United States Patent
Chilov et al.

(10) Patent No.: US 9,522,910 B2
(45) Date of Patent: Dec. 20, 2016

(54) PROTEIN KINASE INHIBITORS (VARIANTS), USE THEREOF IN TREATING ONCOLOGICAL DISEASES AND A PHARMACEUTICAL COMPOSITION BASED THEREON

(71) Applicant: Obshchestvo s ogranichennoy otvetstvennostyou "Fusion Pharma", Moscow (RU)

(72) Inventors: Germes G. Chilov, Domodedovo (RU); Ilya Y. Titov, Moscow (RU)

(73) Assignee: OBSHCHESTVO S OGRANICHENNOY OTVETSTVENNOSTYOU "FUSION PHARMA", Moscow (RU)

( * ) Notice: Subject to any disclaimer, the term of this patent is extended or adjusted under 35 U.S.C. 154(b) by 0 days.

(21) Appl. No.: 14/242,241

(22) Filed: Apr. 1, 2014

(65) Prior Publication Data
US 2014/0213592 A1 Jul. 31, 2014

Related U.S. Application Data

(63) Continuation of application No. PCT/RU2012/000423, filed on May 29, 2012.

(30) Foreign Application Priority Data

Jun. 16, 2011 (RU) .................. 2011124304

(51) Int. Cl.

| | | |
|---|---|---|
| A01N 43/58 | (2006.01) |
| A01N 43/60 | (2006.01) |
| A61K 31/50 | (2006.01) |
| A61K 31/495 | (2006.01) |
| A01N 43/42 | (2006.01) |
| A61K 31/44 | (2006.01) |
| C07D 487/00 | (2006.01) |
| C07D 513/02 | (2006.01) |
| C07D 515/02 | (2006.01) |
| C07D 471/04 | (2006.01) |
| C07D 403/12 | (2006.01) |
| C07D 401/14 | (2006.01) |
| C07D 487/04 | (2006.01) |

(52) U.S. Cl.
CPC .......... C07D 471/04 (2013.01); C07D 401/14 (2013.01); C07D 403/12 (2013.01); C07D 487/04 (2013.01)

(58) Field of Classification Search
None
See application file for complete search history.

(56) References Cited

U.S. PATENT DOCUMENTS

| | | | |
|---|---|---|---|
| 8,088,385 B2 | 1/2012 | Chesney et al. |
| 8,101,604 B2 | 1/2012 | Hepperle et al. |
| 8,148,547 B2 | 4/2012 | Safe |
| 8,158,825 B2 | 4/2012 | Grimm et al. |
| 8,168,650 B2 | 5/2012 | Mach et al. |

(Continued)

FOREIGN PATENT DOCUMENTS

| | | |
|---|---|---|
| RU | 2340611 C2 | 12/2008 |
| RU | 2401265 C2 | 10/2010 |

(Continued)

OTHER PUBLICATIONS

Vieth et al, Kinomics: characterizing the therapeutically validated kinase space, Drug Discovery Today, Jun. 2005, pp. 839-846, vol. 10, No. 12.

(Continued)

*Primary Examiner* — Jeffrey H Murray
(74) *Attorney, Agent, or Firm* — Fish & Richardson P.C.

(57) ABSTRACT

The present invention relates to the treatment of oncological, chronic inflammatory and similar diseases with the aid of new families of chemical compounds having improved efficiency with regard to the inhibition of Abl kinase and mutant forms thereof, as well as other therapeutically significant kinases. It describes protein kinase inhibitors in the form of compounds of general formula (I) and compounds of general formula (II), or a tautomer, an individual isomer, a mixture of isomers, a pharmaceutically acceptable salt, a solvate or a hydrate thereof.

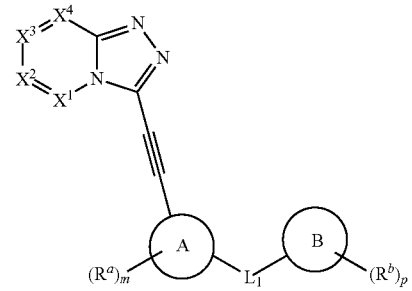

Formula I

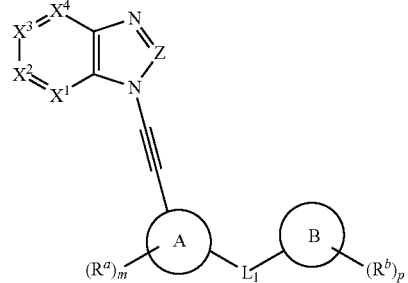

Formula II

50 Claims, No Drawings

(56) References Cited

U.S. PATENT DOCUMENTS

| | | | |
|---|---|---|---|
| 8,178,557 | B2 | 5/2012 | Potashman et al. |
| 8,188,109 | B2 | 5/2012 | Lombardi et al. |
| 8,206,713 | B2 | 6/2012 | Lewicki et al. |
| 8,207,216 | B2 | 6/2012 | Kozikowski et al. |
| 8,211,911 | B2 | 7/2012 | Chen |
| 8,242,282 | B2 | 8/2012 | Wang et al. |
| 8,258,118 | B2 | 9/2012 | Borzilleri et al. |
| 2014/0031354 | A1 | 1/2014 | Yu et al. |

FOREIGN PATENT DOCUMENTS

| | | |
|---|---|---|
| RU | 2011113236 | 10/2012 |
| WO | WO0222607 A1 | 3/2002 |
| WO | WO2005123719 A1 | 12/2005 |
| WO | 2007075869 A2 | 7/2007 |
| WO | WO2007133560 A2 | 11/2007 |
| WO | WO2013170770 A1 | 11/2013 |
| WO | WO2013170774 A1 | 11/2013 |
| WO | WO2014019338 A1 | 2/2014 |

OTHER PUBLICATIONS

Fedorov et al, The (un)targeted cancer kinome, Nature Chemical Biology, Mar. 2010, pp. 166-169, vol. 6.

Gaestel, Targeting innate immunity protein kinase signalling in inflammation, Nature Reviews/Drug Discovery Jun. 2009, pp. 480-499, vol. 8.

Karaman et al, A quantitative analysis of kinase inhibitor selectivity, Nature Biotechnology, Jan. 2008, pp. 127-132,vol. 26, No. 1.

Fabian et al, A small molecule-kinase interaction map for clinical kinase inhibitors, Nature Biotechnology, Mar. 2005, pp. 329-336, vol. 23, No. 3.

Bhagwat, Kinase inhibitors for the treatment of inflammatory and autoimmune disorders, Purinergic Signalling, 2009, pp. 107-115, vo. 5.

Grimminger et al, Targeting non-malignant disorders with tyrosine kinase inhibitors, Nature Reviews/Drug Discovery, Dec. 2010, pp. 956-970, vol. 9.

Hughes et al, Monitoring CML patients responding to treatment with tyrosine kinase inhibitors: review and recommendations for harmonizing current methodology for detecting BCR-ABL transcripts and kinase domain mutations and for expressing results, Blood, Jul. 1, 2006, vol. 108, No. 1, pp. 28-37.

Jabbour, Long-terms outcome of patients with chronic myeloid leukemia treated with second-generation tyrosine kinase inhibitors after imatinib failure is predicted by the in vitro sensitivity of BCR-ABL kinase domain mutations, Blood, Sep. 2009, vol. 114, No. 10, pp. 2037-2043.

Kamath et al, Preclinical pharmacokinetics and in vitro metabolism of dasatinib (BMS-354825): a potent oral multi-targeted kinase inhibitor against SRC and BCR-ABL, Cancer Chemother. Pharmacol, 2008, pp. 365-376, v. 61.

Huang, Discovery of 3-[2-(Imidazo[1,2-b]pyridazin-3-yl)ethynyl]-4-methyl-N-{4-[(4-methylpiperazin-1-yl)-methyl]-3-(trifluoromethyl)phenyl}benzamide (AP24534), a Potent, Orally Active Pan-Inhibitor of Breakpoint Cluster Region-Abelson (BCR-ABL) Kinase Including the T315I Gatekeeper Mutant, Journal of Medical Chemistry, 2010, pp. 4701-4719, vol. 53.

Berge et al, Pharmaceutical Salts, Journal of Pharmaceutical Science, Jan. 1977, vol. 66, No. 11, pp. 1-19.

Guilhot et al, Imatinib in combination with cytarabine for the treatment of Philadelphia-positive chronic myelogenous leukemia chronic-phase patients: rationale and design of phase I/II trails, Seminars in Hematology, Apr. 2003, pp. 92-97, vol. 40, Suppl 2.

Giallongo et al, Imatinib increases cytotoxicity of melphalan and their combination allows an efficient killing of chrnonic myeloid leukemia cells, European Journal of Haematology, 2011, pp. 216-225, vol. 86, No. 3.

Deau et al, The addition of daunorubicin to imatinib mesylate in combination with cytarabine improves the response rate and the survival of patients with myeloid blast crisis chronic myelogenous leukemia (AFR01 study), Leukemia Research, 2001, pp. 777-782, vol. 35.

Pichot et al, Dasatinib synergizes with doxorubicin to block growth, migration, and invasion of breast cancer cells, British Journal of Cancer 2009, pp. 38-47, vol. 101. No. 1.

Coskun et al, Bleomycin, etoposide and cisplatin (BEP) combination with concurrent imatinib mesylate (GLEEVEC) in chronic myeloid leukemia (CML) patient with mesenchymal tumor, Medical Oncology, 2008, pp. 110-112, vol. 25.

Strauss, et al, Three parallel randomized phase II trials of dasatinib plus hormone therapy (HT) in advanced ER+ breast cancer (ER+ABC), Journal of Clinical Oncology, 2010, ASCO Annual Meeting Proceedings (Post-Meeting Edition), 2010, vol. 28, No. 15 (May 20 Supplement).

Lehr et al, Production, purification and characterization of non-myristylated human T-cell protein tyrosine kinase in baculovirus expression system, Gene, 1996; 169(2), 275-279.

Gish et al, Bacterial expression, purification and preliminary kinetic description of the kinase domain of v-fps, Protein Engineering, 1995, pp. 609-614, vol. 8, No. 6.

Braunwalder et al, A Solid-Phase Assay for the Determination of Protein Tyrosine Kinase Activity of c-src Using Scintillating Microtitration Plates, Analytical Biochemistry, 1996, pp. 23-26, vol. 234, Article No. 0044.

Mosmann, Rapid colorimetric Assay for Cellular Growth and Survivial: Application to Proliferation and Cytotoxicity Assays, Journal of Immunological, Methods, 1983, pp. 55-63, vol. 65.

Katritzky et al, Handbook of Heterocyclic Chemistry, Second Edition 2000, Pergamon, Amsterdam, The Netherlands.

Malleron et al, Handbook of Palladium-Catalyzed Organic Reactions, Academic Press, 1997, San Diego, California.

Remington's Pharmaceutical Sciences, 1975, Fifteenth Edition, Mack Publishing Co, Easton, PA.

Bonifacio et al, Current Protocols in Cell Biology, 2003, Wiley and Sons.

Ausubel et al., Current Protocols in Molecular Biology, 2003, Wiley and Sons.

Higuchi et al, Pro-drugs as Novel Drug Delivery Systems, ACS Symposium Series, 1975, v. 14.

International Search Report from International Application No. PCT/RU2012/000423 filed May 29, 2012, mailed Dec. 13, 2012.

Roche, Bioreversible Carriers in Drug Design: Theory and Application, 1987, American Pharmaceutical Association, Pergamon Press, NY.

Cancer Care Ontario, Cisplatin Drug Monograph, Feb. 2015, 11 pp. (https://www.cancercare.on.ca/CCO_DrugFormulary/Pages/DfPdfContent.aspx?itemId=93923, retrieved Dec. 23, 2015).

Cancer Care Ontario, Doxorubicin Drug Monograph, Dec. 2014, 11 pp. (https://www.cancercare.on.ca/CCO_DrugFormulary/Pages/DfPdfContent.aspx?itemId=93879, retrieved Dec. 23, 2015).

Cancer Care Ontario, Paclitaxel Drug Monograph, Aug. 2015, 13 pp. (https://www.cancercare.on.ca/CCO_DrugFormulary/Pages/DfPdfContent.aspx?itemId=94025, retrieved Dec. 23, 2015).

Collins et al., The Cell Cycle and Cancer, Proc. Natl. Acad. Sci. USA, 1997, 94, 2776-78.

Examination Report dated Nov. 9, 2015 for European Patent Application No. 12801171.5 (5 pp.).

Nilotinib Prescribing Information, Novartis, Jan. 2014, 27 pages.

Mian et al., PF-114, a potent and selective inhibitor of native and mutated BCR/ABL is active against Philadelphia chromosome-positive (Ph+) leukemias harboring the T315I mutation, Leukemia. 2015;29(5):1104-14 (including supplementary information).

US 9,522,910 B2

PROTEIN KINASE INHIBITORS (VARIANTS), USE THEREOF IN TREATING ONCOLOGICAL DISEASES AND A PHARMACEUTICAL COMPOSITION BASED THEREON

RELATED APPLICATIONS

This application is a Continuation application of International Application PCT/RU2012/000423, filed on May 29, 2012, which in turn claims priority to Russian Patent Applications No. RU2011124304, filed Jun. 16, 2011, both of which are incorporated herein by reference in their entirety.

FIELD OF THE INVENTION

This invention concerns the therapy of oncologic, chronic inflammatory and other diseases with the use of novel chemical compounds of novel chemical classes possessing improved efficacy in inhibiting Abl-kinase and its mutants as well as other therapeutically relevant kinases, improved selectivity and bioavailability.

BACKGROUND OF THE INVENTION

The protein kinases are a large family of proteins which play a central role in the regulation of key cellular processes. Disregulation of protein kinases activity can lead to oncologic, chronic inflammatory diseases, CNS diseases etc. A list of kinases with validated preclinical or clinical therapeutic impact includes: ABL1, AKT, AKT2, AURKA, BRAF, BCR-ABL, BLK, BRK, C-KIT, C-MET, C-SRC, CAMK2B, CDK1, CDK2, CDK3, CDK4, CDK5, CDK6, CDK7, CDK8, CDK9, CRAF1, CHEK1, CHEK2, CLK1, CLK3, CSF1R, CSK, CSNK1G2, CSNK1G3, CSNK2A1, DAPK1, DAPK2, DAPK3, EGFR, EPHA2, EPHA3, EPHA5, ERBB2, ERBB3, ERBB4, ERK, ERK2, ERK3, FES, FGFR1, FGFR2, FGFR3, FGFR4, FGFR5, FGR, FLT-1, FYN, GSK3B, HCK, IGF1R, INSR, ITK, JAK1, JAK2, JAK3, JNK1, JNK2, JNK3, KIT, LCK, LOK, MAP3K5, MAPKAPK2, MARK1, MEK1, MEK2, MET, MKNK2, MST1, NEK2, p38-alpha, p38-delta, p38-gamma, PAK1, PAK4, PAK6, PAK7, PDPK1, PDGFR, PIK3CG, PIM1, PIM2, PKC, PLK1, PLK4, PRKCQ, PRKR, PTK2, PTK2B, RET, ROCK1, ROS, RPS6KA1, SLK, SRC, SRPK1, STK16, SYK, TAK1, TGFBR1, TIE, TIE2, TNK2, TRK, VEGFR2, WEE1, ZAP70 (Michal Vieth et al, Kinomics: characterizing thetherapeutically validated kinase space, Drug Discov Today•Volume 10, Number 12•June; Oleg Fedorov, The (un)targeted cancer kinome, nature chemical biology, 2010, 6, 166-169; 2005; Matthias Gaestel; Targeting innate immunity protein kinase signalling in inflammation, Nat REv Drug Discov, 480-499, 2009 (8); Karaman M W et al, A quantitative analysis of kinase inhibitor selectivity, Nat. Biotechnol. 2008 January; 26(1):127-132; Fabian M A, et al, A small molecule-kinase interaction map for clinical kinase inhibitors, Nat. Biotechnol. 2005 March; 23(3):329-336; Bhagwat S S, Kinase inhibitors for the treatment of inflammatory and autoimmune disorders. Purinergic Signal. 2009 March; 5(1):107-15; Friedrich Grimminger et al, Targeting non-malignant disorders with tyrosine kinase inhibitors, Nature Reviews Drug Discovery 9, 956-970). With the advent of new experimental data, this list is constantly growing.

Application of small molecule protein kinase inhibitors represents a prospective approach for the treatment of diseases associated with impaired protein kinase activity. Examples of such inhibitors approved for clinical use are: Imatinib, Nilotinib, Dasatinib, Sunitinib, Sorafenib, Lapatinib, Gefitinib, Erlotinib, Flavopiridol. A lot of clinical candidate kinase inhibitors undergoes clinical trials and preclinical development.

Widespread use of small molecule protein kinase inhibitors in clinic revealed several serious issues related to their efficacy and safety. First these problems are connected with low activity of inhibitors towards mutated protein kinase forms that may eventually occur in patients. For instance it is well known that kinase domain of gene product of BCR-ABL chronic myelogenous leukemia target is subjected to mutations that cause resistance to imatinib (mutations Y253H, E255V, T315I) (Timothy Hughes et al, Monitoring CML patients responding to treatment with tyrosine kinase inhibitors: review and recommendations for harmonizing current methodology for detecting BCR-ABL transcripts and kinase domain mutations and for expressing results, BLOOD, 2006; 108:28-37 and second generation inhibitors Nilotinib and Dasatinib (mutation T315I) (Elias Jabbour, Long-term outcome of patients with chronic myelogenous leukemia treated with second-generation tyrosine kinase inhibitors after imatinib failure is predicted by the in vitro sensitivity of BCR-ABL kinase domain mutations, Blood. 2009; 114:2037-2043). Second, kinase inhibition selectivity plays an important role. As a rule decrease in selectivity leads to decrease in inhibitor's safety as can be judged by comparison of more selective imatinib and less selective dasatinib both used for the treatment of chronic myelogenous leukemia. Third, bioavailability of kinase inhibitors has a big impact. Several inhibitors of the same Abl kinase possess low bioavailability: dasatinib (bioavailability 14-34%, Amrita V. K. et al. Cancer Chemoter Pharmacol 2008, 61, 365-376), nilotinib (bioavailability 30%, Nilotinib Prescribing Information, Novartis), ponatinib (bioavailability 20%, J. Med. Chem. 2010, 53, 4701-4719). Thus the development of kinase inhibitors with improved bioavailability is a practically important task.

There are imidazole derivatives which possess inhibiting action upon abnormal activity of kinases selected from Abl, BCR-AbI, PDGF-R, trkB, c-SRC, BMX, FGFR3, b-RAF, SGK, Tie2, Lck, JNK2a2, MKK4, c-RAF, MKK6, SAPK2a and SAPK2P and pharmaceutical composition comprising these compounds for treatment or prevention of such diseases as proliferative disorders and diseases resulting from inadequate activation of immune and nerve systems (Russian patent 2401265). This source may be referred as the nearest analogue.

SUMMARY OF THE INVENTION

This invention is aimed at the development of novel multikinase inhibitors useful as an active ingredients of novel anti-cancer treatments.

The problem solved by this invention deals with novel chemical compounds that possesses improved efficacy in inhibition of Abl-kinase and its mutants, improved selectivity and bioavailability and has a big potential for the treatment of oncologic, chronic inflammatory and other diseases.

The compounds of this invention are protein kinase inhibitors of the general formula I or tautomers or individual isomer or a mixture of isomers, pharmaceutically acceptable salt, solvate or hydrate:

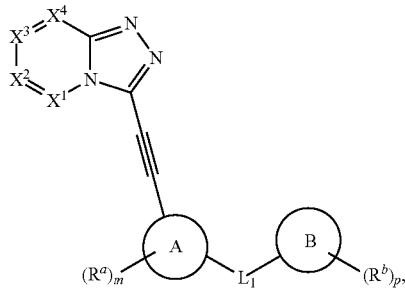

Formula I in which:
$X_1$ represents N, $CR_t^1$; $X_2$ represents N, $CR_t^2$, $X_3$ represents N, $CR_t^3$, $X_4$ represents N, CH. $X^1$, $X^2$, $X^3$ and $X^4$ are each selected independently; preferably $X^1=CR_t^1$, $X^2=CR_t^2$, $X^3=CR_t^3$, $X^4=CH$;

$R_t^1$ represents —H, halo, —$R^1$, —$OR^2$, —$NHR^2$, —$SR^2$, —C(O)CH$_3$, —C(O)CH$_2$CH$_3$, —CH$_2$C(O)CH$_3$, —CH$_2$OH, —CH$_2$CH$_2$OH, —CH$_2$CH$_2$CH$_2$OH, —CH$_2$OCH$_3$, —CH$_2$CH$_2$OCH$_3$, —CH$_2$OCH$_2$CH$_3$, —CH$_2$SH, —CH$_2$SCH$_3$, —CH$_2$SCH$_2$CH$_3$, —CH$_2$CH$_2$SCH$_3$, —CN, —COOH, —CONH$_2$, —C(O)NHCH$_3$, —NHC(O)CH$_3$; preferably $R_t^1$=—H, —Cl, —$R^1$, —$OR^2$, —CH$_2$OCH$_3$, —SCH$_3$;

$R_t^2$ represents —H, halogen, —CH$_3$, —CH$_2$CH$_3$, —CH=CH$_2$, —NH$_2$, —NHCH$_3$, —OH, —OCH$_3$, —SH, —SCH$_3$; preferably $R_t^2$=—H;

$R_t^3$ represents —H, halogen, —CN, —NO$_2$, —$R^6$, —$OR^4$, —$NR^4R^5$, —C(O)$YR^4$, —OC(O)$YR^4$, —$NR^4$C(O)$YR^4$, —SC(O)$YR^4$, —$NR^4$C(=S)$YR^4$, —OC(=S)$YR^4$, —C(=S)$YR^4$, —YC(=$NR^5$)$YR^4$, —YP(=O)($YR^6$)($YR^6$), —Si($R^6$)$_3$, —$NR^4SO_2R^4$, —S(O)$_rR^4$, —SO$_2NR^4R^5$, —$NR^4SO_2NR^4R^5$, where Y is independently selected from chemical bond, —O—, —S—, —$NR^5$—; preferably $R_t^3$=—H, —$NR^4R^5$, —$OR^4$, —$R^6$, —CO(Y)$R^4$.

$R^1$ represents $C_1$-$C_4$-alkyl, $C_2$-$C_4$-alkenyl, $C_2$-$C_4$-alkinyl, $C_3$-$C_{12}$-cycloalkyl, optionally substituted by 1-3 radicals, independently selected from the group consisting of $C_1$-$C_6$ alkyl, hydroxy-$C_1$-$C_6$-alkyl, $C_1$-$C_6$-alkoxy, halogen-substituted $C_1$-$C_6$-alkyl, nitro, cyano, —$NR_7R_8$, where $R_7$ and $R_8$ is independently selected from hydrogen or $C_{1-4}$-alkyl (total number of heavy atoms in $R^1$ should not exceed 4); preferably $R^1$=CH$_3$, CH$_2$CH$_3$, CH$_2$CH$_2$CH$_3$, C≡CCH$_3$, cyclopropyl;

$R^2$ represents $C_1$-$C_3$-alkyl, $C_2$-$C_3$-alkenyl, $C_2$-$C_3$-alkinyl, optionally substituted by 1-3 radicals, independently selected from the group consisting of $C_1$-$C_6$ alkyl, hydroxy-$C_1$-$C_6$-alkyl, $C_1$-$C_6$-alkoxy, halogen-substituted $C_1$-$C_6$-alkyl, nitro, cyano, —$NR_7R_8$, where $R_7$ and $R_8$ are independently selected from hydrogen or $C_{1-4}$-alkyl (total number of heavy atoms in $R^2$ should not exceed 3); preferably $R^2$=CH$_3$, CH$_2$CH$_3$;

ring A represents aryl or 5- or 6-membered heteroaryl cycle, in which heteroaryl contains 1-2 heteroatoms, selected from N, S and O, optionally substituted by 1-4 $R^a$ groups;

ring B represents aryl or 5- or 6-membered heteroaryl cycle, in which heteroaryl contains 1-2 heteroatoms, selected from N, S and O, optionally substituted by 1-5 $R^b$ groups;

$R^a$ and $R^b$ are independently selected from —H, halogen, —CN, —NO$_2$, —$R^6$, —$OR^4$, —$NR^4R^5$), —C(O)$YR^4$, —OC(O)$YR^4$, —$NR^4$C(O)$YR^4$, —SC(O)$YR^4$, —$NR^4$C(=S)$YR^4$, —OC(=S)$YR^4$, —C(=S)$YR^4$, —YC(=$NR^5$)$YR^4$, —YP(=O)($YR^6$)($YR^6$), —Si($R^6$)$_3$, —$NR^4SO_2R^4$, —S(O)$_rR^4$, —SO$_2NR^4R^5$, —$NR^4SO_2NR^4R^5$, where Y is independently selected from chemical bond, —O—, —S—, —$NR^5$—;

$L^1$ represents $NR^3$C(O) or C(O)$NR^3$;

$R^3$, $R^4$ and $R^5$ are independently selected from H, $C_1$-$C_6$-alkyl, $C_2$-$C_6$-alkenyl, $C_2$-$C_6$-alkinyl, $C_3$-$C_{12}$-cycloalkyl, $C_3$-$C_{12}$-cycloalkenyl, $C_3$-$C_{12}$-cycloalkinyl, aryl, heterocyclyl or heteroaryl; in which heterocyclyl represents cyclic system consisting of 1-4 rings and comprising five to fourteen carbon atoms substituted by 1-2 heteroatoms selected from N, S and O, and in which heteroaryl represents heterocyclic or polyheterocyclic aromatic fragment consisting of 5-14 ring atoms connected with one or more aromatic or non-aromatic rings, alternatively $NR^4R^5$ group may represent 5- or 6-membered saturated, partially saturated or unsaturated ring, which may optionally contain 0-2 additional heteroatoms selected from N, O and S(O)$_r$;

each occurrence of $R^6$ is independently selected from $C_1$-$C_6$-alkyl, $C_2$-$C_6$-alkenyl, $C_2$-$C_6$-alkinyl, $C_3$-$C_{12}$-cycloalkyl, $C_3$-$C_{12}$-cycloalkenyl, $C_3$-$C_{12}$-cycloalkinyl, aryl, in which heterocyclyl represents cyclic system consisting of 1-4 rings and comprising five to fourteen carbon atoms substituted by 1-2 heteroatoms selected from N, S and O, and in which heteroaryl represents heterocyclic or polyheterocyclic aromatic fragment consisting of 5-14 ring atoms connected with one or more aromatic or non-aromatic rings;

r is selected from 0, 1 or 2;
m is 0, 1, 2, 3, 4;
p is 0, 1, 2, 3, 4 or 5.

Also the compounds of this invention are protein kinase inhibitors of the general formula II or tautomers or individual isomer or a mixture of isomers, pharmaceutically acceptable salt, solvate or hydrate:

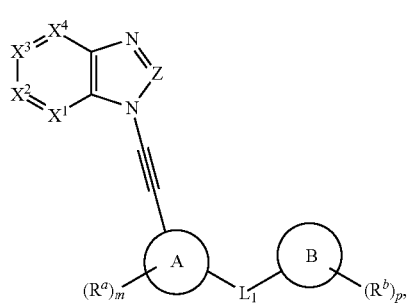

Formula II in which:
Z represents N, CH;
$X_1$ represents N, $CR_t^1$; $X_2$ represents N, $CR_t^2$, $X_3$ represents N, $CR_t^3$, $X_4$ represents N, CH; $X^1$, $X^2$, $X^3$ and $X^4$ are selected independently; preferably $X^1=X^4$ and $X^2=X^3$, Z=CH;

$X_1$ and $X_3$ are not simultaneously N;

$R_t^1$ represents —H, halo, —$R^1$, —$NHR^2$, —$SR^2$, —C(O)CH$_3$, —C(O)CH$_2$CH$_3$, —CH$_2$C(O)CH$_3$, —CH$_2$OH, —CH$_2$CH$_2$OH, —CH$_2$CH$_2$CH$_2$OH, —CH$_2$OCH$_3$, —CH$_2$CH$_2$OCH$_3$, —CH$_2$OCH$_2$CH$_3$, —CH$_2$SH, —CH$_2$SCH$_3$, —CH$_2$SCH$_2$CH$_3$, —CH$_2$CH$_2$SCH$_3$, —CN, —COOH, —CONH$_2$, —C(O)NHCH$_3$, —NHC(O)CH$_3$; preferably $R_t^1$=—H, —Cl, —$R^1$, —$OR^2$, —CH$_2$OCH$_3$, —SCH$_3$;

$R_t^2$ represents —H, halogen, —CH$_3$, —CH$_2$CH$_3$, —CH=CH$_2$, —NHCH$_3$, —OH, —OCH$_3$, —SH, —SCH$_3$; preferably $R_t^2$=—H, —CH$_3$;

$R_t^3$ represents —H, halogen, —CN, —NO$_2$, —R$^6$, —OR$^4$, —NR$^4$R$^5$, —C(O)YR$^4$, —OC(O)YR$^4$, —NR$^4$C(O)YR$^4$, —SC(O)YR$^4$, —NR$^4$C(=S)YR$^4$, —OC(=S)YR$^4$, —C(=S)YR$^4$, —YC(=NR$^5$)YR$^4$, —YP(=O)(YR$^6$)(YR$^6$), —Si(R$^6$)$_3$, —NR$^4$SO$_2$R$^4$, —S(O)$_r$R$^4$, —SO$_2$NR$^4$R$^5$, —NR$^4$SO$_2$NR$^4$R$^5$, where Y is independently selected from chemical bond, —O—, —S—, —NR$^5$—; preferably $R_t^3$=—H, —NR$^4$R$^5$, —OR$^4$, —R$^6$, —CO(Y)R$^4$.

R$^1$ represents C$_1$-C$_4$-alkyl, C$_2$-C$_4$-alkenyl, C$_2$-C$_4$-alkynil, C$_3$-C$_{12}$-cycloalkyl, optionally substituted by 1-3 radicals, independently selected from group including C$_1$-C$_6$ alkyl, hydroxy-C$_1$-C$_6$-alkyl, C$_1$-C$_6$-alkoxy, halogen-substituted C$_1$-C$_6$-alkyl, nitro, cyano, —NR$_7$R$_8$, where R$_7$ and R$_8$ is independently selected from hydrogen or C$_{1-4}$-alkyl (total number of heavy atoms in R$^1$ should not exceed 4); preferably R$^1$=CH$_3$, CH$_2$CH$_3$, CH$_2$CH$_2$CH$_3$, C≡CCH$_3$;

R$^2$ represents C$_1$-C$_3$-alkyl, C$_2$-C$_3$-alkenyl, C$_2$-C$_3$-alkinyl, optionally substituted by 1-3 radicals, independently selected from the group consisting of C$_1$-C$_6$ alkyl, hydroxy-C$_1$-C$_6$-alkyl, C$_1$-C$_6$-alkoxy, halogen-substituted C$_1$-C$_6$-alkyl, nitro, cyano, —NR$_7$R$_8$, where R$_7$ and R$_8$ is independently selected from hydrogen or C$_{1-4}$-alkyl (total number of heavy atoms in R$^2$ should not exceed 3); preferably R$^2$=CH$_3$, CH$_2$CH$_3$;

ring A represents aryl or 5- or 6-membered heteroaryl cycle, in which heteroaryl comprises 1-2 heteroatoms, selected from N, S and O, optionally substituted by 1-4 R$^a$ groups;

ring B represents aryl or 5- or 6-membered heteroaryl cycle, in which heteroaryl comprises 1-2 heteroatoms, selected from N, S and O, optionally substituted by 1-5 R$^b$ groups;

R$^a$ and R$^b$ are independently selected from —H, halo, —CN, —NO$_2$, —R$^6$, —OR$^4$, —NR$^4$R$^5$, —C(O)YR$^4$, —OC(O)YR$^4$, —NR$^4$C(O)YR$^4$, —SC(O)YR$^4$, —NR$^4$C(=S)YR$^4$, —OC(=S)YR$^4$, —C(=S)YR$^4$, —YC(=NR$^5$)YR$^4$, —YP(=O)(YR$^6$)(YR$^6$), —Si(R$^6$)$_3$, —NR$^4$SO$_2$R$^4$, —S(O)$_r$R$^4$, —SO$_2$NR$^4$R$^5$, —NR$^4$SO$_2$NR$^4$R$^5$, where Y is independently selected from chemical bond, —O—, —S—, —NR$^5$—;

L$^1$ represents NR$^3$C(O) or C(O)NR$^3$;

R$^3$, R$^4$ and R$^5$ are independently selected from H, C$_1$-C$_6$-alkyl, C$_2$-C$_6$-alkenyl, C$_2$-C$_6$-alkinyl, C$_3$-C$_{12}$-cycloalkyl, C$_3$-C$_{12}$-cycloalkenyl, C$_3$-C$_{12}$-cycloalkinyl, aryl, heterocyclyl or heteroaryl; in which heterocyclyl represents cyclic system consisting of 1-4 rings and comprising five to fourteen carbon atoms substituted by 1-2 heteroatoms selected from N, S and O, and in which heteroaryl represents heterocyclic or polyheterocyclic aromatic fragment consisting of 5-14 ring atoms connected with one or more aromatic or non-aromatic rings, alternatively NR$^4$R$^5$ group may represent 5- or 6-membered saturated, partially saturated or unsaturated ring, which may optionally contain 0-2 additional heteroatoms selected from N, O and S(O)$_r$;

each occurrence of R$^6$ is independently selected from C$_1$-C$_6$-alkyl, C$_2$-C$_6$-alkenyl, C$_2$-C$_6$-alkinyl, cycloalkyl, C$_3$-C$_{12}$-cycloalkenyl, C$_3$-C$_{12}$-cycloalkinyl, aryl, in which heterocyclyl represents cyclic system consisting of 1-4 rings and comprising five to fourteen carbon atoms substituted by 1-2 heteroatoms selected from N, S and O, and in which heteroaryl represents heterocyclic or polyheterocyclic aromatic fragment consisting of 5-14 ring atoms connected with one or more aromatic or non-aromatic rings;

r is selected from 0, 1 or 2;

m is 0, 1, 2, 3, 4;

p is 0, 1, 2, 3, 4 or 5.

DETAILED DESCRIPTION OF COMPOUNDS OF THE INVENTION

Compounds of formula I which are the subject of current invention contains following heteroaryl cycle:

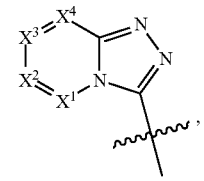

where X$_1$, X$_2$, X$_3$ and X$_4$ are as described above. Examples of bicyclic heteroaryl cycles satisfying this general formula are:

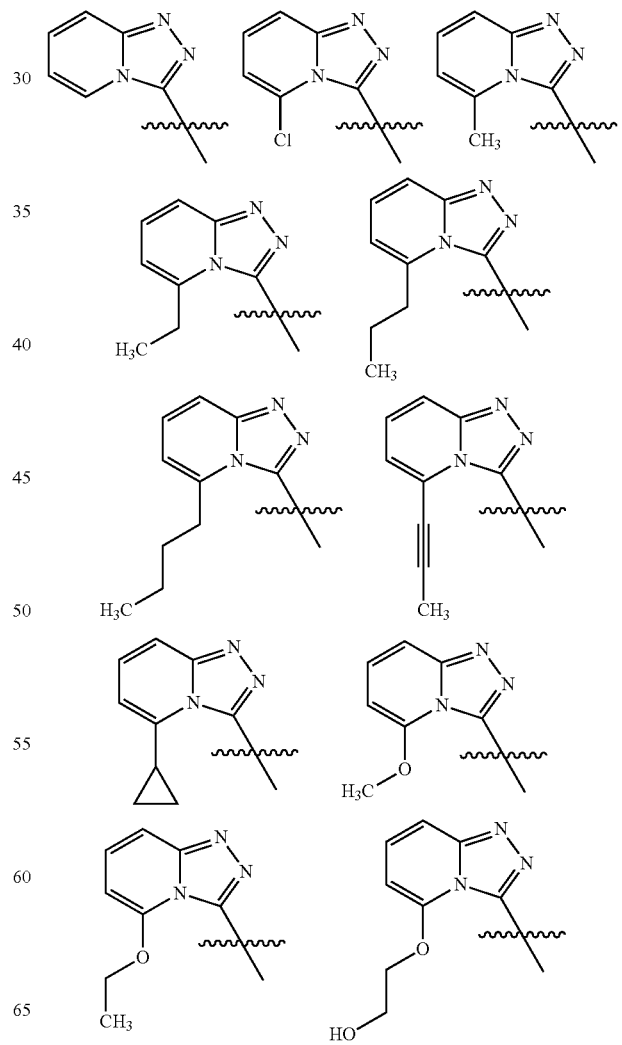

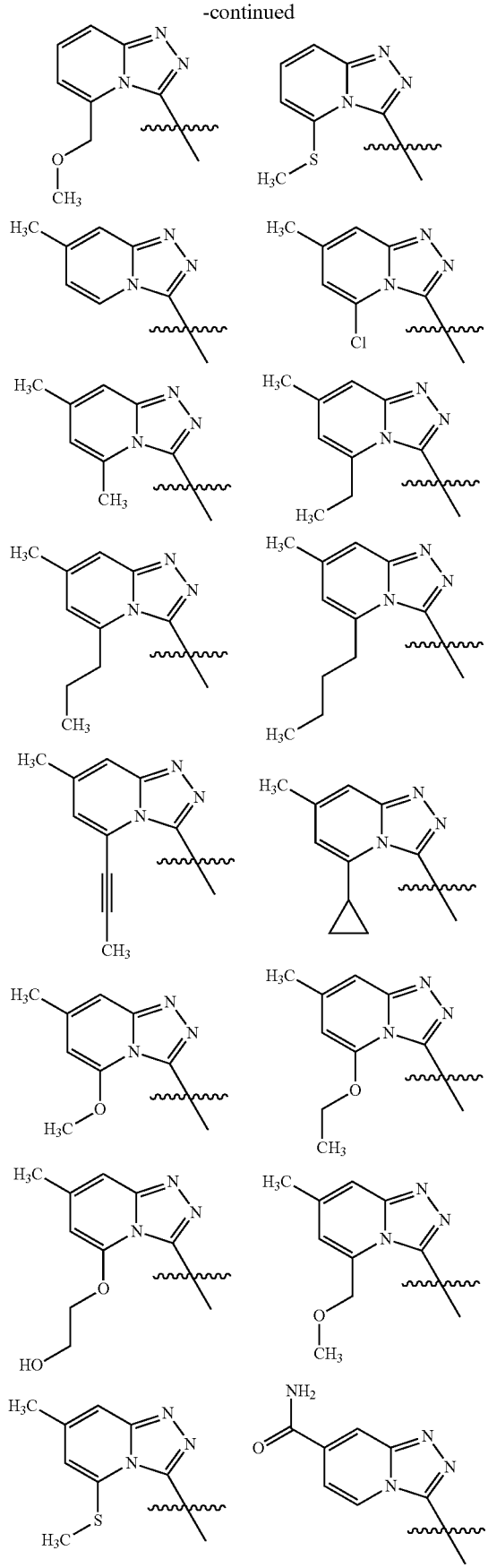
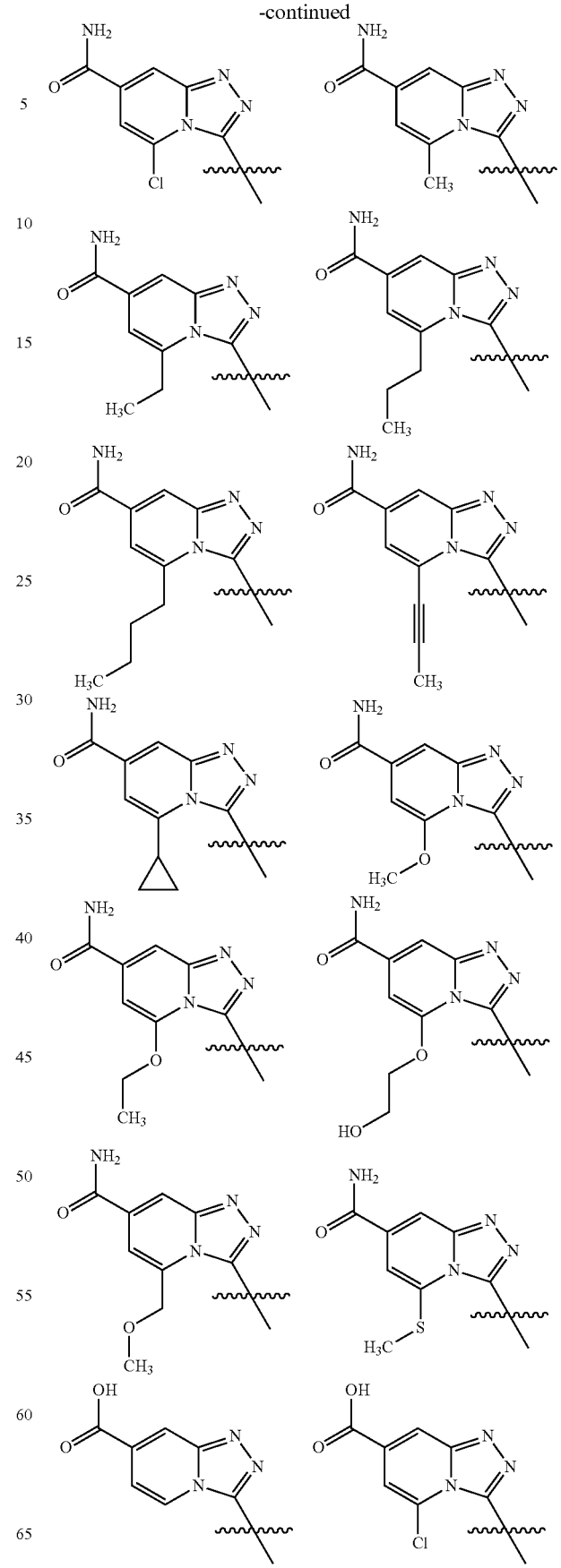

-continued
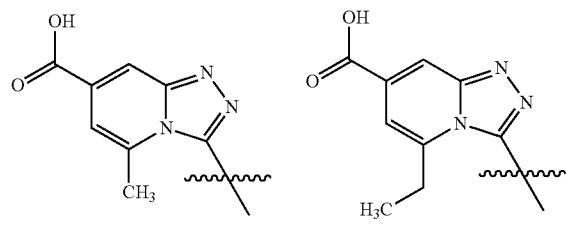
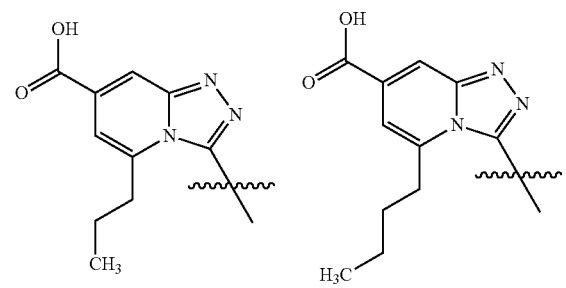
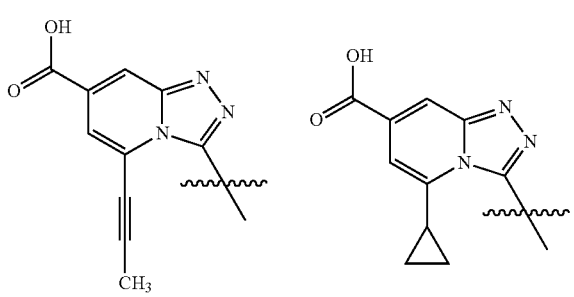
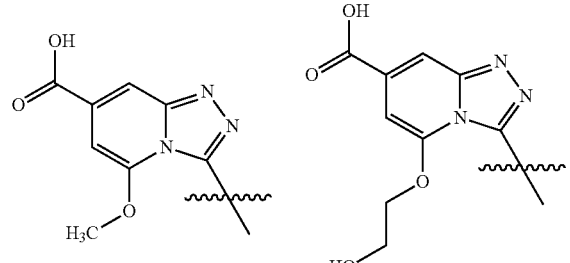
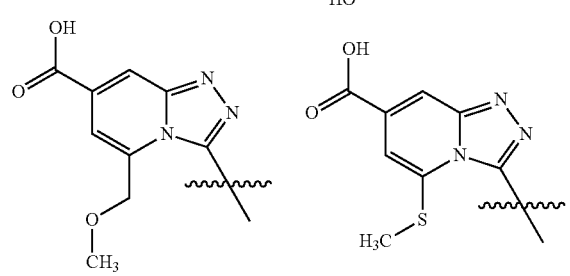
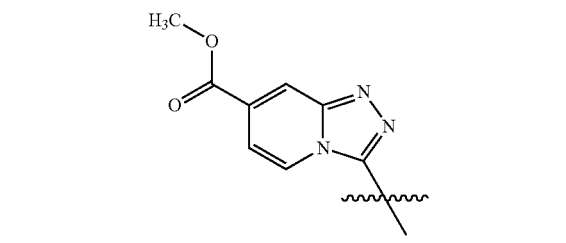
-continued
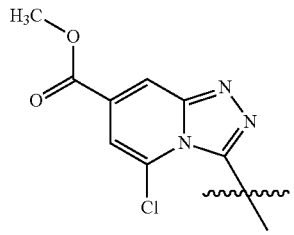
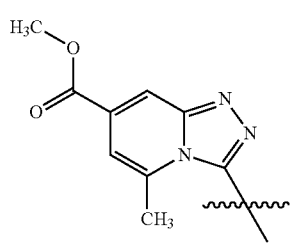
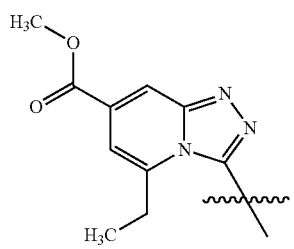
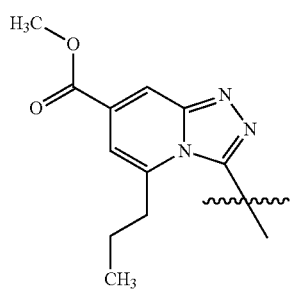
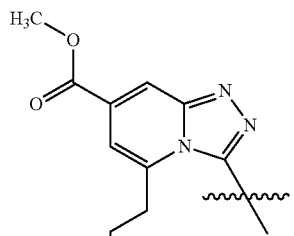
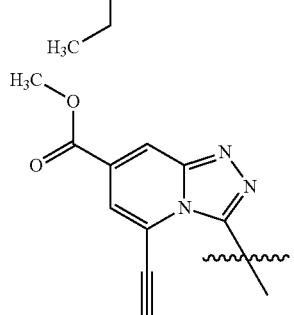

11
-continued
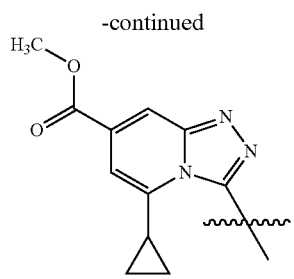
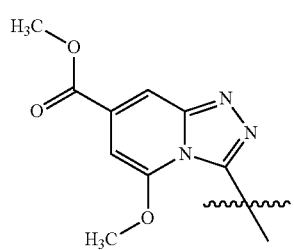
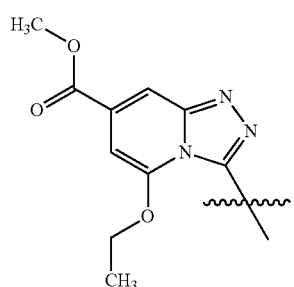
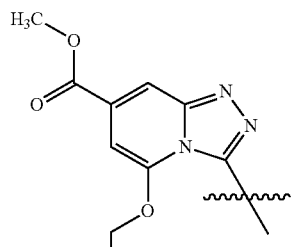
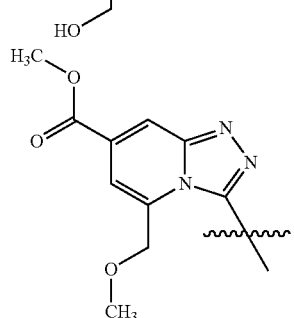
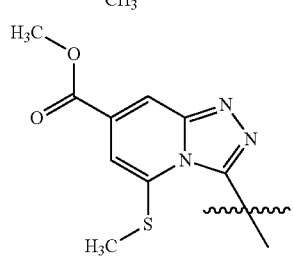
12
-continued
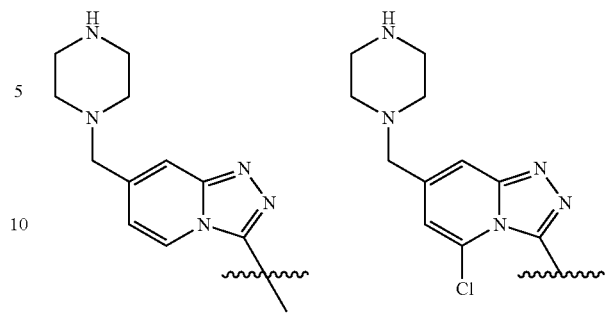
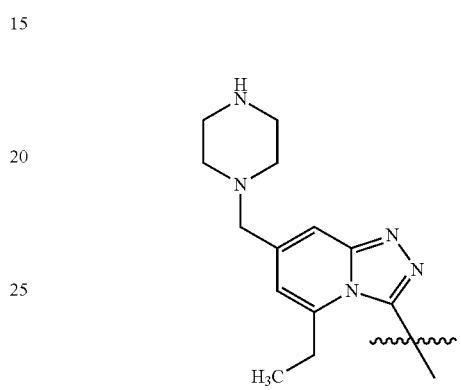
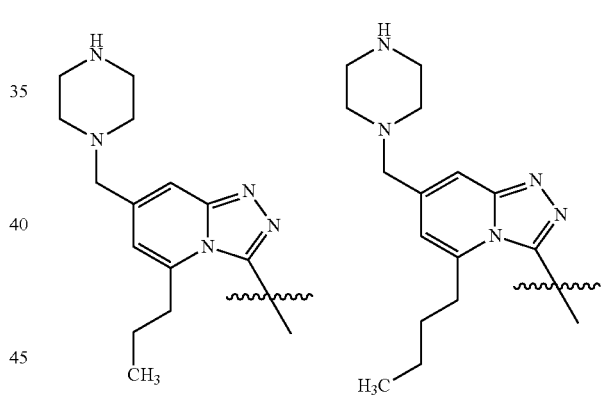
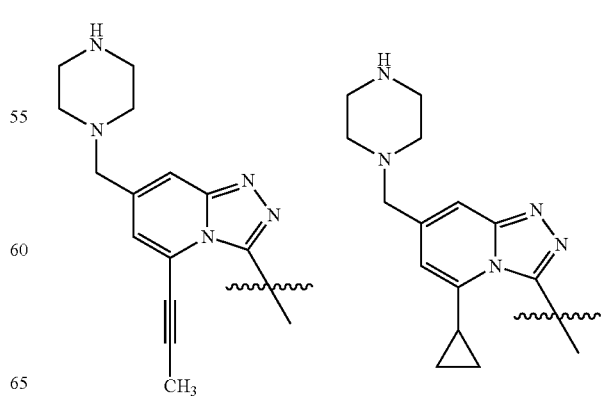

13
-continued

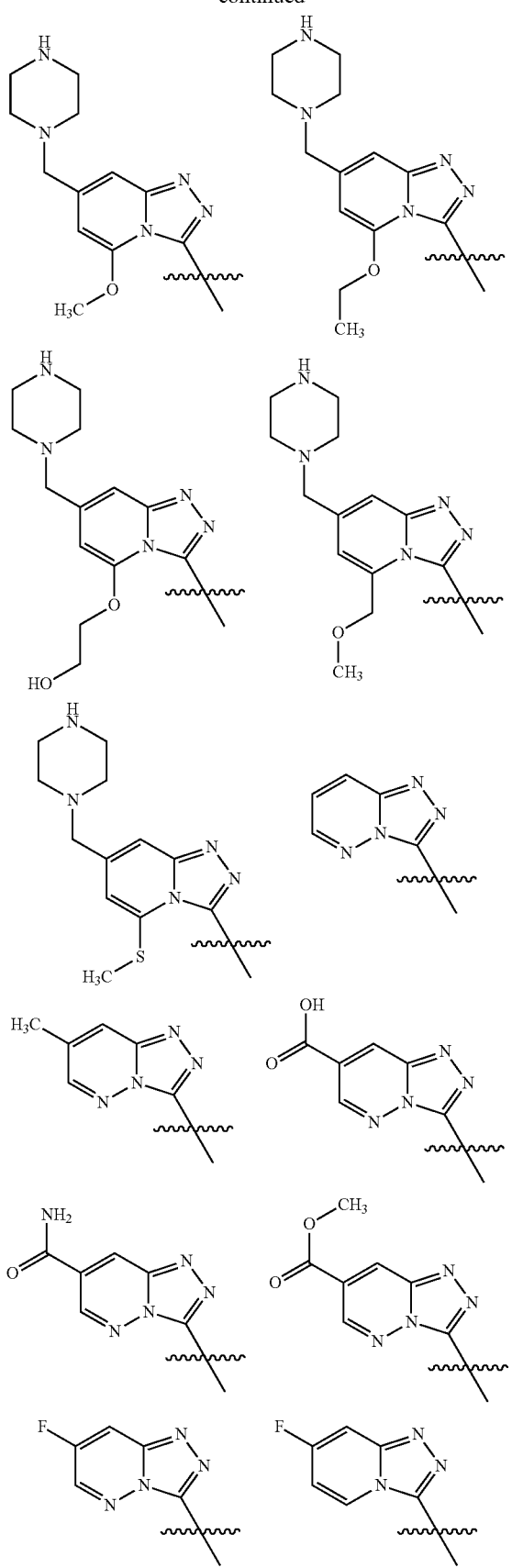

14

Structures of A and B rings for compounds containing represented bicyclic heteroaryl fragments are described in part 1 Description of the invention.

Compounds of general formula II which are the subject of current invention contains following heteroaryl cycle:

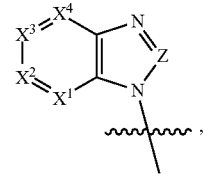

where $X_1$, $X_2$, $X_3$ and $X_4$ are as described above. Examples of bicyclic heteroaryl cycles satisfying this general formula are:

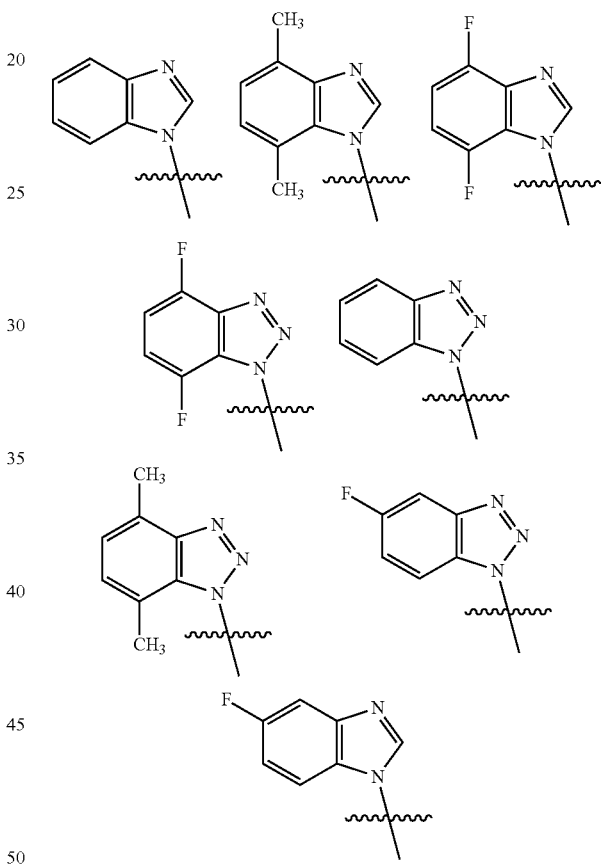

Structures of A and B cycles for compounds containing represented bicyclic heteroaryl fragments are described in part 1 Description of the invention.

Illustrative examples of substituted ring A groups:

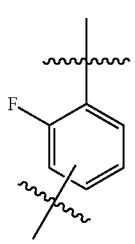

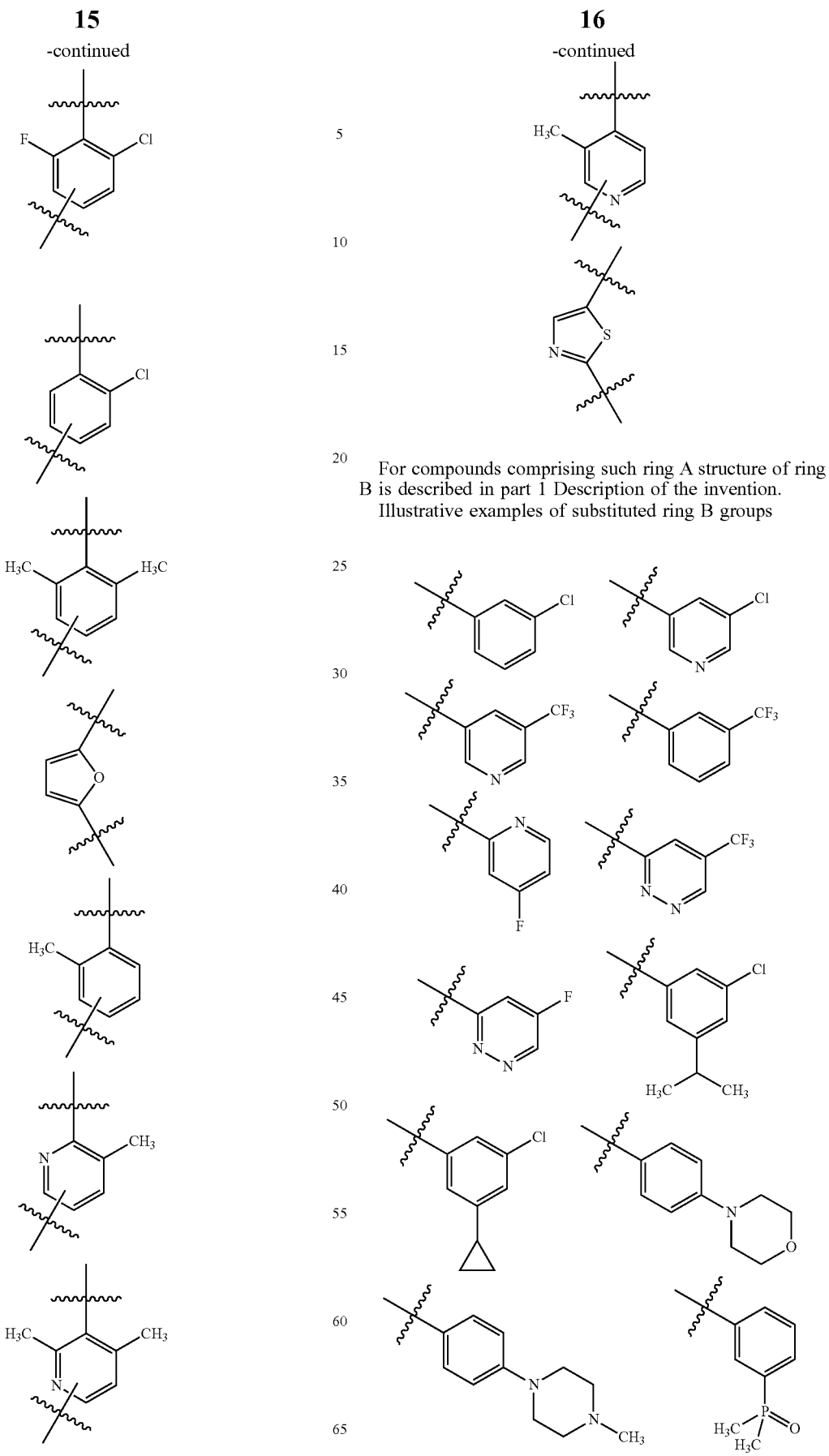
For compounds comprising such ring A structure of ring B is described in part 1 Description of the invention. Illustrative examples of substituted ring B groups -continued

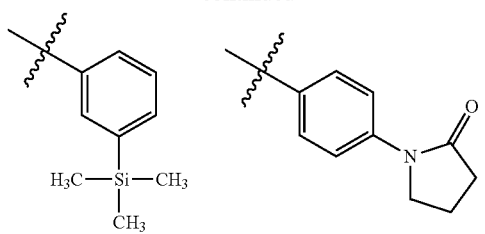

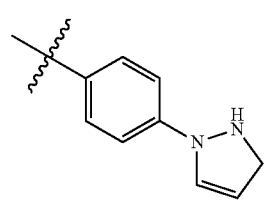

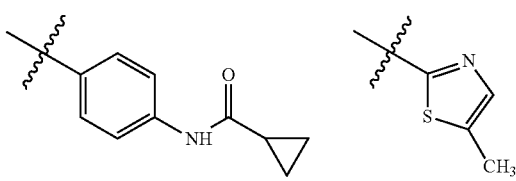

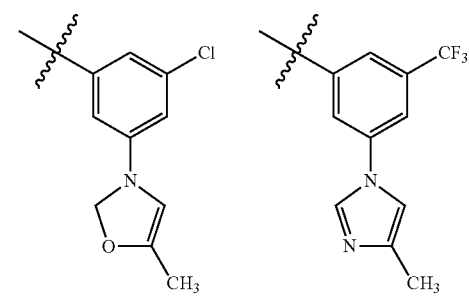

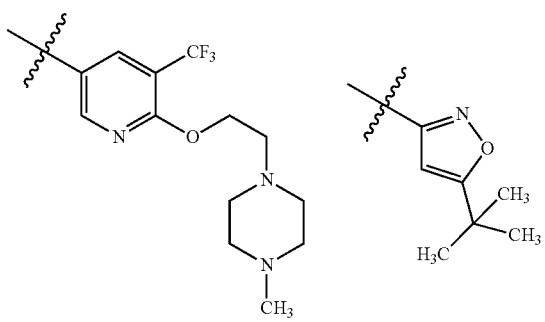

Of special interest is the class of compounds of Formula I as described above in Part 1, in which one of the $R^b$ substituents is a 5- or 6-membered ring (Ring C), which may be heteroaryl or heterocyclic, comprising carbon atoms and 1-3 heteroatoms independently selected from O, N and S(O)r, and Ring C being optionally substituted on carbon or heteroatom(s) with 1 to 5 substituents $R^c$. This class is represented by Formulae III-IV:

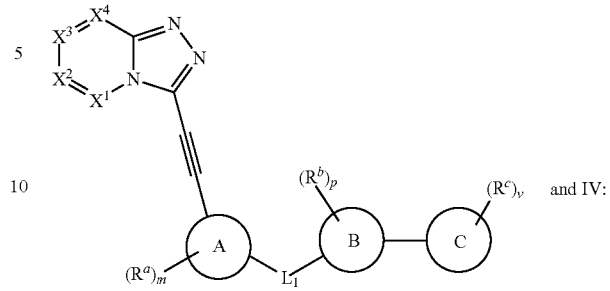

Formula III

Formula IV in which the previously defined variables, e.g., n, m, P, A, B, T, $L^1$, $R^1$, $R_t$, $R_a$ and $R_b$ are as defined above in part 1 and $R^c$ at each occurrence is independently selected from —H, halogen, —CN, —NO$_2$, —$R^6$, —OR$^4$, —NR$^4$R$^5$, —C(O)YR$^4$, —OC(O)YR$^4$, —NR$^4$C(O)YR$^4$, —SC(O)YR$^4$, —NR$^4$C(=S)YR$^4$, —OC(=S)YR$^4$, —C(=S)YR$^4$, —YC(=NR$^5$)YR$^4$, —YP(=O)(YR$^6$)(YR$^6$), —Si(R$^6$)$_3$, —NR$^4$SO$_2$R$^4$, —S(O)$_r$R$^4$, —SO$_2$NR$^4$R$^5$, —NR$^4$SO$_2$NR$^4$R$^5$, wherein each Y is independently a chemical bond, —O—, —S—, —NR$^5$—, $R^4$, $R^5$, $R^6$ are as defined previously in Part 1; and, v is 0, 1, 2, 3, 4 or 5.

Illustrative examples of Ring C systems include:

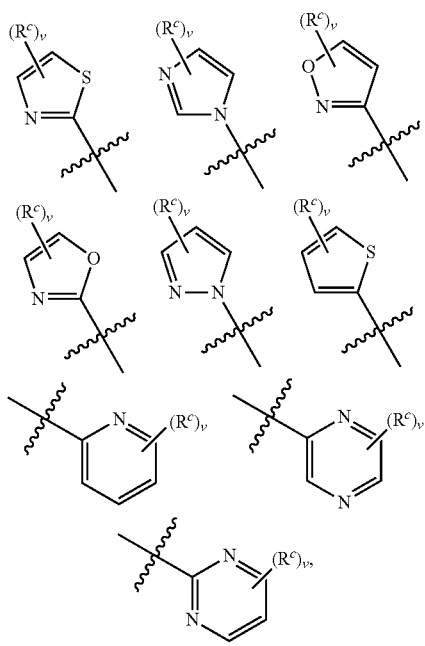

in which v and $R^c$ are as defined above.

Of special interest is the class of compounds of general formula III in which bicyclic heteroaryl ring has the following structure:
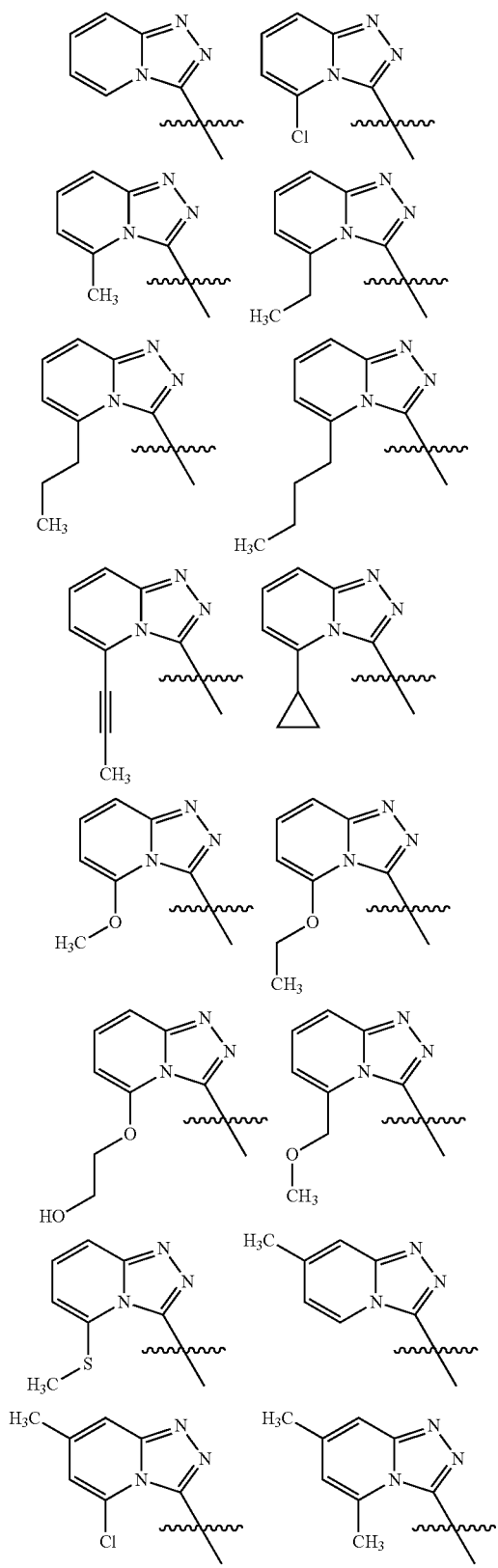
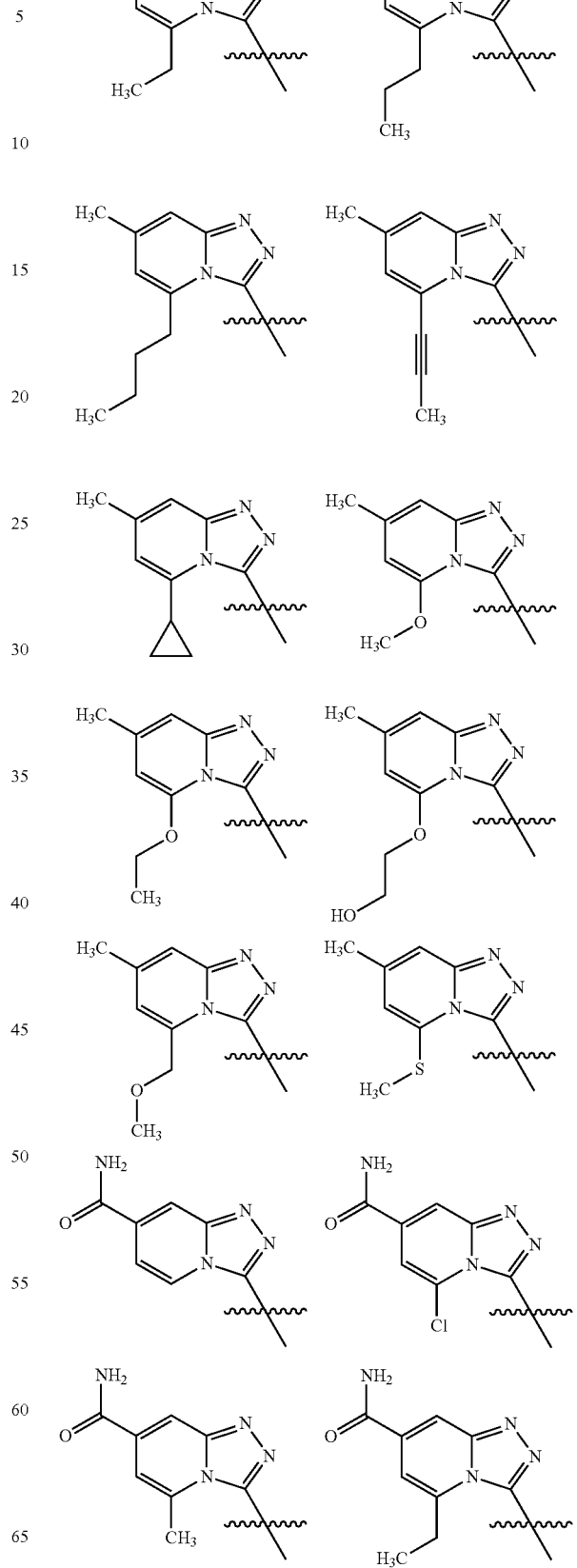

-continued
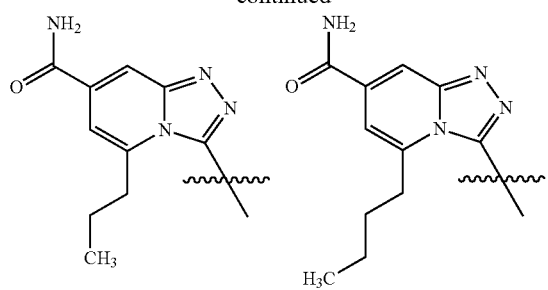
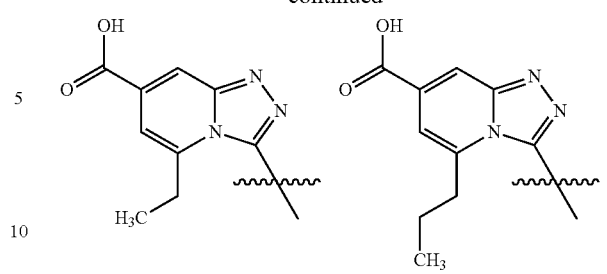
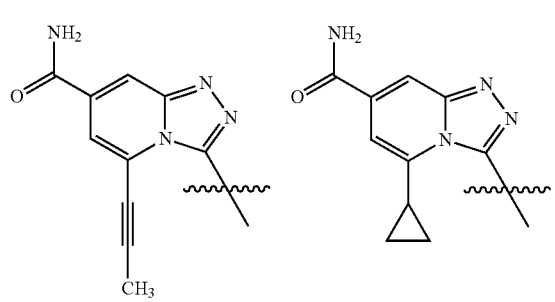
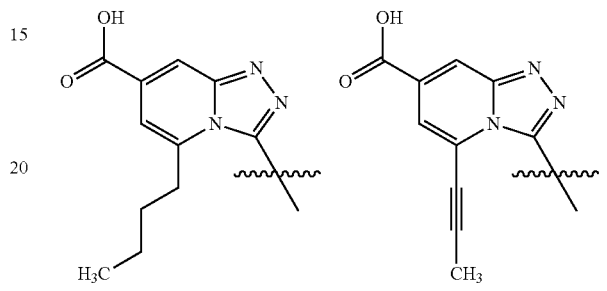
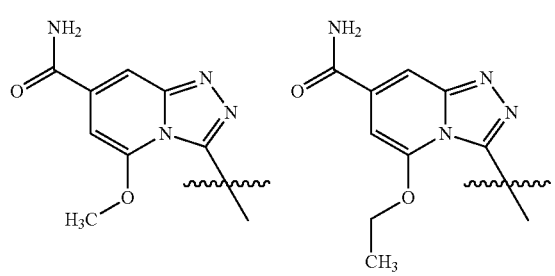
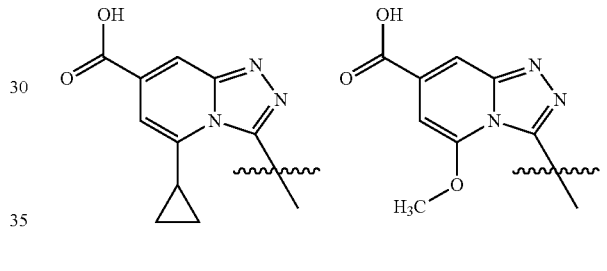
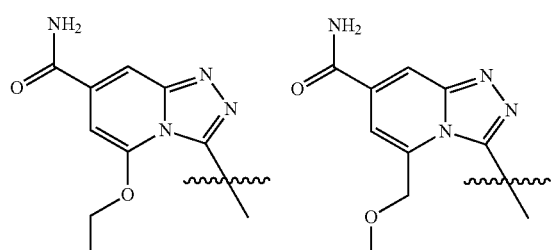
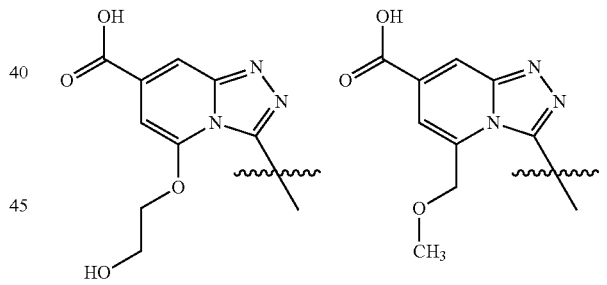
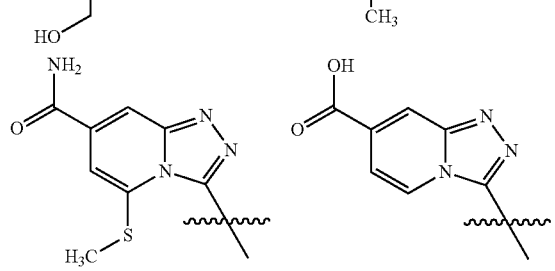
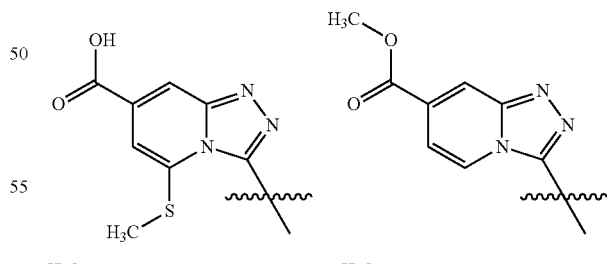
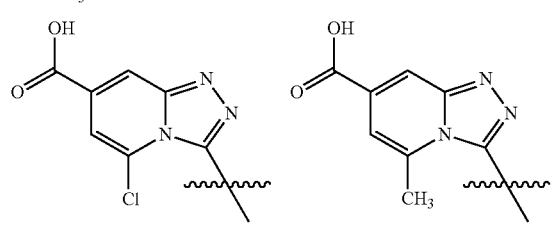
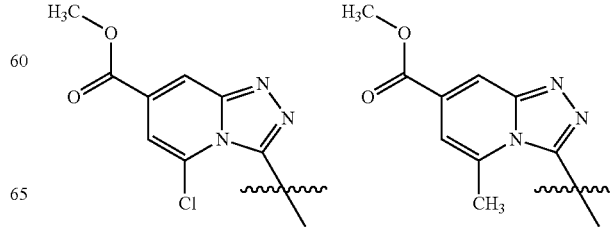

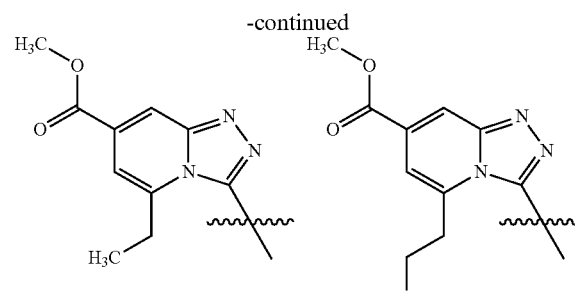
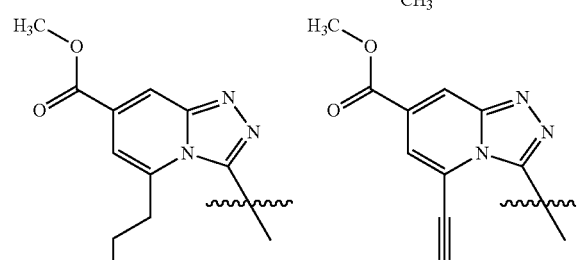
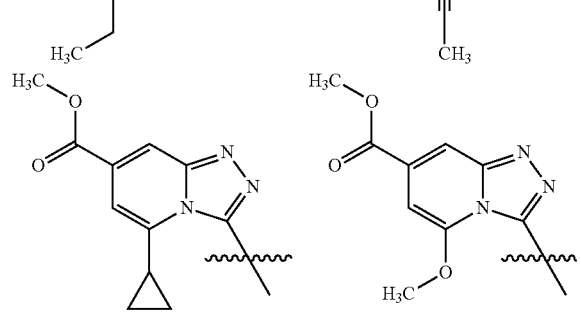
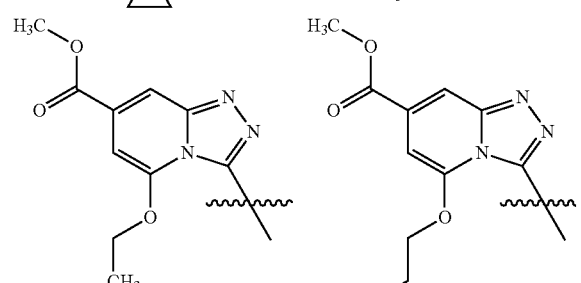
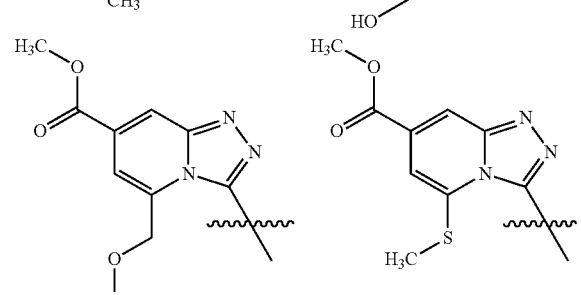
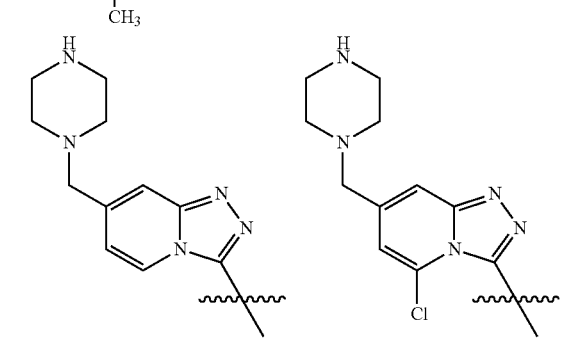
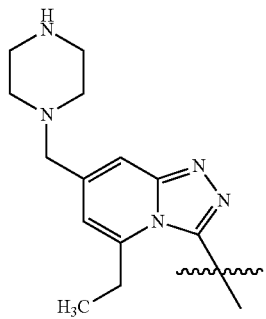
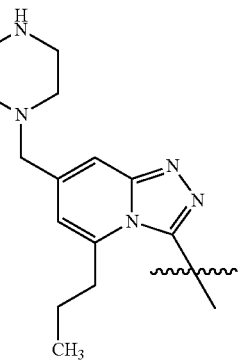
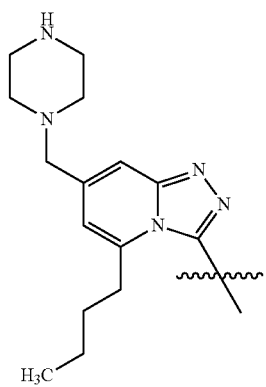
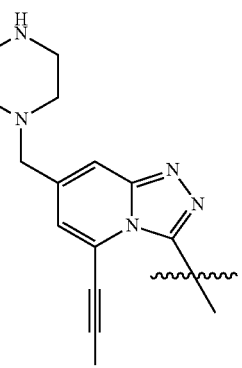
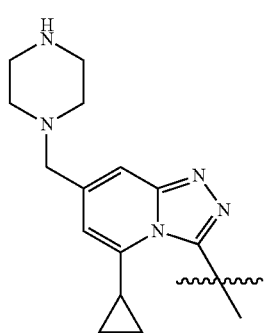
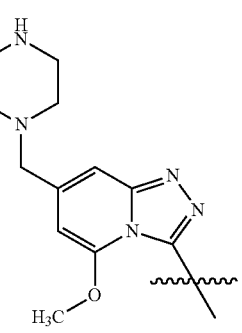
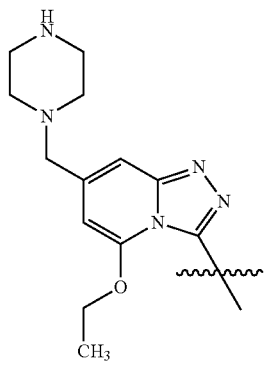
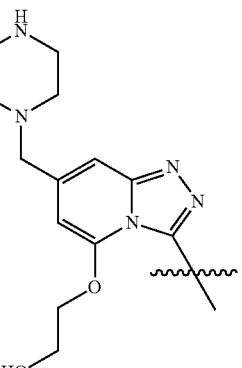

-continued
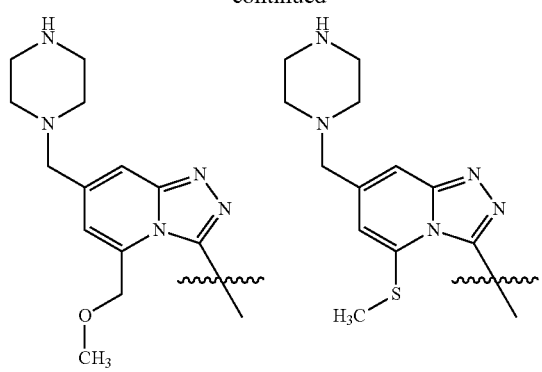
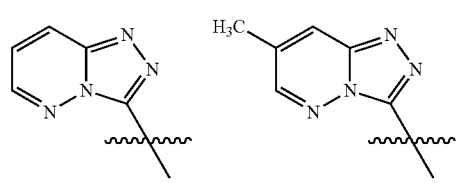
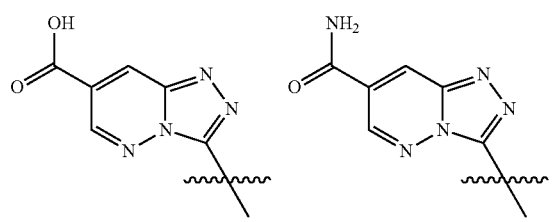
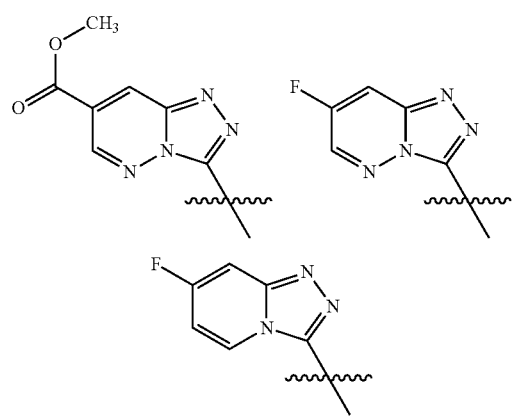
Also of special interest is the class of compounds of general formula IV in which bicyclic heteroaryl ring has the following structure:
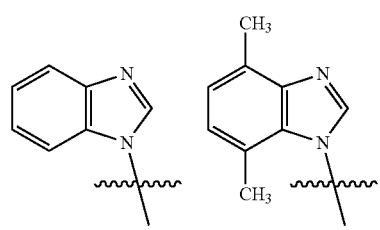
-continued
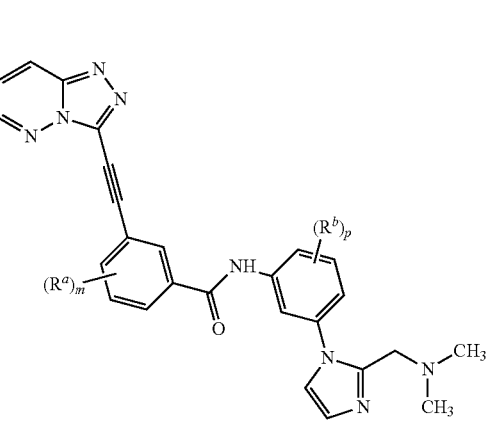
Illustrative subsets of such compounds include those having the following structures:
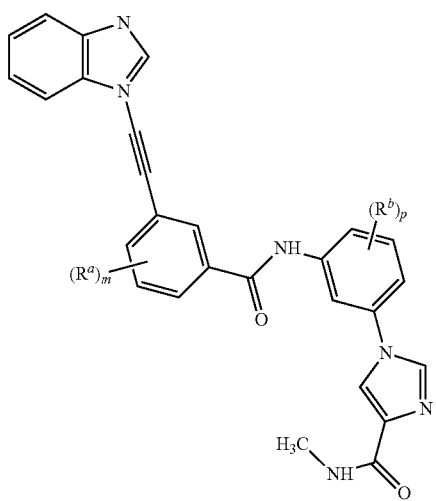

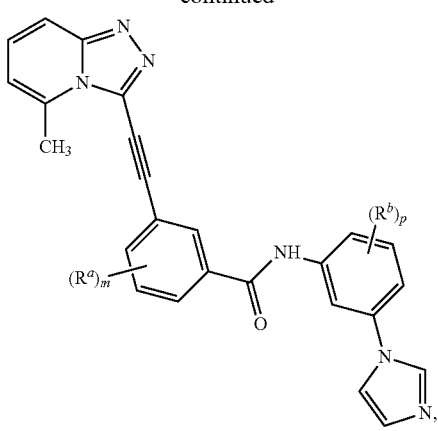

and particular compounds:

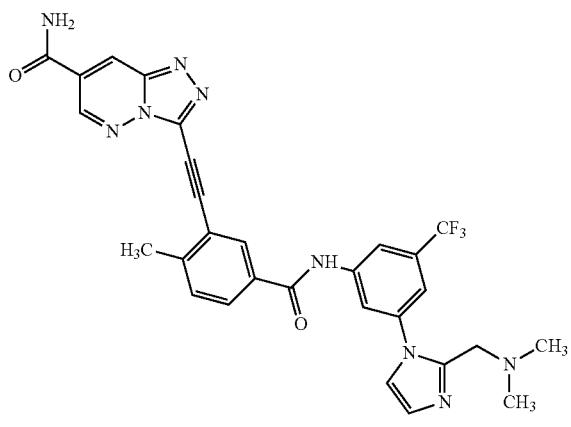

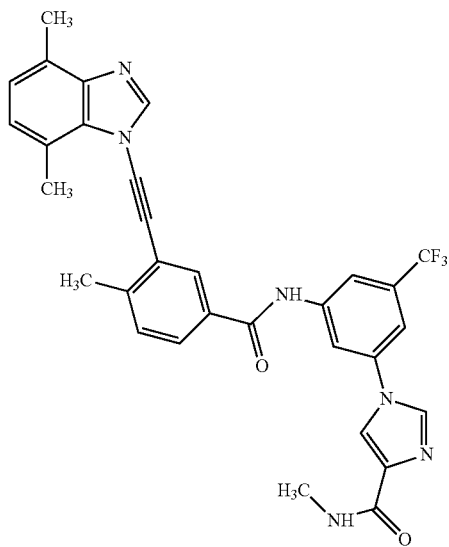

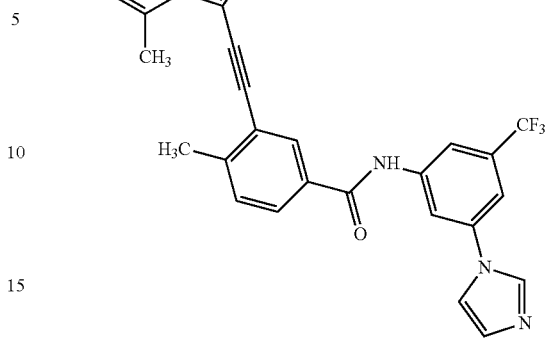

Of special interest among others are compounds of general formulae III and IV in which Ring C is imidazole and is substituted by one or more $R^c$ groups. Of special interest are compounds comprising one $R^c$ group which is lower alkyl (e.g. methyl).

Another class of compounds of general formulae I and II respectively are compounds in which one of $R^b$ groups has structure -$L_2$-Ring D. This class is represented by general formula V:

Formula V

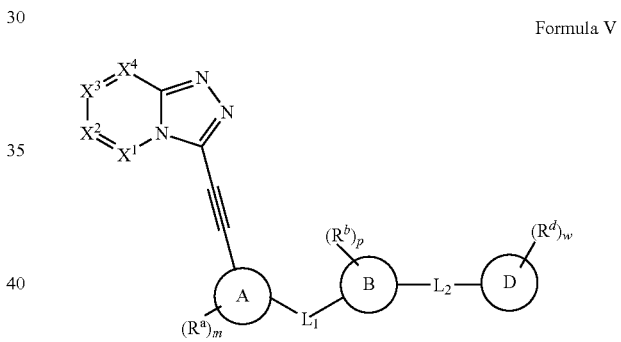

and VI:

Formula VI

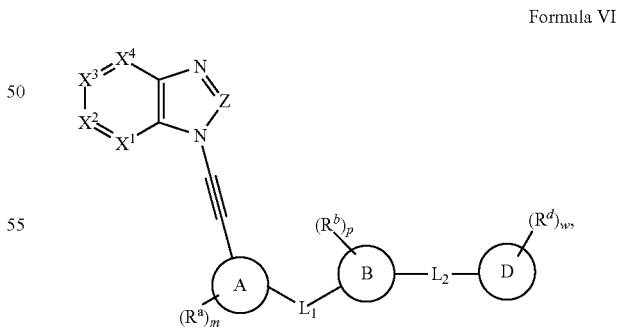

in which the previously defined variables such as n, m, p, A, B, T, $L^1$, $X_1$, $X_2$, $X_3$, $X_4$, Z, are defined above in part 1, and $L_2$ is selected from $(CH_2)_z$, $O(CH_2)_x$, $NR^5(CH_2)_x$, $S(CH_2)_x$, and $(CH_2)_x NR^3 C(O)(CH_2)_x$, and linker moiety $L_2$ can be included in either direction;

Ring D represents 5- or 6-membered heterocyclic or heteroaryl ring comprising carbon atoms and 1-3 heteroatoms independently selected from a, N and S(O)$_r$ and Ring D is optionally substituted on carbon or heteroatom(s) with 1-5 R$^d$ groups;

R$^d$ at each occurrence, is independently selected from —H, halogen, —CN, —NO$_2$, —R$^6$, —OR$^4$, —NR$^4$R$^5$, —C(O)YR$^4$, —OC(O)YR$^4$, —NR$^4$C(O)YR$^4$, —SC(O)YR$^4$, —NR$^4$C(=S)YR$^4$, —OC(=S)YR$^4$, —C(=S)YR$^4$, —YC(=NR$^5$)YR$^4$, —YP(=O)(YR$^6$)(YR$^6$), —Si(R$^6$)$_3$, —NR$^4$SO$_2$R$^4$, —S(O)$_r$R$^4$, —SO$_2$NR$^4$R$^5$, —NR$^4$SO$_2$NR$^4$R$^5$, wherein each Y is independently a chemical bond, —O—, —S—, —NR$^5$—; R$^4$, R$^5$, R$^6$ are as previously defined in Part 1 Description of the invention;

w is 0, 1, 2, 3, 4 or 5;

x is 0, 1, 2, 3;

z is 1, 2, 3 or 4.

Non-limiting, illustrative examples of -[Ring B]-[L$_2$]-[Ring D] moieties in compounds of Formulae V and VI:

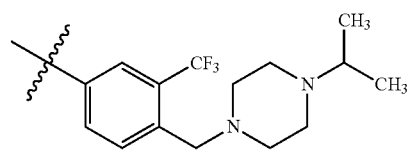

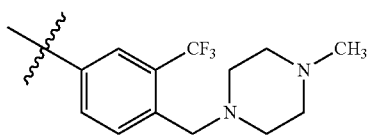

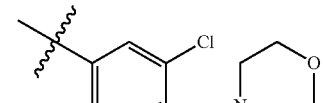

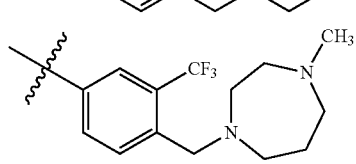

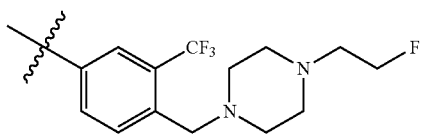

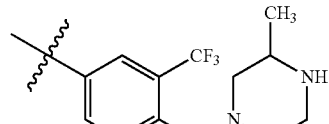

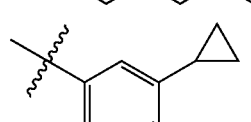

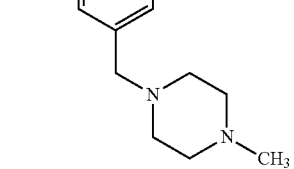

-continued

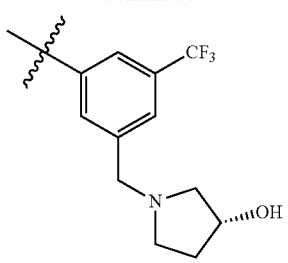

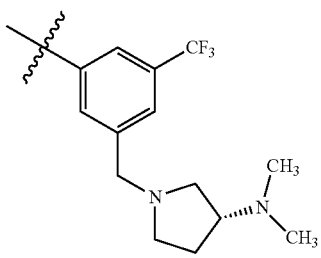

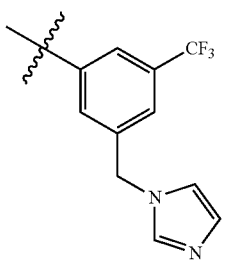

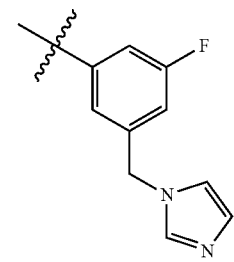

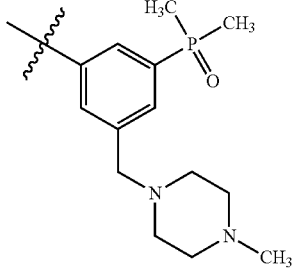

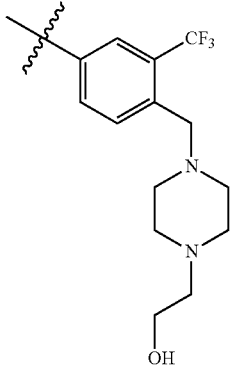

-continued
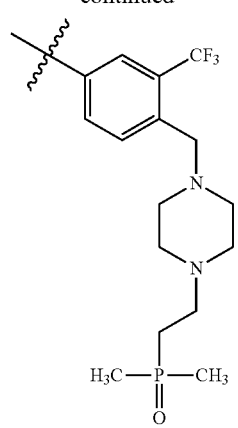
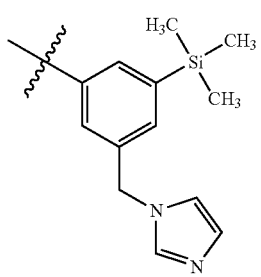
Of special interest are the compounds of general formula V which contains following bicyclic rings:
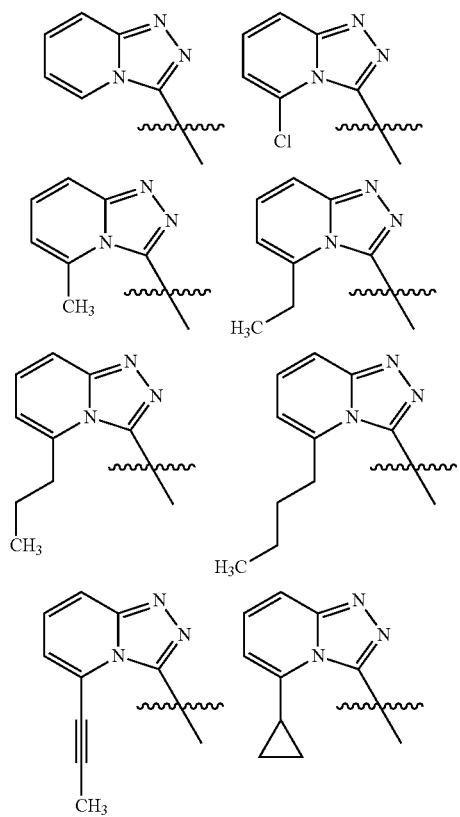
-continued
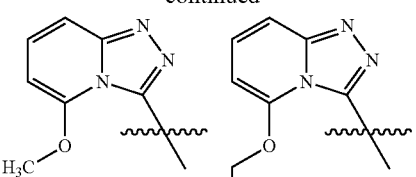
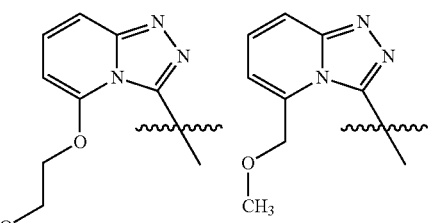
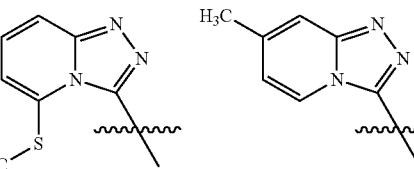
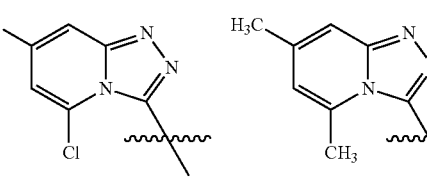
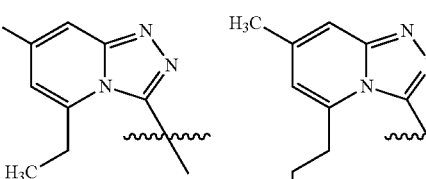
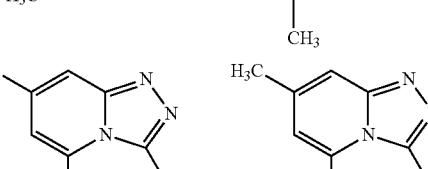
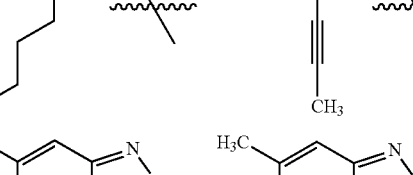
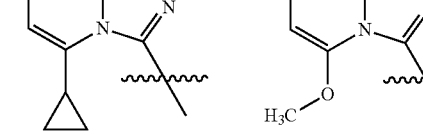
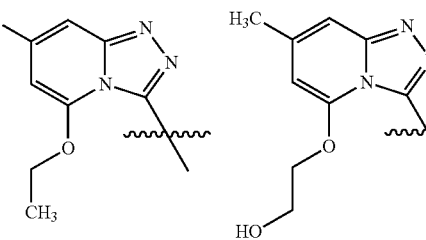

-continued
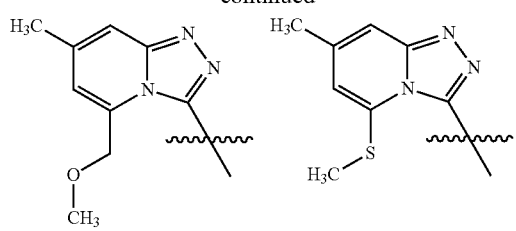
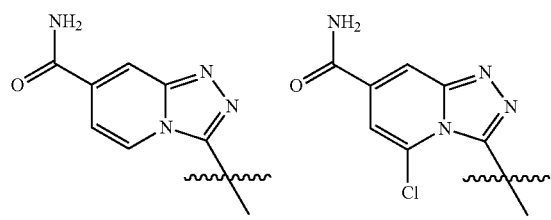
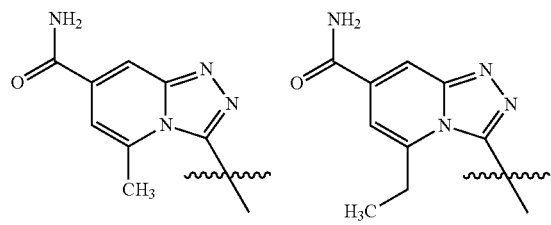
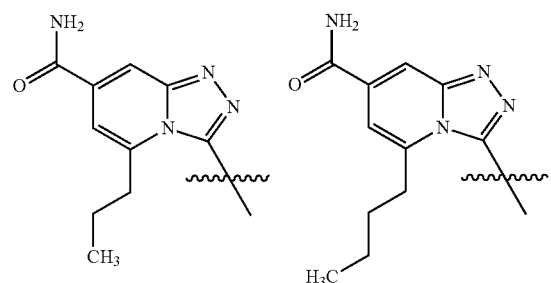
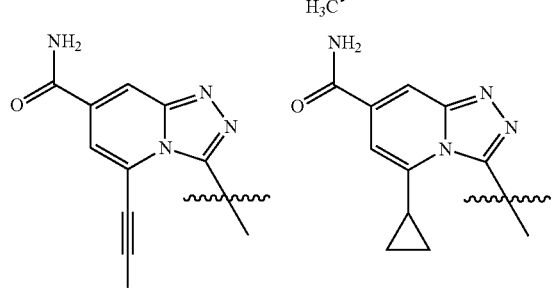
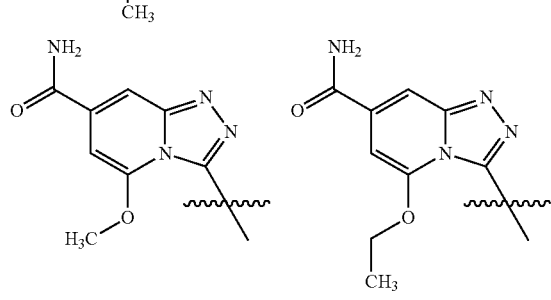
-continued
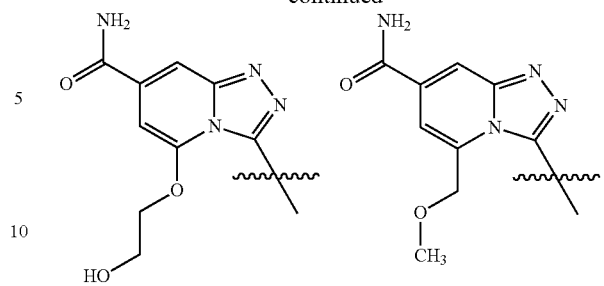

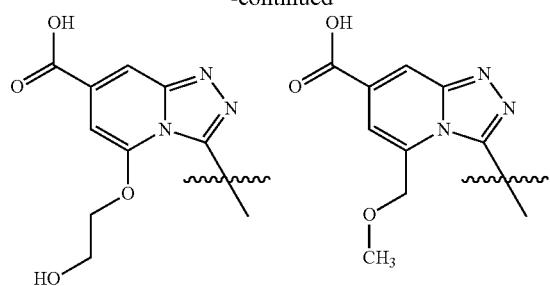
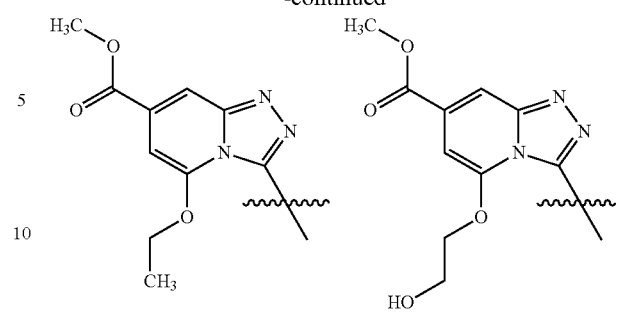
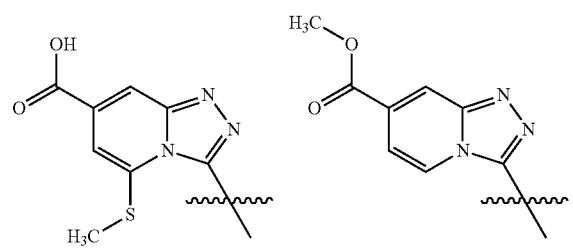
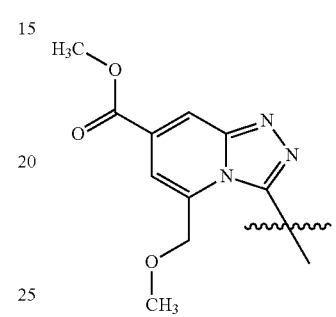
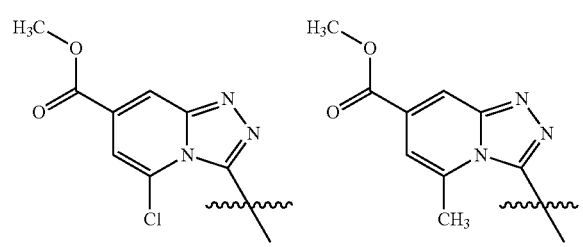
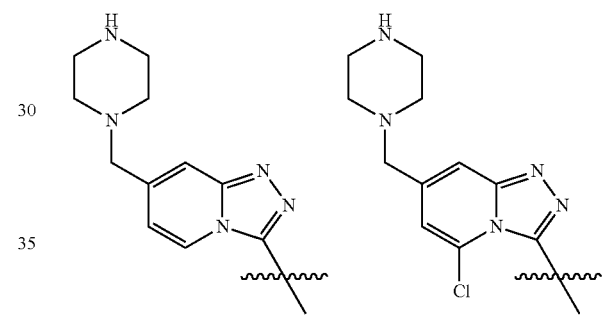
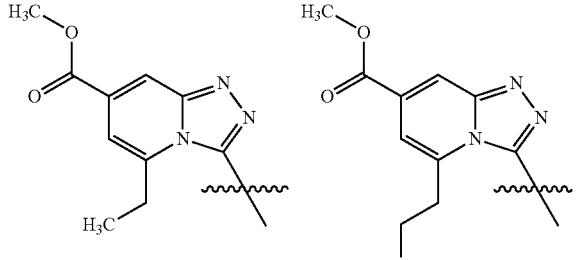
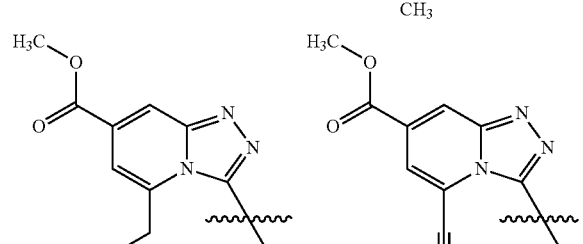
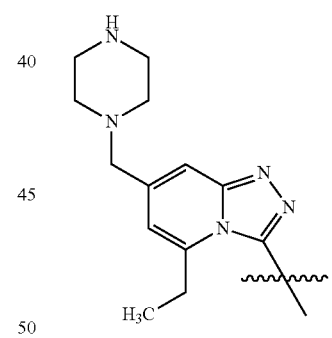
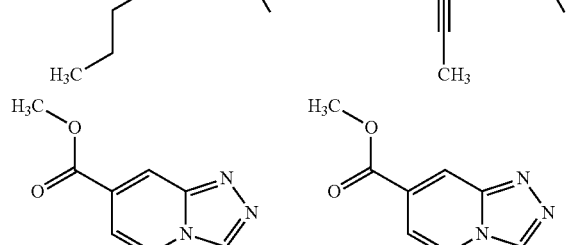
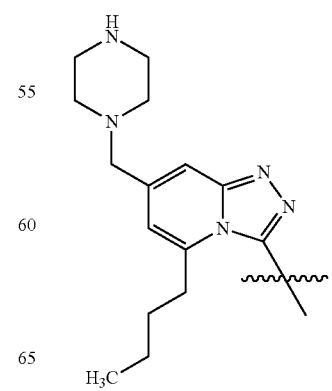

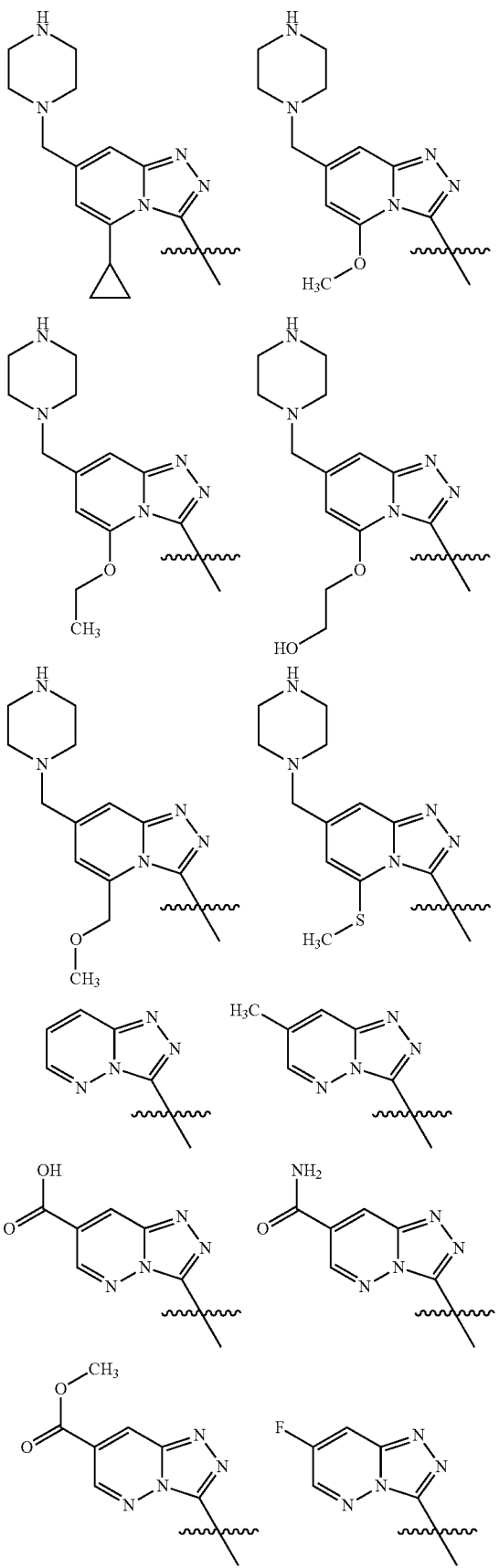

Also of special interest are compounds of general formula VI in which bicyclic heteroaryl ring has the following structure:

Illustrative examples of general formulae of such compounds:
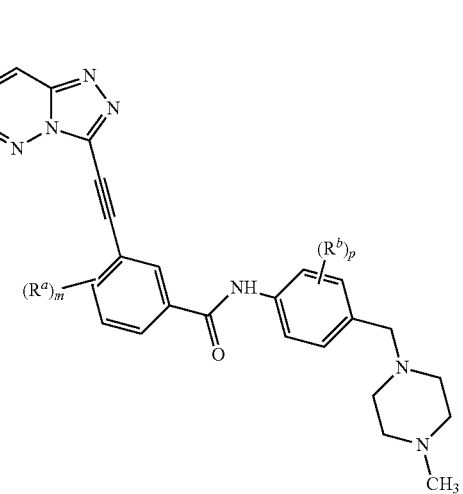

-continued
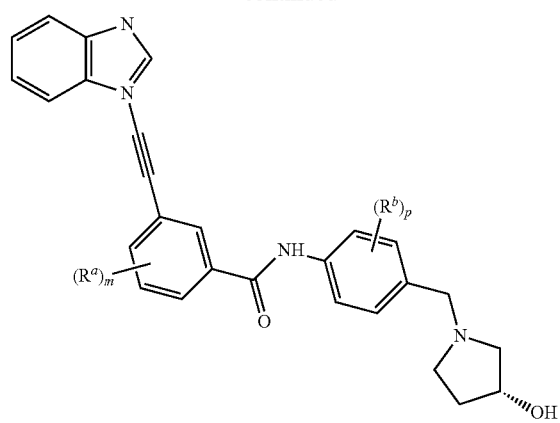
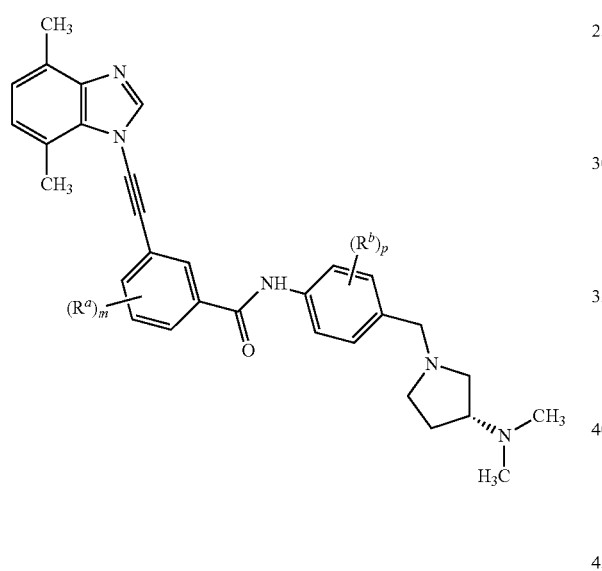
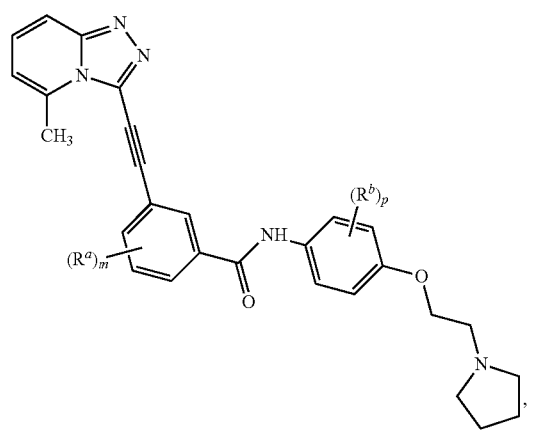
and specific compounds:
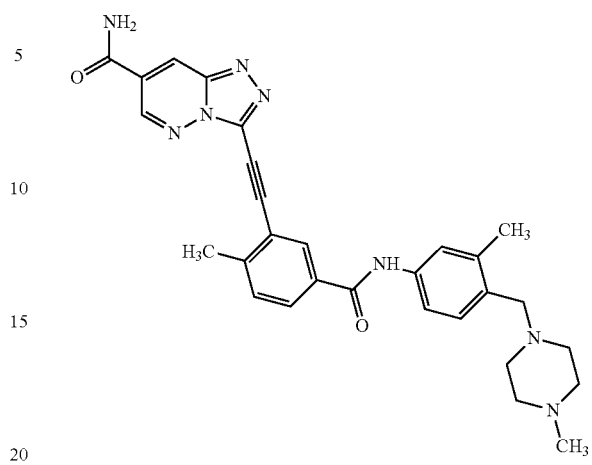
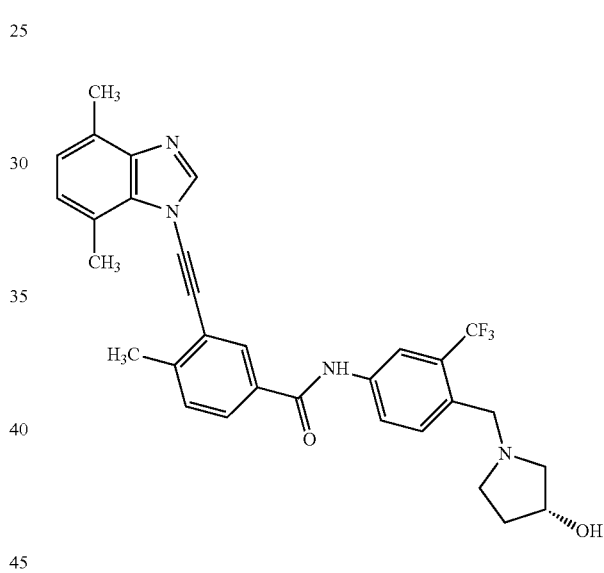
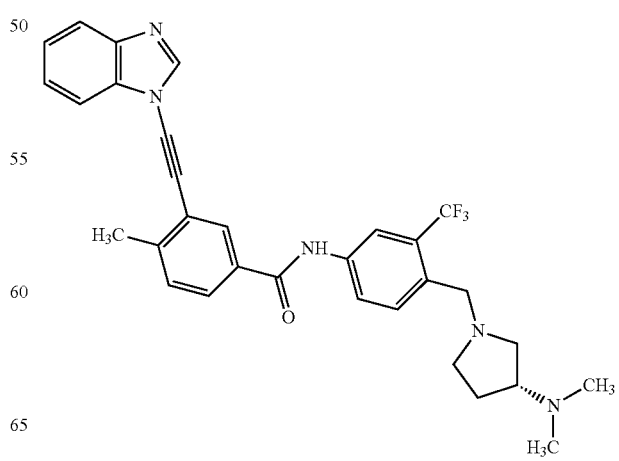

-continued

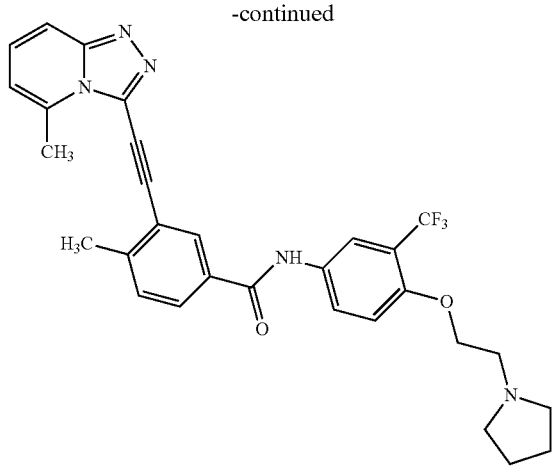

Compounds of interest include among others, compounds of Formulae V and VI in which Ring D is a piperazine ring, substituted on nitrogen with $R^d$. Of particular interest are compounds of this subclass in which $R^d$ is a substituted or unsubstituted lower (i.e., 1-6 carbon) alkyl as illustrated by N-methylpiperazine moieties in some of the foregoing examples.

Of special interest are compounds of formulae V and VI in which bicyclic heteroaryl ring is an optionally substituted 1H-benzimidazole, 1H-benzotriazole, [1,2,4]triazolo[4,3-a]pyridine, [1,2,4]triazolo[4,3-b]pyridazine.

Also of interest are compounds of formulae III, IV, V and VI in which Rings A and B are aryl.

Compounds of this invention of particular interest include those with one or more of the following characteristics:

a molecular weight of less than 1000, preferably less than 750 and more preferably less than 600 mass units (not including the weight of any solvating or co-crystallizing species, of any counter-ion in the case of a salt); or inhibitory activity against a wild type or mutant (especially a clinically relevant mutant) kinase, especially a Src family kinase such as Src, Yes, Lyn or Lck; a VEGF-R such as VEGF-R1 (Flt-1), VEGF-R2 (kdr), or VEGF-R3; a PDGF-R; an Abl kinase or another kinase of interest with an $IC_{50}$ value of 1 µM or less (as determined using any scientifically acceptable kinase inhibition assay), preferably with an $IC_{50}$ of 500 nM or better, and optimally with an IG50 value of 250 nM or better; or inhibitory activity against a given kinase with an $IC_{50}$ value at least 100-fold lower than their $IC_{50}$ values for other kinases of interest; or a cytotoxic or growth inhibitory effect on cancer cell lines maintained in vitro, or in animal studies using a scientifically acceptable cancer cell xenograft model, (especially preferred are compounds of the invention which inhibit proliferation of cultured KS62 cells with a potency at least as great as Gleevec, preferably with a potency at least twice that of Gleevec, and more preferably with a potency at least 10 times that of Gleevec as determined by comparative studies.)

Also provided is a composition comprising at least one compound of the invention or a salt, hydrate or other solvate thereof, and at least one pharmaceutically acceptable excipient or additive. Such compositions can be administered to a subject in need thereof to inhibit the growth, development and/or metastasis of cancers, including solid tumors (e.g., breast, colon, pancreatic, CNS and head and neck cancers, among others) and various forms of leukemia, including leukemias and other cancers which are resistant to other treatment, including those which are resistant to treatment with Gleevec or another kinase inhibitor, and generally for the treatment and prophylaxis of diseases or undesirable conditions mediated by one or more kinases which are inhibited by a compound of this invention.

The cancer treatment method of this invention involves administering (as a monotherapy or in combination with one or more other anti-cancer agents, one or more agents for ameliorating side effects, radiation, etc) a therapeutically effective amount of a compound of the invention to a human or animal in need of it in order to inhibit, slow or reverse the growth, development or spread of cancer, including solid tumors or other forms of cancer such as leukemias, in the recipient. Such administration constitutes a method for the treatment or prophylaxis of diseases mediated by one or more kinases inhibited by one of the disclosed compounds or a pharmaceutically acceptable derivative thereof. "Administration" of a compound of this invention encompasses the delivery to a recipient of a compound of the sort described herein, or a prodrug or other pharmaceutically acceptable derivative thereof, using any suitable formulation or route of administration, as discussed herein. Typically the compound is administered one or more times per month, often one or more times per week, e.g. daily, every other day, 5 days/week, etc. Oral and intravenous administrations are of particular current interest.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue (MW >300) thereof. Pharmaceutically acceptable derivatives thus include among others prodrugs. A prodrug is a derivative of a compound, usually with significantly reduced pharmacological activity, which contains an additional moiety which is susceptible to removal in vivo yielding the parent molecule as the pharmacologically active species. An example of a prodrug is an ester which is cleaved in vivo to yield a compound of interest. Prodrugs of a variety of compounds, and materials and methods for derivatizing the parent compounds to create the prodrugs, are known and may be adapted to the present invention.

Particularly favored derivatives and prodrugs of a parent compound are those derivatives and prodrugs that increase the bioavailability of the compound when administered to a mammal (e.g., by permitting enhanced absorption into the blood following oral administration) or which enhance delivery to a biological compartment of interest (e.g., the brain or lymphatic system) relative to the parent compound. Preferred prodrugs include derivatives of a compound of this invention with enhanced aqueous solubility or active transport through the gut membrane, relative to the parent compound.

One important aspect of this invention is a method for treating cancer in a subject in need thereof, which comprises administering to the subject a treatment effective amount of a composition containing a compound of this invention. Various cancers which may be thus treated are noted elsewhere herein and include, among others. cancers which are or have become resistant to another anticancer agent such as Gleevec, Iressa, Tarceva or one of the other agents noted herein. Treatment may be provided in combination with one or more other cancer therapies, include surgery, radiotherapy (e.g., gamma-radiation, neutron beam radiotherapy. electron beam radiotherapy, proton therapy, brachytherapy, and systemic radioactive isotopes, etc.), endocrine therapy, biologic response modifiers (e.g., interferons, interleukins, and tumor necrosis factor (TNF) to name a few), hyperthermia, cryotherapy, agents to attenuate any adverse effects (e.g., antiemetics), and other cancer chemotherapeutic drugs. The other agent(s) may be administered using a formulation, route of administration and dosing schedule the same or different from that used with the compound of this invention.

This invention further comprises the preparation of a compound of any of Formulas I, II, III, IV, V, VI or of any other compounds of this invention.

The invention also comprises the use of a compound of the invention, or a pharmaceutically acceptable derivative thereof, in the manufacture of a medicament for the treatment either acutely or chronically cancer (including leukemias and solid tumors, primary or metastatic, including cancers such as noted elsewhere herein and including cancers which are resistant or refractory to one or more other therapies). The compounds of this invention are useful in the manufacture of an anti-cancer medicament. The compounds of the present invention are also useful in the manufacture of a medicament to attenuate or prevent disorders through inhibition of one or more kinases such as Src, kdr, abl. etc.

Other disorders which may be treated with a compound of this invention include metabolic disorders, inflammatory disorders and osteoporosis and other bone disorders. In such cases the compound of this invention may be used as a monotherapy or may be administered in conjunction with administration of another drug for the disorder, e.g., a bisphosphonate in the case of osteoporosis or other bone-related illnesses.

This invention further encompasses a composition comprising a compound of the invention, including a compound of any of the described classes or subclasses, including those of any of the formulas noted above, among others, preferably in a therapeutically-effective amount, in association with a least one pharmaceutically acceptable carrier, adjuvant or diluent.

Compounds of this invention are also useful as standards and reagents for characterizing various kinases, especially but not limited to kdr and Src family kinases, as well as for studying the role of such kinases in biological and pathological phenomena; for studying intracellular signal transduction pathways mediated by such kinases, for the comparative evaluation of new kinase inhibitors; and for studying various cancers in cell lines and animal models.

DEFINITIONS

Unless otherwise specified, the term "alkyl", other aliphatic, alkoxy, and acyl groups usually contains 1-6 (<<$C_1$-$C_6$>>) adjacent carbon atoms. Examples of alkyl include, but are not limited to methyl, ethyl, n-propyl, isopropyl, cyclopropyl, —$CH_2$—, cyclopropyl allyl, n-butyl, sec-butyl, cyclobutyl, —$CH_2$-cyclobutyl, n-pentyl, cis-pentyl, cyclopentyl, tert-pentyl, isopentyl, —$CH_2$-cyclopentyl, n-hexyl, sec-hexyl, cyclohexyl, —$CH_2$-cyclohexyl, etc derivatives that may contain one or more substituents.

The term "Alkyl" is intended to include linear (i.e., unbranched or acyclic), branched, cyclic, or polycyclic non aromatic hydrocarbon groups. Analogous conditions are applied to other common definitions such as <<alkenyl>>, <<alkinyl>> etc.

Moreover, <<alkyl>>, <<alkenyl>>, <<alkinyl>> and relative groups may be either substituent or not.

<<Alkyl>> represents groups usually containing one to six carbon atoms unless otherwise specified. $C_{1-6}$ alkyl, is intended to include $C_1$, $C_2$, $C_3$, $C_4$, $C_5$, and $C_6$ alkyl groups. Lower alkyl refers to alkyl groups containing 1 to 6 carbon atoms. Examples of Alkyl include, but are not limited to, methyl, ethyl, n-propyl, isopropyl, cyclopropyl, butyl, isobutyl, sec-butyl, tert-butyl, cyclobutyl, pentyl, isopentyl tert-pentyl, cyclopentyl, hexyl, isohexyl, cyclohexyl, etc. Alkyl may be substituted or unsubstituted. Illustrative substituted alkyl groups include, but are not limited to, fluoromethyl, difluoromethyl, trifluoromethyl, 2-fluoroethyl, 3-fluoropropyl, hydroxymethyl, 2-hydroxyethyl, 3-hydroxypropyl, benzyl, substituted benzyl, phenethyl, substituted phenethyl, etc.

<<Alkenyl>> represents groups usually containing one to six carbon atoms. For example, "alkenyl" may refer to prop-2-enyl, but-2-enyl, but-3-enyl, 2-methylprop-2-enyl, hex-2-enyl, hex-5-enyl. 2,3-dimethylbut-2-enyl, and the like. <<Alkinyl>> represents groups usually containing one to six carbon atoms include, but are not limited to prop-2-ynyl, but-2-ynyl, but-3-ynyl, pent-2-ynyl, 3-methylpent-4-ynyl, hex-2-ynyl, hex-5-ynyl. etc.

Cycloalkyl represents groups containing 3 to 12 carbon atoms, preferably 3 to 10, in mono-, bi- or polycyclic ring structure. Examples of such cycloalkyl include, but are not limited to cyclopropyl, cyclobutyl, cyclopentyl, cyclohexyl, cycloheptyl, norbornyl and the like, which, as in the case of other alkyl moieties, may optionally be substituted.

"Heterocycle", "heterocyclyl", or "heterocyclic" as used herein refers to non-aromatic ring systems having five to fourteen ring atoms, preferably five to ten, in which one or more ring carbons, preferably one to four, are each replaced by a heteroatom such as N, O, or S, Non limiting examples of heterocyclic rings include 3-1H-benzimidazol-2-one, (1-substituted)-2-oxo-benzimidazol-3-yl, 2-tetrahydrofuranyl, 3-tetrahydrofuranyl, 2-tetrahydrothiophenyl, 3-tetrahydrothiophenyl, 2-morpholinyl, 3-morpholinyl, 4-morpholinyl, 2-thiomorpholinyl, 3thiomorpholinyl, 4-thiomorpholinyl, 1-pyrrolidinyl, 2-pyrrolidinyl, 3-pyrrolidinyl, 1-piperazinyl, 2piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclyl" or "heterocyclic" as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. The term "heterocycle". "heterocyclyl", or "heterocyclic" whether saturated or partially unsaturated, also refers to rings that are optionally substituted.

The term "aryl" used alone or as part of a larger moiety as in "aralkyl", "aralkoxy". or "aryloxyalkyl", refers to aromatic ring groups having six to fourteen carbon ring atoms, such as phenyl, 1-naphthyl, 2-naphthyl, 1-anthracyl and 2-anthracyl. An "aryl" ring may contain one or more substituents. The term "aryl" may be used interchangeably with the term "aryl ring". "Aryl" also includes fused polycyclic aromatic ring systems in which an aromatic ring is fused to one or more rings. Non-limiting examples of useful aryl ring groups include phenyl, hydroxyphenyl, halophenyl; alkoxyphenyl, dialkoxyphenyl, trialkoxyphenyl, alkylenedioxyphenyl, naphthyl, phenanthryl, anthryl, phenanthro and the like, as well as 1-naphthyl, 2-naphthyl, 1-anthracyl group in which an aromatic ring is fused to one or more non-aromatic rings, such as in a indanyl, phenanthridinyl, or tetrahydronaphthyl, where the radical or point of attachment is on the aromatic ring. and 2-anthracyl. Also included within the scope of the term "aryl", as it is used herein, is a group in which an aromatic ring is fused to one or more non-aromatic rings, such as in a indanyl, phenanthridinyl, or tetrahydronaphthyl, where the radical or point of attachment is on the aromatic ring.

The term "heteroaryl" as used herein refers to stable heterocyclic, and polyheterocyclic aromatic moieties having 5-14 ring atoms. Heteroaryl groups may be substituted or unsubstituted and may comprise one or more rings. Examples of typical heteroaryl rings include 5-membered monocyclic ring groups such as thienyl, pyrrolyl, imidazolyl, pyrazolyl, furyl, isothiazolyl, furazanyl, isoxazolyl, thiazolyl and the like; 6-membered monocyclic groups such as pyridyl, pyrazinyl, pyrimidinyl, pyridazinyl, triazinyl and the like; and polycyclic heterocyclic ring groups such as benzo[b]thienyl, naphtho[2,3-b]thienyl, thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxalinyl, quinazolinyl, benzothiazole, benzimidazole, tetrahydroquinoline cinnolinyl, pteridinyl, carbazolyl. beta-carbolinyl, phenanthridinyl, acridinyl, perimidinyl, phenanthrolinyl, phenazinyl, isothiazolyl, phenothiazinyl, phenoxazinyl, and the like (see e.g. Katritzky, Handbook of Heterocyclic Chemistry). Further specific examples of heteroaryl rings include 2-furanyl, 3-furanyl, Nimidazolyl, 2-imidazolyl, 4-imidazolyl, 5-imidazolyl, 3-isoxazolyl, 4-isoxazolyl, 5-isoxazolyl, 2oxadiazolyl, 5-oxadiazolyl, 2-oxazolyl, 4-oxazolyl, 5-oxazolyl, 1-pyrrolyl, 2-pyrrolyl, 3-pyrrolyl, 2-pyridyl, 3-pyridyl, 4-pyridyl, 2-pyrimidyl, 4-pyrimidyl. 5-pyrimidyl, 3-pyridazinyl, 2-thiazolyl, 4thiazolyl, 5-thiazolyl, 5-tetrazolyl. 2-triazolyl, 5-triazolyl, 2-thienyl, 3-thienyl, carbazolyl, benzimidazolyl, benzothienyl, benzofuranyl, indolyl, quinolinyl, benzotriazolyl. benzothiazolyl. benzooxazolyl, benzimidazolyl, isoquinolinyl, indolyl, isoindolyl, acridinyl, or benzoisoxazolyl. Heteroaryl groups further include a group in which a heteroaromatic ring is fused to one or more aromatic or nonaromatic rings where the radical or point of attachment is on the heteroaromatic ring. Examples include tetrahydroquinoline, tetrahydroisoquinoline, and pyrido[3,4-d]pyrimidinyl. imidazo[1,2-a]pyrimidyl, imidazo[1,2-a]pyrazinyl, imidazo[1,2a]pyiridinyl, imidazo[1,2-c]pyrimidyl, pyrazolo[1,5-a][1,3,5]triazinyl, pyrazolo[1,5-c]pyrimidyl, imidazo[1,2-b]pyridazinyl, imidazo[1,5-a]pyrimidyl, pyrazolo[1,5-b][1,2,4]triazine, quinolyl, 30 isoquinolyl, quinoxalyl, imidazotriazinyl, pyrrolo[2,3-d]pyrimidyl, triazolopyrimidyl, pyridopyrazinyl. The term "heteroaryl" also refers to rings that are optionally substituted. The term "heteroaryl" may be used interchangeably with the term "heteroaryl ring" or the term "heteroaromatic".

An aryl group (including the aryl portion of an aralkyl, aralkoxy, or aryloxyalkyl moiety and the like) or heteroaryl group (including the heteroaryl portion of a heteroaralkyl or heteroarylalkoxy moiety and the like) may contain one or more substituents. Non limiting list of such substituents: amino, alkylamino, dialkilamino moieties, aminocarbonyl, halogen such as fluorine, chlorine, iodine, alkyl, alkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy and haloalkyl-groups.

This invention encompasses only those combinations of substituents and variables that result in a stable or chemically feasible compound. A stable compound or chemically feasible compound is one that has stability sufficient to permit its preparation and detection. Preferred compounds of this invention are sufficiently stable that they are not substantially altered when kept at a temperature of 40° C. or less, in the absence of moisture or other chemically reactive conditions, for at least a week.

Certain compounds of this invention may exist in tautomeric forms, and this invention includes all such tautomeric forms of those compounds unless otherwise specified.

Unless otherwise stated, structures depicted herein are also meant to include all stereochemical forms of the structure; i.e., the R and S configurations for each asymmetric center. Thus, single stereochemical isomers as well as enantiomeric and diastereomeric mixtures of the present compounds are within the scope of the invention. Thus, this invention encompasses each diasteriomer or enantiomer substantially free of other isomers (>90%, and preferably >95%, free from other stereoisomers on a molar basis) as well as a mixture of such isomers.

Particular optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound Optically active compounds of the invention can be obtained by using optically active starting materials. These isomers may be in the form of a free acid, a free base, an ester or a salt.

The compounds of this invention can exist in radiolabeled form, i.e., said compounds may contain one or more atoms containing an atomic mass or mass number different from the atomic mass or mass number ordinarily found in nature. Radioisotopes of hydrogen, carbon, phosphorous, fluorine and chlorine include $^3H$, $^{14}C$, $^{32}P$, $^{35}S$, and $^{36}Cl$, respectively. Compounds of this invention which contain those radioisotopes and/or other radioisotopes of other atoms are within the scope of this invention. Tritiated, i.e., $^3H$, and carbon-14, i.e., $^{14}C$, radioisotopes are particularly preferred for their ease of preparation and detectability.

Radiolabelled compounds of this invention can generally be prepared by methods well known to those skilled in the art. Conveniently, such radiolabelled compounds can be prepared by carrying out the procedures disclosed herein except substituting a readily available radiolabelled reagent for a non-radiolabelled reagent.

IMPLEMENTATION OF THE INVENTION

The compounds of the this invention can be synthesized using the methods described below, together with synthetic methods known in the art of synthetic organic chemistry or by a variation thereon as appreciated by those skilled in the art. Preferred methods include, but are not limited to those described below. The reactions are performed in a solvent appropriate to the reagents and materials employed and suitable for the transformation being effective. It will be understood by those skilled in the art of organic synthesis that the functionality present on the molecule should be consistent with the transformations proposed. This will sometimes require some judgment to modify the order of the synthetic steps or to select one particular process scheme over another in order to obtain a desired compound of the invention.

A compound of the present invention could be prepared as outlined in Scheme I to Scheme XXII and via standard methods known to those skilled in the art.

A palladium catalyzed Sonogashira coupling reaction is used to link the 'top' bicyclic heteroaryl ring to the 'bottom' [Ring A]-[L1]-[Ring B] moiety as illustrated in Scheme I and II. In Scheme I the Sonogashira coupling reaction is performed with an acetylenic 'top' and a [Ring A]-[L1]-[Ring B] moiety which has been activated by the presence of a reactive group, W, which is an I, a Br or another reactive group permitting the desired coupling reaction. The variables in the W-[Ring A]-[L1]-[Ring B] are as defined previously, rings A and B being substituted with permitted $R^a$ and $R^b$ groups, respectively.

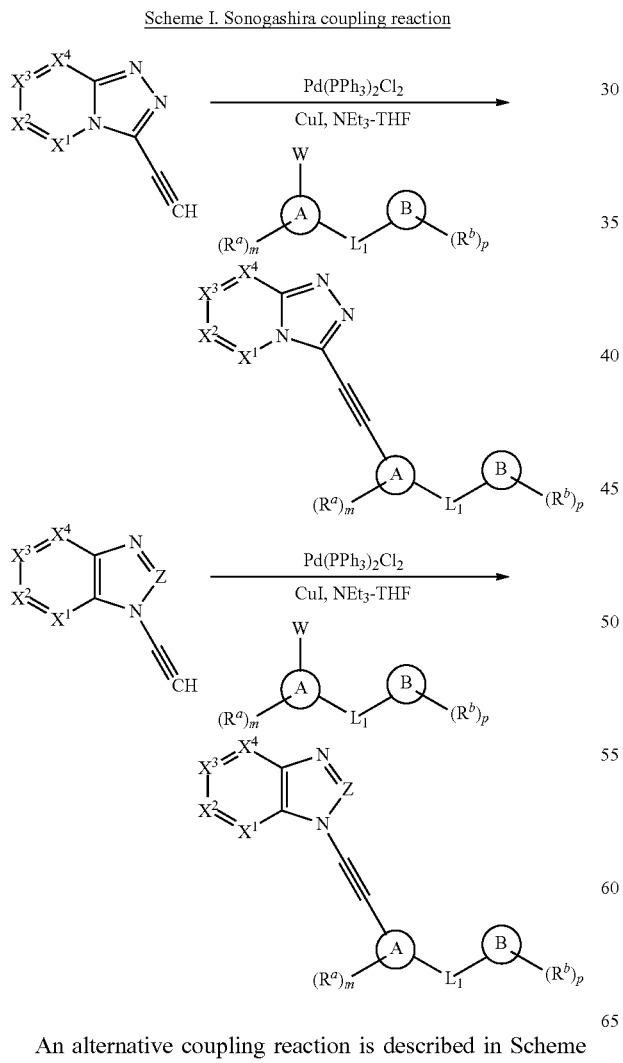

An alternative coupling reaction is described in Scheme II, in which bicyclic heteroaryl ring is "activated" by the presence of a reactive group W (such as I or Br) and is coupled to the 'bottom' acetylenic [Ring A]-L1-[Ring B] under similar Palladium catalyzed coupling conditions.

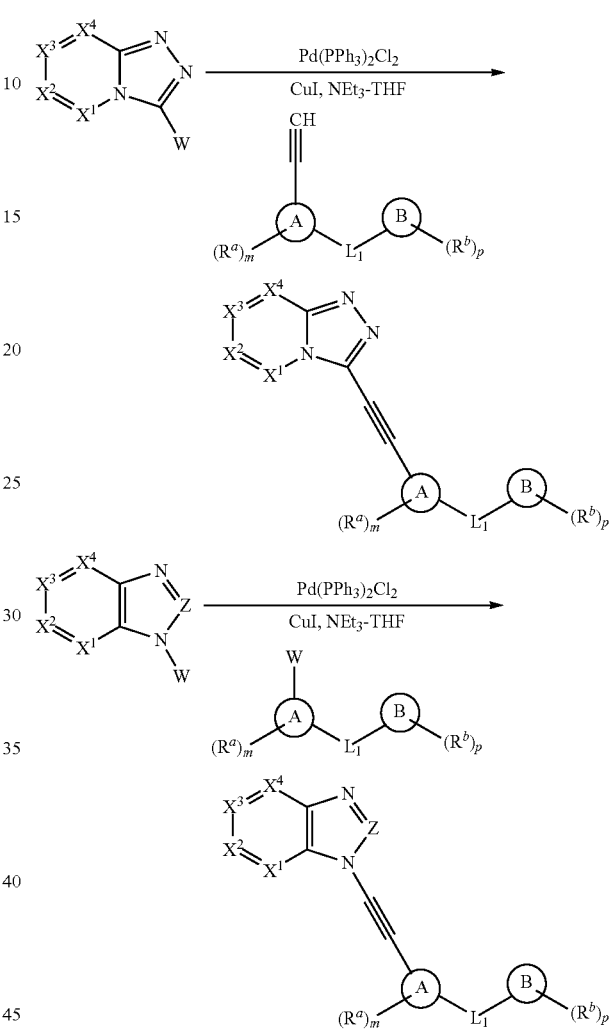

The Sonogashira coupling conditions described in Scheme I and II are applicable to all bicyclic heteroaryl Rings and useful to synthesize all compounds of this invention.

Several illustrative overall synthetic approaches to the preparation of the acetylenic bicyclic heteroaryl ring moieties, based on known transformations, are illustrated below in Schemes III to X:

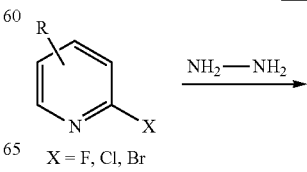

X = F, Cl, Br

Scheme IV
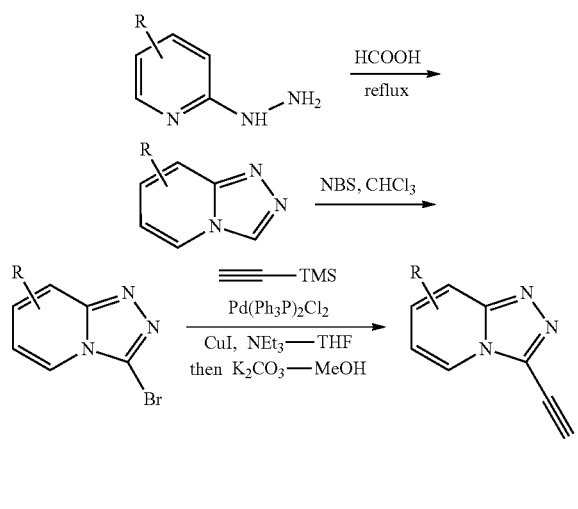
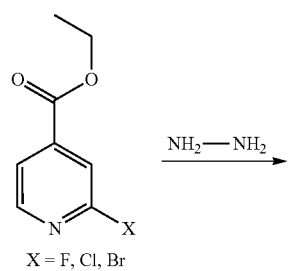
Scheme V
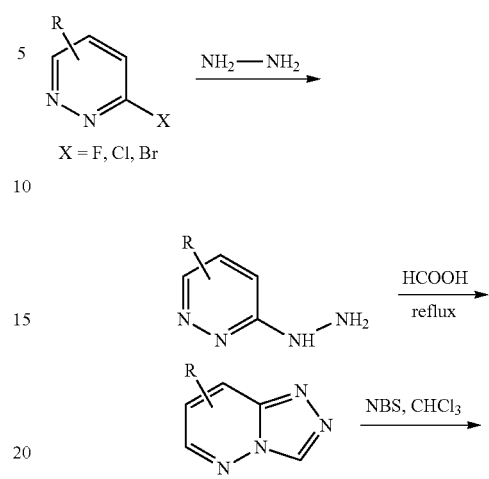
Scheme VI
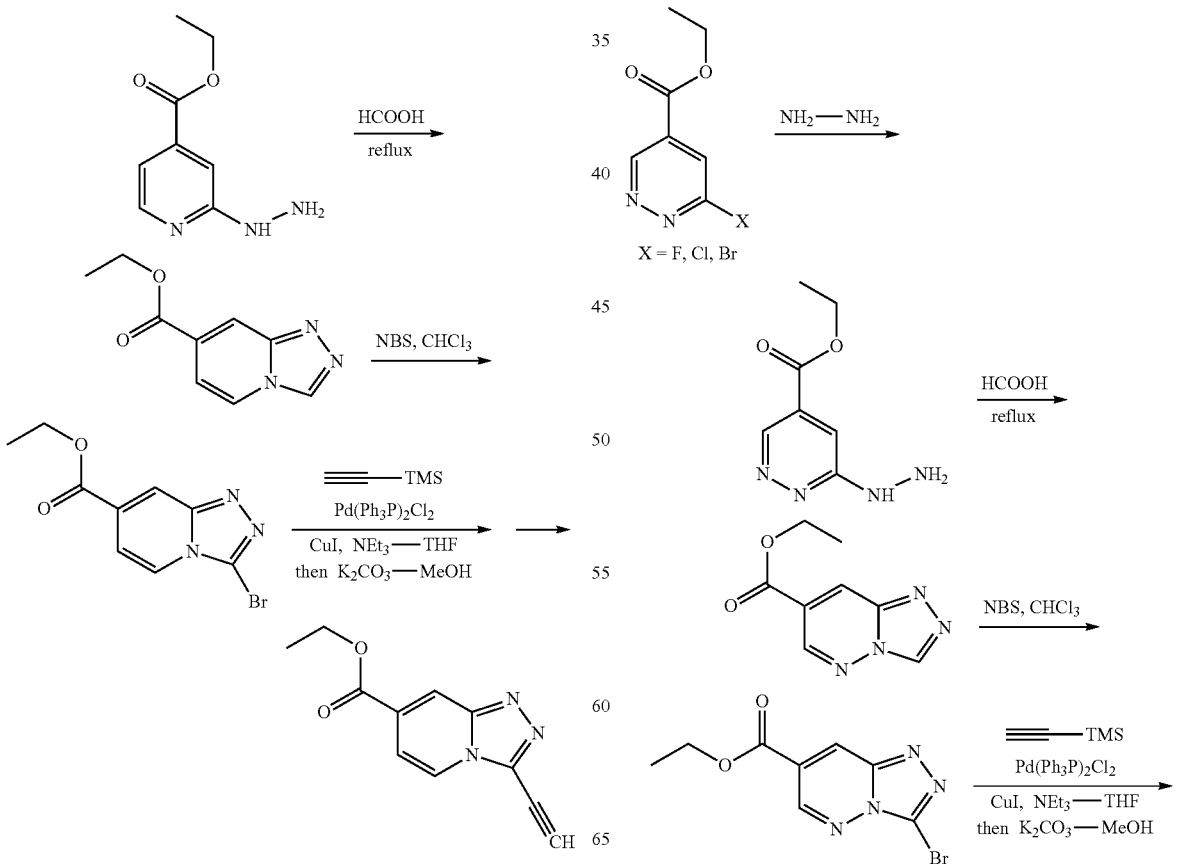

-continued
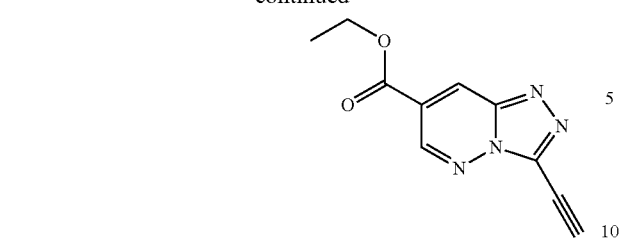
Scheme VIII
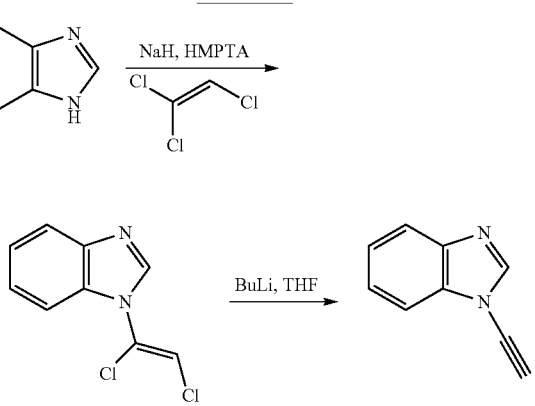
Scheme VII
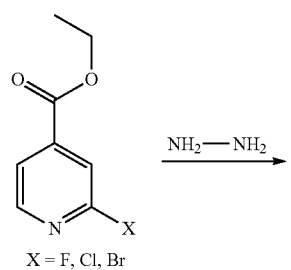
X = F, Cl, Br
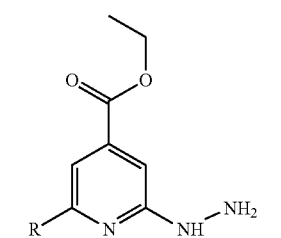
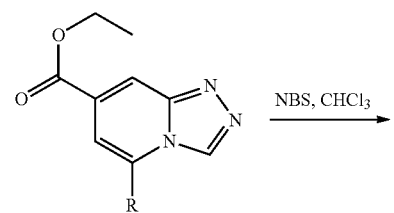
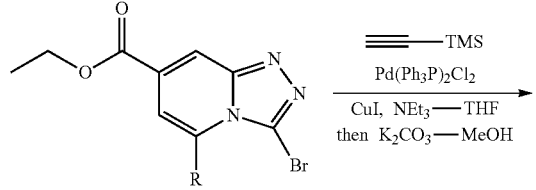
Scheme IX
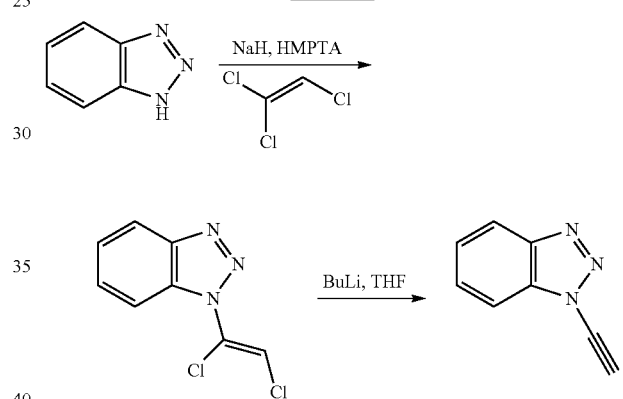
Scheme X
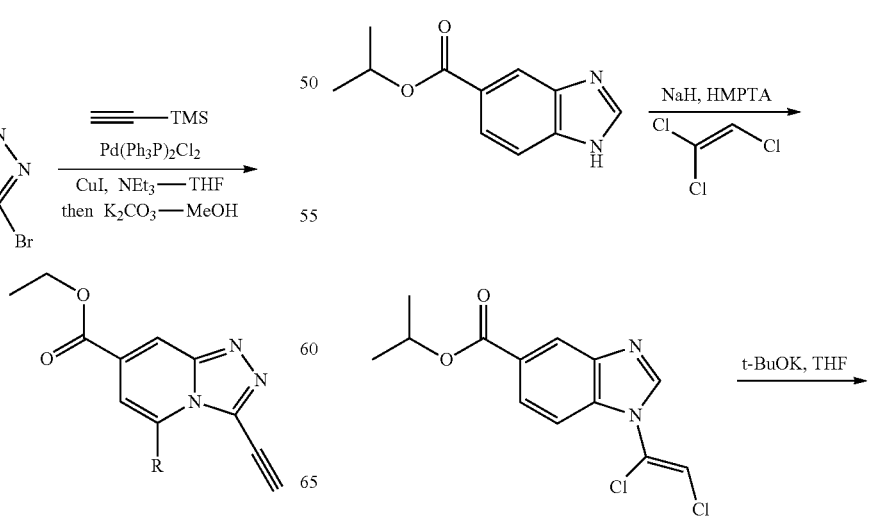

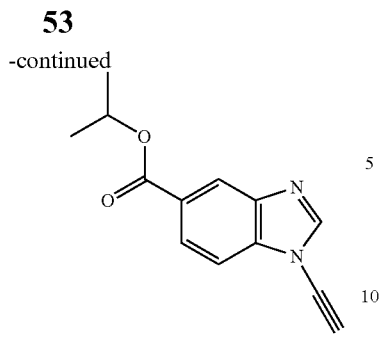

For the coupling step, see Malleron, J.-L., Fiaud, J.-C., Legros, J.-Y. Handbook of Palladium Catalyzed Organic Reactions. San Diego: academic Press, 1997.

As one of ordinary skill in the art would recognize, these methods for the preparation of various substituted acetylenic bicyclic heteroaryl ring groups, are widely applicable to various other fused bicyclic ring systems not shown.

Schemes XI to XXII below depict the synthesis of compounds of the formula W-[Ring A][L1]-[Ring B] which are useful as intermediates in the coupling reaction described in Scheme I (Scheme I).

Illustrative such intermediates include among others those of those following structures:

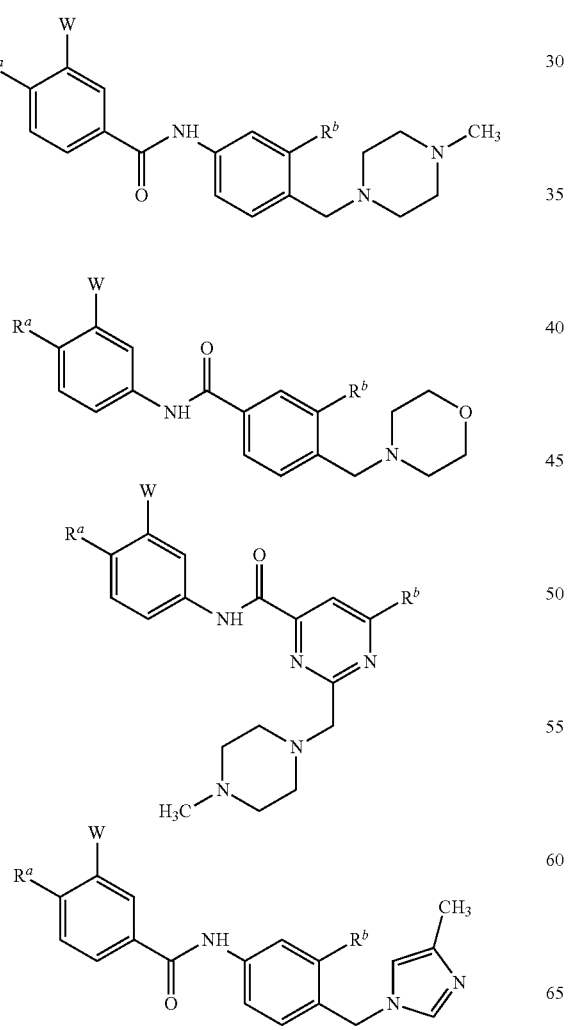

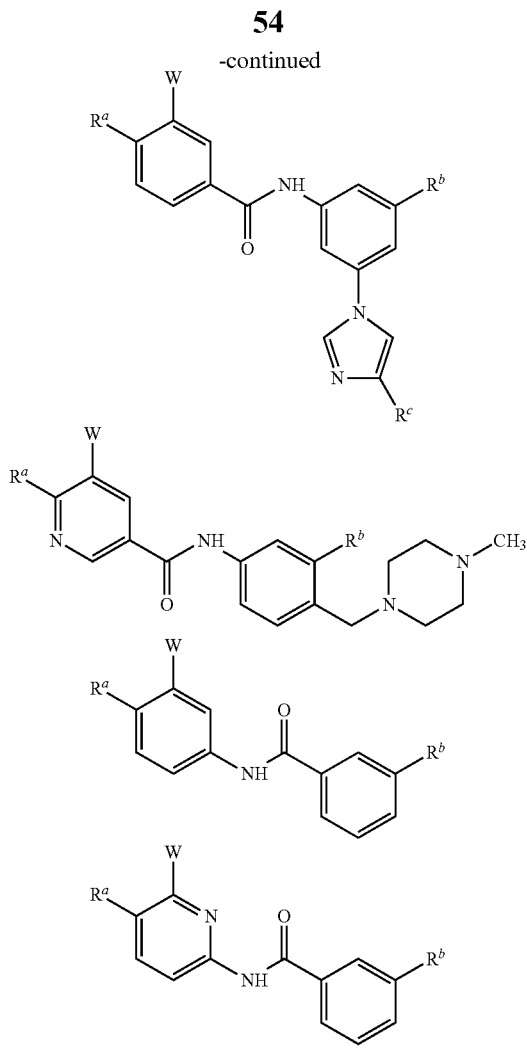

wherein the previously defined variables $R^a$, $R^b$ and $R^c$ are as previously defined. For instance, $R^a$ in some embodiments is chosen from F or alkyl, e.g., Me, among others, and $R^b$ in some embodiments is chosen from Cl, F, Me, t-butyl, —$CF_3$ or $OCF_3$ among others.

Those and other compounds of the formula W-[Ring A]-[L1]-[Ring B] with the various permitted substituents are useful for preparing the corresponding compounds of the invention.

Scheme XI describes an illustrative synthesis of W-[Ring A]-[L1]-[Ring B] in which Rings A and B are phenyl derivatives and L1 is NHC(O).

Scheme XI

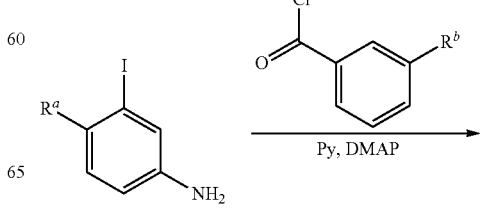

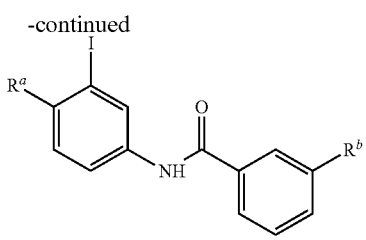

Scheme XII depicts the synthesis of a variant of the foregoing in which Ring B is a 2-pyridine and $L_1$ is C(O)NH (i.e., in the other orientation).

Schemes XI and XII, below illustrate the synthesis of W-[Ring A]-[L1]-[Ring B] in which Rings A and B are phenyl and Ring C is a heteroaryl ring.

Scheme XIII describes the preparation of intermediates in which Ring C is an imidazole ring:

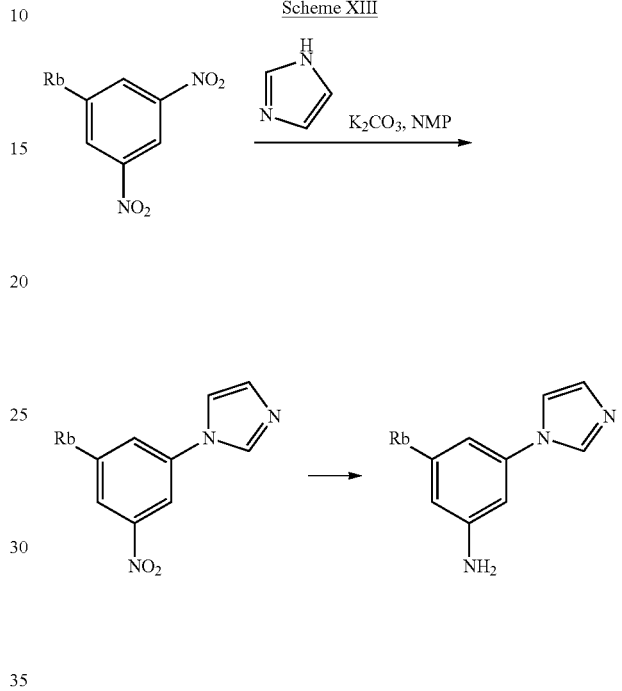

Scheme XIV describes the preparation of intermediates in which Ring C is an oxazole ring:

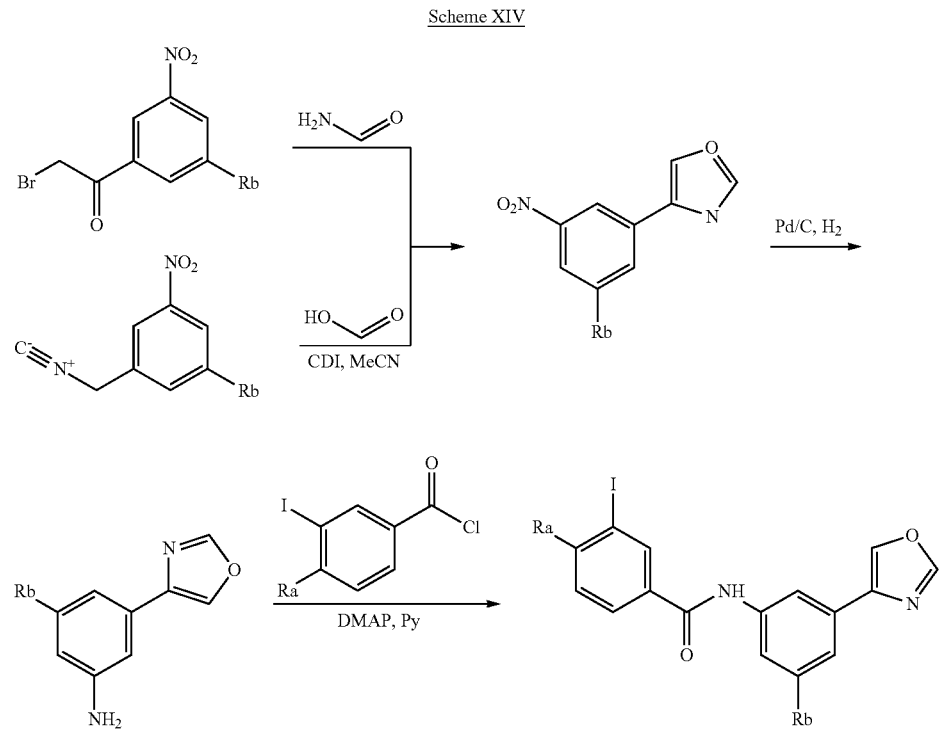

Scheme XV describes the preparation of W-[Ring A-L1-Ring B], containing saturated 5- or 6-membered ring C which contains 1 or 2 heteroatoms.

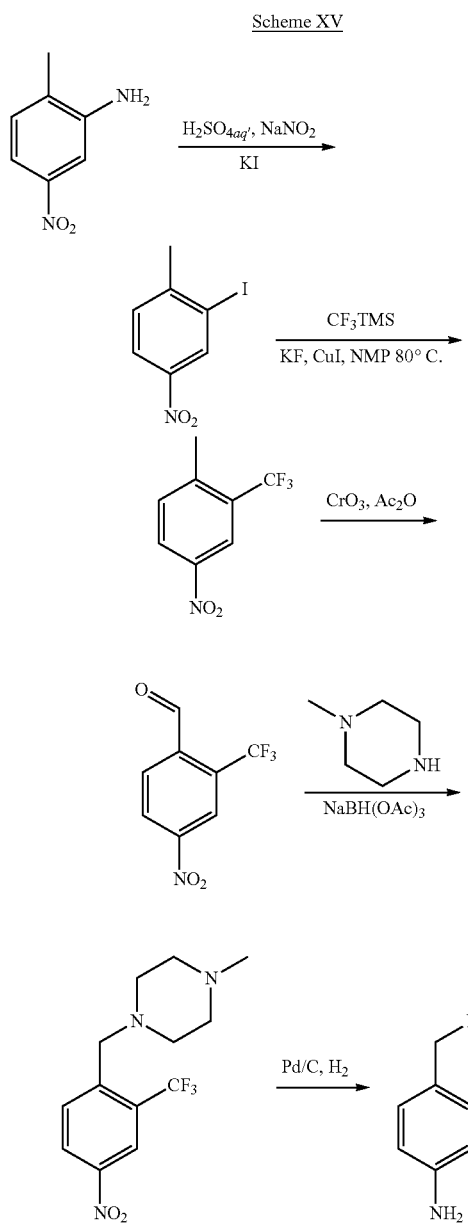

In this scheme, non-limiting examples of substituents $R^b$ on Ring B are halo, e.g., Cl; lower alkyl groups, e.g., isopropyl; and substituted lower alkyl groups, e.g. —$CF_3$; and non-limiting examples of Ring C are N,N-dimethylpyrrolidine, N-(2-hydroxyethyl)piperazine, and N-methylpiperazine.

Intermediates W-[Ring A]-[L1]-[Ring B], such as those presented in the various synthetic schemes above, can be reacted with an acetylenic derivative of bicyclic heteroaryl ring using the Sonogashira coupling conditions described in the general Scheme I. Specific example is depicted below in Scheme XVI.

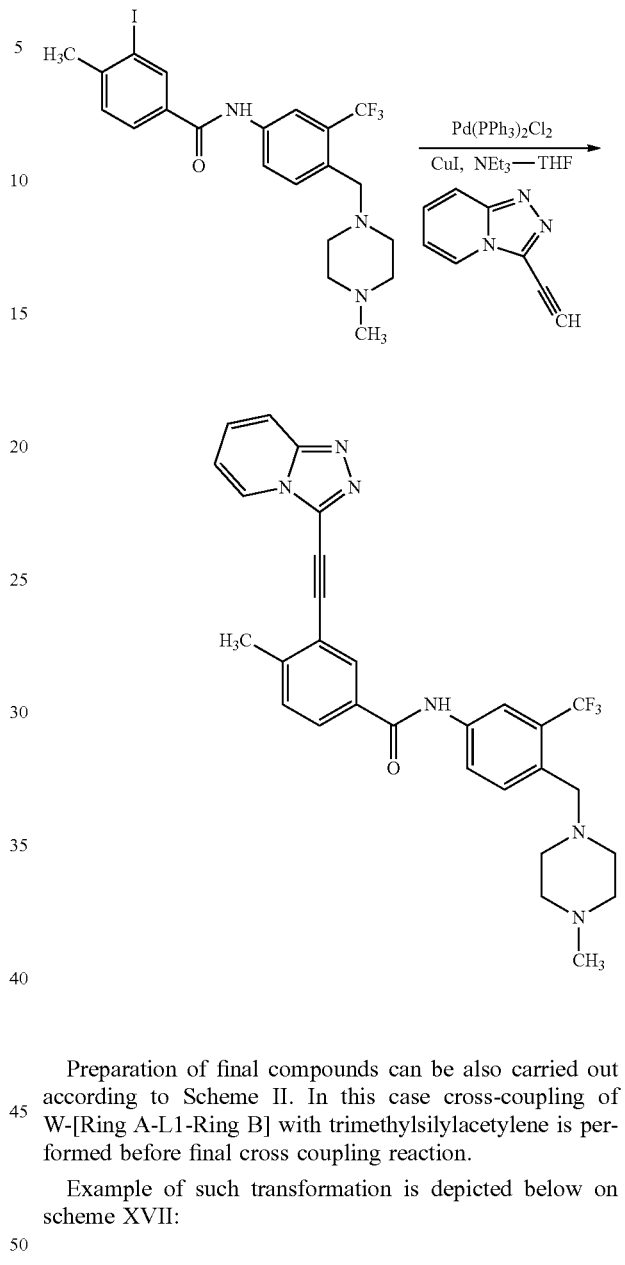

Preparation of final compounds can be also carried out according to Scheme II. In this case cross-coupling of W-[Ring A-L1-Ring B] with trimethylsilylacetylene is performed before final cross coupling reaction.

Example of such transformation is depicted below on scheme XVII:

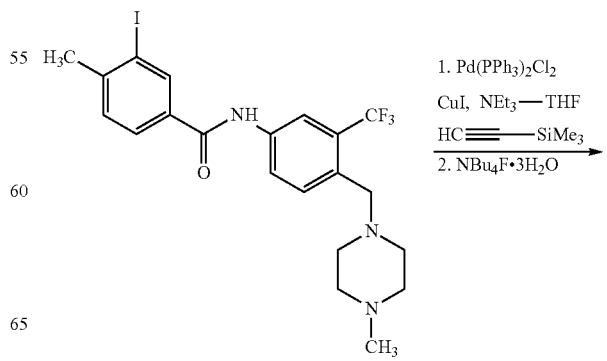

-continued

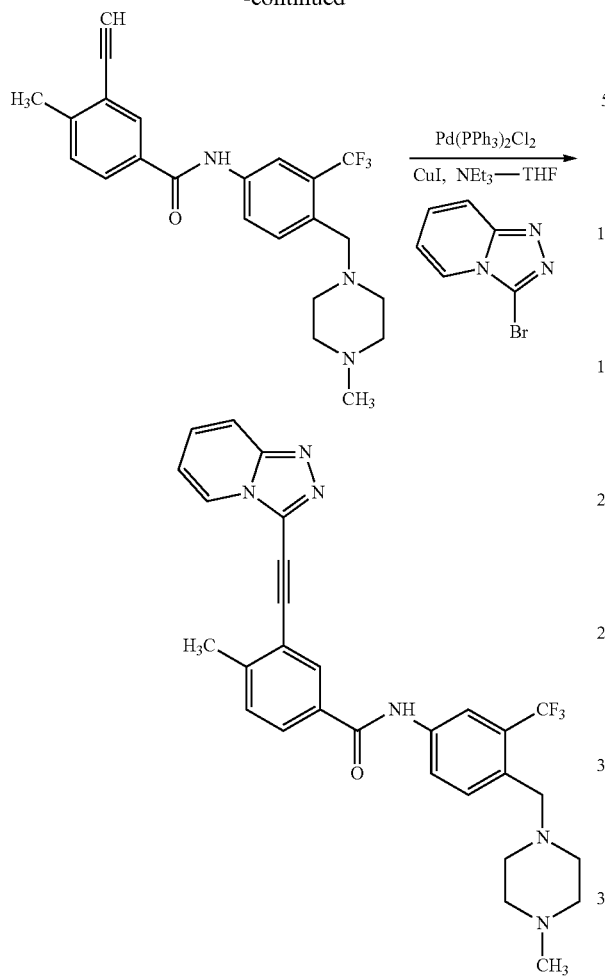

In other embodiments, the steps can be carried out in a different order. For example, the Sonogashira Coupling reaction can be used to link bicyclic heteroaryl ring to Ring A prior to linking that portion to Ring B Scheme XIX.

Scheme XVIII

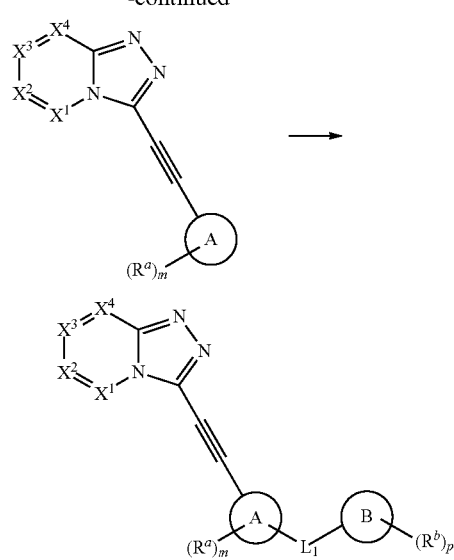

-continued

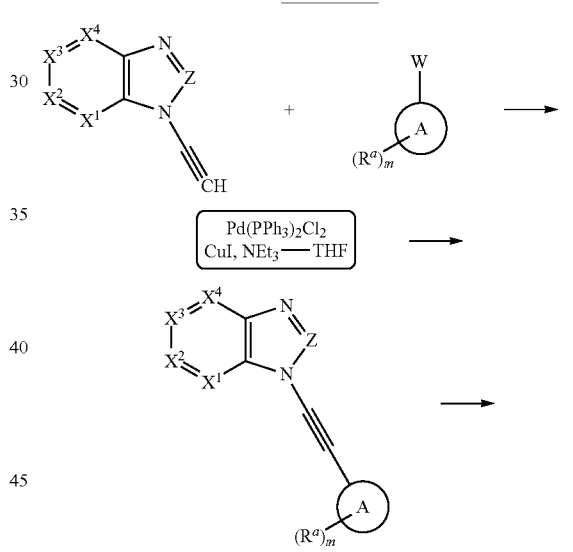

Scheme XIX

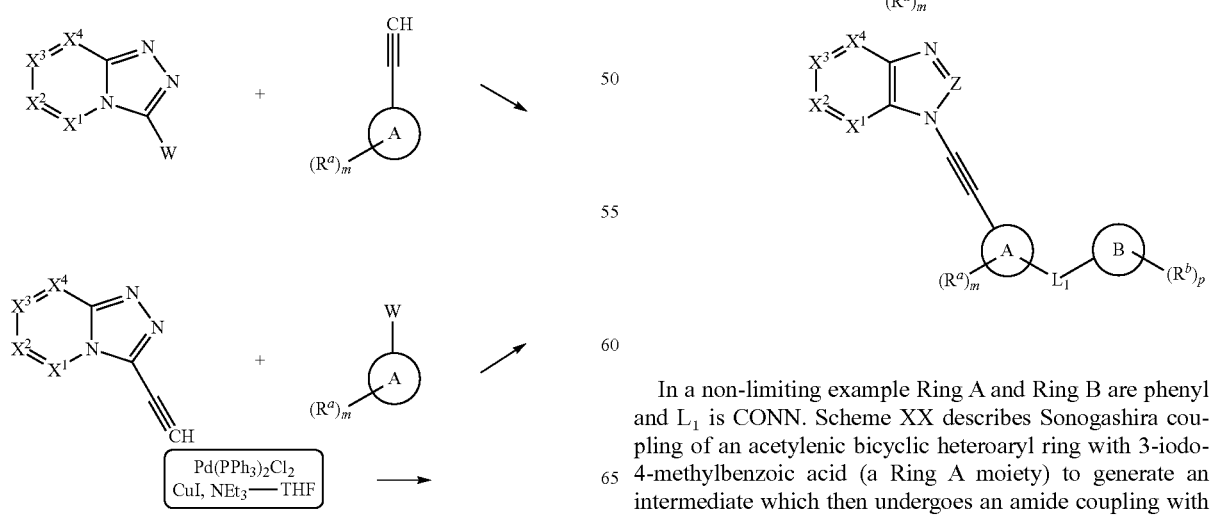

In a non-limiting example Ring A and Ring B are phenyl and $L_1$ is CONN. Scheme XX describes Sonogashira coupling of an acetylenic bicyclic heteroaryl ring with 3-iodo-4-methylbenzoic acid (a Ring A moiety) to generate an intermediate which then undergoes an amide coupling with an optionally substituted Ring B moiety.

Scheme XX

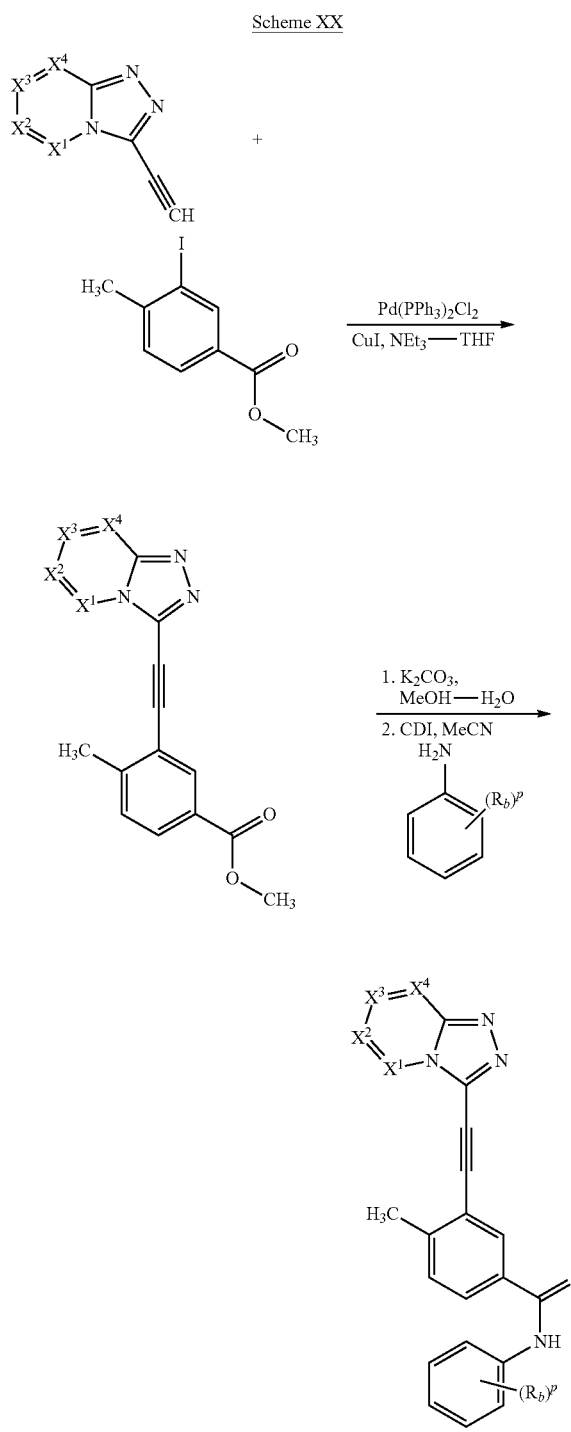

Scheme XXI

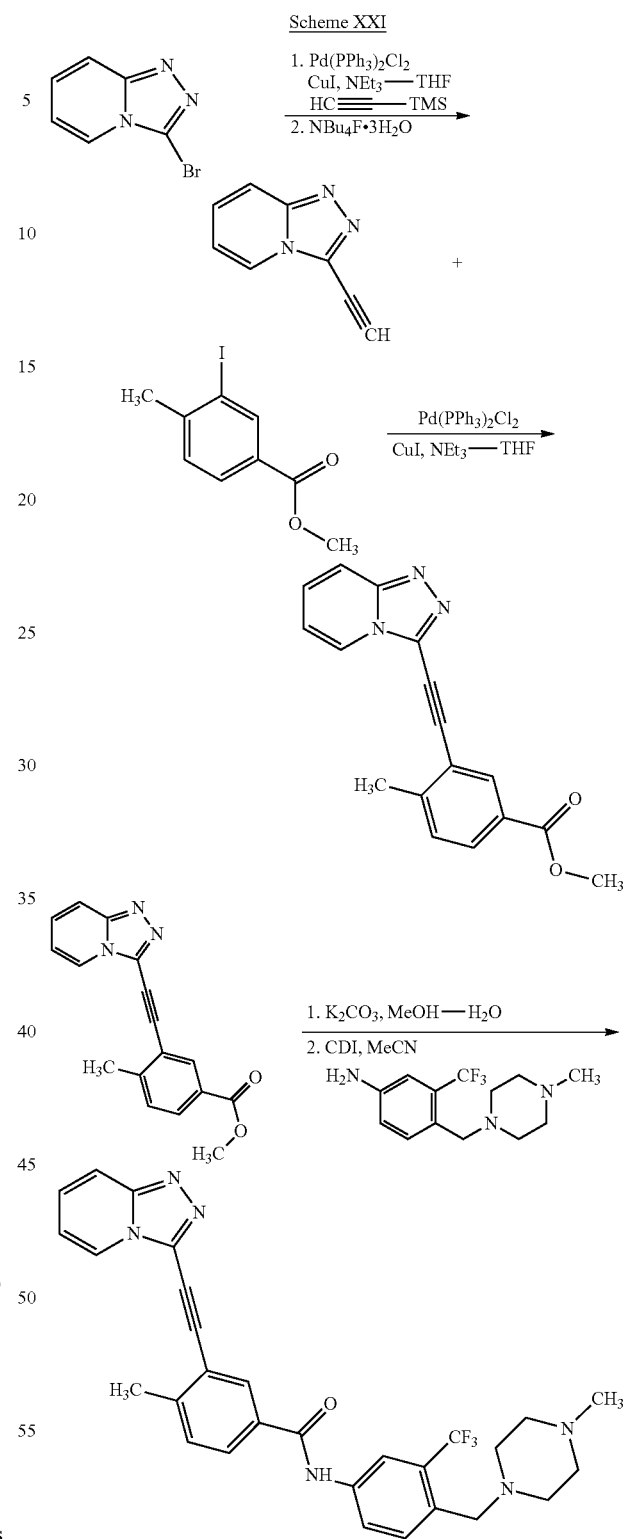

This approach is illustrated in Scheme XXI which depicts the coupling of an acetylenic bicyclic heteroaryl ring (i.e., 3-ethynylimidazo[1,2,4]triazolo[4,3-a]-pyridine) with a substituted W-[Ring A] (i.e., 3-iodo-4-methylbenzoic acid) followed by an amide coupling of the resultant [Ring T]-[Ring A]-COOH intermediate with a H2N-[Ring B]-L2-[Ring C] moiety (i.e., 4-(4-methylpiperazin-1-yl)methyl)-3-(trifluoromethylaniline):

Alternative approach may arise from Sonogashira coupling between acetylenic Ring A and halogenated bicyclic heteroaryl moiety. Alternatively, as another illustration of the practitioner's range of assembly options, the 3-iodo-4-methylbenzoic acid Ring A intermediate can be reacted in a Sonogashira reaction with trimethylsilylacetylene, which after silyl deprotection, can undergo second Sonogashira coupling reaction with an halogenated bicyclic heteroaryl ring as illustrated in Scheme XXII.

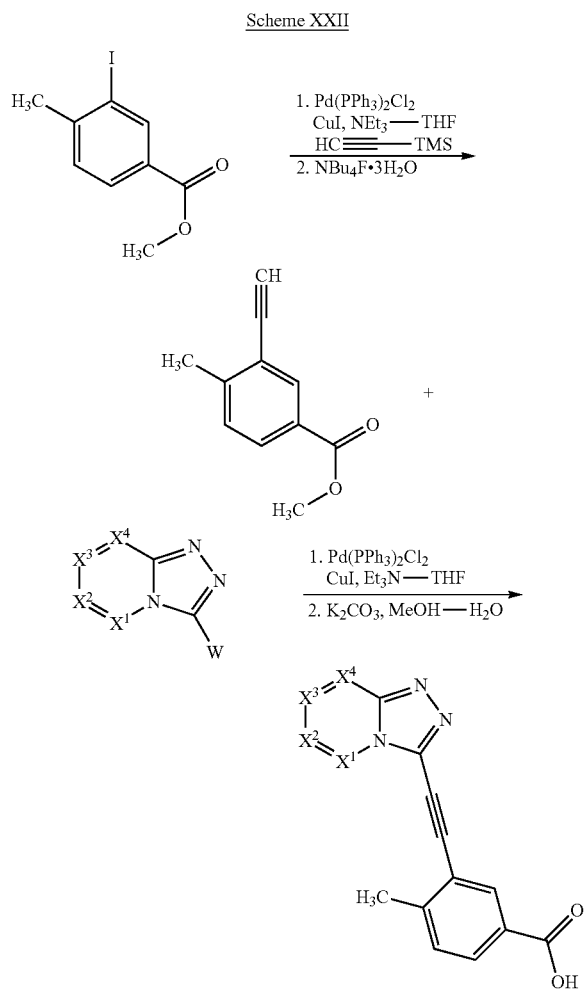

With synthetic approaches such as the foregoing, combined with the examples which follow, additional information provided herein and conventional methods and materials, the practitioner can prepare the full range of compounds disclosed herein.

Uses of Chemical Compounds of the Invention
Pharmaceutical Uses

Compounds of the present invention may be used for treatment of diseases which pathogenesis involves protein kinases. According to current knowledge such diseases are represented by many oncological diseases (Michal Vieth et al, Kinomics: characterizing thetherapeutically validated kinase space, Drug Discov Today•Volume 10, Number 12•June; Oleg Fedorov, The (un)targeted cancer kinome, nature chemical biology, 2010, 6, 166-169; 2005; Fabian M A, et al, A small molecule-kinase interaction map for clinical kinase inhibitors, Nat. Biotechnol. 2005 March; 23(3):329-336) and chronic inflammatory diseases (Matthias Gaestel; Targeting innate immunity protein kinase signaling in inflammation, Nat REv Drug Discov, 480-499, 2009 (8); Bhagwat S S, Kinase inhibitors for the treatment of inflammatory and autoimmune disorders. Purinergic Signal. 2009 March; 5(1):107-15.; Friedrich Grimminger et al, Targeting non-malignant disorders with tyrosine kinase inhibitors, Nature Reviews Drug Discovery 9, 956-970).

Compounds can be used for therapy of primary and metastatic cancer, solid and hematologic tumors, associated with impaired protein kinase activity, specifically head and neck tumors, gastrointestinal tumors, lung, breast, pancreas, prostate, rectum, colon, cervix, ovaries tumors and such oncologic diseases as melanoma, multiple myeloma, non-Hodgkin lymphoma, leukemia.

Of special interest these compounds may be used for treatment of chronic myelogenous leukemia associated with increased activity of Abl protein kinase including its forms resistant to such drugs as Imatinib, Dasatinib and Nilotinib due to mutations in Abl catalytic domain.

Therapeutic Use of Compounds

The method of the invention comprises administering to a subject in need thereof a therapeutically effective amount of a compound of the invention.

A "therapeutically effective amount" is that amount effective for detectable killing or inhibition of the growth or spread of cancer cells; the size or number of tumors; or other measure of the level, stage, progression or severity of the cancer. The exact amount required will vary from subject to subject, depending on the species, age, and general condition of the subject, the severity of the disease, the particular anticancer agent, its mode of administration, combination treatment with other therapies, and the like.

The compound, or a composition containing the compound, may be administered using any amount and any route of administration effective for killing or inhibiting the growth of cancer cells.

The anticancer compounds of the invention are preferably formulated in dosage unit form for ease of administration and uniformity of dosage. The expression "dosage unit form" as used herein refers to a physically discrete unit of anticancer agent appropriate for the patient to be treated. As is normally the case, the total daily usage of the compounds and compositions of the present invention will be decided by the attending physician using routine reliance upon sound medical judgment. The specific therapeutically effective dose level for any particular patient or organism will depend upon a variety of factors including the disorder being treated; the severity of the disorder; the potency of the specific compound employed; the specific composition employed; the age, body weight, general health, sex and diet of the patient; the route and schedule of administration; the rate of metabolism and/or excretion of the compound; the duration of the treatment; drugs used in combination or coincident with administration of the compound of this invention; and like factors well known in the medical arts.

Furthermore, after formulation with an appropriate pharmaceutically acceptable carrier in a desired dosage, the compositions of this invention can be administered to humans and other animals orally, rectally, parenterally, intracisternally, intravaginally, intraperitoneally, topically (as by transdermal patch, powders, ointments, or drops), sublingually, bucally, as an oral or nasal spray, or the like.

The effective systemic dose of the compound will typically be in the range of 0.01 to 500 mg of compound per kg of patient body weight, preferably 0.1 to 125 mg/kg and in some cases 1 to 25 mg/kg, administered in single or multiple doses. Generally, the compound may be administered to patients in need of such treatment in a daily dose range of about 50 to about 2000 mg per patient. Administration may be once or multiple times daily, weekly (or at some other multiple-day interval) or on an intermittent schedule. For example, the compound may be administered one or more times per day on a weekly basis (e.g. every Monday) indefinitely or for a period of weeks, e.g. 4-10 weeks.

Alternatively, it may be administered daily for a period of days (e.g. 2-10 days) followed by a period of days (e.g. 1-30 days) without 10 administration of the compound, with that cycle repeated indefinitely or for a given number of repititions, e.g. 4-10 cycles. As an example, a compound of the invention may be administered daily for 5 days, then discontinued for 9 days, then administered daily for another 5 day period, then discontinued for 9 days, and so on, repeating the cycle indefinitely or for a total of 4-10 times.

The amount of compound which will be effective in the treatment or prevention of a particular disorder or condition will depend in part on well known factors affecting drug dosage. In addition, in vitro or in vivo assays may optionally be employed to help identify optimal dosage ranges. A rough guide to effective doses may be extrapolated from dose-response curves derived from in vitro or animal model test systems. The precise dosage level should be determined by the attending physician or other health care provider and will depend upon well known factors, including route of administration, and the age, body weight, sex and general health of the individual; the nature, severity and clinical stage of the disease; the use (or not) of concomitant therapies; and the nature and extent of genetic engineering of cells in the patient.

When administered for the treatment or inhibition of a particular disease state or disorder, the effective dosage of the compound of this invention may vary depending upon the particular compound utilized, the mode of administration, the condition, and severity thereof, of the condition being treated, as well as the various physical factors related to the individual being treated. In many cases, satisfactory results may be obtained when the compound is administered in a daily dosage of from about 0.01 mg/kg-500 mg/kg, preferably between 0.1 and 125 mg/kg, and more preferably between 1 and 25 mg/kg. The projected daily dosages are expected to vary with route of administration. Thus, parenteral dosing will often be at levels of roughly 10% to 20% of oral dosing levels.

When the compound of this invention is used as part of a combination regimen, dosages of each of the components of the combination are administered during a desired treatment period. The components of the combination may be administered at the same time; either as a unitary dosage form containing both components, or as separate dosage units; the components of the combination can also be administered at different times during a treatment period, or one may be administered as a pretreatment for the other.

Compounds of present invention can exist in free form for treatment, or where appropriate, as a pharmaceutically acceptable salt or other derivative. As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, phosphonates and other types of compounds, are well known in the art. For example, S. M. Berge, et al. describe pharmaceutically acceptable salts in detail in J. Pharmaceutical Sciences, 66: 1-19 (1977), incorporated herein by reference. The salts can be prepared in situ during the isolation and purification of the compounds of the invention, or separately by reacting the free base or free acid of a compound of the invention with a suitable base or acid, respectively. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, 'citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate. camphorate, camphorsulfonate, citrate, cyclopentanepropionate. Digluconate, dodecylsulfate, ethanesulfonate, formate, fumarate, glucoheptonate, glycerophosphate, gluconate, hernisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate. tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium. and amine cations formed using counterions such as halide, hydroxide, carboxylate, sulfate, phosphate, nitrate, lower alkyl sulfonate and aryl sulfonate.

Additionally, as used herein, the term "pharmaceutically acceptable ester" refers preferably to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates. Obviously, esters can be formed with a hydroxyl or carboxylic acid group of the compound of the invention.

Furthermore, the term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are transformed in vivo to yield the parent compound of the above formula, for example by hydrolysis in blood. See, e.g., T. Higuchi and V. Stella, Prodrugs as Novel Delivery Systems, Vol. 14 of the AC.S. Symposium Series, and Edward B. Roche, ed., Bioreversible Carriers in Drug Design, American Pharmaceutical Assocn. and Pergamon Press, 1987.

Compositions.

Compositions are provided which comprise anyone of the compounds described herein (or a prodrug, pharmaceutically acceptable salt or other pharmaceutically acceptable derivative thereof), and one or more pharmaceutically acceptable carriers or excipients. These compositions optionally further comprise one or more additional therapeutic agents. Alternatively, a compound of this invention may be administered to a patient in need thereof in combination with the administration of one or more other therapeutic regimens (e.g. Imatinib or other kinase inhibitors, interferon, bone marrow transplant, farnesyl transferase inhibitors, bisphosphonates, thalidomide, cancer vaccines, hormonal therapy, antibodies, radiation, etc). For example, additional therapeutic agents for conjoint administration or inclusion in a pharmaceutical composition with a compound of this invention may be another one or more anticancer agents.

As described herein, the compositions of the present invention comprise a compound of the invention together with a pharmaceutically acceptable carrier, which, as used herein, includes any and all solvents, diluents, or other vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyllaurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition.

Formulations

This invention also encompasses a class of compositions comprising the active compounds of this invention in association with one or more pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly, intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient.

Examples of such dosage units are tablets or capsules. For example, these may contain an amount of active ingredient from about 1 to 2000 mg, preferably from about 1 to 500 mg, more commonly from about 5 to 200 mg. A suitable daily dose for a human or other mammal may vary depending on the condition of the patient and other factors.

For therapeutic purposes, the active compounds of this invention are ordinarily combined with one or more adjuvants, excipients or carriers appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. In the case of skin conditions, it may be preferable to apply a topical preparation of compounds of this invention to the affected area two to four times a day. Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs.

The compounds of this invention can also be administered by a transdermal device. Preferably transdermal administration will be accomplished using a patch either of the reservoir and porous membrane type or of a solid matrix variety. In either case, the active agent is delivered—continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The oily phase of the emulsions of this invention may be constituted from known ingredients in a known manner.

While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl ~onostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable nonirritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Pharmaceutical compositions of this invention comprise a compound of the formulas described herein or a pharmaceutically acceptable salt thereof; an additional agent selected from a kinase inhibitory agent (small molecule, polypeptide, antibody, etc.), an immunosuppressant, an anti-cancer agent, an anti-viral agent, antiinflammatory agent, antifungal agent, antibiotic, or an anti-vascular hyperproliferation compound; and any pharmaceutically acceptable carrier, adjuvant or vehicle.

The term "pharmaceutically acceptable carrier or adjuvant" refers to a carrier or adjuvant that may be administered to a patient, together with a compound of this invention and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDOS) such as d-atocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethelene glycol, sodium carboxymethylcellulose, polyacrylates, waxes, polyethylene-polyoxypropylene-block polymers, polyethylene glycol and wool fat. Cyclodextrins such as U•, P-, and y-cyclodextrin, or chemically modified derivatives such as hydroxyalkylcyclodextrins, including 2 and 3-hydroxypropyl-cyclodextrins, or other solubilized derivatives may also be advantageously used to enhance delivery of compounds of the formulae described herein.

The pharmaceutical compositions may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents.

If desired, certain sweetening, flavoring and/or coloring agents may be added. The pharmaceutical compositions may comprise formulations utilizing liposome or microencapsulation techniques, various examples of which are known in the art.

Combination Therapy Use of Compounds of the Invention

While the compounds of the invention can be administered as the sole active pharmaceutical agent, they can also be used in combination with one or more other compounds of the invention or with one or more other agents. When administered as a combination, the therapeutic agents can be formulated as separate compositions that are administered at the same time or sequentially at different times, or the therapeutic agents can be given as a single composition.

The phrase "combination therapy", in referring to the use of a compound of this invention together with another pharmaceutical agent, means the coadministration of each agent in a substantially simultaneous manner as well as the administration of each agent in a sequential manner, in either case, in a regimen that will provide beneficial effects of the drug combination. Coadministration includes inter alia the simultaneous delivery, e.g., in a single tablet, capsule, injection or other dosage form having a fixed ratio of these active agents, as well as the simultaneous delivery in multiple, separate dosage forms for each agent respectively.

Thus, the administration of compounds of the present invention may be in conjunction with additional therapies known to those skilled in the art in the prevention or treatment of cancer, such as radiation therapy or cytostatic agents, cytotoxic agents, other anti-cancer agents an other drugs to ameliorate symptoms of the cancer or side effects of any of the drugs.

If formulated as a fixed dose, such combination products employ the compounds of this invention within the accepted dosage ranges. Compounds of this invention may also be administered sequentially with other anticancer or cytotoxic agents when a combination formulation is inappropriate. The invention is not limited in the sequence of administration; compounds of this invention may be administered prior to, simultaneously with, or after administration of the other anticancer or cytotoxic agent.

Currently, standard treatment of primary tumors consists of surgical excision, when appropriate, followed by either radiation or chemotherapy, and typically administered intravenously (i.v.). The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of cancer by combination drug chemotherapy. And there are several major categories of such antineoplastic agents, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention includes antimetabolite-type/thymidilate synthase inhibitor such as cytarabine (Guilhot F et al., Imatinib in combination with cytarabine for the treatment of Philadelphia-positive chronic myelogenous leukemia chronic-phase patients: rationale and design of phase I/II trials, Semin Hematol, 2003, 40 (2 Suppl), 92-97).

A second family of antineoplastic agents which may be used in combination with compounds of the present invention consists of alkylating-type antineoplastic agents, e.g. hydroxyurea and melfalan (Giallongo, C et al, Imatinib increases cytotoxicity of melphalan and their combination allows an efficient killing of chronic myelogenous leukemia cells, European Journal of Haematology, 2011, 86, 3, 216-225).

A third family of antineoplastic agents which may be used in combination with compounds of the present invention consists of antibiotic-type antineoplastic agents such as daunorubicin (Deau B et al, The addition of daunorubicin to imatinib mesylate in combination with cytarabine improves the response rate and the survival of patients with myelogenous blast crisis chronic myelogenous leukemia (AFR01 study), Leukemia Researches, 8 Dec. 2010) and doxorubicin (Pichot C S et al, Dasatinib synergizes with doxorubicin to block growth, migration, and invasion of breast cancer cells, British Journal of Cancer (2009) 101, 38-47).

A fourth family of antineoplastic agents which may be used in combination with compounds of the present invention consists of a miscellaneous family of antineoplastic agents, including tubulin interacting agents, topoisomerase II inhibitors, topoisomerase I inhibitors such as etoposide (Coskun H S et al, Bleomycin, etoposide and cisplatin (BEP) combination with concurrent imatinib mesylate (GLEEVEC) in chronic myelogenous leukemia (CML) patient with mesenchymal tumor, Medical Oncology, 2008, 25, 1, 110-112) and hormonal agents (Strauss L. C. et al, Three parallel randomized phase II trials of dasatinib plus hormone therapy (HT) in advanced ER+ breast cancer (ER+ ABC), Journal of Clinical Oncology, 2010 ASCO Annual Meeting Proceedings (Post-Meeting Edition), Vol 28, Suppl 15.

Treatment Kits

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Optionally associated with such container(s) can be a notice in the form prescribed by a governmental agency regulating the manufacture, use or sale of pharmaceutical products, which notice reflects approval by the agency of manufacture, use or sale for human administration.

EXAMPLES

Synthesis Examples

Example 1

Synthesis of potassium 3-((2-methyl-5-(4-((4-methylpiperazin-1-yl)methyl)-3-(trilluoromethyl)phenylcarbamoyl)phenyl)ethynyl)-[1,2,4]-triazolo[4,3-b]pyridazine-7-carboxylate 4-methyl-3,6-pyridazinediol

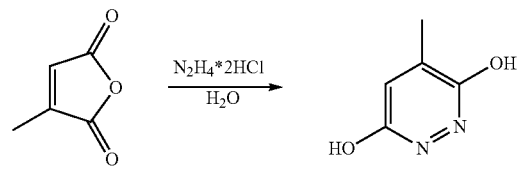

Citraconic anhydride (336 g, 3 mol) is added to a boiling solution of hydrazine dihydrochloride (313 g, 3 mol) in water (700 ml). The reaction mixture is refluxed for 10 h and cooled. The precipitate is filtered out, washed with a small amount of cold water and dried, yielding the desired product (270 g, 71.4%).

4-methyl-3,6-dichloropyridazine

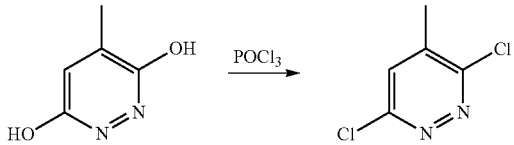

A solution of 4-methyl-3,6-pyridazinediol (252 g, 2 mol) in phosphorous oxychloride (2000 ml) is refluxed on an oil bath for 7 h. The excess amount of POCl$_3$ is removed in vacuum, the residue is cooled and added to 5 kg of ice. The reaction mixture is then neutralized with aqueous ammonia and extracted with chloroform (8×500 ml). The combined organic extract is washed with brine (4×500 ml), dried over MgSO$_4$ and the solvent is removed in vacuum, yielding the desired product (290 g, 89%).

3,6-dichloropyridazine-4-carboxylic acid

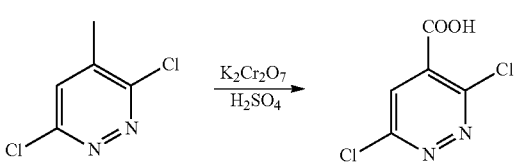

Potassium bichromate (214 g, 1.5 mol) is added in small portions (0.2-0.5 g) to a solution of 4-methyl-3,6-dichloropyridazine (200 g, 1.2 mol) in conc. sulphuric acid (600 ml) keeping the temperature around 35° C. The reaction mixture is then stirred for 4 h, poured into ice (1.5 kg), alkalized to pH~3 with aqueous NaHCO$_3$ and extracted with ether (5×500 ml). The combined organic extract is washed with brine (5×200 ml) and dried. The solvent is evaporated, and the residue is recrystallized from water, yielding the desired product (167 g).

Ethyl 3,6-dichloropyridazine-4-carboxylate

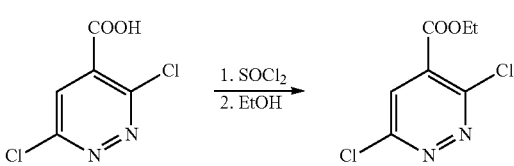

A suspension of 3,6-dichloropyridazine-4-carboxylic acid (50 g, 260 mmol) in a mixture of thionyl chloride (40 ml) and dry DCM (2 l) is refluxed to complete dissolution. Dry ethanol (150 ml) is then added dropwise under intensive stirring and cooling. Solvents are removed in vacuum, yielding the desired product (55.7 g, 97%).

Ethyl 6-chloro-3-hydrazinylpyridazine-4-carboxylate

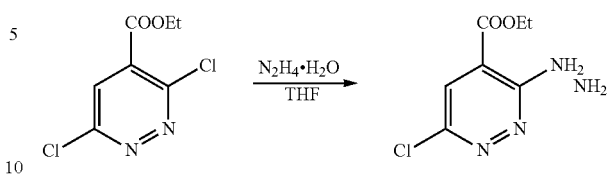

Hydrazine hydrate (66.8 ml, 1.37 mol) is added to a solution of ethyl 3,6-dichloropyridazine-4-carboxylate (138 g, 1.37 mol) in THF (600 ml). When the addition is completed, the clear yellowish solution immediately turns reddish brown and turbid. A brown suspension is then formed, and a reddish brown oil deposits on the tube walls. The mixture is stirred for 80 min and the suspension is decanted from the dark oily residue. The latter is washed with THF (2×100 ml). Water (600 ml) is added to the combined THF fraction, and the obtained mixture is heated to almost boiling and then cooled to room temperature under stirring. The precipitate is filtered out and washed with water (2×200 ml), giving a brownish-yellow solid (99.3 g). A part of this solid (87.6 g) is dissolved in ethanol (1000 ml), heated to boiling and stirred at RT for 2 h (crystallization starts to occur after 10-20 min). The precipitate is filtered out, washed with ethanol (3×50 ml) and hexanes (3×50 ml), giving the desired product (59.9 g) as orange needles.

Ethyl 3-chloropyridazine-5-carboxylate

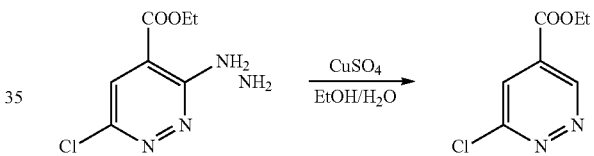

Copper sulfate (120 g, 480 mmol) is added to a mixture of ethyl 6-chloro-3-hydrazinylpyridazine-4-carboxylate (52 g, 240 mmol) and 70% aqueous ethanol (1500 ml). The reaction mixture is refluxed for 20 h, and the residue is purified chromatographically, using hexanes:ethyl acetate mixture of increasing polarity. Yield: 21 g (47%).

Ethyl 3-hydrazopyridazine-5-carboxylate

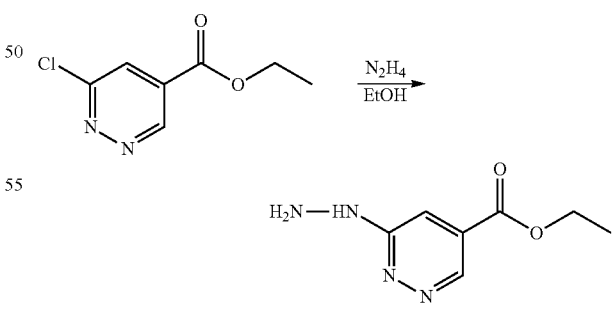

Hydrazine hydrate (70 ml, 1.42 mol) is added to a solution of ethyl 3-chloropyridazine-5-carboxylate (121 g, 648 mmol) in ethanol (1000 ml). The reaction mixture is stirred at 30° C. for 20 h and cooled. The precipitate is filtered out and dried, yielding the desired product of ~85% purity which is taken into the next step without further purification.

Ethyl [1,2,4]triazolo[4,3-b]pyridazine-7-carboxylate

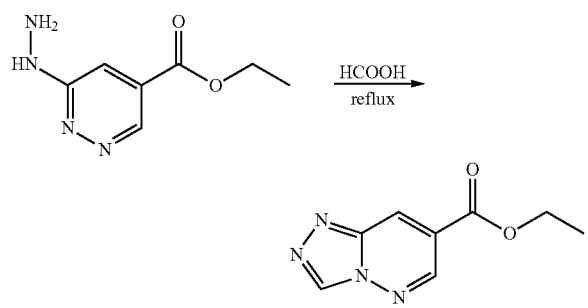

A mixture of ethyl 3-hydrazopyridazine-5-carboxylate (56 g, 307 mmol), 97% formic acid (500 ml) and HC(OEt)$_3$ (50 ml) is refluxed for 15 h. The reaction mixture is evaporated in vacuum. Water (200 ml) is added and the mixture is neutralized with NaHCO$_3$. The mixture is extracted with ethyl acetate (3×300 ml). The combined organic extract is dried over Na$_2$SO$_4$ and the solvent is evaporated in vacuum. The residue is purified chromatographically using chloroform:methanol mixture of increasing polarity, yielding the desired product (36.6 g, 62%).

Ethyl 3-bromo[1,2,4]triazolo[4,3-b]pyridazine-7-carboxylate

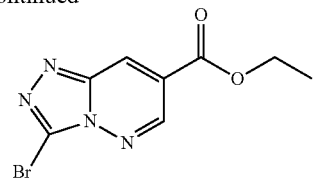

A solution of bromine (11.5 g, 72 mmol) in dry pyridine (100 ml) is added to a suspension of ethyl [1,2,4]triazolo[4,3-b]pyridazine-7-carboxylate (12.6 g, 65.5 mmol) in chloroform (200 ml), keeping the temperature about 0° C. The reaction mixture is stirred at room temperature for 2 h, after which a solution of K2CO$_3$ (50 g) in brine (100 ml) is added and the precipitate is filtered out. The organic layer is separated and the aqueous layer is extracted with ethyl acetate (3×300 ml). The combined organic extract is dried over Na$_2$SO$_4$ and evaporated in vacuum. The residue is combined with the previously filtered precipitate and purified chromatographically, using chlorophorm:methanol mixture of increasing polarity, giving the desired product (12.2 g, 69%).

Potassium 3-((2-methyl-5-(4-((4-methylpiperazin-1-yl)methyl)-3-(trifluoromethyl)phenylcarbamoyl)phenyl)ethynyl)-[1,2,4]triazolo[4,3-b]pyridazine-7-carboxylate

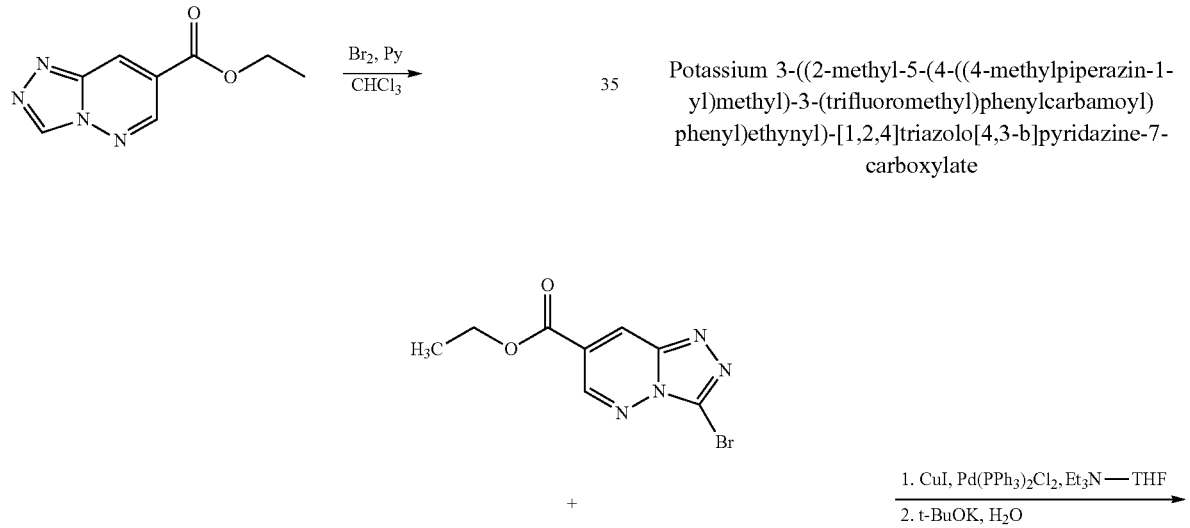

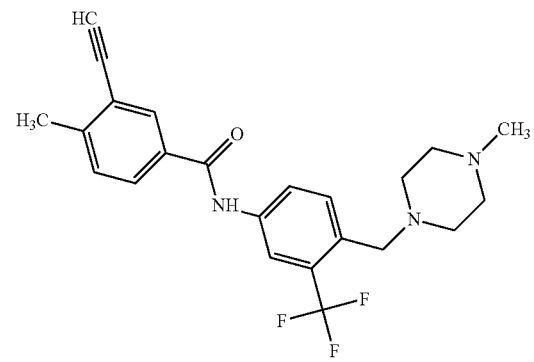

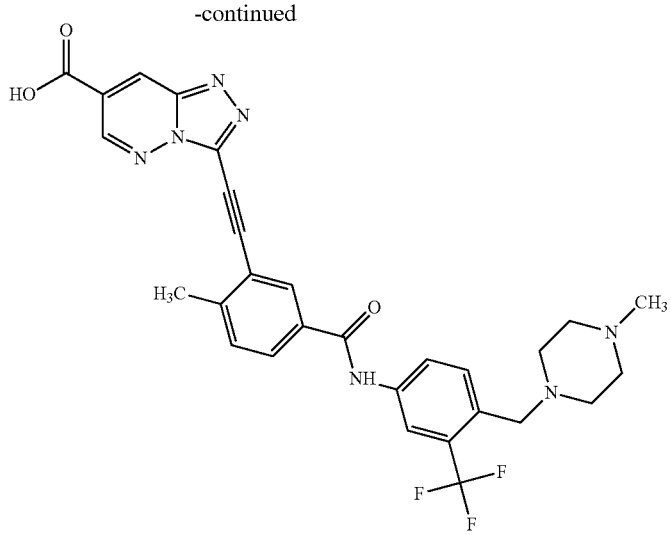

Copper (I) iodide (396 mg, 4 mol. %) is added to a suspension of acetylene derivative (21.6 g, 52 mmol) and ethyl 3-bromo[1,2,4]triazolo[4,3-b]pyridazine-7-carboxylate (14.1 g, 52 mmol) in a mixture of degassed dry triethylamine (100 ml) and degassed dry THF (40 ml) and the reaction mixture is stirred for 10 min. Pd(Ph$_3$P)$_2$Cl$_2$ (730 mg, 2 mol. %), PPh$_3$ (1.1 g) and di-tert-butyl(2',6'-dimethoxybiphenyl-2-yl)phosphine (100 mg) are then added, the reaction mixture is degassed twice and stirred at 65° C. for 130 h under inert atmosphere. Solvents are evaporated and the residue is purified chromatographically, using chloroform:methanol mixture of increasing polarity. The obtained product is dissolved in dry DMSO (50 ml). Water (1 ml) and potassium tert-butylate (0.6 g) are added and the mixture is stirred for 4 h. The desired product is purified on an ion exchange resin (16.3 g, 52%).

Example 2

Synthesis of 3-([1,2,4]triazolo[4,3-b]pyridazin-3-ylethynyl)-4-methyl-N-(4-((4-methylpiperazinyl-1-yl)methyl)-3-(trifluoromethyl)phenyl)benzamide 3-hydroxypyridazine

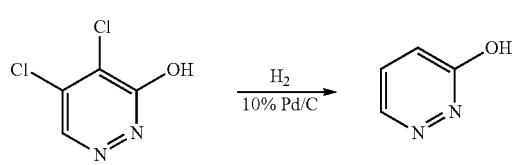 [SMILES: Oc1nncc(Cl)c1Cl ; "10% Pd/C" ; "H2" ; Oc1cccnn1]

A suspension of 3-hydroxy-4,5-dichloropyridazine (168 g, 1.02 mol) in abs. ethanol is hydrogenized on 10% Pd/C at 45° C. and 30 atm for 120 h. The catalyst is filtered out and the solvent is evaporated, yielding the desired product (96 g, 98%).

3-chloropyridazine

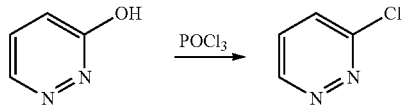

A solution of 3-hydroxypyridazine (96 g, 1 mol) in phosphorous oxychloride (800 ml) is refluxed on an oil bath for 4 h. The excess amount of POCl$_3$ is removed in vacuum, the residue is cooled and added to 2 kg of ice. The reaction mixture is then neutralized with aqueous ammonia and extracted with chloroform (4×500 ml). The combined organic extract is washed with brine (3×200 ml), dried over MgSO4 and the solvent is removed in vacuum, yielding the desired product (76 g, 67%).

3-hydrazopyridazine

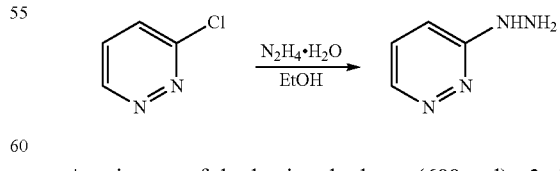

A mixture of hydrazine hydrate (600 ml), 3-chloropyridazine (67 g, 587 mmol) and ethanol (500 ml) is refluxed for 50 h, evaporated in vacuum, treated with water (100 ml) and extracted with ether (4×500 ml). The combined organic extract is dried over Na$_2$SO$_4$ and evaporated in vacuum, giving the desired product (39 g, 61%).

[1,2,4]triazolo[4,3-b]pyridazine

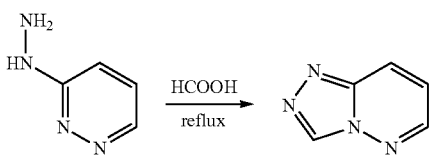 [SMILES: NNc1cccnn1 ; "HCOOH" ; c1cnn2cnnc2c1]

A mixture of ethyl 3-hydrazopyridazine (89.2 g, 810 mmol), 97% formic acid (1500 ml) and HC(OEt)$_3$ (50 ml) is refluxed for 8 h. The reaction mixture is evaporated in vacuum. Water (100 ml) is added and the mixture is neutralized with NaHCO$_3$. The mixture is extracted with ethyl acetate (4×300 ml). The combined organic extract is dried over Na$_2$SO$_4$ and the solvent is evaporated in vacuum. The residue is purified chromatographically using chloroform:methanol mixture of increasing polarity, yielding the desired product (66 g, 68%).

3-bromo-[1,2,4]triazolo[4,3-b]pyridazine

A mixture of [1,2,4]triazolo[4,3-b]pyridazine (73.5 g, 0.61 mol), NBS (120.0 g, 0.67 mol) and chloroform is refluxed for 10 h. A solution of potassium carbonate (100 g) in brine (300 ml) is added and the organic layer is separated. The aqueous layer is extracted with DCM (4×400 ml). The combined organic extract is dried over Na$_2$SO$_4$ and the solvent is evaporated in vacuum. The residue is purified chromatographically using hexane:ethyl acetate mixture of increasing polarity, yielding the desired product (57.1 g, 47%).

3-([1,2,4]triazolo[4,3-b]pyridazin-3-ylethynyl)-4-methyl-N-(4-((4-methylpiperazinyl-1-yl)methyl)-3-(trifluoromethyl)phenyl)benzamide

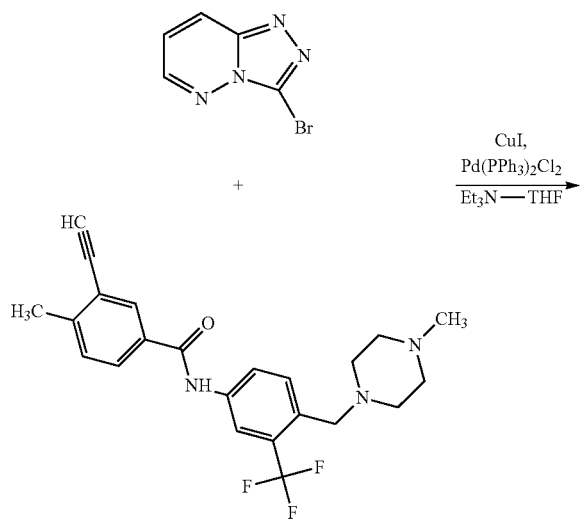

-continued

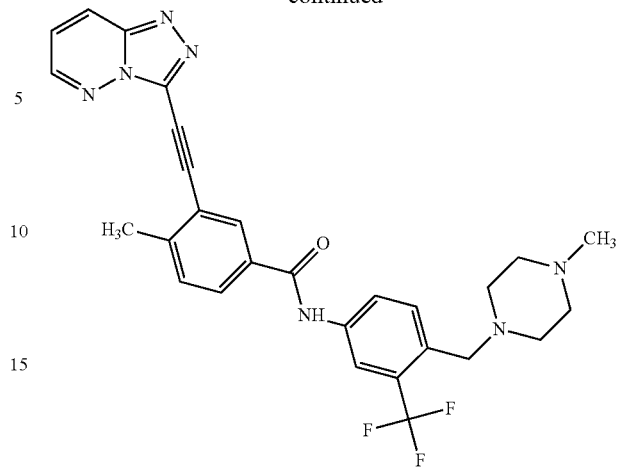

Copper (I) iodide (396 mg, 4 mol. %) is added to a suspension of acetylene derivative (21.6 g, 52 mmol) and 3-bromo-[1,2,4]triazolo[4,3-b]pyridazine (10.3 g, 52 mmol) in a mixture of degassed dry triethylamine (100 ml) and degassed dry THF (40 ml) and the reaction mixture is stirred for 10 min. Pd(Ph$_3$P)$_2$Cl$_2$ (730 mg, 2 mol. %), PPh$_3$ (1.1 g) and di-tert-butyl(2',6'-dimethoxybiphenyl-2-yl)phosphine (100 mg) are then added, the reaction mixture is degassed twice and stirred at 65° C. for 80 h under inert atmosphere. Solvents are evaporated and the residue is purified chromatographically, using chloroform:methanol mixture of increasing polarity, yielding the desired product (17.4 g, 63%).

Example 3

Synthesis of 3-([1,2,4]-triazolo[4,3-a]pyridin-3-yl-ethynyl)-4-methyl-N-(4-((4-methylpiperazin-1-yl)methyl)-3-(trifluoromethyl)phenyl)benzamide 2-hydrazopyridine

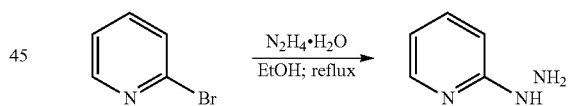

A mixture of hydrazine hydrate (600 ml) and 2-bromopyridine (250 g, 1.6 mol) with ethanol (500 ml) is refluxed for 30 h and then evaporated in vacuum. Water (1500 ml) is added and the mixture is extracted with ether (4×400 ml). The combined organic extract is dried over Na$_2$SO$_4$ and the solvent is evaporated in vacuum, yielding the desired product as an oil (100 g, 58%).

[1,2,4]-triazolo[4,3-a]pyridine

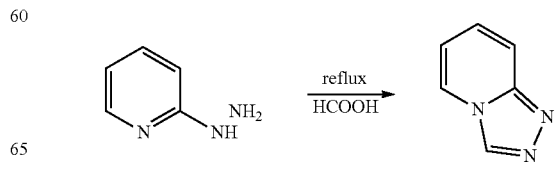

A mixture of 2-hydrazopyridine hydrate (23.3 g, 183 mmol), 97% formic acid (500 ml) and HC(OEt)$_3$ (100 ml) is refluxed for 15 h. The reaction mixture is evaporated in vacuum. Water (100 ml) is added and the mixture is neutralized with NaHCO$_3$. The mixture is extracted with ethyl acetate (4×400 ml). The combined organic extract is dried over Na$_2$SO$_4$ and the solvent is evaporated in vacuum. The residue is treated with heptane (500 ml) and left for 5 h at −18° C. The formed precipitate is filtered out, washed with hexanes and dried, giving the desired product with 65% yield.

3-bromo[1,2,4]triazolo[4,3-a]pyridine

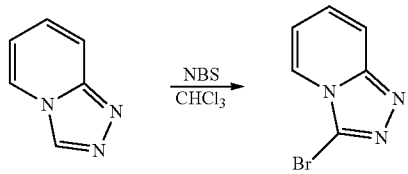

A mixture of [1,2,4]triazolo[4,3-a]pyridine (1.26 g) and NBS (1.98 g) with chloroform is refluxed for 5 h and then left for 14 h at room temperature. A saturated aqueous solution of potassium carbonate (200 ml) and KOH (20 g) are added, the mixture is shaken and the organic layer is separated. The aqueous layer is extracted with DCM twice. The combined organic extract is dried over Na$_2$SO$_4$ and the solvent is evaporated in vacuum giving the desired product with 60% yield.

3-([1,2,4]triazolo[4,3-a]pyridin-3-ylethynyl)-4-methyl-N-(4-((4-methylpiperazin-1-yl)methyl)-3-(trifluoromethyl)phenyl)benzamide

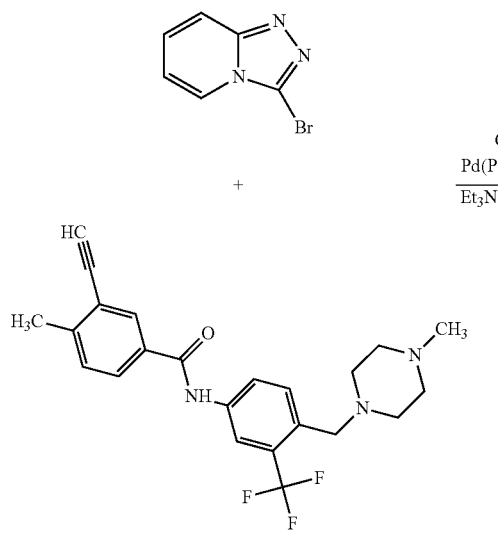

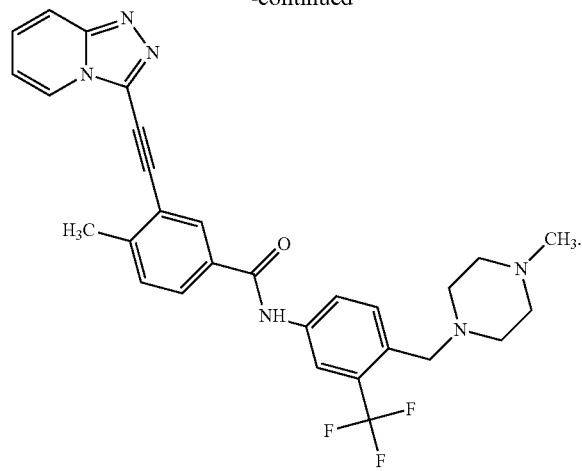

Copper (I) iodide (396 mg, 4 mol. %) is added to a suspension of acetylene derivative (21.6 g, 52 mmol) and 3-bromo-[1,2,4]triazolo[4,3-b]pyridine (10.3 g, 52 mmol) in a mixture of degassed dry triethylamine (100 ml) and degassed dry THF (40 ml) and the reaction mixture is stirred for 10 min. Pd(Ph$_3$P)$_2$Cl$_2$ (730 mg, 2 mol. %), PPh$_3$ (1.1 g) and di-tert-butyl(2',6'-dimethoxybiphenyl-2-yl)phosphine (100 mg) are then added, the reaction mixture is degassed twice and stirred at 65° C. for 80 h under inert atmosphere. Solvents are evaporated and the residue is purified chromatographically, using chloroform:methanol mixture of increasing polarity, yielding the desired product (10.2 g, 37%).

Example 4

Synthesis of potassium 3-((2-methyl-5-(4-((4-methylpiperazin-1-yl)methyl)-3-(trifluoromethyl)phenylcarbamoyl)phenyl)ethynyl)-[1,2,4]triazolo[4,3-a]pyridine-7-carboxylate Ethyl 2-hydrazopyridine-4-carboxylate

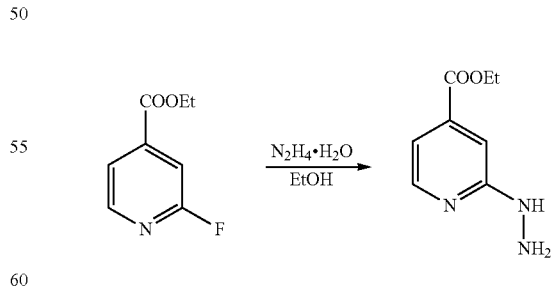

A mixture of hydrazine hydrate (150 ml, 3.2 mol) and ethyl 2-fluoroisonicotinate (215 g, 1.28 mol) with ethanol (2000 ml) is stirred at 50° C. for 20 h and cooled. The precipitate is filtered out and dried, yielding the desired product of ~70% purity which is taken into the next step without further purification.

Ethyl [1,2,4]-triazolo[4,3-a]pyridine-7-carboxylate

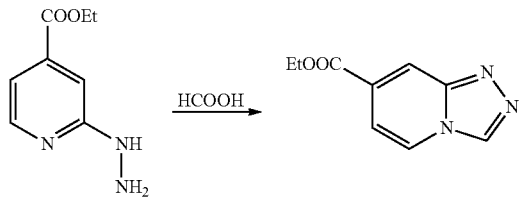 [SMILES: CCOC(=O)c1ccnc(NN)c1 ; "HCOOH" ; CCOC(=O)c1ccn2cnnc2c1]

A mixture of ethyl 2-hydrazopyridine-4-carboxylate (100 g, 413 mmol), 97% formic acid (2500 ml) and HC(OEt)$_3$ (200 ml) is refluxed for 25 h. The reaction mixture is evaporated in vacuum. Water (200 ml) is added and the mixture is neutralized with NaHCO$_3$. The mixture is extracted with ethyl acetate (4×400 ml). The combined organic extract is dried over Na$_2$SO$_4$ and the solvent is evaporated in vacuum. The residue is treated with heptane (500 ml) and left for 5 h at −18° C. The formed precipitate is filtered out, washed with hexanes and dried, giving the desired product with 65% yield.

Ethyl 3-bromo-[1,2,4]triazolo[4,3-a]pyridine-7-carboxylate

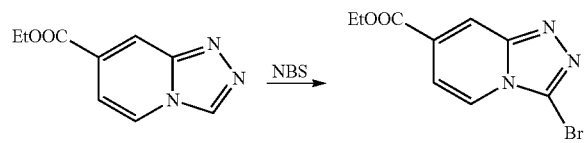

A mixture of ethyl [1,2,4]triazolo[4,3-a]pyridine-7-carboxylate (60 g, 314 mmol) and NBS (57 g, 320 mmol) with dry chloroform (2000 ml) is refluxed for 5 h and then stirred for 24 h at room temperature. A saturated aqueous solution of potassium carbonate (100 ml) is added, the mixture is shaken and the organic layer is separated. The aqueous layer is extracted with chloroform (4×400 ml). The combined organic extract is dried over Na$_2$SO$_4$ and the solvent is evaporated in vacuum. The residue is purified chromatographically (CH$_2$Cl$_2$/MeOH 19:1→9:1→4:1) giving the desired product (41 g, 54%).

Potassium 3-((2-methyl-5-(4-((4-methylpiperazin-1-yl)methyl)-3-(trifluoromethyl)phenylcarbamoyl)phenyl)ethynyl)-[1,2,4]triazolo[4,3-a]pyridine-7-carboxylate

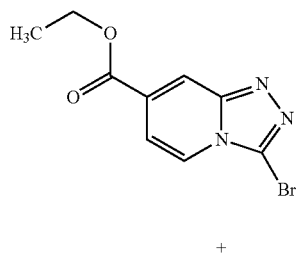

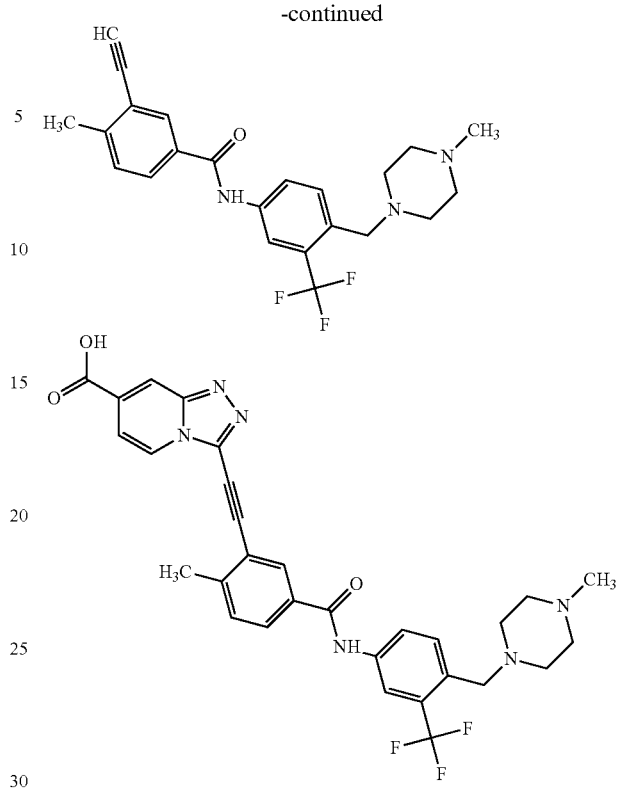

Copper (I) iodide (396 mg, 4 mol. %) is added to a suspension of acetylene derivative (21.6 g, 52 mmol) and ethyl 3-bromo[1,2,4]triazolo[4,3-b]pyridine-7-carboxylate (14.0 g, 52 mmol) in a mixture of degassed dry triethylamine (100 ml) and degassed dry THF (40 ml) and the reaction mixture is stirred for 10 min. Pd(Ph$_3$P)$_2$Cl$_2$ (730 mg, 2 mol. %), PPh$_3$ (1.1 g) and di-tert-butyl(2',6'-dimethoxybiphenyl-2-yl)phosphine (100 mg) are then added, the reaction mixture is degassed twice and stirred at 65° C. for 130 h under inert atmosphere. Solvents are evaporated and the residue is purified chromatographically, using chloroform:methanol mixture of increasing polarity. The obtained product is dissolved in dry DMSO (50 ml). Water (1 ml) and potassium tert-butylate (0.6 g) are added and the mixture is stirred for 4 h. The desired product is purified on an ion exchange resin (15.1 g, 47%).

Example 5

Synthesis of 3-((1H-benzimidazol-1-yl)ethynyl)-4-methyl-N-(4-((4-methylpiperazin-1-yl)methyl)-3-(trifluoromethyl)phenyl)benzamide

1-(1,2-dichlorovinyl)benzimidazole

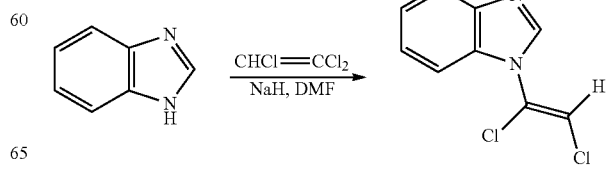

A solution of benzimidazole (106.5 g, 0.9 mol) in DMF (3.5 l) is stirred at 60° C. until the mixture becomes clear. Sodium hydride (25 g, 1 mol, 60% in mineral oil) is then added and the mixture is stirred for 1.5 h, the solution becomes clear and brownish. The heating is stopped, and trichloroethylene (162.5 ml, 1.8 mol) is added (gray precipitate is formed immediately). The mixture is stirred overnight at room temperature and the solvent is removed in vacuum. A mixture of ethyl acetate, methanol and DCM is added, the precipitate is filtered out and the filtrate is evaporated in vacuum, giving the desired product (50 g, 35%) as a yellow oil that is taken to the next step without further purification.

1-ethynyl-1H-benzimidazole

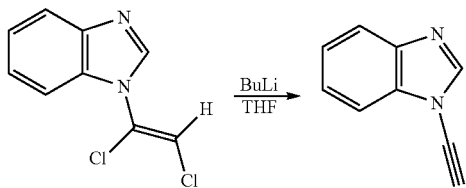

To a cooled to −78° C. solution of 1-(1,2-dichlorovinyl) benzimidazole (48 g, 252 mmol) in THF (6 l) n-BuLi solution in hexanes (1.2M, 843 ml, 1.02 mol) is added over a period of 60 min, keeping the temperature around −70° C. The reaction mixture is stirred at the same temperature for 1 h, then 5 min at room temperature, and quenched with ice-cold aqueous NH₄Cl/MeOH (3:1) (900 ml). The mixture is allowed to warm to room temperature and poured into ethyl acetate (3000 ml). The organic layer is separated, washed with brine (3×400 ml), dried over MgSO₄ and evaporated in vacuum. The residue is purified with flash chromatography, giving the desired product (11.4 g, 32%).

3-((1H-benzimidazol-1-yl)ethynyl)-4-methyl-N-(4-((4-methylpiperazin-1-yl)methyl)-3-(trifluoromethyl) phenyl)benzamide

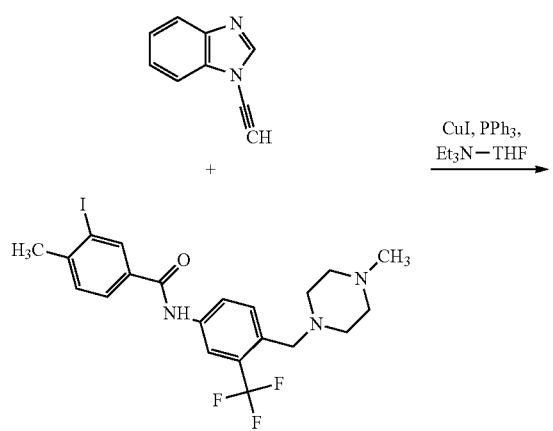

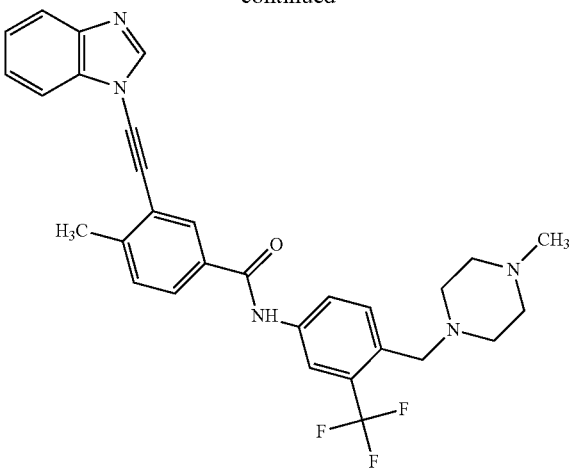

Copper (I) iodide (396 mg, 4 mol. %) is added to a suspension of iododerivative (26.9 g, 52 mmol) and 1-ethynyl-1H-benzimidazole (7.4 g, 52 mmol) in a mixture of degassed dry triethylamine (100 ml) and degassed dry THF (40 ml) and the reaction mixture is stirred for 10 min. Pd(Ph₃P)₂Cl₂ (730 mg, 2 mol. %), PPh₃ (1.1 g) and di-tert-butyl(2',6'-dimethoxybiphenyl-2-yl)phosphine (100 mg) are then added, the reaction mixture is degassed twice and stirred at 65° C. for 80 h under inert atmosphere. Solvents are evaporated and the residue is purified chromatographically, using chloroform:methanol mixture of increasing polarity, yielding the desired product (13 g, 47%).

Synthesis of Common Intermediates 4-(2,2,2-trifluoroacetamido)-2-(trifluoromethyl)benzoic acid

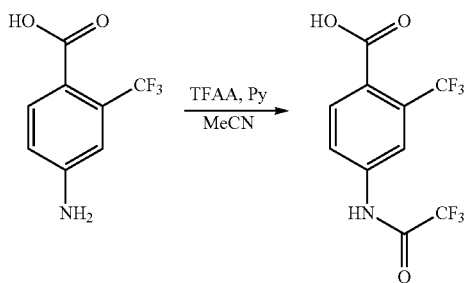 [SMILES: "MeCN" ; Nc1ccc(C(=O)O)c(C(F)(F)F)c1 ; O=C(O)c1ccc(NC(=O)C(F)(F)F)cc1C(F)(F)F]

The starting acid (70 g, 0.34 mol) is dissolved in dry acetonitrile (1200 ml) under inert atmosphere. Pyridine (51.6 ml, 0.68 mol) is added and the reaction mixture is cooled to 0° C. Trifluoroacetic anhydride (61.7 ml, 0.44 mol) is added dropwise keeping the temperature below 5° C. The reaction mixture is stirred at 0° C. for 30 min and another 1 h at room temperature. Solvents are evaporated in vacuum and the residue is treated with 6N HCl (3000 ml) and ether (5000 ml) and shaken. The organic layer is separated, washed with water (5×500 ml), dried over sodium sulphate and evaporated in vacuum. The residue is dried in vacuum, yielding the desired product (82.4 g, 81%).

4-(2,2,2-trifluoroacetamido)-2-(trifluoromethyl)benzoyl chloride

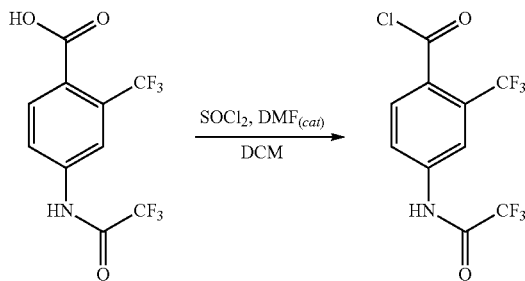 [SMILES: O=C(O)c1ccc(NC(=O)C(F)(F)F)cc1C(F)(F)F ; O=C(Cl)c1ccc(NC(=O)C(F)(F)F)cc1C(F)(F)F]

The starting acid (40 g, 133 mmol) is dissolved in dry DCM (50 ml) under inert atmosphere. 2 drops of DMF are added to the mixture, followed by dropwise addition of $SOCl_2$ (15.4 ml, 0.21 mol). The reaction mixture is stirred at room temperature for 1 h and then refluxed for 30 min (the solution becomes clear). The mixture is then cooled, evaporated in vacuum and the residue is dried in vacuum yielding the desired product (41.9 g, 100%).

2,2,2-trifluoro-N-(4-(4-methylpiperazin-1-carbonyl)-3-(trifluoromethyl)phenyl)acetamide

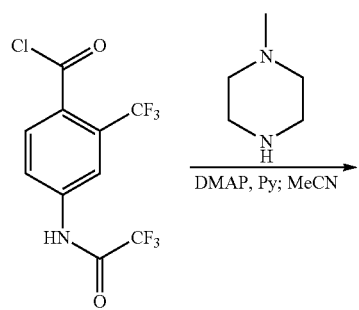

DMAP (1.59 g, 13 mmol) is added to a solution of the chloranhydride (41.9 g, 133 mmol) in dry DCM (500 ml) under inert atmosphere. The reaction mixture is cooled to 0° C. and N-methylpiperazine is added slowly, keeping the temperature below 5° C. The mixture is stirred at 0° C. for 30 min and another 1.5 h at room temperature. The solvent is evaporated in vacuum and the residue is treated with ethyl acetate (500 ml) and saturated aqueous $NaHCO_3$ (500 ml). Potassium carbonate (50 g) is then added and the mixture is shaken. Another portion of ethyl acetate (1500 ml) is added and the mixture is again shaken. The organic layer is separated, washed with water (5×400 ml), dried over sodium sulphate and the solvent is evaporated. The residue is dried in vacuum, giving the desired product (47.9 g, 94%).

(4-amino-2-(trifluoromethyl)phenyl)(4-methylpiperazin-1-yl)methanone

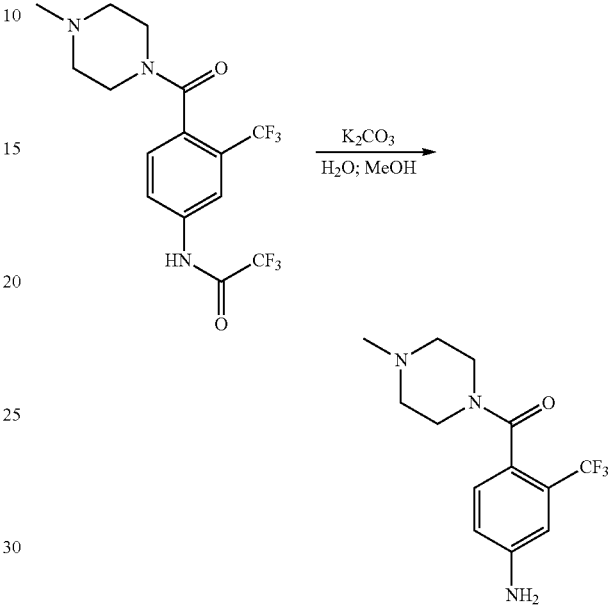

A mixture of the amide (45 g, 117 mmol). potassium carbonate (64.9 g, 470 mmol), water (5 ml) and methanol (1000 ml) is refluxed for 15 h and cooled. Water (250 ml) is added and methanol is evaporated in vacuum. The residue is extracted with ethyl acetate (3×500 ml). The combined extract is dried, solvent is evaporated and the residue is dried in vacuum, giving the desired product (28.9 g, 86%).

4-((4-methylpiperazin-1-yl)methyl)-3-(trifluoromethyl)aniline

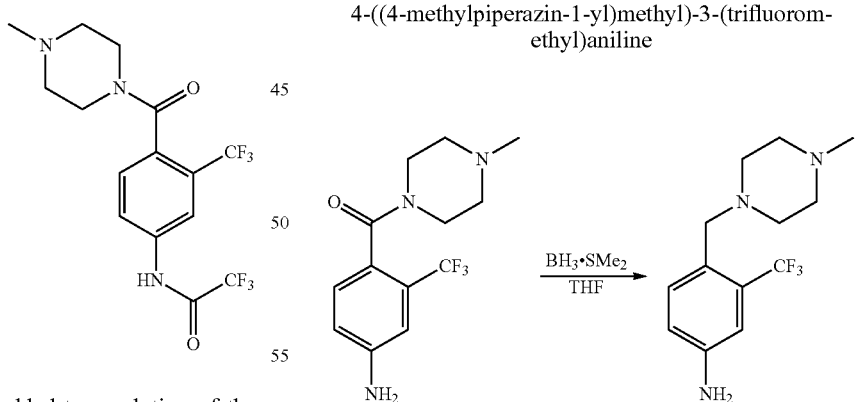

To a cooled to 0° C. solution of the amide (110 g, 383 mmol) in dry THF (3000 ml) under inert atmosphere a 2M solution of $BH_3.SMe_2$ in THF (680 ml, 1.34 mol) is added slowly under vigorous stirring, keeping the temperature below 5° C. The reaction mixture is stirred at 0° C. for 3 h, then refluxed for another 12 h and cooled to 0° C. 2N aqueous HCl (1.1 l) is added dropwise. The mixture is stirred for 30 min and then refluxed for 3 h. 4N aqueous KOH (1.2 l) is added and the mixture is stirred for 10 min. THF is removed in vacuum and the residue is extracted with ethyl acetate (5×500 ml). The combined organic extract is washed with brine (4×300 ml), dried over sodium sulphate, evaporated and the residue is dried in vacuum. According to ¹H NMR, the product contains 4-chlorobutanol-1 and should be purified as follows. The mixture is dissolved in 6N HCl (1000 ml), stirred for 10 min and washed with ethyl acetate (5×500 ml). The aqueous layer is alkalized to pH=10 with 10N KOH and extracted with ethyl acetate (5×500 ml). The combined organic extract is washed with brine (3×400 ml), dried over sodium sulphate, evaporated and the residue is dried in vacuum, yielding the desired product (52.7 g, 51%) as a yellow oil that crystallizes in course of time.

3-ethynyl-4-methylbenzoyl chloride

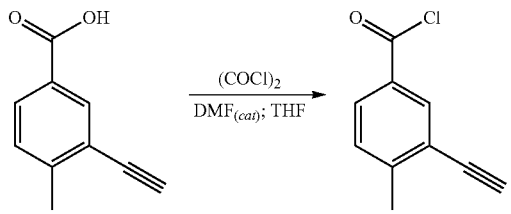

Oxalyl chloride (2.95 ml, 34.3 mmol) is added dropwise do dry THF (50 ml) under inert atmosphere, keeping the temperature around 0° C., and the mixture is stirred for 20 min at the same temperature. A solution of the acid (5 g, 31.2 mmol) in dry THF (120 ml) is added over a period of 10 min, keeping the temperature below 5° C., and 1 drop of DMF is then added. The reaction mixture is stirred for 30 min at 0° C. and then left overnight. Solvents are evaporated and the residue is dried giving the desired product (5.57 g, 100%).

3-ethynyl-4-methyl-N-(4-((4-methylpiperazin-1-yl)methyl)-3-(trifluoromethyl)phenyl)benzamide

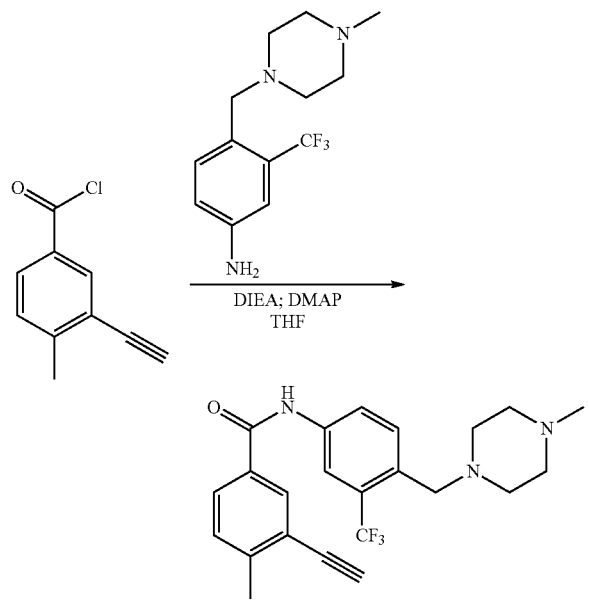

Chloranhydride (5.57 g, 31.2 mmol) and DMAP (590 mg, 4.8 mmol) are dissolved in dry THF (50 ml) under inert atmosphere and the solution is cooled to 0° C. A mixture of aniline (6.56 g, 24 mmol), DIEA (7.93 ml, 48 mmol) and dry THF (40 ml) is added dropwise, keeping the temperature below 5° C. The mixture thickens upon the completion of the addition. Another portion of dry THF (20 ml) is added and the reaction mixture is stirred for 30 min at 0° C. and left overnight. The solvent is evaporated in vacuum, the residue is treated with water (500 ml) and the mixture is extracted with ethyl acetate (3×500 ml). The combined organic extract is dried and concentrated in vacuum. The residue is purified on silica gel (CH₂Cl₂/MeOH 10:1→7:1→5:1) yielding the desired product (3.2 g, 20%).

3-iodo-4-methylbenzoyl chloride

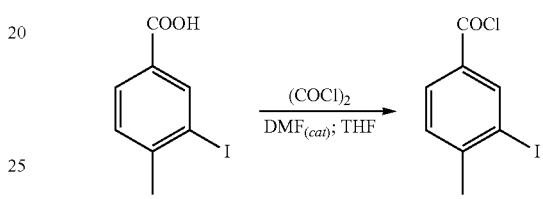

A solution of oxalyl chloride (2.95 ml, 34.3 mmol) in dry THF (50 ml) is added dropwise to a suspension of the acid (5 g, 31.2 mmol) in dry THF (120 ml) under inert atmosphere, keeping the temperature around 0° C., 1 drop of DMF is then added and the reaction mixture is stirred for 30 min at 0° C. and then left overnight. Solvents are evaporated and the residue is dried giving the desired product (9.6 g, 100%).

3-iodo-4-methyl-N-(4-((4-methylpiperazin-1-yl)methyl)-3-(trifluoromethyl)phenyl)benzamide

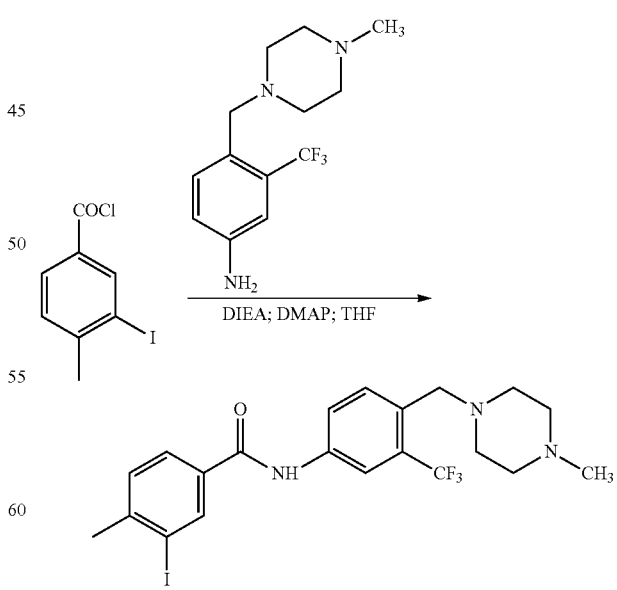

A solution of chloranhydride (8.76 g, 31.2 mmol) in dry THF (30 ml) is added dropwise to a mixture of aniline (6.56 g, 24 mmol), DIEA (7.93 ml, 48 mmol), DMAP (590 mg, 4.8 mmol) and dry THF (50 ml), keeping the temperature below 5° C. The mixture thickens upon the completion of the addition. Another portion of dry THF (20 ml) is added and the reaction mixture is stirred for 30 min at 0° C. and left overnight. The solvent is evaporated in vacuum, the residue is treated with water (500 ml) and the mixture is extracted with ethyl acetate (3×100 ml). The combined organic extract is dried and concentrated in vacuum. The residue is purified on silica gel (CH$_2$Cl$_2$/MeOH 10:1→7:1→5:1) yielding the desired product (2.48 g, 20%).

Common Method for Synthesis of AB System

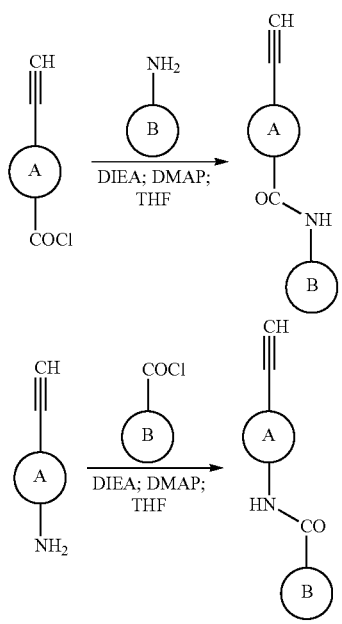

A solution of chloranhydride (1.3 mol) in dry THF (125 ml) is added dropwise to a mixture of aniline (1 mol), DIEA (2 mol), DMAP (0.2 mol) and dry THF (2000 ml), keeping the temperature below 5° C. The mixture thickens upon the completion of the addition. Another portion of dry THF (80 ml) is added and the reaction mixture is stirred for 30 min at 0° C. and left overnight. The solvent is evaporated in vacuum, the residue is treated with water (2000 ml) and the mixture is extracted with ethyl acetate (3×500 ml). The combined organic extract is dried and concentrated in vacuum. The residue is purified on silica gel (CH$_2$Cl$_2$/MeOH 10:1→7:1→5:1). Examples of the compounds obtained according to this method can be found in Table 6.

Common Method for Synthesis of Brominated Cycle T, Corresponding to Formula I

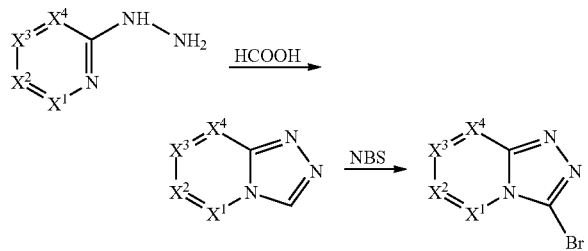

A mixture of heteroarylhydrazine (1 mol), 97% formic acid (6000 ml) and HC(OEt)$_3$ (500 ml) is refluxed for 25 h. The reaction mixture is evaporated in vacuum. Water (500 ml) is added and the mixture is neutralized with NaHCO$_3$. The mixture is extracted with ethyl acetate (5×500 ml). The combined organic extract is dried over Na$_2$SO$_4$ and the solvent is evaporated in vacuum. The residue is treated with heptane (1200 ml) and left for 5 h at −18° C. The formed precipitate is filtered out, washed with hexanes and dried.

In order to perform bromination, a mixture of heterocycle (1 mol) and NBS (1.1 mol) with dry chloroform (6000 ml) is refluxed for 5 h and then stirred for 24 h at room temperature. A saturated aqueous solution of potassium carbonate (300 ml) is added, the mixture is shaken and the organic layer is separated. The aqueous layer is extracted with chloroform (5×500 ml). The combined organic extract is dried over Na$_2$SO$_4$ and the solvent is evaporated in vacuum. The residue is purified chromatographically (CH$_2$Cl$_2$/MeOH 19:1→9:1→4:1). Examples of the compounds obtained according to this method can be found in Table 7.

Common Method for Synthesis of Acetylene Derivative of Cycle T, Corresponding to Formula II

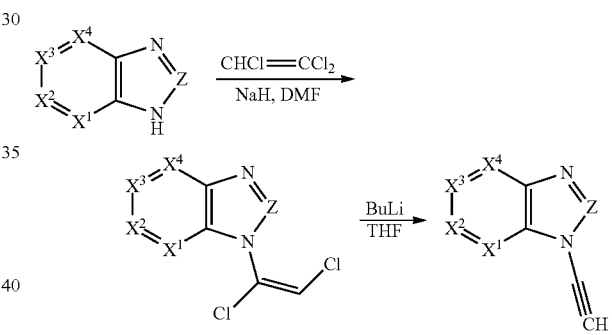

A solution of heterocycle (1 mol) in DMF (4 l) is stirred at 60° C. until the mixture becomes clear. Sodium hydride (1.1 mol, 60% in mineral oil) is then added and the mixture is stirred for 1.5 h, the solution becomes clear and brownish. The heating is stopped, and trichloroethylene (2 mol) is added (gray precipitate is formed immediately). The mixture is stirred overnight at room temperature and the solvent is removed in vacuum. A mixture of ethyl acetate, methanol and DCM is added, the precipitate is filtered out and the filtrate is evaporated in vacuum, giving the product as a yellow oil that is taken to the next step without further purification.

To a cooled to −78° C. solution of 1-(1,2-dichlorovinyl) derivative (250 mmol) in THF (6 l) n-BuLi solution in hexanes (1.2M, 843 ml, 1.02 mol) is added over a period of 60 min, keeping the temperature around −70° C. The reaction mixture is stirred at the same temperature for 1 h, then 5 min at room temperature, and quenched with ice-cold aqueous NH$_4$Cl/MeOH (3:1) (900 ml). The mixture is allowed to warm to room temperature and poured into ethyl acetate (3000 ml). The organic layer is separated, washed with brine (3×400 ml), dried over MgSO$_4$ and evaporated in vacuum. The residue is purified with flash chromatography, giving the desired product. Examples of the compounds obtained according to this method can be found in Appendix 2.

Common Method for Synthesis of Compound Corresponding to Formula I

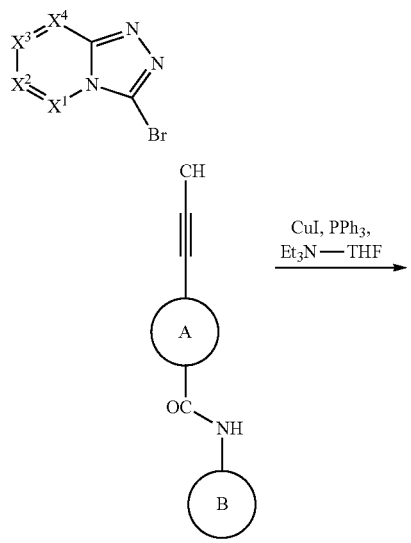

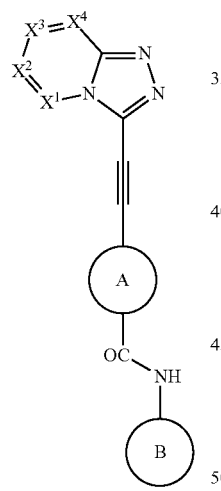

Copper (I) iodide (800 mg, 4 mol. %) is added to a suspension of acetylene derivative (100 mmol) and brominated cycle T (100 mmol) in a mixture of degassed dry triethylamine (200 ml) and degassed dry THF (80 ml) and the reaction mixture is stirred for 10 min. Pd(Ph$_3$P)$_2$Cl$_2$ (1.46 g, 2 mol. %), PPh$_3$ (2.2 g) and di-tert-butyl(2',6'-dimethoxybiphenyl-2-yl)phosphine (200 mg) are then added, the reaction mixture is degassed twice and stirred at 65° C. for 130 h under inert atmosphere. Solvents are evaporated and the residue is purified chromatographically, using chloroform:methanol mixture of increasing polarity. Examples of the compounds obtained according to this method can be found in Table 8.

Common Method for Synthesis of Compound Corresponding to Formula II

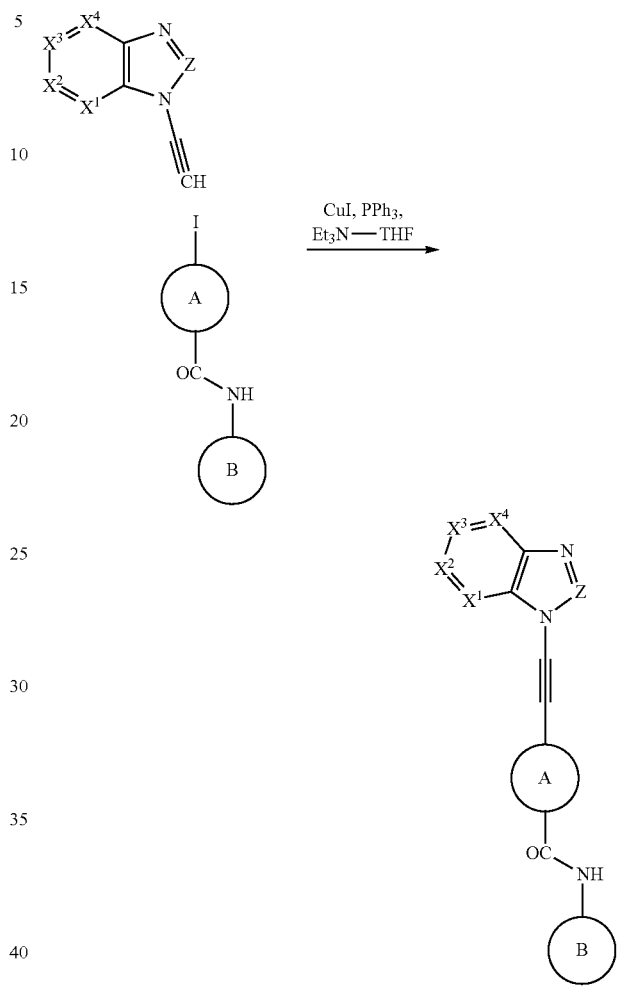

Copper (I) iodide (800 mg, 4 mol. %) is added to a suspension of iododerivative (100 mmol) and ethynylheterocycle (100 mmol) in a mixture of degassed dry triethylamine (200 ml) and degassed dry THF (80 ml) and the reaction mixture is stirred for 10 min. Pd(Ph$_3$P)$_2$Cl$_2$ (1.46 g, 2 mol. %), PPh$_3$ (2.2 g) and di-tert-butyl(2',6'-dimethoxybiphenyl-2-yl)phosphine (200 mg) are then added, the reaction mixture is degassed twice and stirred at 65° C. for 80 h under inert atmosphere. Solvents are evaporated and the residue is purified chromatographically, using chloroform:methanol mixture of increasing polarity. Examples of the compounds obtained according to this method can be found in Table 8.

Evaluation of Biological Activity of the Compounds

Compounds of this invention were evaluated in a variety of assays to determine their biological activities. For example the compounds' ability to inhibit kinase activity was studied. Some of the compounds tested displayed potent nanomolar activity against the following kinases: Abl, Abl (T315I). Src and FGFR. Furthermore some compounds possessed significant antiproliferative activity against CML K562 cells in concentrations 1-100 nM.

Illustrative examples of compounds possessing potent inhibitory and antiproliferative activity are depicted in Table 1.

TABLE 1
| Structure | Abl IC$_{50}$, nM [a] | Abl (T315I) IC$_{50}$, nM [a] | K562 IC$_{50}$, nM [b] |
|---|---|---|---|
| 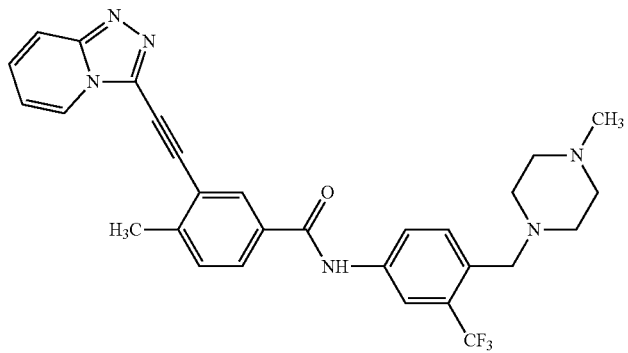 | <20 | <20 | <100 |
| 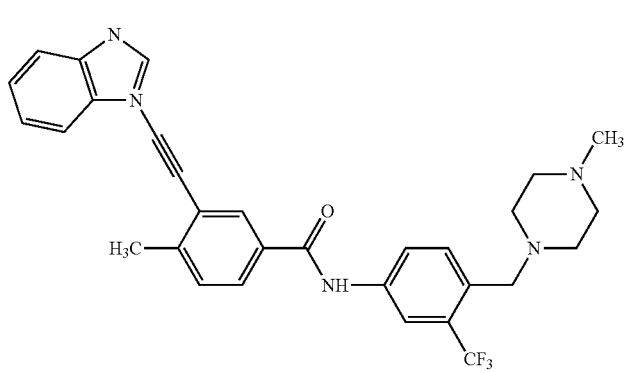 | <20 | <20 | <100 |
| 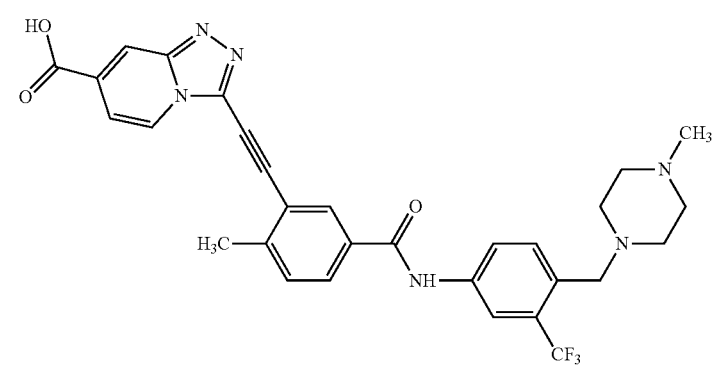 | <20 | <20 | <100 |
| 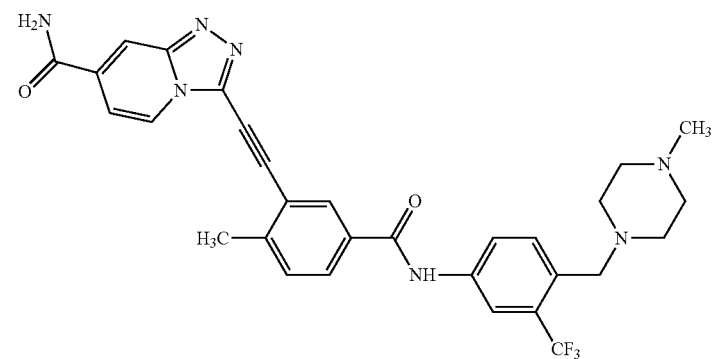 [SMILES: Cc1ccc(C(=O)Nc2ccc(CN3CCN(C)CC3)c(C(F)(F)F)c2)cc1C#Cc1nnc2cc(C(=O)O)ccn12] | <20 | <20 | <100 |

TABLE 1-continued
| Structure | Abl IC$_{50}$, nM [a] | Abl (T315I) IC$_{50}$, nM [a] | K562 IC$_{50}$, nM [b] |
|---|---|---|---|
| 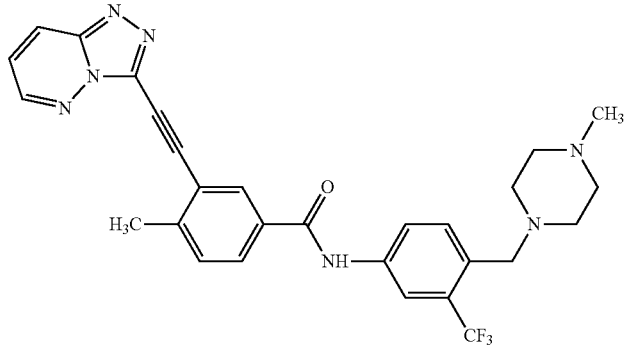 [SMILES: Cc1ccc(C(=O)Nc2ccc(CN3CCN(C)CC3)c(C(F)(F)F)c2)cc1C#Cc1nnc2cccnn12] | <20 | <20 | <100 |
| 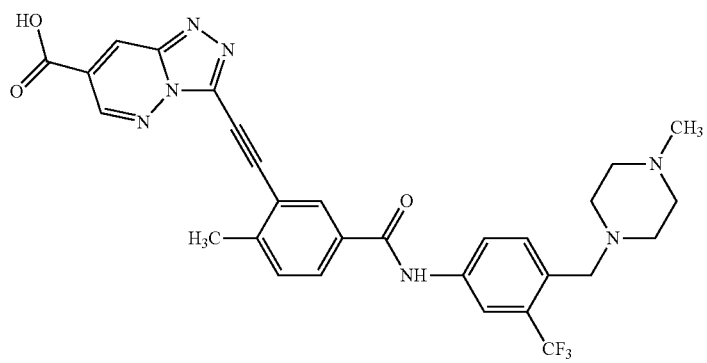 [SMILES: Cc1ccc(C(=O)Nc2ccc(CN3CCN(C)CC3)c(C(F)(F)F)c2)cc1C#Cc1nnc2cc(C(=O)O)cnn12] | <20 | <20 | <100 |
| 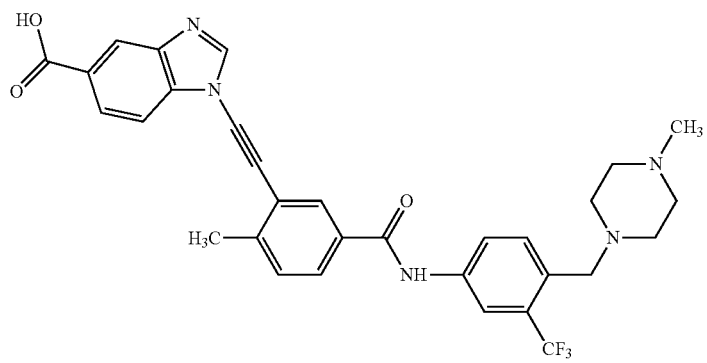 [SMILES: Cc1ccc(C(=O)Nc2ccc(CN3CCN(C)CC3)c(C(F)(F)F)c2)cc1C#Cn1cnc2cc(C(=O)O)ccc21] | <20 | <20 | <100 |
| 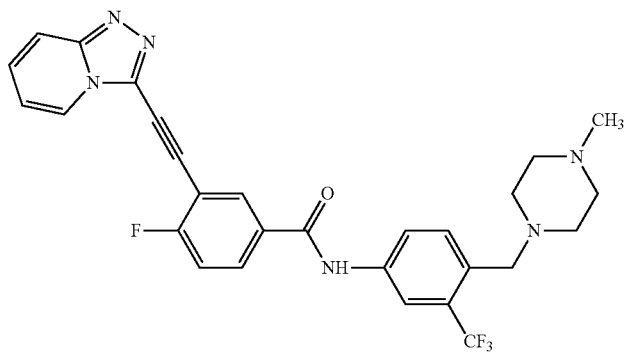 [SMILES: CN1CCN(Cc2ccc(NC(=O)c3ccc(F)c(C#Cc4nnc5ccccn45)c3)cc2C(F)(F)F)CC1] | <20 | <20 | <100 |
[a] compound concentration that causes 2-times reduction of kinase enzymatic activity
[b] compound concentration that causes 2-times reduction of viable cells Kinase Inhibition The ability the compounds of the invention to inhibit kinases related to oncologic, chronic inflammatory and other diseases was studied. Kinases studied accordingly to the represented protocol includes (but is not principally limited to) kinases Abl1, Abl2/Arg, Ack1, Akt2, Alk, AurA, AurB, AurC, Axl, Blk, Bmx, Brk, Btk, c-Kit, c-Mer, c-Src, Cdk2, Csk, Ctk, Ddr2, EGFR, EPHA1, EPHA2, EPHA3, EPHA4, EPHA5, EPHA6, EPHA7, EPHA8, EPHB1, EPHB2, EPHB3, EPHB4, ERBB2, ERBB4, Fer, Fes, FGFR1, FGFR2, FGFR3, FGFR4, FGR, FLT1/VEGFR1, FLT3, FLT4/VEGFR3, FMS, FRK, Fyn, Hck, IGF1R, IR, IRR, ITK, Jak1, Jak2, Jak3, KDR/VEGFR2, Lck, Lyn, mTor, Musk, PDGFRa, PDGFRb, PKA, PKCθ, PYK2, RET, RON, ROS1, SRMS, Syk, TEC, TIE2/TEK, TRKA, TRKB, TRKC, TXK, TYK1/LTK, TYK2, TYRO3, Yes, Zap70, as well as their mutants.

Kinases as either kinase domain or full construct fused to glutathione S-transferase (GST) or poly-Histidine tagged fusion proteins were expressed in baculovrius-infected insect cells (e.g. Sf21) or in *E. Coli*. They are purified to near homogeneity by affinity chromatography as previously described (Lehr et al., Production, purification and characterization of non-myristylated human T-cell protein tyrosine kinase in a baculovirus expression system, Gene, 1996; 169(2), 275-279; Gish et al., Bacterial expression, purification and preliminary kinetic description of the kinase domain of v-fps, Protein Eng. 8, 6, 609-614). In some instances, kinases are co-expressed or mixed with purified or partially purified regulatory polypeptides prior to measurement of activity.

Kinase activity and inhibition was measured by established protocols (see e.g. Braunwalder et al., A Solid-Phase Assay for the Determination of Protein Tyrosine Kinase Activity of c-src Using Scintillating Microtitration Plates, Anal Biochem. 234, 1, 23-26). In such cases, the transfer of $^{33}PO_4$ from ATP to the synthetic substrates poly(Glu, Tyr) 4:1 or poly(Arg, Ser) 3:1 attached to the bioactive surface of microtiter plates is taken as a measure of enzyme activity. After an incubation period, the amount of phosphate transferred is measured by first washing the plate with 0.5% phosphoric acid, adding liquid scintillant, and then counting in a liquid scintillation detector. The IC50 is determined by the concentration of compound that causes a 50% reduction in the amount of $^{33}P$ incorporated onto the substrate bound to the plate.

Other methods for evaluation of kinase inhibition can be employed particularly those based on determination of the degree of phosphate transfer to peptide or polypeptide containing tyrosine, serine or threonine in soluble or immobilized state.

Compounds of the invention have shown nanomolar IC50 values towards different kinases including Abl, Src and kdr. Moreover compounds of the invention are selective and in concentrations up to 1000 nM shows no significantly inhibition of such kinases as AKT2, ALK, AurA, AurC, AXL, c-MER, c-MET, CDK2, CTK, FAK, IGF1R, IR, IRR, ITK, mTOR, MUSK, PKA, PKCθ, RON, ROS, Syk, TYRO3, Zap70 Compounds with IC50<10 nM towards Abl and Abl (T315I) are depicted below.

Cell-Based Assays

Certain compounds of this invention have also been demonstrated cytotoxic or growth inhibitory effects on tumor and other cancer cell lines and thus may be useful in the treatment of cancer and other cell proliferative diseases.

Cell-based methods for measuring antiproliferative activity are well known and can be used for comparative characterization of compounds of this invention. In general, cell proliferation and cell viability assays are designed to provide a detectable signal when cells are metabolically active. Compounds may be tested for antiproliferative activity by measuring any observed decrease in metabolic activity of the cells after exposure of the cells to compound. Commonly used methods include, for example, measurement of membrane integrity (as a measure of cell viability) (e.g. using trypan blue exclusion) or measurement of DNA synthesis (e.g. by measuring incorporation of BrdU or $^3$H-thymidine).

Some methods for assaying cell proliferation use a reagent that is converted into a detectable compound during cell proliferation. Particularly preferred compounds are tetrazolium salts and include without limitation MTT (3-(4,5-dimethylthiazol-2-yl)-2,5diphenyltetrazolium bromide), MTS (3-(4,5-dimethylthiazol-2-yl)-5-(3-carboxymethoxyphenyl)-2-(4-sulfophenyl)-2H-tetrazolium), XTT (2,3-bis (2-Methoxy-4-nitro-5-sulfophenyl)-2H-tetrazolium-5-carboxanilide), INT (2-(4-iodophenyl)-3-(4-nitrophenyl)-5-phenyl tetrazolium), NBT (2H-tetrazolium, 2,2'-(3,3'-dimethoxy[1,1'-biphenyl]-4,4'-dyyl)bis[3-(4-nitrophenyl)-5-phenyl, dichloride). Preferred assays utilizing tetrazolium salts detect cell proliferation by detecting the product of the enzymatic conversion of the tetrazolium salts into blue formazan derivatives, which are readily detected by spectroscopic methods (Mosman J., J. Immunol. Methods, 65:55-63, 1983).

Generally, preferred methods for assaying cell proliferation involve incubating cells in a desired growth medium with and without the compounds to be tested. Growth conditions for various prokaryotic and eukaryotic cells are well-known to those of ordinary skill in the art (Ausubel et al. Current Protocols in Molecular Biology. Wiley and Sons. 1999; Bonifacio et al. Current Protocols in Cell Biology. Wiley and Sons. 1999). To detect cell proliferation, the tetrazolium salts are added to the incubated cultured cells to allow enzymatic conversion to the detectable product by active cells.

An example of cell-based assay is shown as below. The cell lines used in this assay are Ba/F3, a murine pro-B cell line stably transduced with full-length wild type Bcr-Abl and Bcr-Abl, with point mutation in kinase domain (including T315I mutation). Parental Ba/F3 cell line is used as control. Ba/F3 cell expressing Bcr-Abl or Bcr-Abl mutants were maintained in RPMI 1640 growth medium with 200 μM L-glutamine, 10% FCS, penicillin (200 U/ml) and streptomycin (200 μg/ml). Parental Ba/F3 cells were culture in the same medium supplemented with 10 ng/ml IL-3.

Parental Ba/F3 cells (supplemented with IL-3) or Ba/F3 cells expressing WT or mutant Bcr-Abl are plated in duplicate at $1\times10^4$ cells/well in 96-well plates with the compounds in different concentrations in the media. Solid compounds were first dissolved in DMSO, then the solution was diluted with DMSO to necessary concentration, mixed with equal volume of growth medium and was transferred to cell plates. The final compound concentrations of compounds was 0.5 nM to 10 μM. DMSO at same percentage is used as control. After compound was incubated with cells for 3 days, the numbers of active cells are measured. The MTT solution was added, cells were incubated and resulting optical density was determined at 540 and 620 nm (number of viable cells is proportional to the relation of optical densities at these wavelengths). IC50s were determined from best fit curves that adequately represented experimental data. Most potent compounds of the present invention possess IC50<10 nM.

Moreover, antiproliferative activity of the compounds of the present invention can be studied on K562 human chronic myelogenous leukemia cells.

Human myelogenous leukemia K562 cells K562 were cultivated in RPMI 1640 growth medium. K562 cells were transferred to 96-well plated in duplicated (final concentration 2×10⁴ cells/ml) and testing compound solution in growth medium was added at different concentrations (final volume is 100 μl per well). Solid compounds were first dissolved in DMSO, then the solution was diluted with DMSO to necessary concentration, mixed with equal volume of growth medium and was transferred to cell plates. The final compound concentrations of compounds was 0.5 nM to 10 μM. DMSO at same percentage is used as control. After compound was incubated with cells for 3 days, the numbers of active cells are measured. It was achieved by removing old medium, addition of 100 μl of fresh medium and 20 μl MIT solution containing 5 mg/ml PBS. Plates was incubated for 2 h at 37° C., then 100 μl DMSO was added at each well and stirred for 1 min. Then the absorbance was measured at 570 nm and percent of proliferation inhibition related to the control (without testing compounds) was determined.

Animal Experiments

Compounds that have shown antiproliferative activity in cell experiments were further tested in in vivo mammal studies. Usually in vivo experiments are carried out in rodents such as mice and rats.

Animal Models of Chronic Myelogenous Leukemia

Ba/F3 cells expressing either native or mutant (T315I) Bcr-Abl kinase, were inoculated in the right flank of nude balb/c mouse (100 μl of cell suspension in serum-free medium, 3×10⁶ cells/ml). Mice were randomly assigned to the groups upon tumor volume of ~500 mm³. Once daily vehicle (0.5% methylcellulose I in water) was given using oral gavage to the control group, and substance suspension was given to therapeutic group during 10 days. In a typical experiment malignant cells (e.g., K562 cells, or Ba/F3 cells, expressing native of mutated Bcr-Abl kinase) are injected to mouse with reduced immunity (e.g. nude or SCID mice). Tumor volume (mm³) was calculated as follows: $V = L \times W^2 \times 0.5$, where L—tumor length in mm, W—width in mm. Ratio of the mean tumor volume in therapeutic and control groups (% T/C) was used to evaluate efficacy of tumor growth inhibition. Obtained data was subjected to statistical reliability Dunnet test. Efficacies of tested compounds in 30 mg/kg dose are depicted in Table 2.

TABLE 2

| Compound | % T/C |
|---|---|
|  | <40 |
|  | <40 |
| 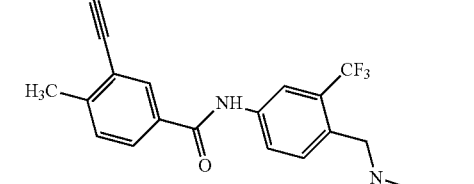 | <40 |
| | <40 |
| | <40 |

TABLE 2-continued

| Compound | % T/C |
|---|---|
| [Structure: 7-fluoro-[1,2,4]triazolo[4,3-a]pyridine connected via alkyne to H₃C-phenyl-C(O)NH-phenyl(CF₃)-CH₂-N-methylpiperazine] | <40 |
| [Structure: 6-methyl-[1,2,4]triazolo[4,3-b]pyridazine connected via alkyne to H₃C-phenyl-C(O)NH-phenyl(CF₃)-CH₂-N-methylpiperazine] | <40 |

Animal Models of Acute Myelogenous Leukemia

MV4-11 cells (1×10$^7$ in serum-free medium) were subcutaneously injected in right flank of SCID female mice. When tumor volume achieved ~200 mm$^3$ mice were separated into two groups: control and therapeutic. Control group mice received 0.3 ml of 0.5% methylcellulose solution, therapeutic group received 0.3 ml of 0.5% methylcellulose with suspended therapeutic compound. Tumor volume (mm$^3$) was calculated as follows: V=L×W$^2$×0.5, where L—tumor length in mm, W—width in mm. Ratio of the mean tumor volume in therapeutic and control groups (% T/C) on the end of the therapy (20 days) was used to evaluate efficacy of tumor growth inhibition. Obtained data was subjected to statistical reliability Dunnet test. Efficacies of tested compounds in 30 mg/kg dose are depicted in Table 3.

Animal Models of Solid Intestine Tumors

200 µl of HCT116 cells (2.5×10$^7$ cells/ml) were subcutaneously injected in right flank of SCID mice. When tumor volume achieved ~200 mm$^3$ mice were randomized and separated into two groups: control and therapeutic. Control group mice received 0.3 ml of 0.5% methylcellulose solution, therapeutic group received 0.5% methylcellulose with suspended therapeutic compound (30 mg/kg). Twice a week animals animal weight, toxic effects and tumor volume were measured. Experiment was stopped upon tumor reached volume of 1200 mm3 of when animal lost 10% of body weight, or 20% of body weight upon 2 consecutive weightings. Ratio of the mean tumor volume in therapeutic and control groups (% T/C) was used to evaluate efficacy of tumor growth inhibition upon the end of the therapy (20 days). Obtained data was subjected to statistical reliability Dunnet test. Efficacies of tested compounds in 30 mg/kg dose are depicted in Table 4.

TABLE 3

| Compound | % T/C |
|---|---|
| [Structure: [1,2,4]triazolo[4,3-a]pyridine connected via alkyne to H₃C-phenyl-C(O)NH-phenyl(CF₃)-CH₂-N-methylpiperazine] | <40 |
| [Structure: 5-chloro-[1,2,4]triazolo[4,3-a]pyridine connected via alkyne to H₃C-phenyl-C(O)NH-phenyl(CF₃)-CH₂-N-methylpiperazine] | <40 |
| [Structure: benzimidazole connected via alkyne to H₃C-phenyl-C(O)NH-phenyl(CF₃)-CH₂-(3R)-N,N-dimethylpyrrolidin-3-amine] | <40 |

TABLE 3-continued
| Compound | % T/C |
|---|---|
| 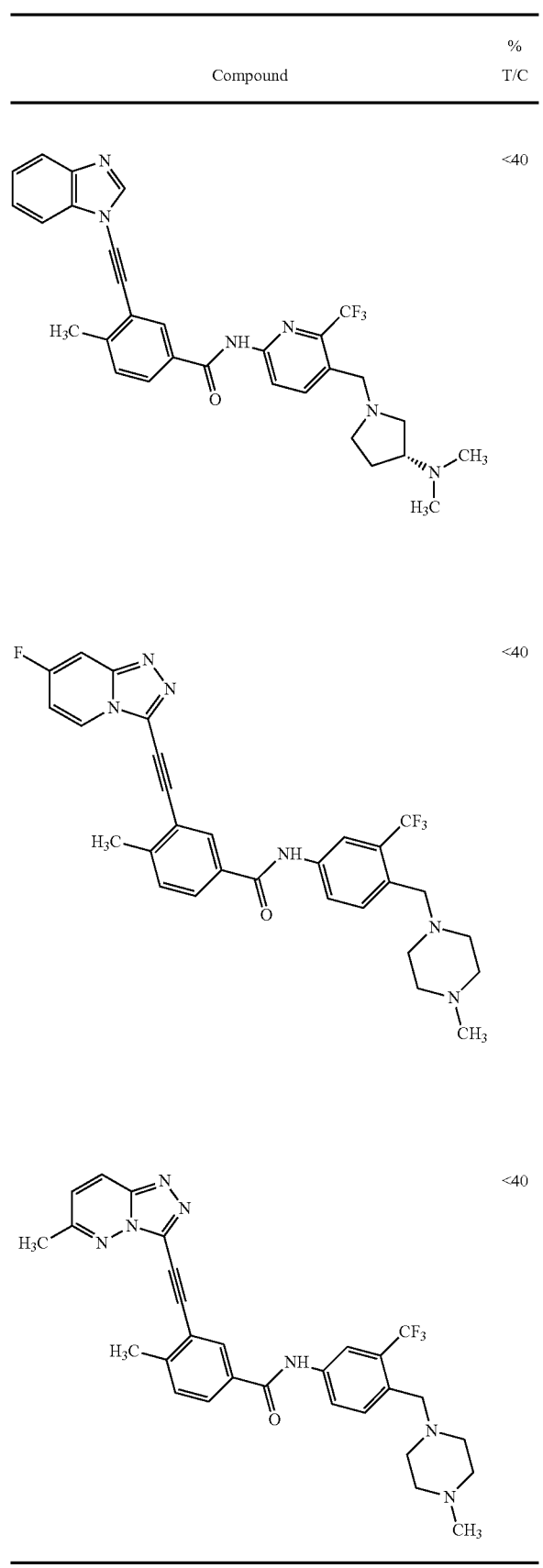 | <40 |
| | <40 |
| | <40 |
TABLE 4
| Compound | % T/C |
|---|---|
| 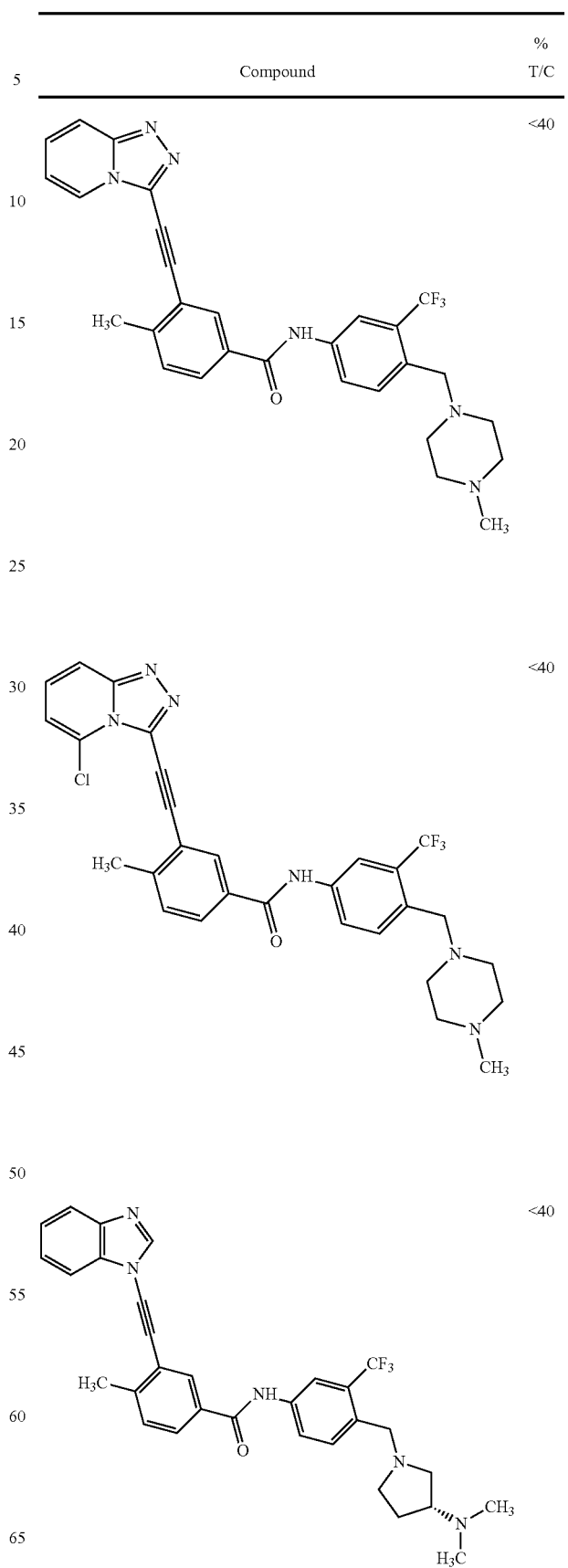 | <40 |
| | <40 |
| | <40 |

TABLE 4-continued

| Compound | % T/C |
|---|---|
| (structure: benzimidazole-alkyne-tolyl-benzamide-NH-pyridine(CF3)-CH2-pyrrolidine-N(CH3)2) | <40 |
| (structure: 7-fluoro-[1,2,4]triazolo[4,3-a]pyridine-alkyne-tolyl-benzamide-NH-aryl(CF3)-CH2-N-methylpiperazine) | <40 |
| (structure: 6-methyl-[1,2,4]triazolo[4,3-b]pyridazine-alkyne-tolyl-benzamide-NH-aryl(CF3)-CH2-N-methylpiperazine) | <40 |

Animal Models of Non-Small Cell Lung Cancer

Male nude mice were used for this experiment. A549 cells ($1 \times 10^7$) in 0.2 ml of Matrigel (BD Pharmingen) solution were injected in left mice leg upon ketamine-xylazine anesthesia. After a week of cell inoculation mice were separated into control and therapeutic groups. Control group mice received 0.3 ml of 0.5% methylcellulose solution, therapeutic group received 0.3 ml of 0.5% methylcellulose with suspended therapeutic compound (30 mg/kg). Tumor volume (mm$^3$) was calculated as follows: $V = L \times W^2 \times 0.5$. Compounds were administered using oral gavage. Treatment continued for 20 days. Ratio of the mean tumor volume in therapeutic and control groups (% T/C) was used to evaluate efficacy of tumor growth inhibition upon the end of the therapy (20 days). Obtained data was subjected to statistical reliability Dunnet test. Efficacies of tested compounds in 30 mg/kg dose are depicted in Table 5.

TABLE 5

| Compound | % T/C |
|---|---|
| (structure: [1,2,4]triazolo[4,3-a]pyridine-alkyne-tolyl-benzamide-NH-aryl(CF3)-CH2-N-methylpiperazine) | <40 |
| (structure: 5-chloro-[1,2,4]triazolo[4,3-a]pyridine-alkyne-tolyl-benzamide-NH-aryl(CF3)-CH2-N-methylpiperazine) | <40 |
| (structure: benzimidazole-alkyne-tolyl-benzamide-NH-aryl(CF3)-CH2-pyrrolidine-N(CH3)2) | <40 |

TABLE 5-continued

| Compound | % T/C |
|---|---|
| 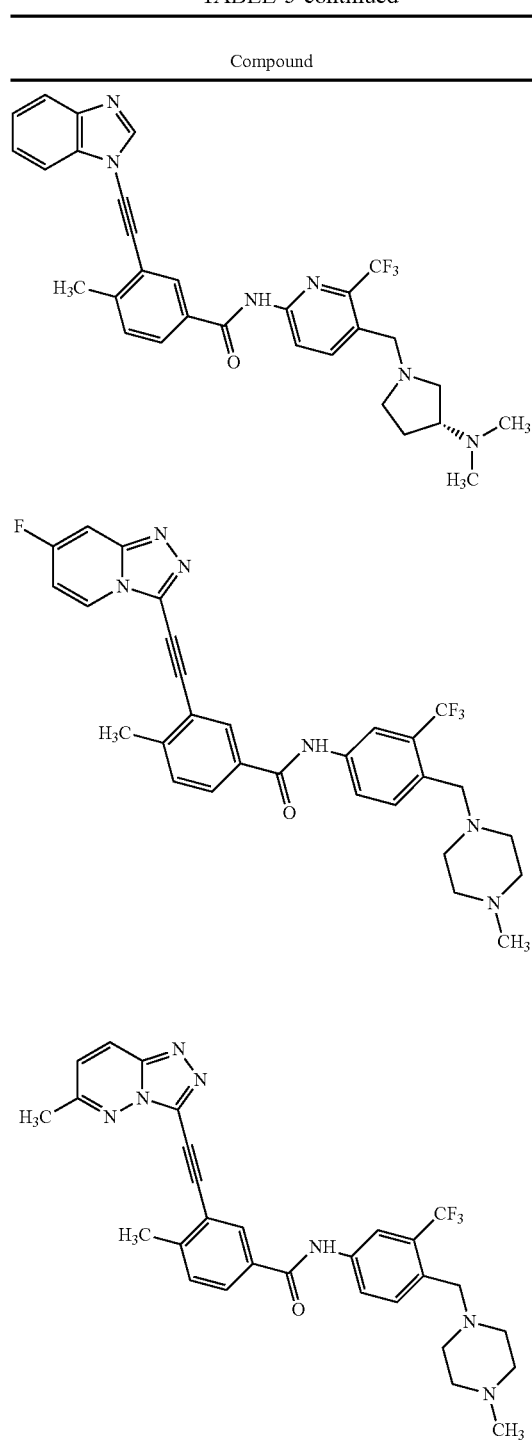 | <40 |
| | <40 |
| | <40 |

Pharmaceutical Compositions

Compounds of this invention may be used for prophylaxis and treatment of human disease in following pharmaceutical compositions ("Compound" is an active ingredient):

| Tablet I | mg/tablet |
|---|---|
| Compound of example 1 | 100 |
| Lactose Ph. Eur | 182.75 |
| Croscarmellose sodium | 12.0 |
| Maize starch paste (5% w/v paste) | 2.25 |
| Magnesium stearate | 3.0 |

| Tablet II | mg/tablet |
|---|---|
| Compound of example 2 | 50 |
| Lactose Ph. Eur | 223.75 |
| Croscarmellose sodium | 6.0 |
| Maize starch | 15 |
| Polyvinylpyrrolidone (5% w/v paste) | 2.25 |
| Magnesium stearate | 3.0 |

| Tablet III | mg/tablet |
|---|---|
| Compound of example 3 | 1.0 |
| Lactose Ph. Eur | 93.25 |
| Croscarmellose sodium | 4.0 |
| Maize starch paste (5% w/v paste) | 0.75 |
| Magnesium stearate | 1.0-76 |

| Capsule | mg/capsule |
|---|---|
| Compound of example 4 | 10 |
| Lactose Ph. Eur | 488.5 |
| Magnesium | 1.5 |

| Injection I | (50 mg/ml) |
|---|---|
| Compound of example 4 | 5.0% w/v |
| 1M Sodium hydroxide solution | 15.0% w/v |
| M Hydrochloric acid (to adjust pH to 7.6) | |
| Polyethylene glycol 400 | 4.5% w/v |
| Water for injection to 100% | |

| Injection II | (10 mg/ml) |
|---|---|
| Compound of example 2 | 1.0% w/v |
| Sodium phosphate BP | 3.6% w/v |
| M Sodium hydroxide solution | 15.0% w/v |
| Water for injection to 100% | |
| Injection III | (1 mg/ml, buffer with pH 6) |
| Compound of example 1 | 0.1% w/v |
| Sodium phosphate BP | 2.26% w/v |
| Citric acid | 0.38% w/v |
| Polyethylene glycol 400 | 3.5% w/v |

| Aerosol I | mg/ml |
|---|---|
| Compound of example 2 | 10 |
| Sorbitan trioleate | 13.5 |
| Trichlorofluoromethane | 910.0 |
| Dichlorodifluoromethane | 490.0 |

| Aerosol II | mg/ml |
|---|---|
| Compound of example 1 | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

| Aerosol III | mg/ml |
|---|---|
| Compound of example 3 | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

-continued

| Aerosol IV | mg/ml |
|---|---|
| Compound of example 1 | 2.5 |
| Soya lecithin | 2.7 |
| Trichlorofluoromethane | 67.5 |
| Dichlorodifluoromethane | 1086.0 |
| Dichlorotetrafluoroethane | 191.6 |

| Ointment | ml |
|---|---|
| Compound of example 2 | 40 mg |
| Ethanol | 300 μl |
| Water | 300 μl |
| 1-Dodecylazacycloheptanone | 50 μl |
| Propylene glycol | to 1 ml |

Note:
These formulations may be prepared using conventional procedures well known in the pharmaceutical art. The tablets (a)-(c) may be enteric coated by conventional means, if desired to provide a coating of cellulose acetate phthalate, for example. The aerosol formulations (h)-(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

TABLE 6

| Structure | MW | m/z |
|---|---|---|
|  | 401.42 | 402 |
|  | 419.42 | 420 |
|  | 426.43 | 427 |
| 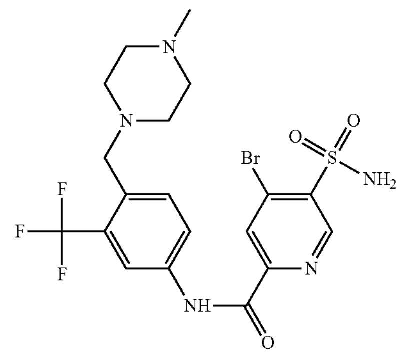 [SMILES: CN1CCN(Cc2ccc(NC(=O)c3cc(Br)c(S(N)(=O)=O)cn3)cc2C(F)(F)F)CC1] | 536.37 | 537 |
| 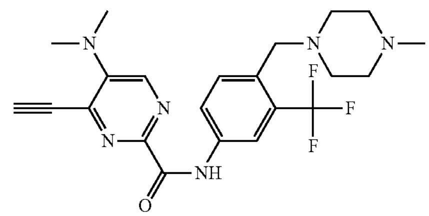 [SMILES: C#Cc1nc(C(=O)Nc2ccc(CN3CCN(C)CC3)c(C(F)(F)F)c2)ncc1N(C)C] | 446.47 | 447 |
| 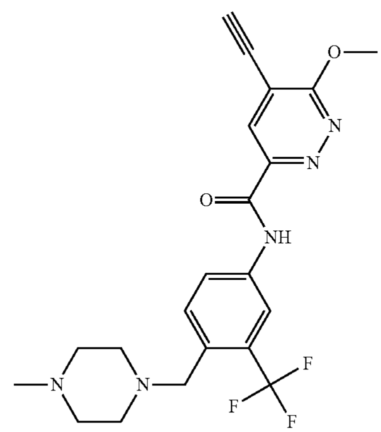 | 433.43 | 434 |
| 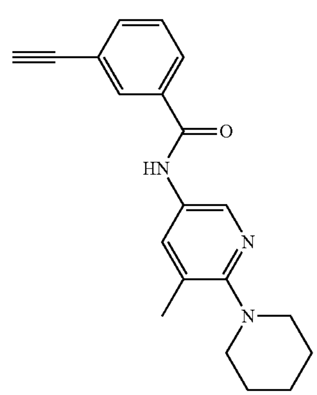 [SMILES: C#Cc1cccc(C(=O)Nc2cnc(N3CCCCC3)c(C)c2)c1] | 319.40 | 320 |

TABLE 6-continued

| Structure | MW | m/z |
|---|---|---|
| (4-fluoro-3-ethynylbenzamide-pyridine-piperidine) | 337.39 | 338 |
| (piperidine-pyridine-NH-benzamide-3,5-diethynyl/cyano) | 344.41 | 345 |
| (sulfamoyl-bromo-pyridine-carboxamide-pyridine-methyl-piperidine) | 454.34 | 455 |
| (piperidine-methyl-pyridine-NH-pyrimidine carboxamide-dimethylamino-ethynyl) | 364.44 | 365 |

TABLE 6-continued

| Structure | MW | m/z |
|---|---|---|
| (methoxy-ethynyl-pyridazine carboxamide-pyridine-methyl-piperidine) | 351.40 | 352 |
| (methyl-imidazole-NH-3-ethynylbenzamide) | 224.24 | 225 |
| (methyl-imidazole-NH-3-ethynyl-4-fluorobenzamide) | 242.23 | 243 |
| (methyl-imidazole-NH-3-cyano-5-ethynylbenzamide) | 249.25 | 250 |
| (methyl-imidazole-NH-pyridine carboxamide-bromo-sulfamoyl) | 359.18 | 360 |

TABLE 6-continued

| Structure | MW | m/z |
|---|---|---|
| (structure) | 269.28 | 270 |
| (structure) | 256.24 | 257 |
| (structure) | 253.26 | 254 |
| (structure) | 271.25 | 272 |
| (structure) | 278.27 | 279 |
| (structure) | 388.20 | 389 |
| (structure) | 298.30 | 299 |
| (structure) | 285.26 | 286 |
| (structure) | 263.29 | 264 |
| (structure) | 281.28 | 282 |

TABLE 6-continued
| Structure | MW | m/z |
|---|---|---|
| 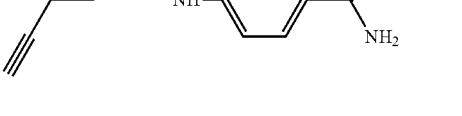 | 288.30 | 289 |
| 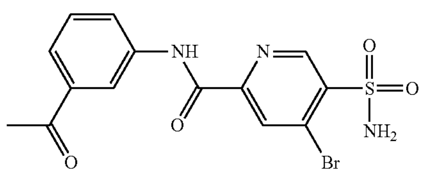 [SMILES: CC(=O)c1cccc(NC(=O)c2cc(Br)c(S(N)(=O)=O)cn2)c1] | 398.23 | 399 |
| 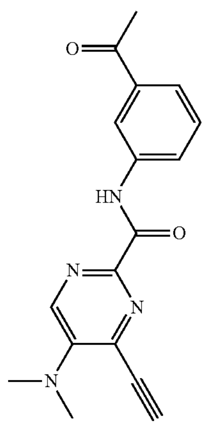 [SMILES: C#Cc1nc(C(=O)Nc2cccc(C(C)=O)c2)ncc1N(C)C] | 308.33 | 309 |
| 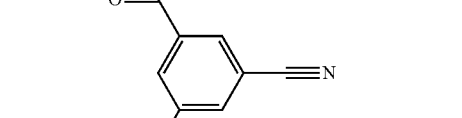 | 295.29 | 296 |
| 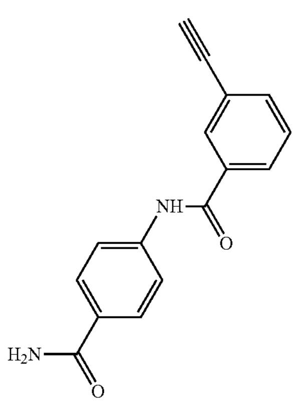 [SMILES: C#Cc1cccc(C(=O)Nc2ccc(C(N)=O)cc2)c1] | 264.28 | 265 |
TABLE 6-continued
| Structure | MW | m/z |
|---|---|---|
| 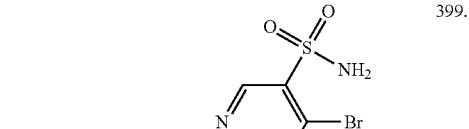 | 282.27 | 283 |
| 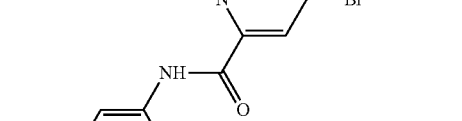 | 289.29 | 290 |
| 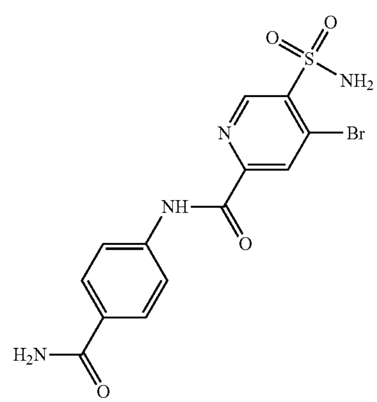 [SMILES: NC(=O)c1ccc(NC(=O)c2cc(Br)c(S(N)(=O)=O)cn2)cc1] | 399.22 | 400 |
| 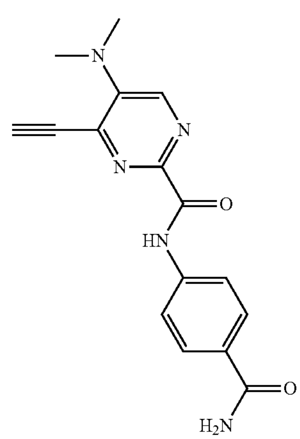 [SMILES: C#Cc1nc(C(=O)Nc2ccc(C(N)=O)cc2)ncc1N(C)C] | 309.32 | 310 |

TABLE 6-continued
| Structure | MW | m/z |
|---|---|---|
| 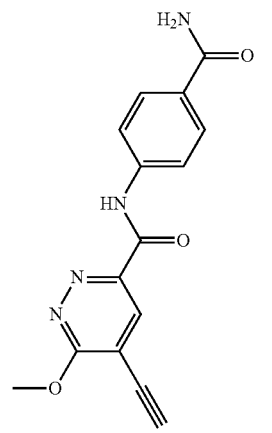 [SMILES: C#Cc1cc(C(=O)Nc2ccc(C(N)=O)cc2)nnc1OC] | 296.28 | 297 |
| 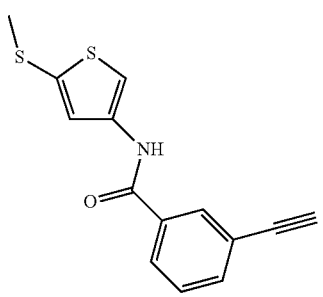 [SMILES: C#Cc1cccc(C(=O)Nc2csc(SC)c2)c1] | 273.38 | 274 |
| 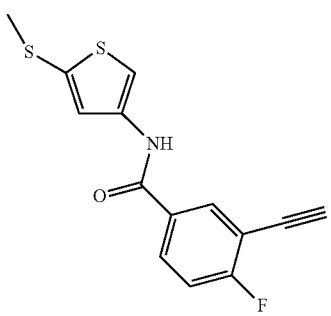 [SMILES: C#Cc1cc(C(=O)Nc2csc(SC)c2)ccc1F] | 291.37 | 292 |
| 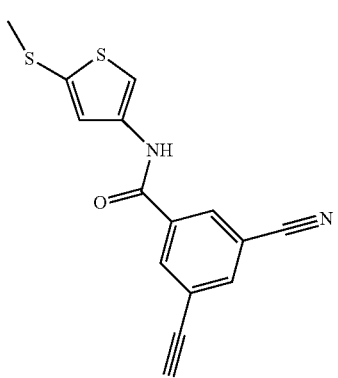 [SMILES: C#Cc1cc(C#N)cc(C(=O)Nc2csc(SC)c2)c1] | 298.38 | 299 |
TABLE 6-continued
| Structure | MW | m/z |
|---|---|---|
| 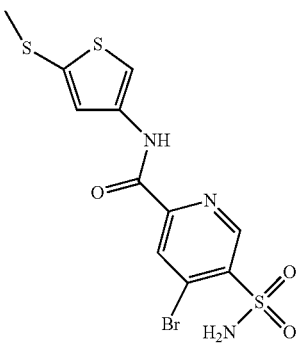 [SMILES: CSc1cc(NC(=O)c2cc(Br)c(S(N)(=O)=O)cn2)cs1] | 408.32 | 409 |
| 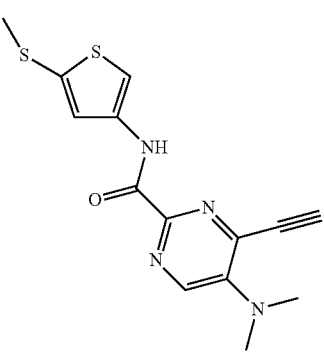 [SMILES: C#Cc1nc(C(=O)Nc2csc(SC)c2)ncc1N(C)C] | 318.42 | 319 |
| 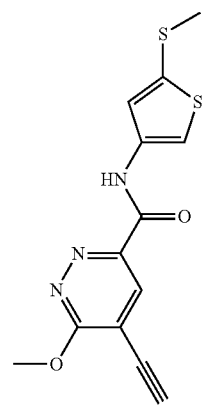 | 305.38 | 306 |
| 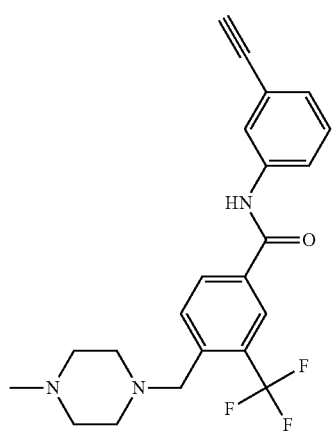 [SMILES: C#Cc1cccc(NC(=O)c2ccc(CN3CCN(C)CC3)c(C(F)(F)F)c2)c1] | 401.42 | 402 |

TABLE 6-continued
| Structure | MW | m/z |
|---|---|---|
| 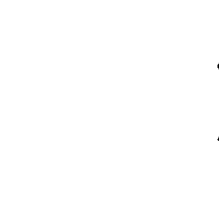 | 319.40 | 320 |
| 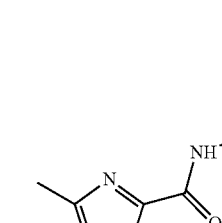 | 224.24 | 225 |
| 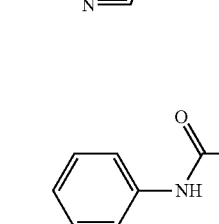 | 253.26 | 254 |
| 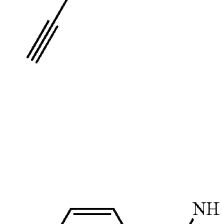 | 263.29 | 264 |
| 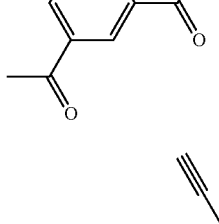 | 264.28 | 265 |
TABLE 6-continued
| Structure | MW | m/z |
|---|---|---|
| 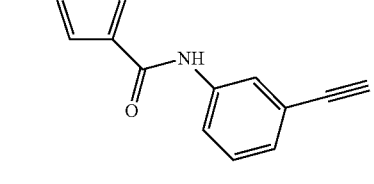 | 273.38 | 274 |
| 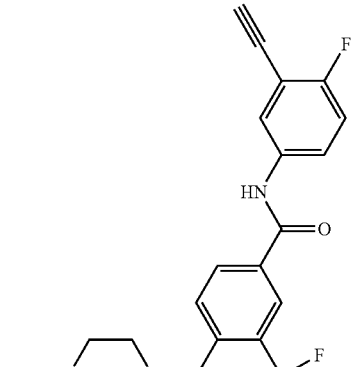 | 419.42 | 420 |
| 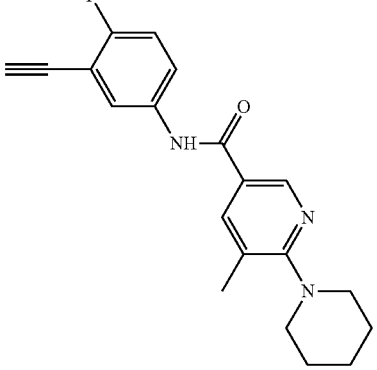 | 337.39 | 338 |
| 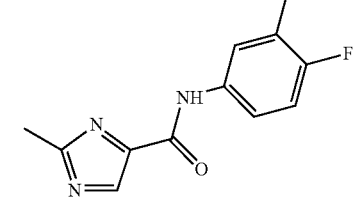 | 242.23 | 243 |

TABLE 6-continued
| Structure | MW | m/z |
|---|---|---|
| 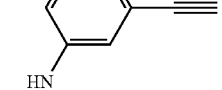 | 271.25 | 272 |
| 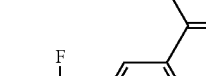 | 281.28 | 282 |
| 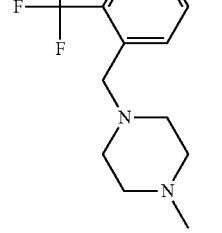 | 282.27 | 283 |
| 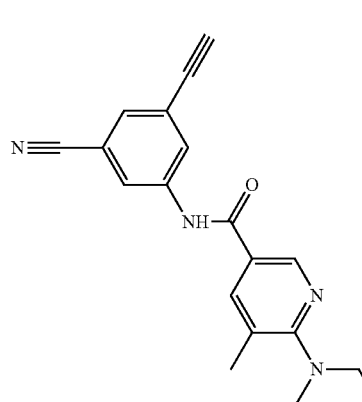 | 291.37 | 292 |
TABLE 6-continued
| Structure | MW | m/z |
|---|---|---|
| 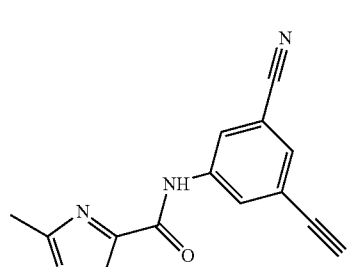 | 426.43 | 427 |
| 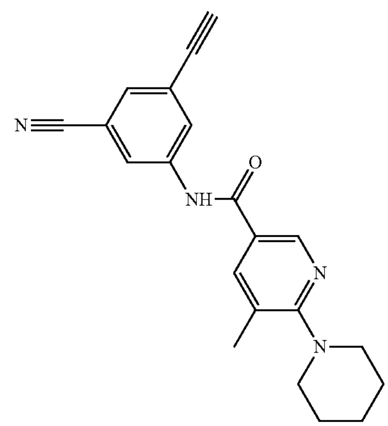 [SMILES: C#Cc1cc(C#N)cc(NC(=O)c2cnc(N3CCCCC3)c(C)c2)c1] | 344.41 | 345 |
| 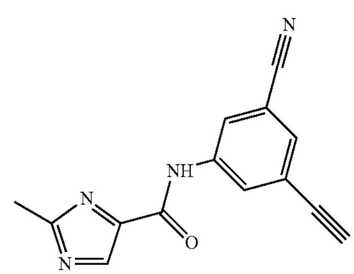 | 249.25 | 250 |
| 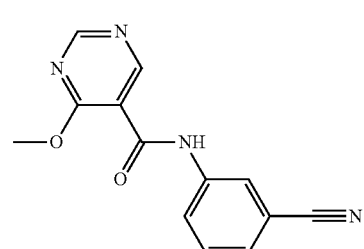 | 278.27 | 279 |

TABLE 6-continued
| Structure | MW | m/z |
|---|---|---|
| 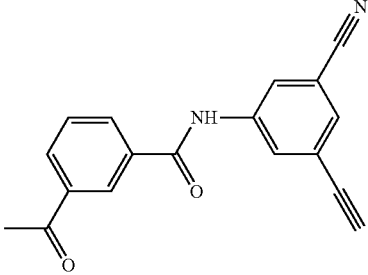 [SMILES: C#Cc1cc(C#N)cc(NC(=O)c2cccc(C(C)=O)c2)c1] | 288.30 | 289 |
| 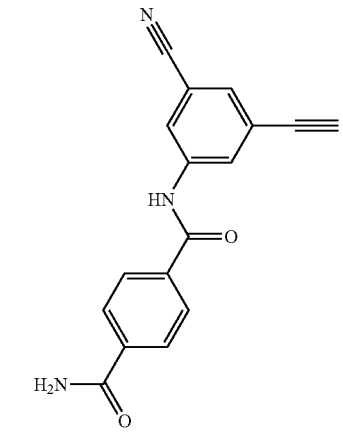 [SMILES: C#Cc1cc(C#N)cc(NC(=O)c2ccc(C(N)=O)cc2)c1] | 289.29 | 290 |
| 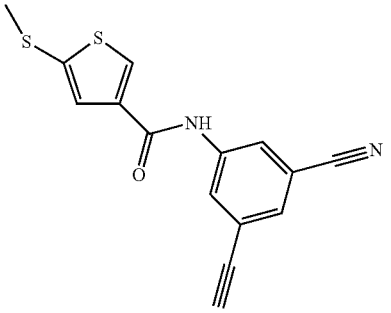 [SMILES: C#Cc1cc(C#N)cc(NC(=O)c2csc(SC)c2)c1] | 298.38 | 299 |
| 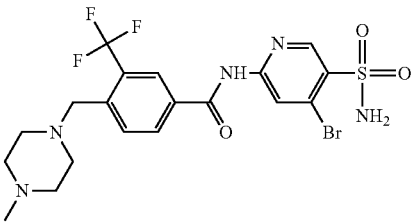 [SMILES: CN1CCN(Cc2ccc(C(=O)Nc3cc(Br)c(S(N)(=O)=O)cn3)cc2C(F)(F)F)CC1] | 536.37 | 537 |
TABLE 6-continued
| Structure | MW | m/z |
|---|---|---|
| 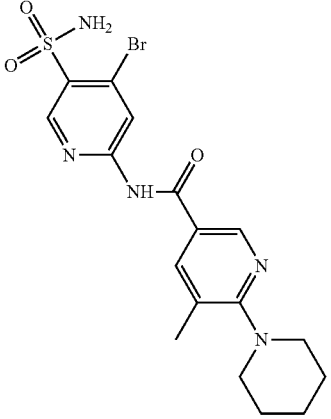 [SMILES: Cc1cc(C(=O)Nc2cc(Br)c(S(N)(=O)=O)cn2)cnc1N1CCCCC1] | 454.34 | 455 |
| 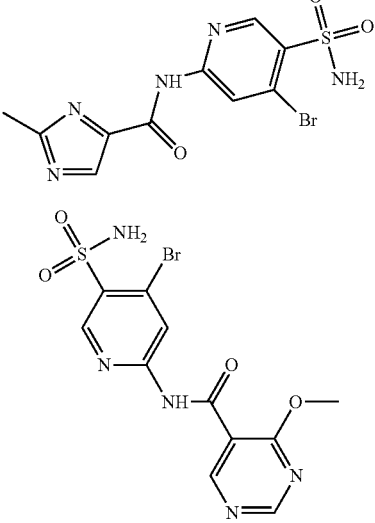 | 359.18 | 360 |
| 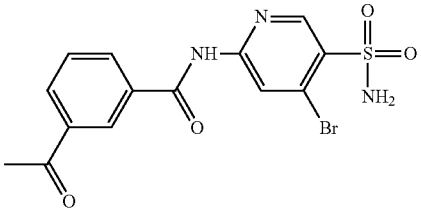 [SMILES: CC(=O)c1cccc(C(=O)Nc2cc(Br)c(S(N)(=O)=O)cn2)c1] | 388.20 | 389 |
| 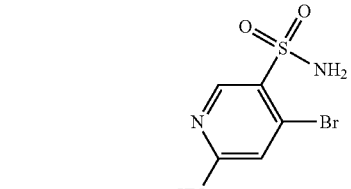 | 398.23 | 399 |
| 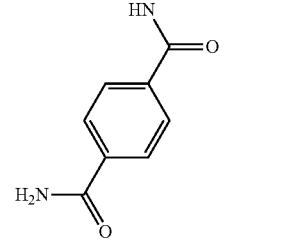 | 399.22 | 400 |

TABLE 6-continued

| Structure | MW | m/z |
|---|---|---|
| (structure) | 408.32 | 409 |
| (structure) | 446.47 | 447 |
| (structure) | 364.44 | 365 |
| (structure) | 269.28 | 270 |

TABLE 6-continued

| Structure | MW | m/z |
|---|---|---|
| (structure) | 298.30 | 299 |
| (structure) | 308.33 | 309 |
| (structure) | 309.32 | 310 |
| (structure) | 318.42 | 319 |
| (structure) | 433.43 | 434 |

TABLE 6-continued
| Structure | MW | m/z |
|---|---|---|
| 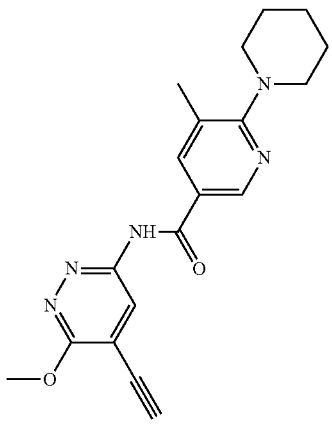 [SMILES: C#Cc1cc(NC(=O)c2cnc(N3CCCCC3)c(C)c2)nnc1OC] | 351.40 | 352 |
| 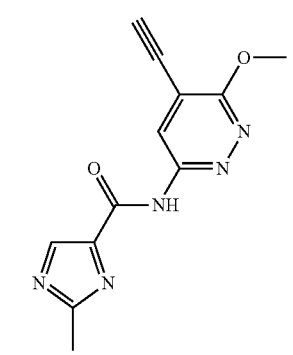 | 256.24 | 257 |
| 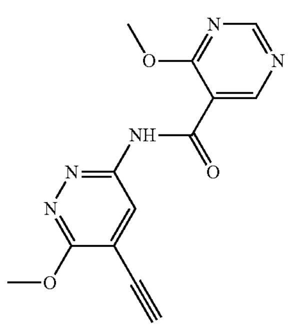 [SMILES: C#Cc1cc(NC(=O)c2cncnc2OC)nnc1OC] | 285.26 | 286 |
TABLE 6-continued
| Structure | MW | m/z |
|---|---|---|
| | 295.29 | 296 |
| | 296.28 | 297 |
| | 305.38 | 306 |
TABLE 7
| Structure | MW | m/z |
|---|---|---|
| 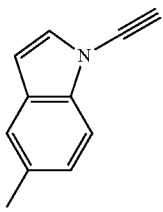 | 156.18 | 157 |

TABLE 7-continued

| Structure | MW | m/z |
|---|---|---|
| 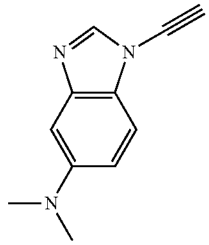 | 185.23 | 186 |
| 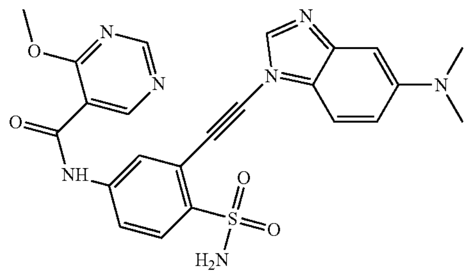 | 492.51 | 493 |
| 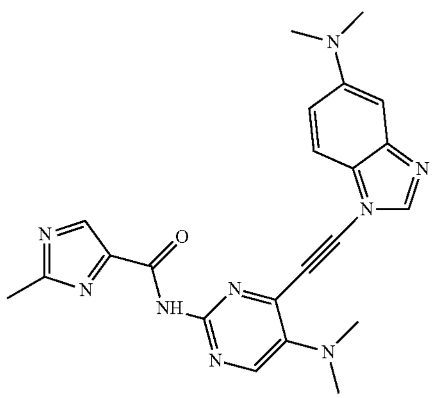 | 428.47 | 429 |
| 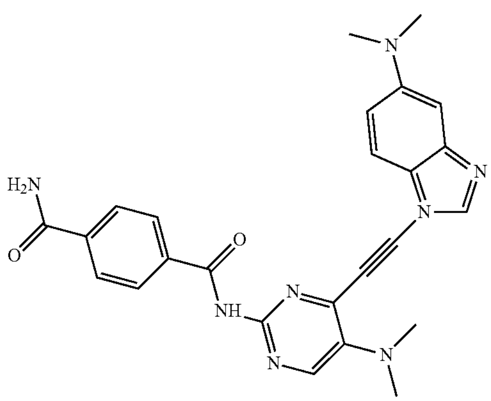 | 468.51 | 469 |
| 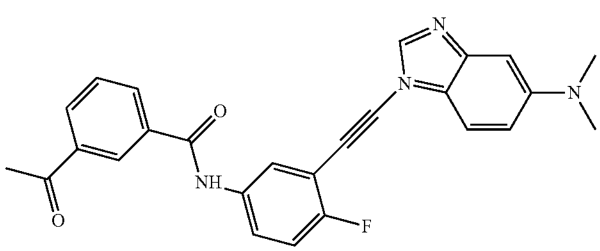 | 440.47 | 441 |

TABLE 7-continued
| Structure | MW | m/z |
|---|---|---|
| 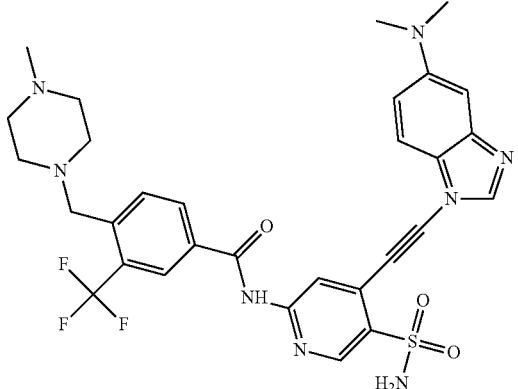 | 640.68 | 641 |
| 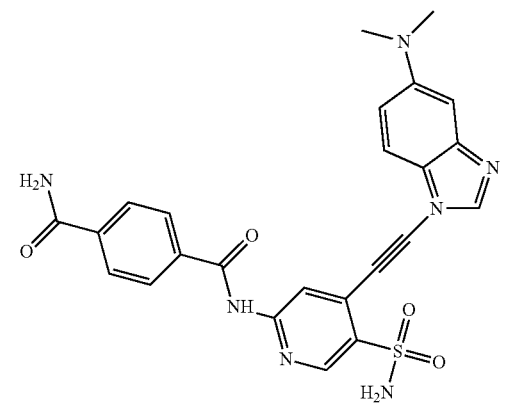 | 503.53 | 504 |
TABLE 8
| Structure | MW | m/z |
|---|---|---|
| 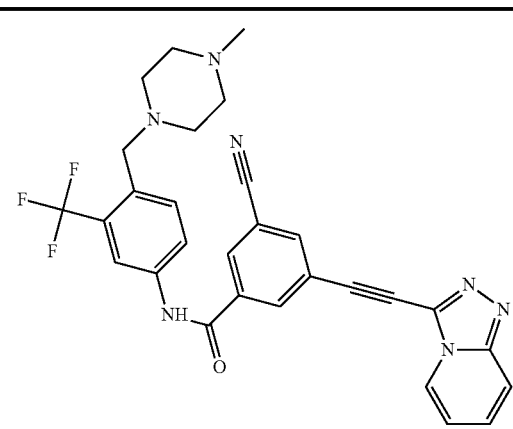 | 543.54 | 544 |

TABLE 8-continued

| Structure | MW | m/z |
|---|---|---|
| 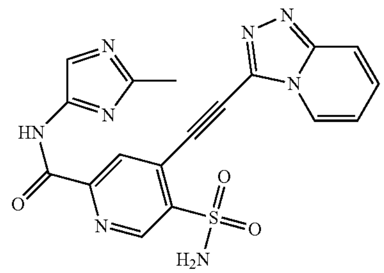 | 421.41 | 422 |
| 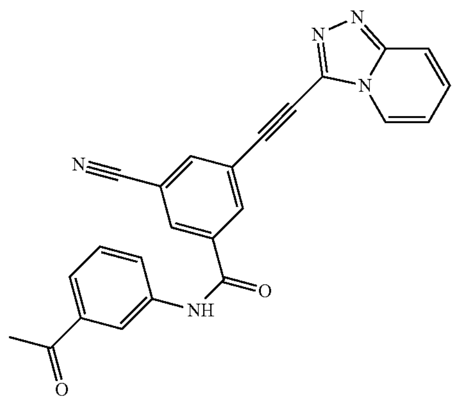 [SMILES: CC(=O)c1cccc(NC(=O)c2cc(C#N)cc(C#Cc3nnc4ccccn34)c2)c1] | 405.41 | 406 |
| 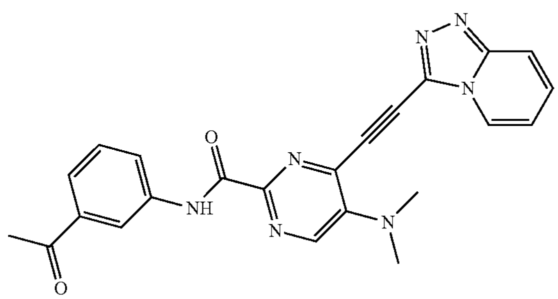 [SMILES: CC(=O)c1cccc(NC(=O)c2ncc(N(C)C)c(C#Cc3nnc4ccccn34)n2)c1] | 425.44 | 426 |
| 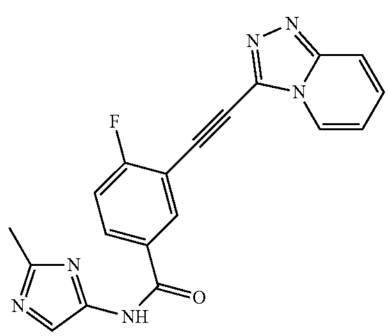 | 359.34 | 360 |
| 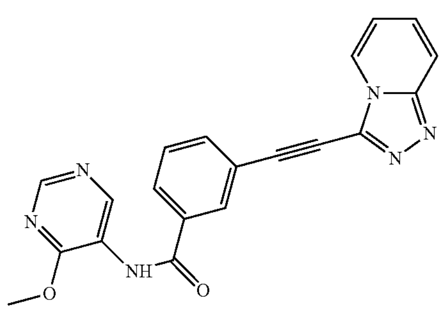 [SMILES: COc1ncncc1NC(=O)c1cccc(C#Cc2nnc3ccccn23)c1] | 370.36 | 371 |

TABLE 8-continued
| Structure | MW | m/z |
|---|---|---|
| 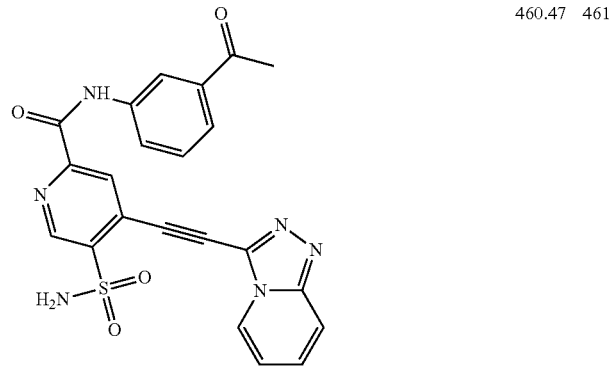 | 460.47 | 461 |
| 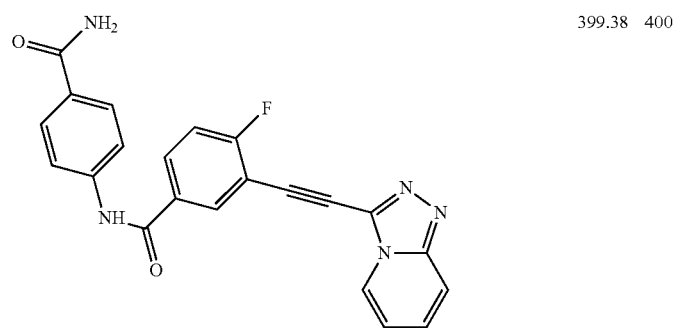 | 399.38 | 400 |
| 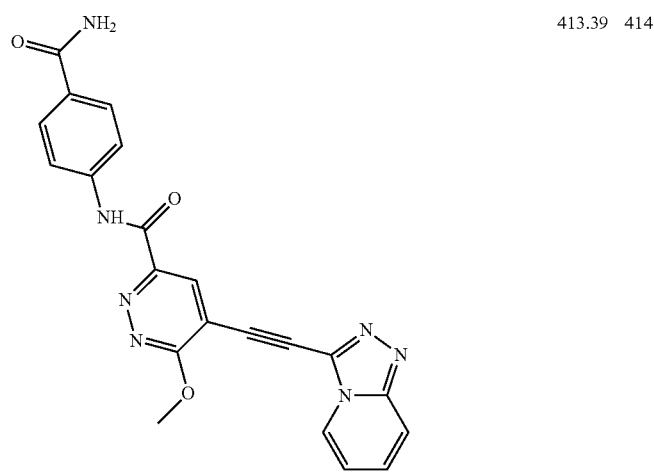 | 413.39 | 414 |

TABLE 8-continued
| Structure | MW | m/z |
|---|---|---|
| 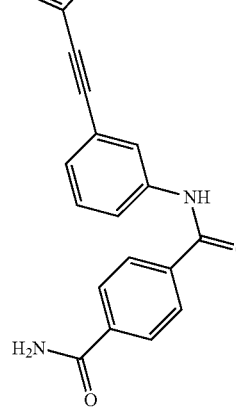 | 381.39 | 382 |
| 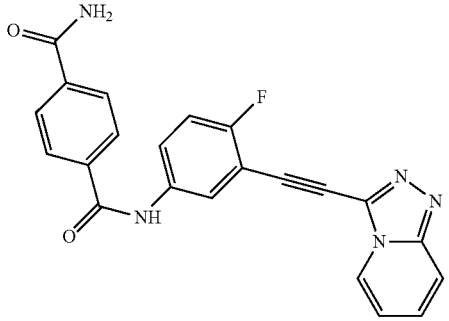 [SMILES: NC(=O)c1ccc(C(=O)Nc2ccc(F)c(C#Cc3nnc4ccccn34)c2)cc1] | 399.38 | 400 |
| 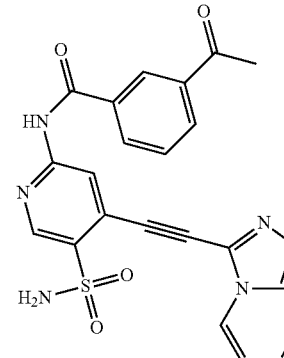 | 460.47 | 461 |
| 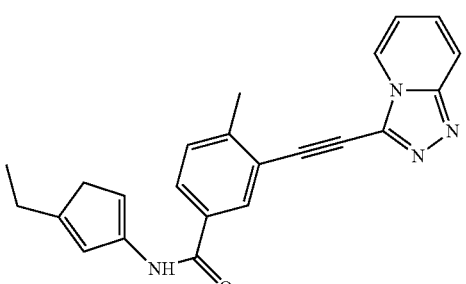 | 408.47 | 409 |

TABLE 8-continued
| Structure | MW | m/z |
|---|---|---|
| 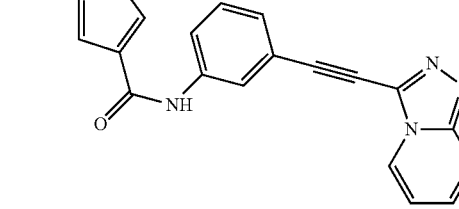 | 390.48 | 391 |
| 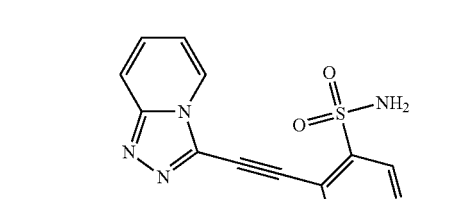 | 516.58 | 517 |
| 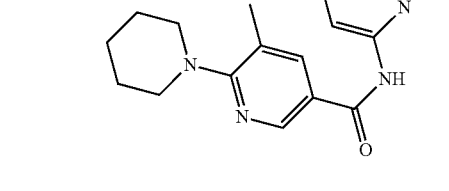 | 470.55 | 471 |
| 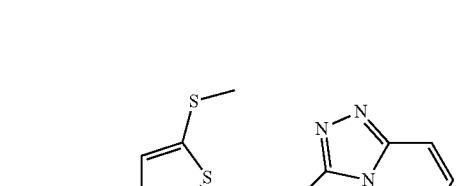 | 386.39 | 387 |

TABLE 8-continued
| Structure | MW | m/z |
|---|---|---|
| 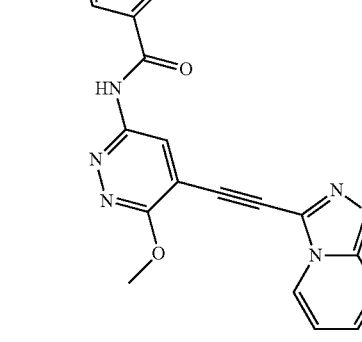 | 412.40 | 413 |
| 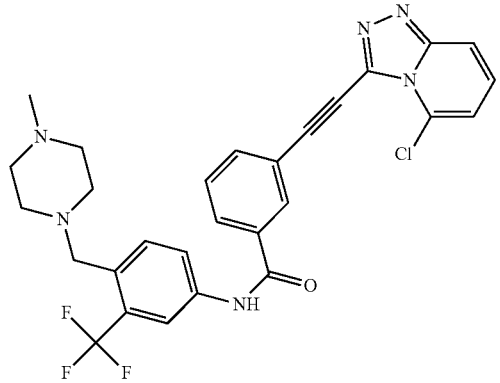 [SMILES: CN1CCN(Cc2ccc(NC(=O)c3cccc(C#Cc4nnc5cccc(Cl)n45)c3)cc2C(F)(F)F)CC1] | 552.98 | 553 |
| 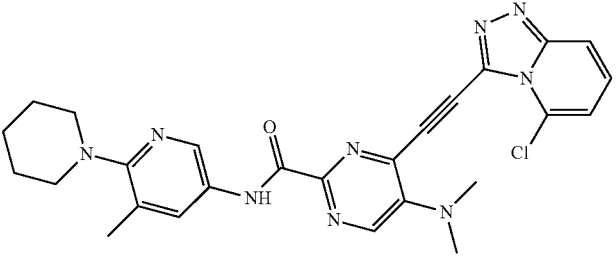 [SMILES: Cc1cc(NC(=O)c2ncc(N(C)C)c(C#Cc3nnc4cccc(Cl)n34)n2)cnc1N1CCCCC1] | 516.00 | 516 |

145
146

TABLE 8-continued

| Structure | MW | m/z |
|---|---|---|
| 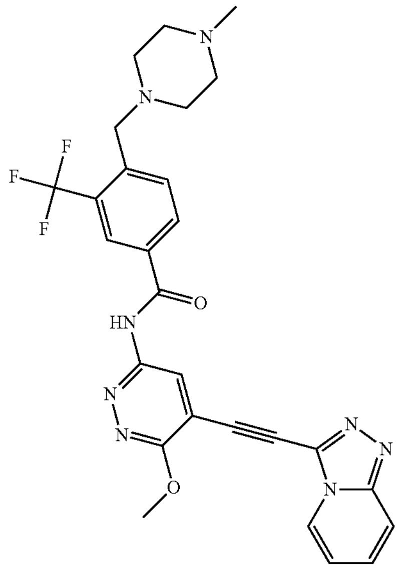 [SMILES: COc1nnc(NC(=O)c2ccc(CN3CCN(C)CC3)c(C(F)(F)F)c2)cc1C#Cc1nnc2ccccn12] | 550.54 | 551 |
| 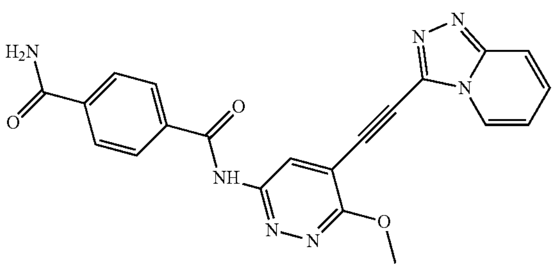 [SMILES: COc1nnc(NC(=O)c2ccc(C(N)=O)cc2)cc1C#Cc1nnc2ccccn12] | 413.39 | 414 |
| 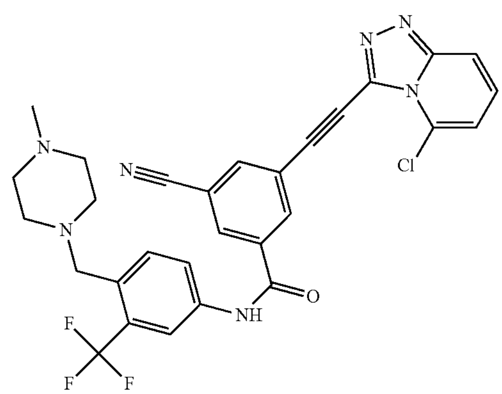 [SMILES: CN1CCN(Cc2ccc(NC(=O)c3cc(C#N)cc(C#Cc4nnc5cccc(Cl)n45)c3)cc2C(F)(F)F)CC1] | 577.99 | 578 |
| 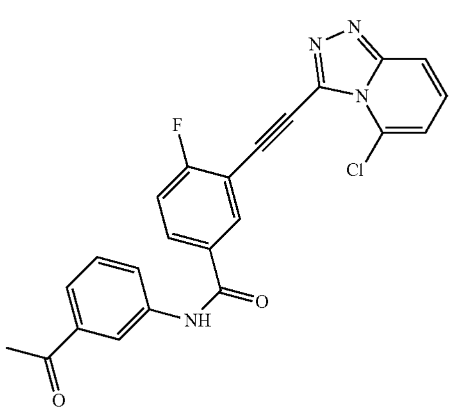 [SMILES: CC(=O)c1cccc(NC(=O)c2ccc(F)c(C#Cc3nnc4cccc(Cl)n34)c2)c1] | 432.83 | 433 |

TABLE 8-continued
| Structure | MW | m/z |
|---|---|---|
| 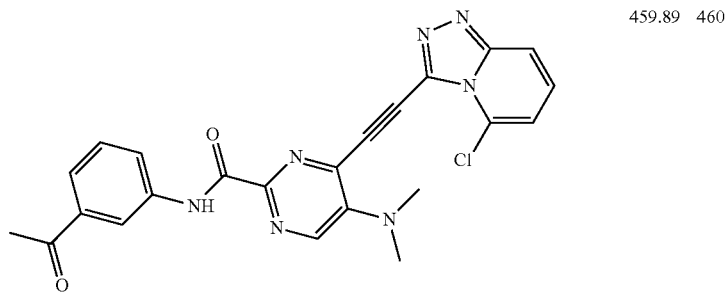 | 459.89 | 460 |
| 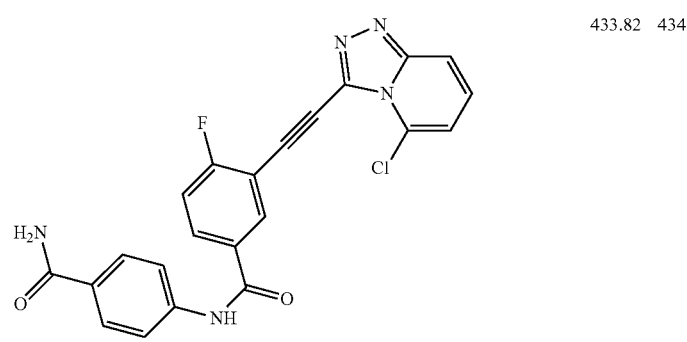 | 433.82 | 434 |
| 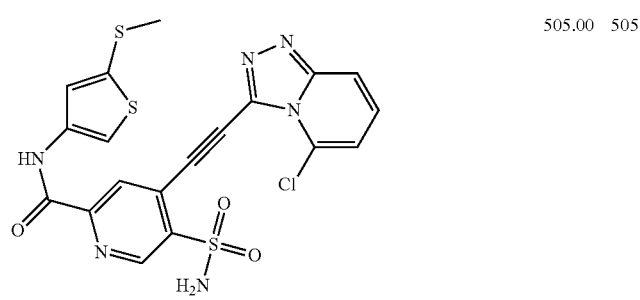 | 505.00 | 505 |
| 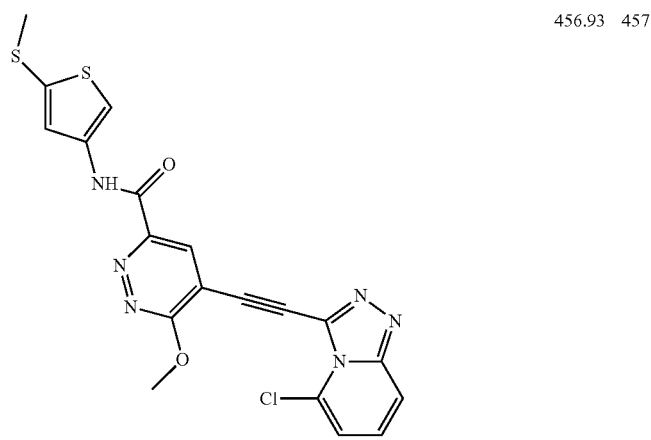 | 456.93 | 457 |

TABLE 8-continued

| Structure | MW | m/z |
|---|---|---|
| 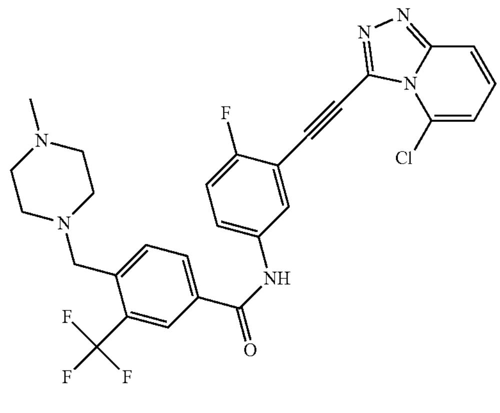 [SMILES: CN1CCN(Cc2ccc(C(=O)Nc3ccc(F)c(C#Cc4nnc5cccc(Cl)n45)c3)cc2C(F)(F)F)CC1] | 570.97 | 571 |
| 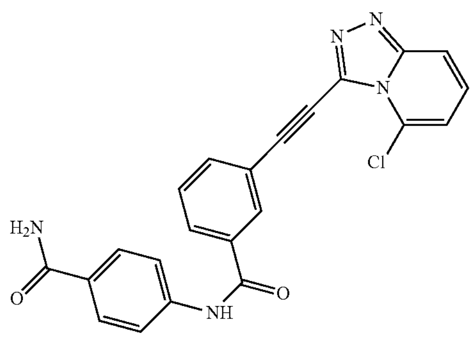 [SMILES: NC(=O)c1ccc(NC(=O)c2cccc(C#Cc3nnc4cccc(Cl)n34)c2)cc1] | 415.83 | 416 |
| 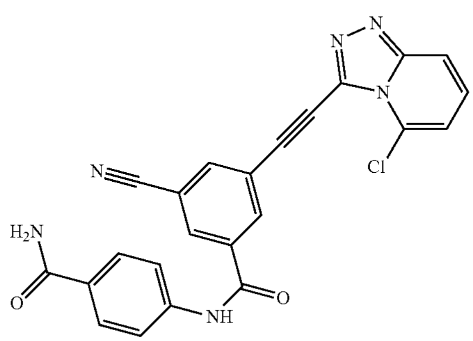 [SMILES: N#Cc1cc(C#Cc2nnc3cccc(Cl)n23)cc(C(=O)Nc2ccc(C(N)=O)cc2)c1] | 440.84 | 441 |
| 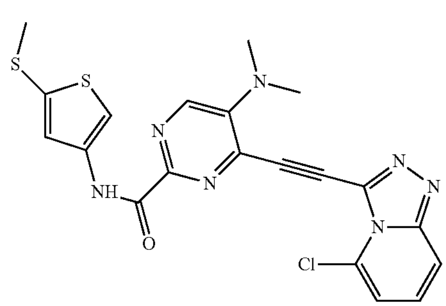 [SMILES: CSc1cc(NC(=O)c2ncc(N(C)C)c(C#Cc3nnc4cccc(Cl)n34)n2)cs1] | 469.97 | 470 |

TABLE 8-continued

| Structure | MW | m/z |
|---|---|---|
| 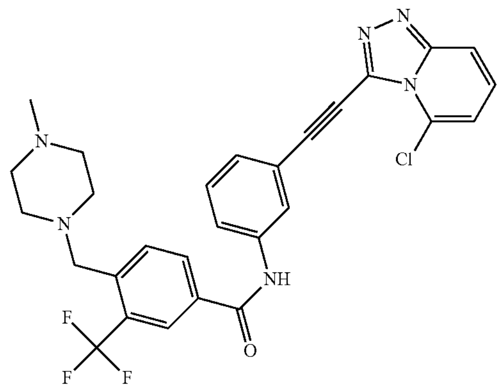 [SMILES: CN1CCN(Cc2ccc(C(=O)Nc3cccc(C#Cc4nnc5cccc(Cl)n45)c3)cc2C(F)(F)F)CC1] | 552.98 | 553 |
| 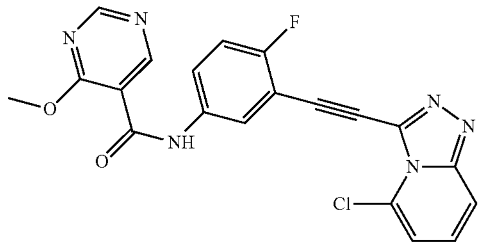 [SMILES: COc1ncncc1C(=O)Nc1ccc(F)c(C#Cc2nnc3cccc(Cl)n23)c1] | 422.80 | 423 |
| 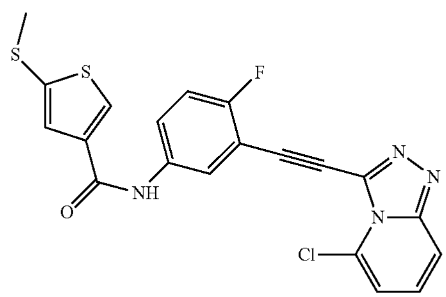 [SMILES: CSc1cc(C(=O)Nc2ccc(F)c(C#Cc3nnc4cccc(Cl)n34)c2)cs1] | 442.92 | 443 |
| 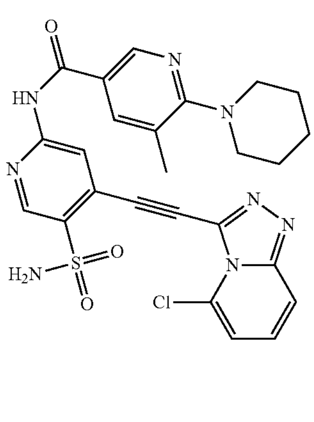 [SMILES: Cc1cc(C(=O)Nc2cc(C#Cc3nnc4cccc(Cl)n34)c(S(N)(=O)=O)cn2)cnc1N1CCCCC1] | 551.02 | 552 |

TABLE 8-continued
| Structure | MW | m/z |
|---|---|---|
| 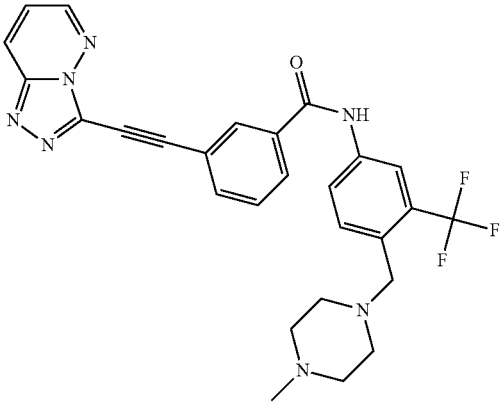 [SMILES: CN1CCN(Cc2ccc(NC(=O)c3cccc(C#Cc4nnc5cccnn45)c3)cc2C(F)(F)F)CC1] | 519.52 | 520 |
| 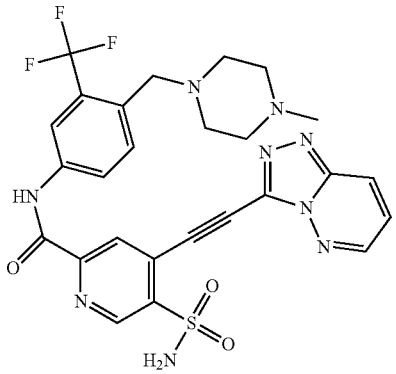 [SMILES: CN1CCN(Cc2ccc(NC(=O)c3cc(C#Cc4nnc5cccnn45)c(S(N)(=O)=O)cn3)cc2C(F)(F)F)CC1] | 599.59 | 600 |
| 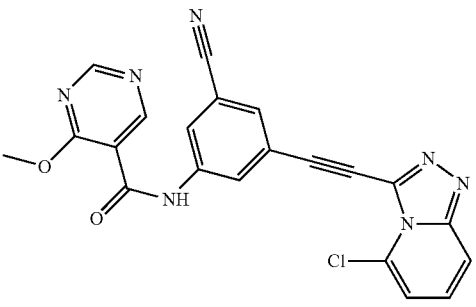 [SMILES: COc1ncncc1C(=O)Nc1cc(C#N)cc(C#Cc2nnc3cccc(Cl)n23)c1] | 429.82 | 430 |
| 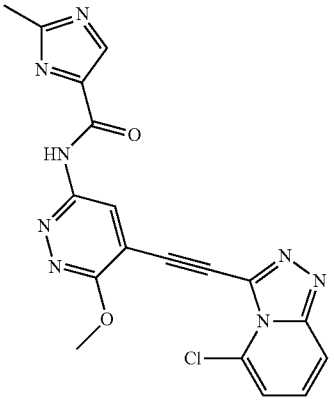 | 407.79 | 408 |

TABLE 8-continued

| Structure | MW | m/z |
|---|---|---|
| 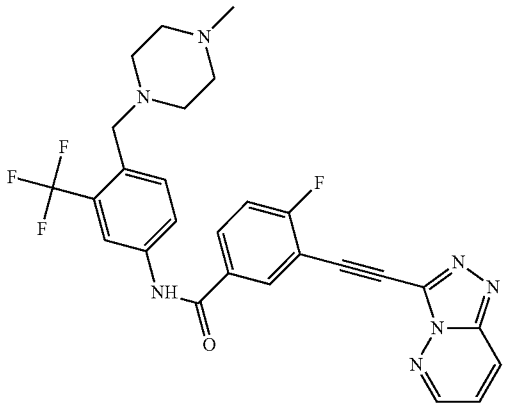 [SMILES: CN1CCN(Cc2ccc(NC(=O)c3ccc(F)c(C#Cc4nnc5cccnn45)c3)cc2C(F)(F)F)CC1] | 537.51 | 538 |
| 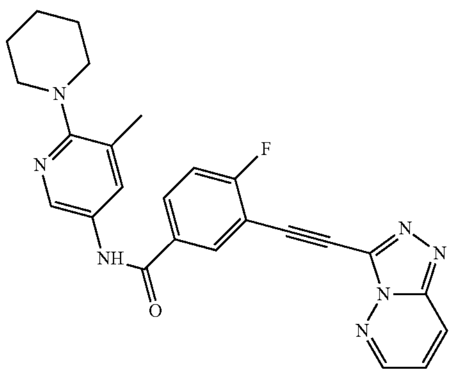 [SMILES: Cc1cc(NC(=O)c2ccc(F)c(C#Cc3nnc4cccnn34)c2)cnc1N1CCCCC1] | 455.49 | 456 |
| 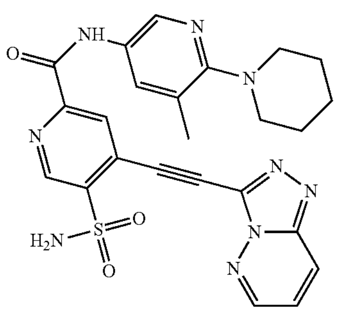 [SMILES: Cc1cc(NC(=O)c2cc(C#Cc3nnc4cccnn34)c(S(N)(=O)=O)cn2)cnc1N1CCCCC1] | 517.56 | 518 |
| 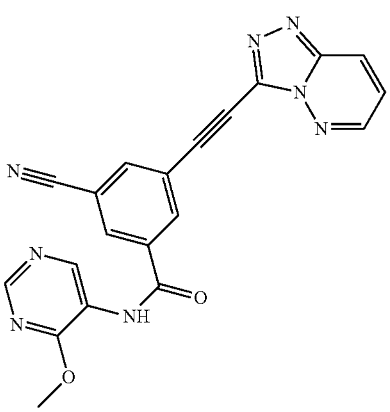 [SMILES: COc1ncncc1NC(=O)c1cc(C#N)cc(C#Cc2nnc3cccnn23)c1] | 396.36 | 397 |

TABLE 8-continued

| Structure | MW | m/z |
|---|---|---|
| 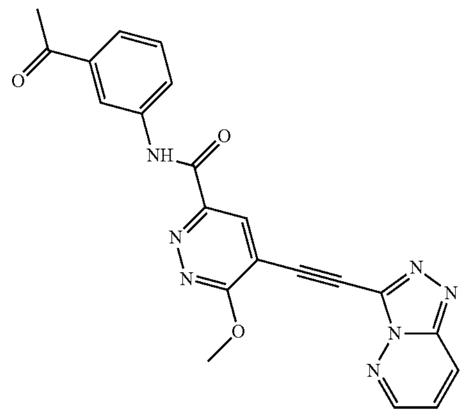 [SMILES: COc1nnc(C(=O)Nc2cccc(C(C)=O)c2)cc1C#Cc1nnc2cccnn12] | 413.39 | 414 |
| 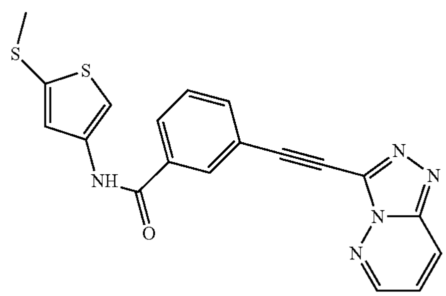 [SMILES: CSc1cc(NC(=O)c2cccc(C#Cc3nnc4cccnn34)c2)cs1] | 391.47 | 392 |
| 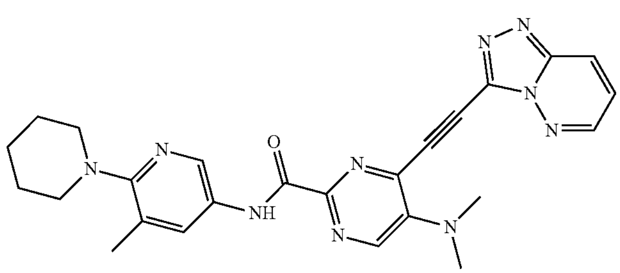 [SMILES: Cc1cc(NC(=O)c2ncc(N(C)C)c(C#Cc3nnc4cccnn34)n2)cnc1N1CCCCC1] | 482.54 | 483 |
| 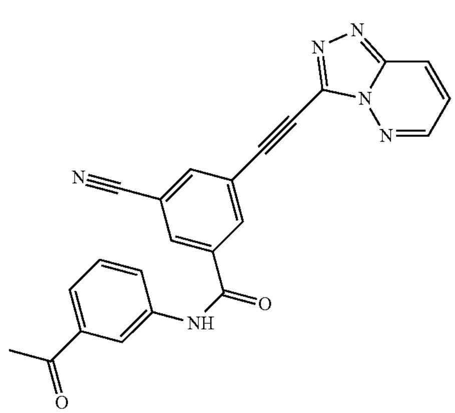 [SMILES: CC(=O)c1cccc(NC(=O)c2cc(C#N)cc(C#Cc3nnc4cccnn34)c2)c1] | 406.40 | 407 |

TABLE 8-continued

| Structure | MW | m/z |
|---|---|---|
| 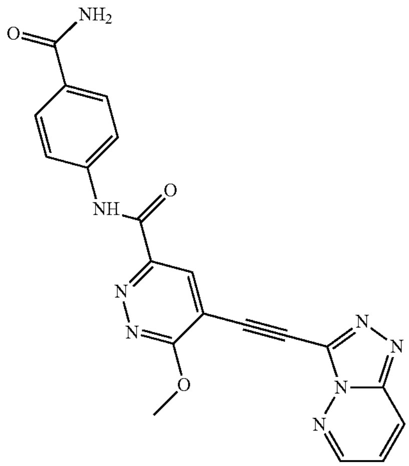 [SMILES: COc1nnc(C(=O)Nc2ccc(C(N)=O)cc2)cc1C#Cc1nnc2cccnn12] | 414.38 | 415 |
| 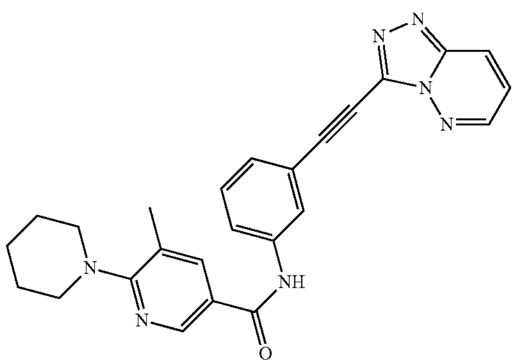 [SMILES: Cc1cc(C(=O)Nc2cccc(C#Cc3nnc4cccnn34)c2)cnc1N1CCCCC1] | 437.50 | 438 |
| 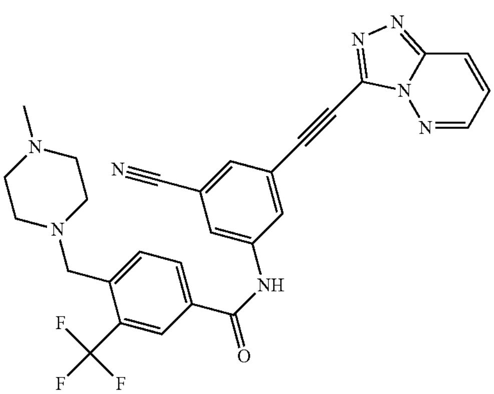 [SMILES: CN1CCN(Cc2ccc(C(=O)Nc3cc(C#N)cc(C#Cc4nnc5cccnn45)c3)cc2C(F)(F)F)CC1] | 544.53 | 545 |
| 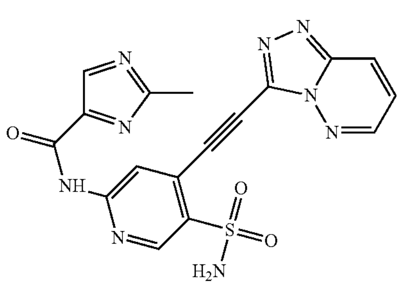 | 422.40 | 423 |

TABLE 8-continued
| Structure | MW | m/z |
|---|---|---|
| 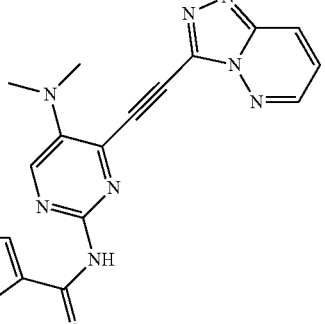 | 436.52 | 437 |
| 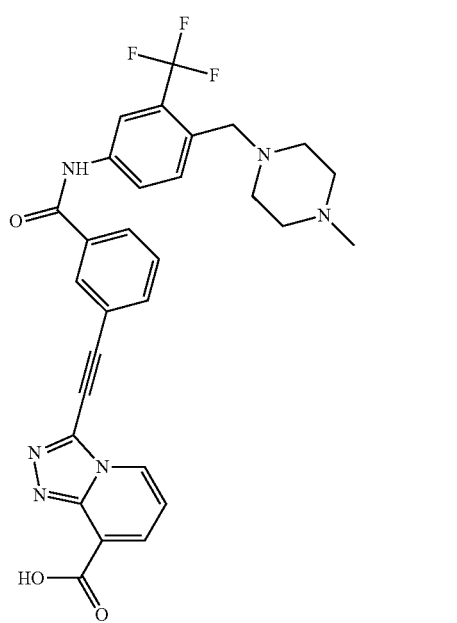 [SMILES: CN1CCN(Cc2ccc(NC(=O)c3cccc(C#Cc4nnc5c(C(=O)O)cccn45)c3)cc2C(F)(F)F)CC1] | 562.54 | 563 |
| 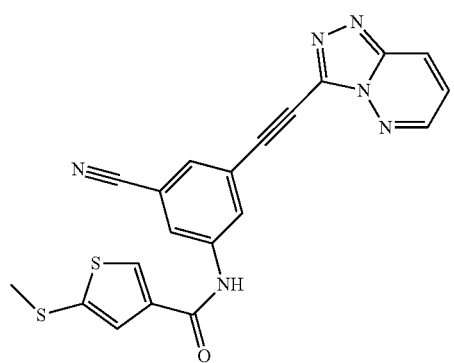 [SMILES: CSc1cc(C(=O)Nc2cc(C#N)cc(C#Cc3nnc4cccnn34)c2)cs1] | 416.48 | 417 |

TABLE 8-continued

| Structure | MW | m/z |
|---|---|---|
| 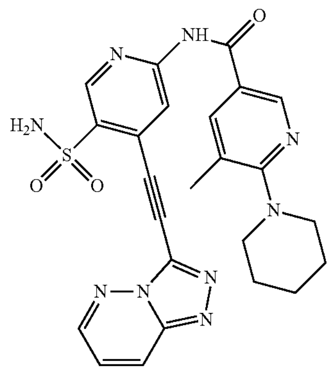 [SMILES: Cc1cc(C(=O)Nc2cc(C#Cc3nnc4cccnn34)c(S(N)(=O)=O)cn2)cnc1N1CCCCC1] | 517.56 | 518 |
| 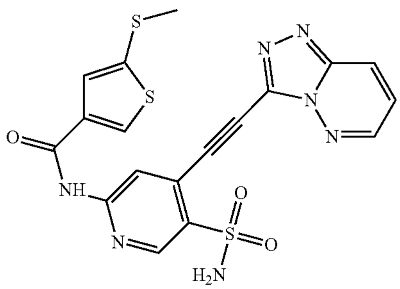 | 471.54 | 472 |
| 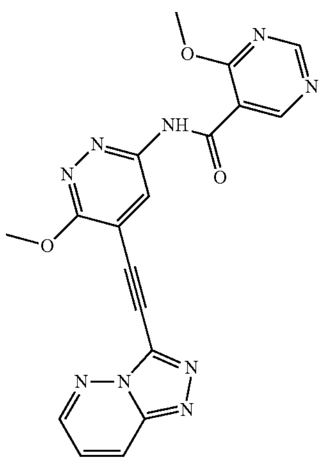 [SMILES: COc1nnc(NC(=O)c2cncnc2OC)cc1C#Cc1nnc2cccnn12] | 403.35 | 404 |
| 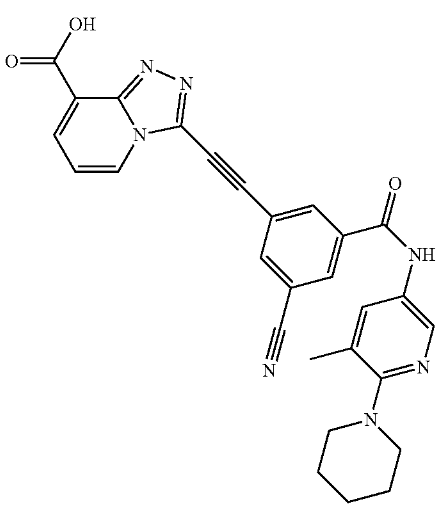 [SMILES: Cc1cc(NC(=O)c2cc(C#N)cc(C#Cc3nnc4c(C(=O)O)cccn34)c2)cnc1N1CCCCC1] | 505.53 | 506 |

TABLE 8-continued
| Structure | MW | m/z |
|---|---|---|
| 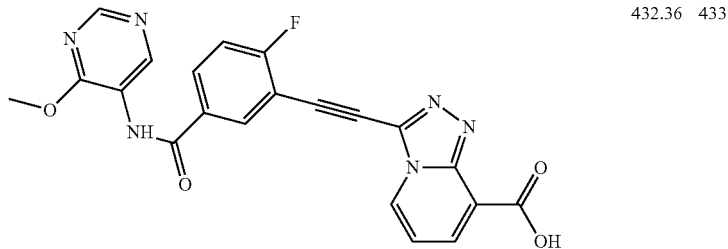 | 432.36 | 433 |
| 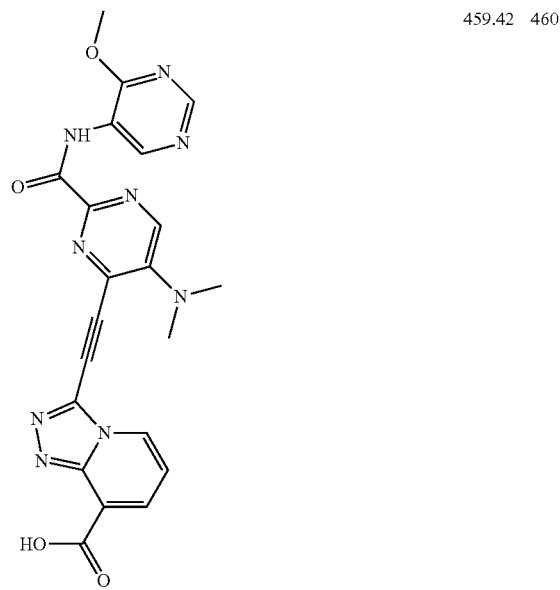 | 459.42 | 460 |
| 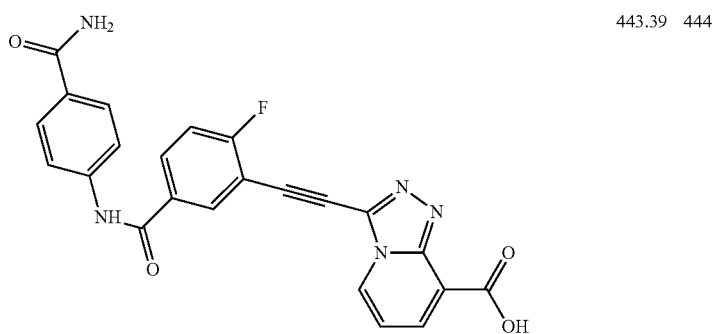 | 443.39 | 444 |

TABLE 8-continued
| Structure | MW | m/z |
|---|---|---|
| 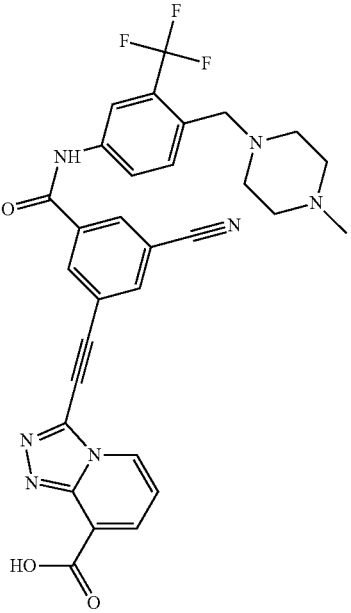 [SMILES: CN1CCN(Cc2ccc(NC(=O)c3cc(C#N)cc(C#Cc4nnc5c(C(=O)O)cccn45)c3)cc2C(F)(F)F)CC1] | 587.55 | 588 |
| 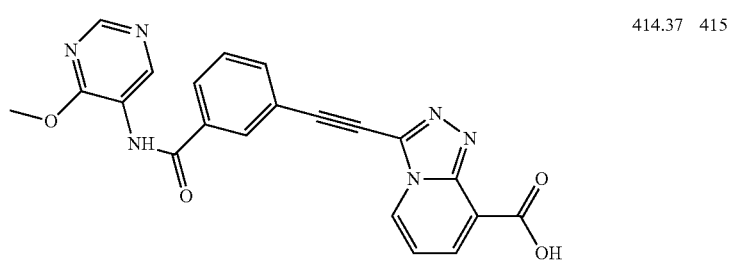 | 414.37 | 415 |
| 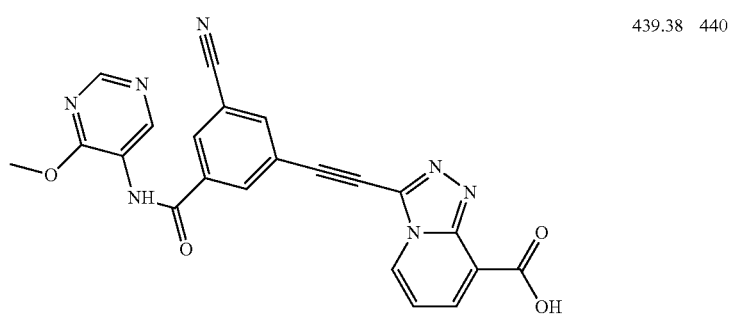 | 439.38 | 440 |

TABLE 8-continued
| Structure | MW | m/z |
|---|---|---|
| 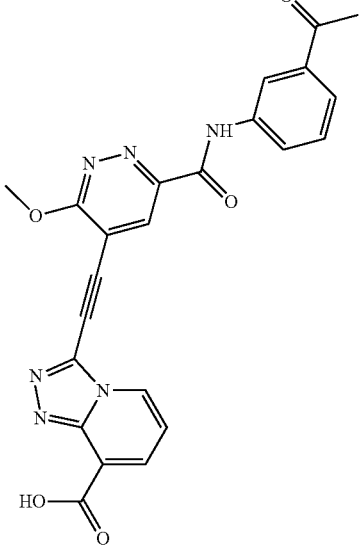 | 456.41 | 457 |
| 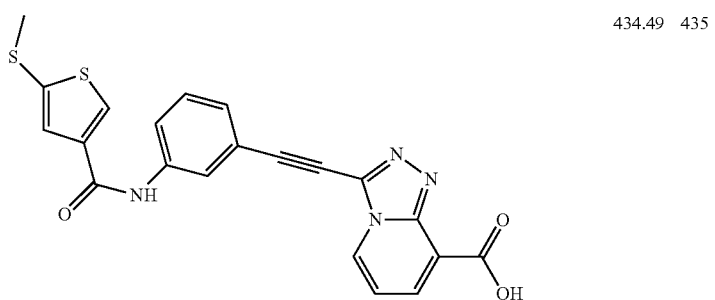 | 434.49 | 435 |
| 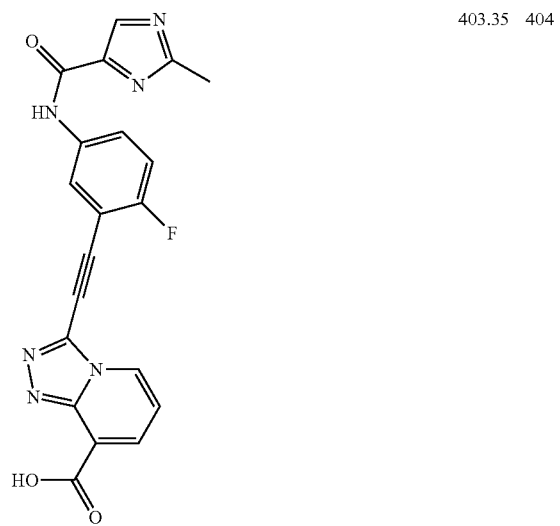 | 403.35 | 404 |

TABLE 8-continued
| Structure | MW | m/z |
|---|---|---|
| 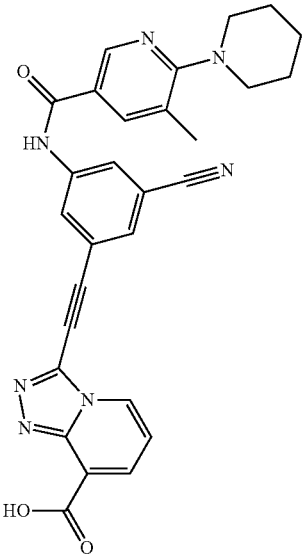 [SMILES: Cc1cc(C(=O)Nc2cc(C#N)cc(C#Cc3nnc4c(C(=O)O)cccn34)c2)cnc1N1CCCCC1] | 505.53 | 506 |
| 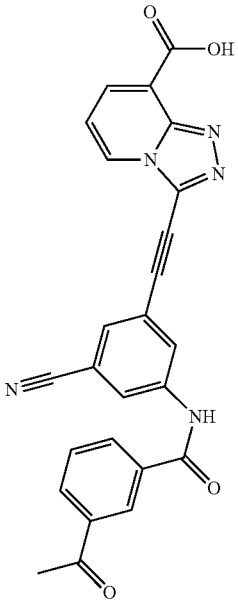 [SMILES: CC(=O)c1cccc(C(=O)Nc2cc(C#N)cc(C#Cc3nnc4c(C(=O)O)cccn34)c2)c1] | 449.42 | 450 |
| 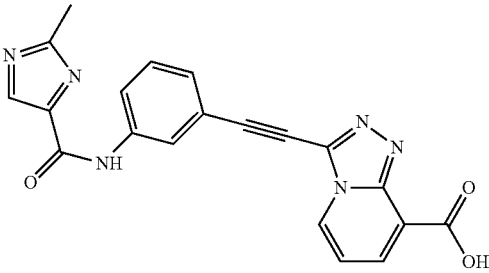 | 385.36 | 386 |

TABLE 8-continued

| Structure | MW | m/z |
|---|---|---|
| 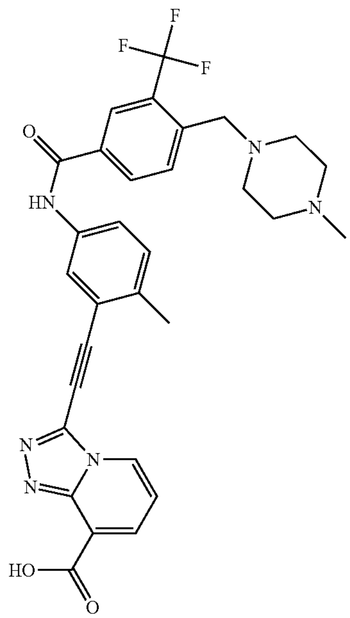 [SMILES: Cc1ccc(NC(=O)c2ccc(CN3CCN(C)CC3)c(C(F)(F)F)c2)cc1C#Cc1nnc2c(C(=O)O)cccn12] | 580.53 | 581 |
| 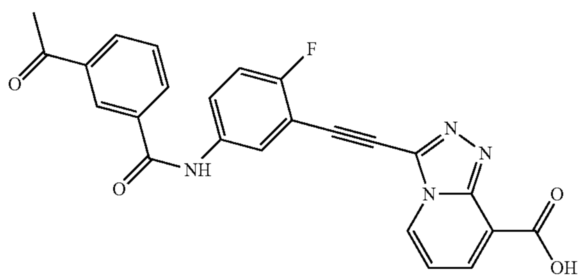 [SMILES: CC(=O)c1cccc(C(=O)Nc2ccc(F)c(C#Cc3nnc4c(C(=O)O)cccn34)c2)c1] | 442.40 | 443 |
| 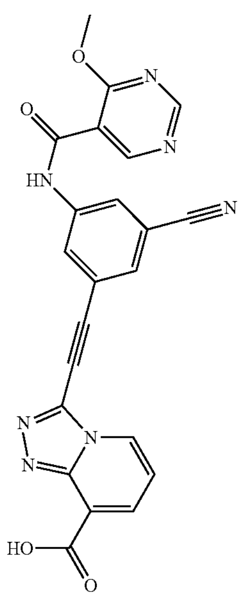 [SMILES: COc1ncncc1C(=O)Nc1cc(C#N)cc(C#Cc2nnc3c(C(=O)O)cccn23)c1] | 439.38 | 440 |

TABLE 8-continued
| Structure | MW | m/z |
|---|---|---|
| 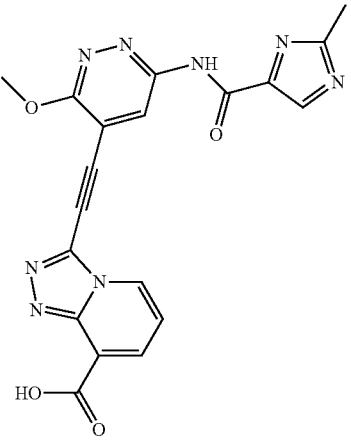 | 417.36 | 418 |
| 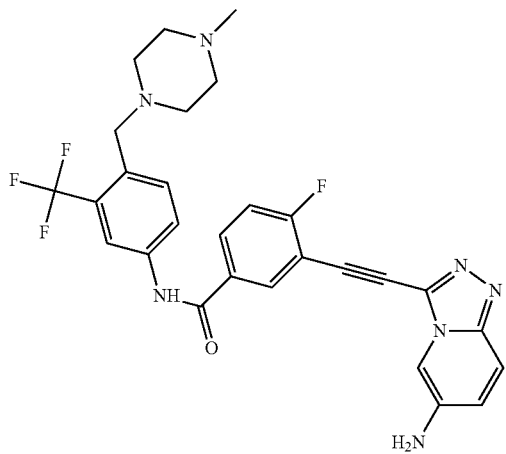 [SMILES: CN1CCN(Cc2ccc(NC(=O)c3ccc(F)c(C#Cc4nnc5ccc(N)cn45)c3)cc2C(F)(F)F)CC1] | 551.54 | 552 |
| 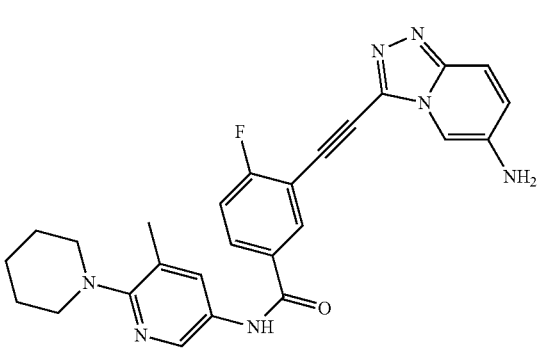 [SMILES: Cc1cc(NC(=O)c2ccc(F)c(C#Cc3nnc4ccc(N)cn34)c2)cnc1N1CCCCC1] | 469.51 | 470 |
| 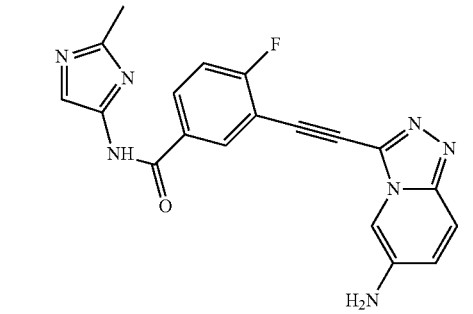 | 374.35 | 375 |

TABLE 8-continued
| Structure | MW | m/z |
|---|---|---|
| 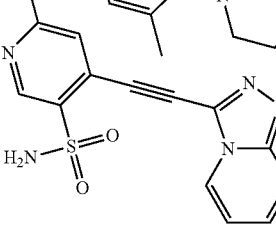 | 560.59 | 561 |
| 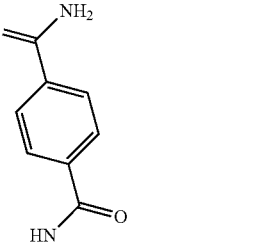 | 457.40 | 458 |
| 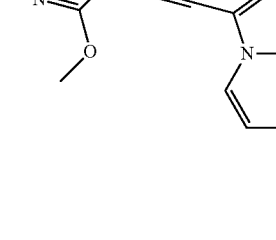 | 565.55 | 566 |

TABLE 8-continued

| Structure | MW | m/z |
|---|---|---|
| 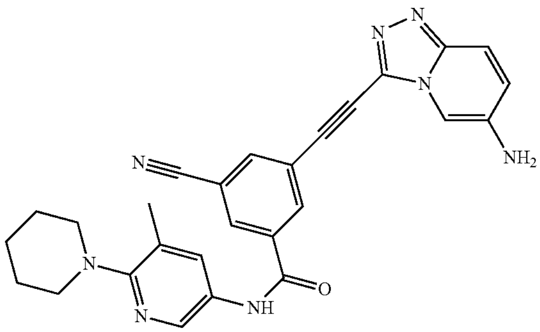 [SMILES: Cc1cc(NC(=O)c2cc(C#N)cc(C#Cc3nnc4ccc(N)cn34)c2)cnc1N1CCCCC1] | 476.53 | 477 |
| 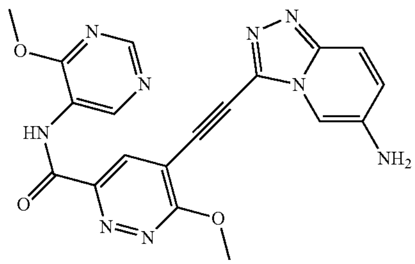 [SMILES: COc1nnc(C(=O)Nc2cncnc2OC)cc1C#Cc1nnc2ccc(N)cn12] | 417.38 | 418 |
| 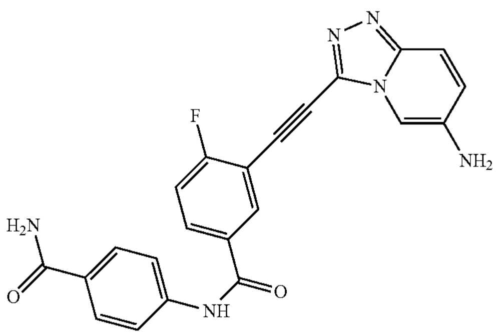 [SMILES: NC(=O)c1ccc(NC(=O)c2ccc(F)c(C#Cc3nnc4ccc(N)cn34)c2)cc1] | 414.39 | 415 |
| 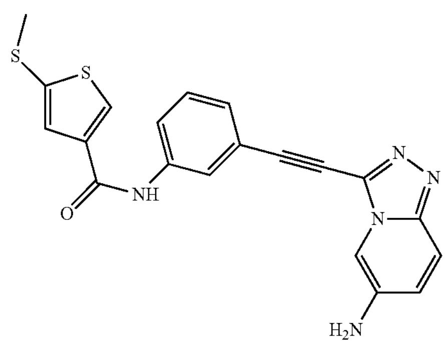 [SMILES: CSc1cc(C(=O)Nc2cccc(C#Cc3nnc4ccc(N)cn34)c2)cs1] | 405.50 | 406 |
| 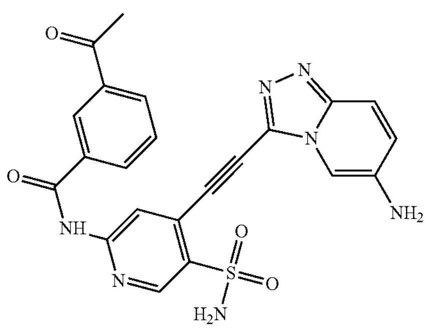 [SMILES: CC(=O)c1cccc(C(=O)Nc2cc(C#Cc3nnc4ccc(N)cn34)c(S(N)(=O)=O)cn2)c1] | 475.48 | 476 |

181
TABLE 8-continued
| Structure | MW | m/z |
|---|---|---|
| 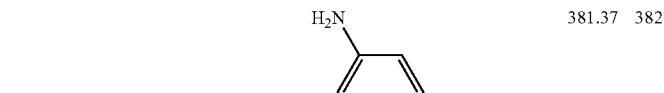 | 381.37 | 382 |
| 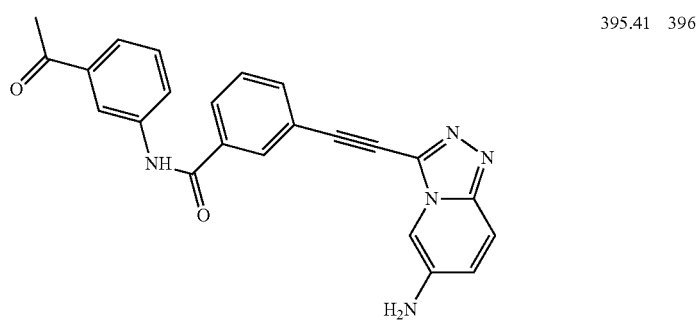 | 395.41 | 396 |
| 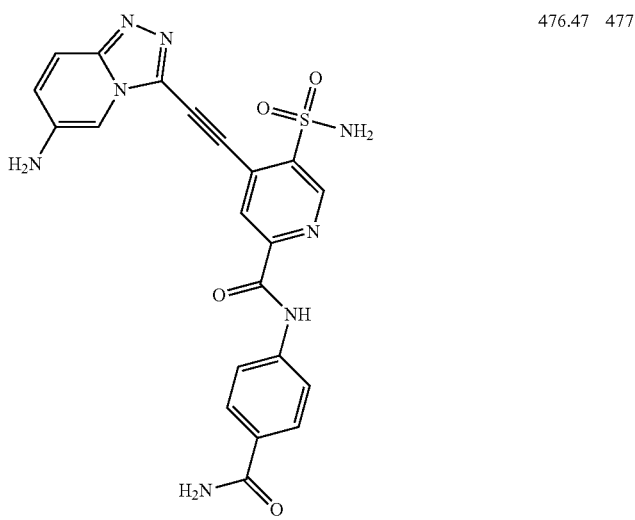 | 476.47 | 477 |
| 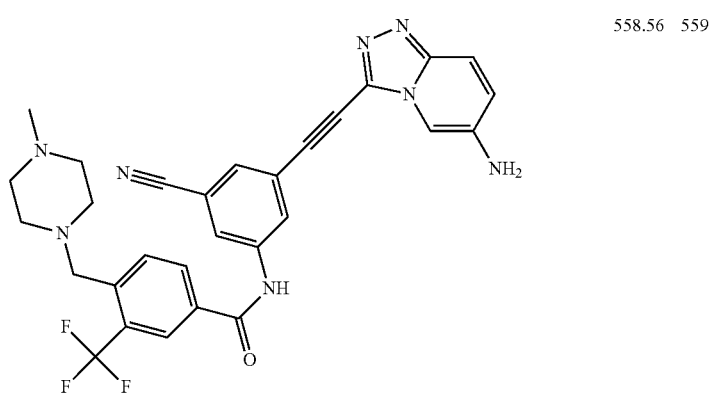 | 558.56 | 559 |

TABLE 8-continued
| Structure | MW | m/z |
|---|---|---|
| 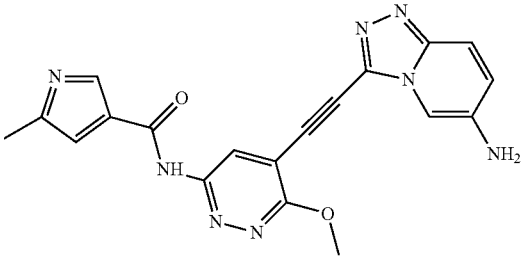 | 388.36 | 389 |
| 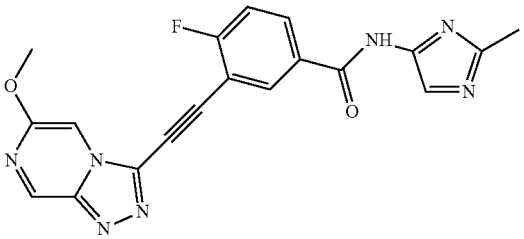 | 390.35 | 391 |
| 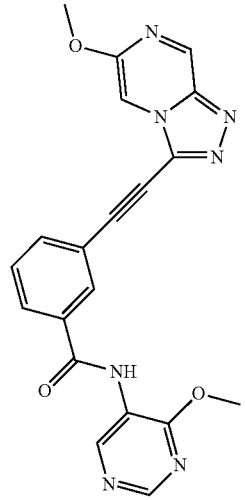 [SMILES: COc1cn2c(C#Cc3cccc(C(=O)Nc4cncnc4OC)c3)nnc2cn1] | 401.38 | 402 |
| 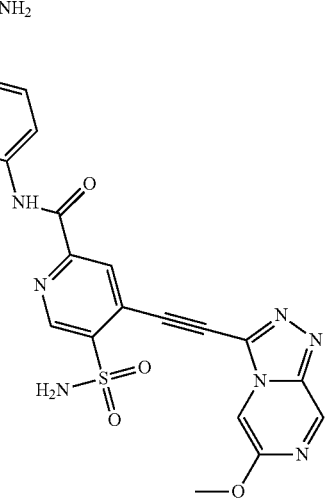 | 492.47 | 493 |

TABLE 8-continued

| Structure | MW | m/z |
|---|---|---|
| 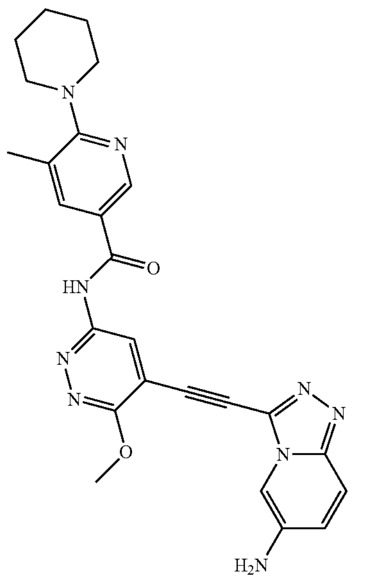 [SMILES: COc1nnc(NC(=O)c2cnc(N3CCCCC3)c(C)c2)cc1C#Cc1nnc2ccc(N)cn12] | 483.53 | 484 |
| 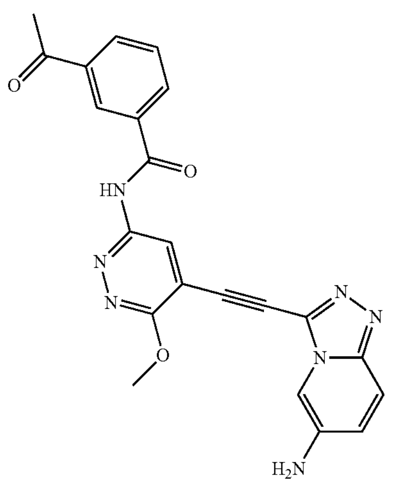 [SMILES: COc1nnc(NC(=O)c2cccc(C(C)=O)c2)cc1C#Cc1nnc2ccc(N)cn12] | 427.42 | 428 |
| 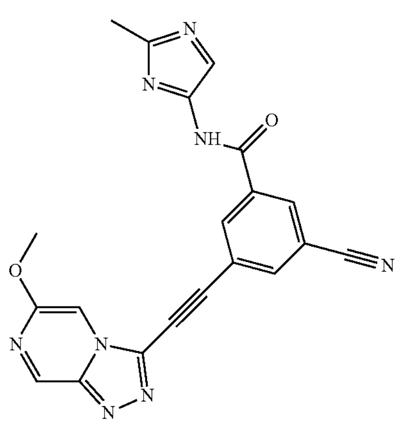 | 397.37 | 398 |

TABLE 8-continued
| Structure | MW | m/z |
|---|---|---|
| 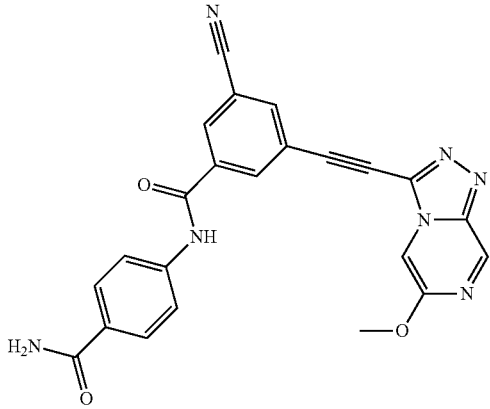 [SMILES: COc1cn2c(C#Cc3cc(C#N)cc(C(=O)Nc4ccc(C(N)=O)cc4)c3)nnc2cn1] | 437.41 | 438 |
| 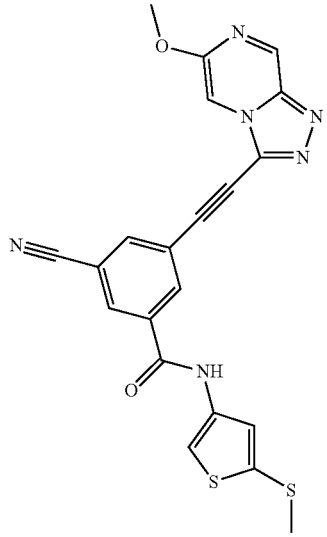 [SMILES: COc1cn2c(C#Cc3cc(C#N)cc(C(=O)Nc4csc(SC)c4)c3)nnc2cn1] | 446.51 | 447 |
| 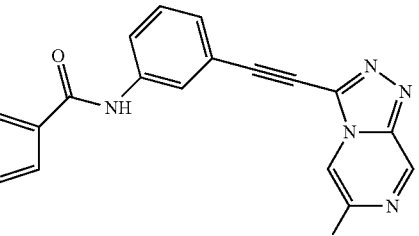 | 421.50 | 422 |
| 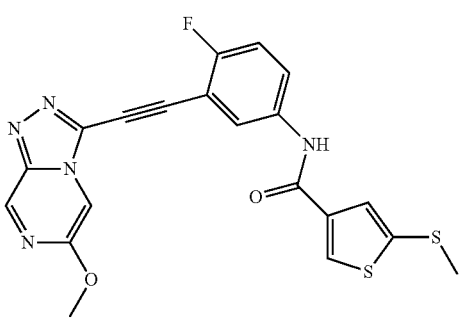 [SMILES: COc1cn2c(C#Cc3cc(NC(=O)c4csc(SC)c4)ccc3F)nnc2cn1] | 439.49 | 440 |

TABLE 8-continued

| Structure | MW | m/z |
|---|---|---|
| 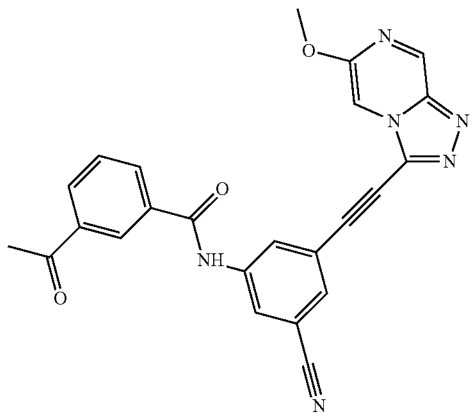 [SMILES: COc1cn2c(C#Cc3cc(C#N)cc(NC(=O)c4cccc(C(C)=O)c4)c3)nnc2cn1] | 436.42 | 437 |
| 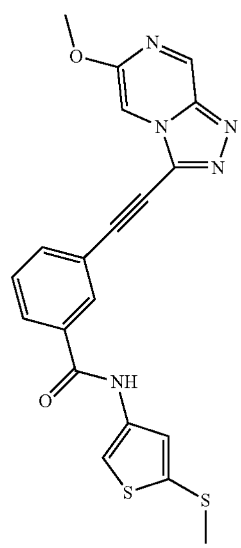 [SMILES: COc1cn2c(C#Cc3cccc(C(=O)Nc4csc(SC)c4)c3)nnc2cn1] | 421.50 | 422 |
| 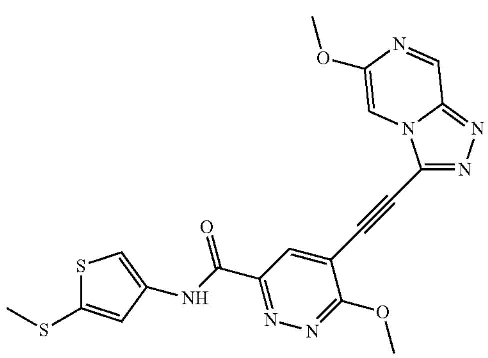 [SMILES: COc1cn2c(C#Cc3cc(C(=O)Nc4csc(SC)c4)nnc3OC)nnc2cn1] | 453.50 | 454 |

TABLE 8-continued
| Structure | MW | m/z |
|---|---|---|
| 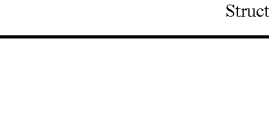 | 390.35 | 391 |
| 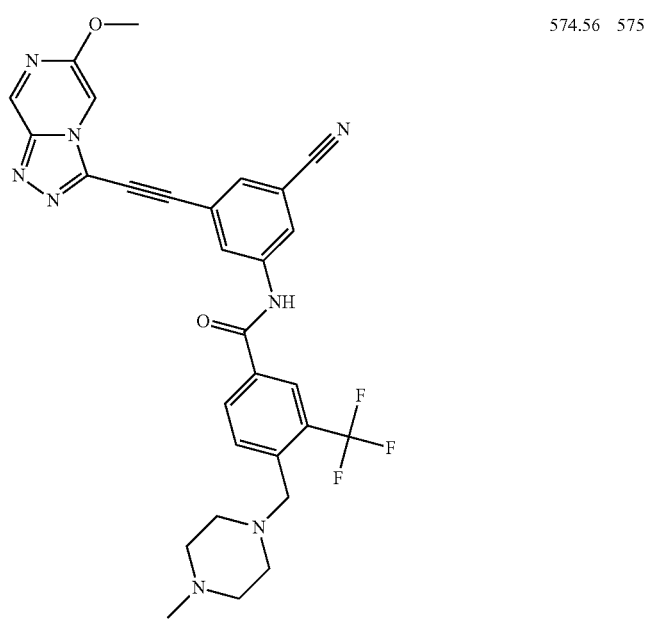 | 574.56 | 575 |
| 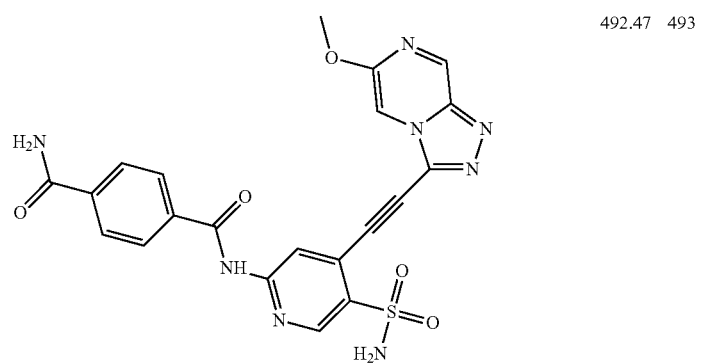 | 492.47 | 493 |

TABLE 8-continued
| Structure | MW | m/z |
|---|---|---|
| 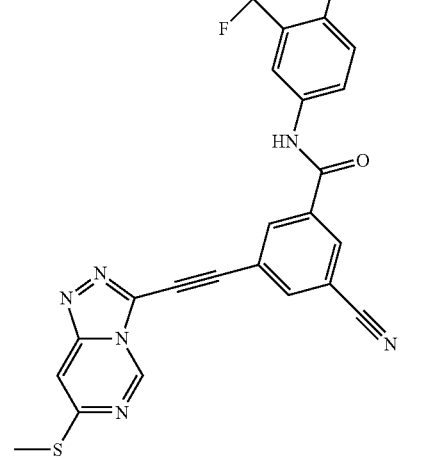 | 590.62 | 591 |
| 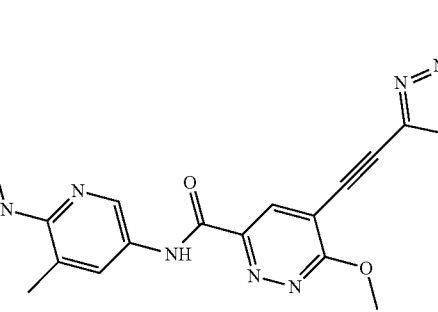 | 515.59 | 516 |
| 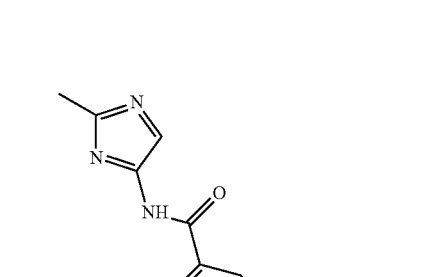 | 420.43 | 421 |

TABLE 8-continued

| Structure | MW | m/z |
|---|---|---|
| 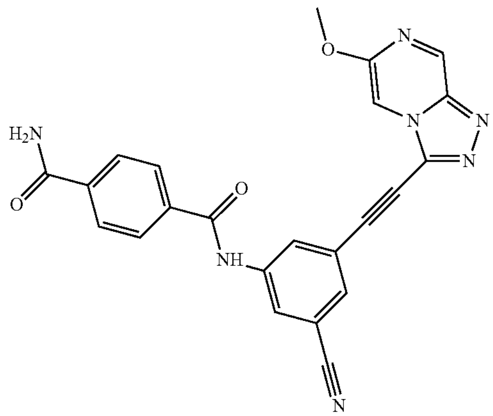 [SMILES: COc1cn2c(C#Cc3cc(C#N)cc(NC(=O)c4ccc(C(N)=O)cc4)c3)nnc2cn1] | 437.41 | 438 |
| 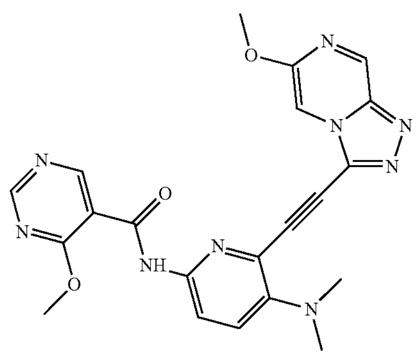 [SMILES: COc1cn2c(C#Cc3nc(NC(=O)c4cncnc4OC)ccc3N(C)C)nnc2cn1] | 446.42 | 447 |
| 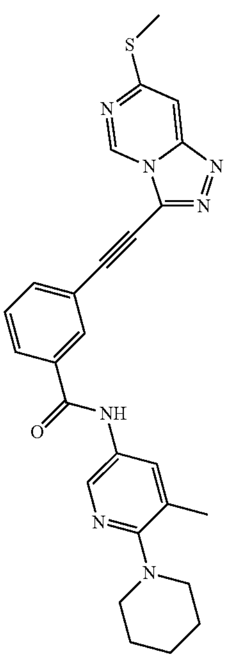 | 483.59 | 484 |

TABLE 8-continued

| Structure | MW | m/z |
|---|---|---|
| 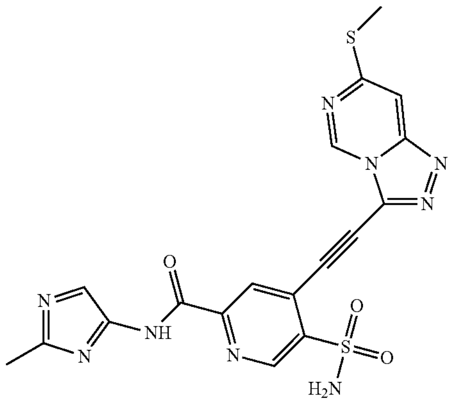 | 468.49 | 469 |
| 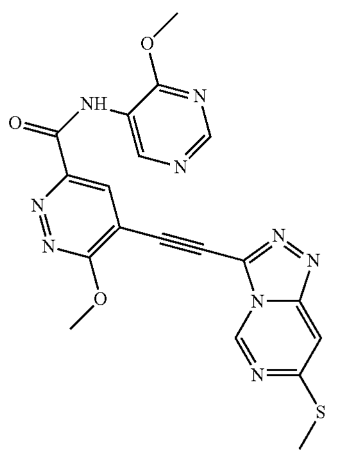 | 449.45 | 450 |
| 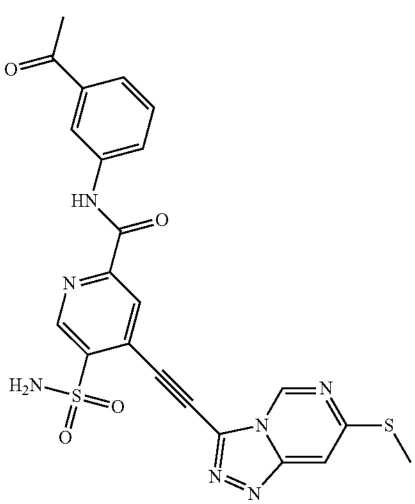 | 507.55 | 508 |

TABLE 8-continued
| Structure | MW | m/z |
|---|---|---|
| 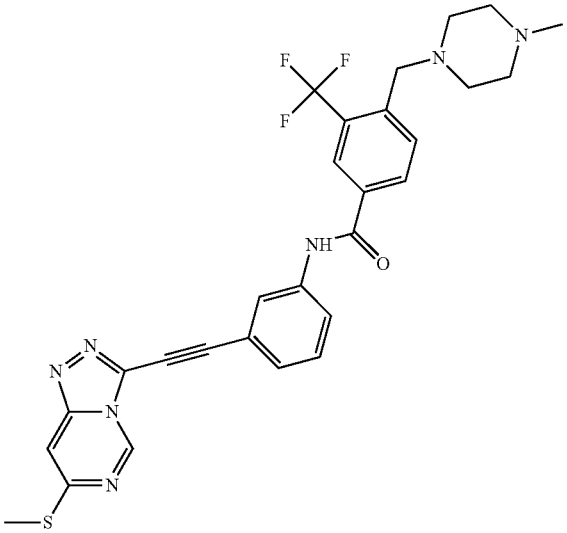 | 565.61 | 566 |
| 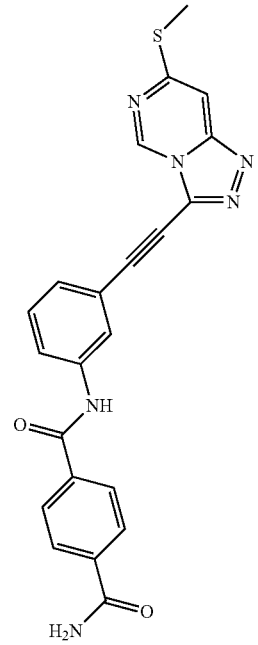 | 428.47 | 429 |
| 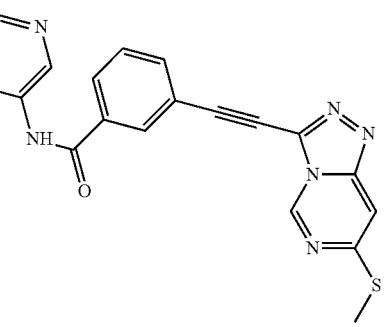 | 417.45 | 418 |

TABLE 8-continued

| Structure | MW | m/z |
|---|---|---|
| 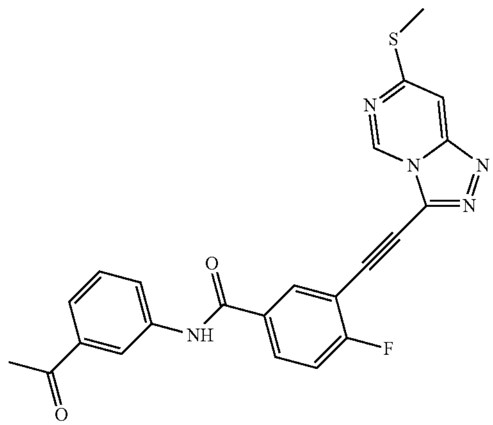 | 445.47 | 446 |
| 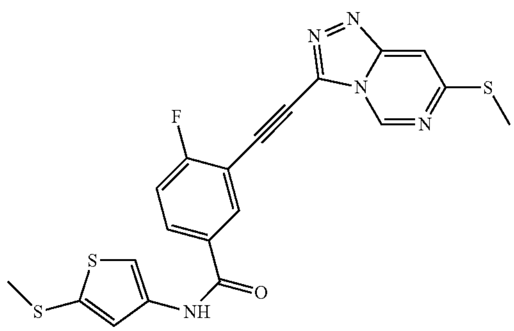 | 455.55 | 456 |
| 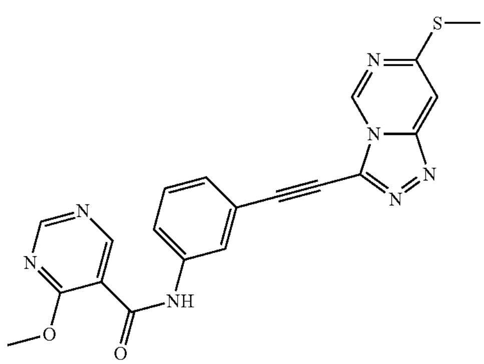 | 417.45 | 418 |
| 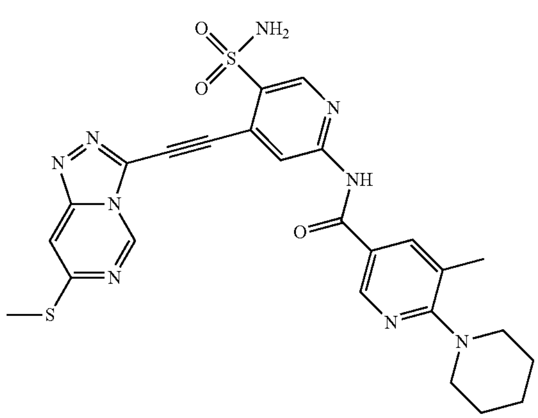 | 563.66 | 564 |

TABLE 8-continued
| Structure | MW | m/z |
|---|---|---|
| 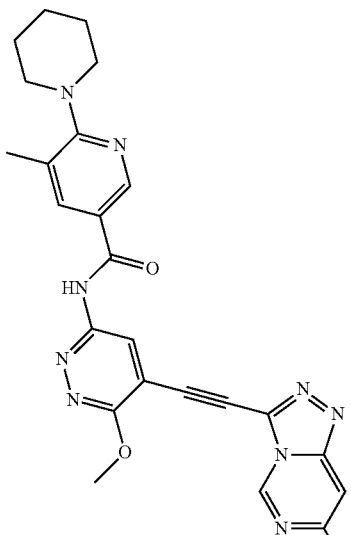 | 515.59 | 516 |
| 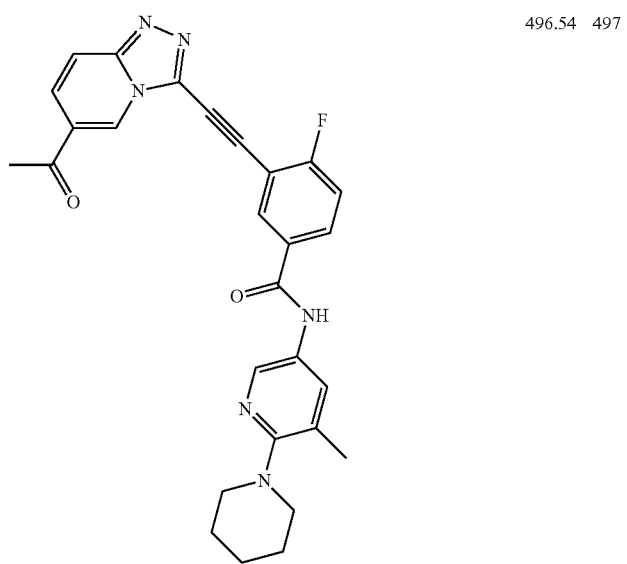 | 496.54 | 497 |

TABLE 8-continued
| Structure | MW | m/z |
|---|---|---|
| 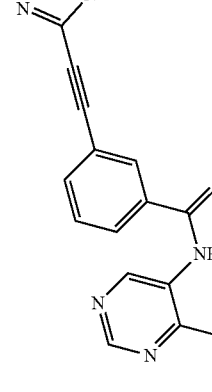 | 412.40 | 413 |
| 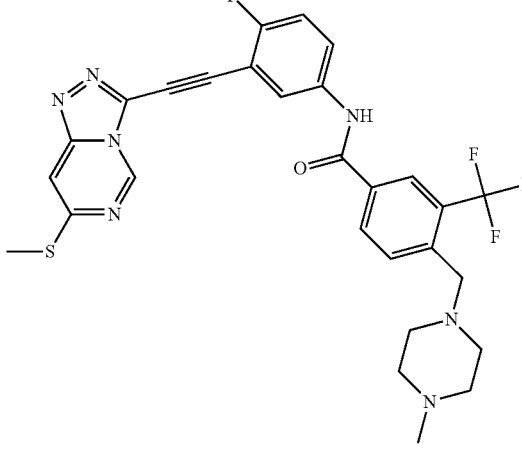 | 583.60 | 584 |
| 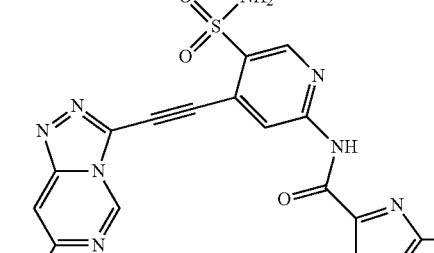 | 468.49 | 469 |

TABLE 8-continued
| Structure | MW | m/z |
|---|---|---|
| 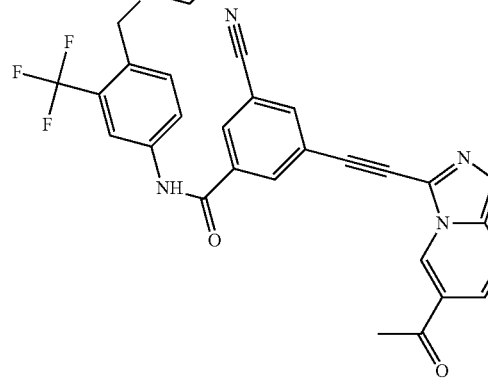 | 585.58 | 586 |
| 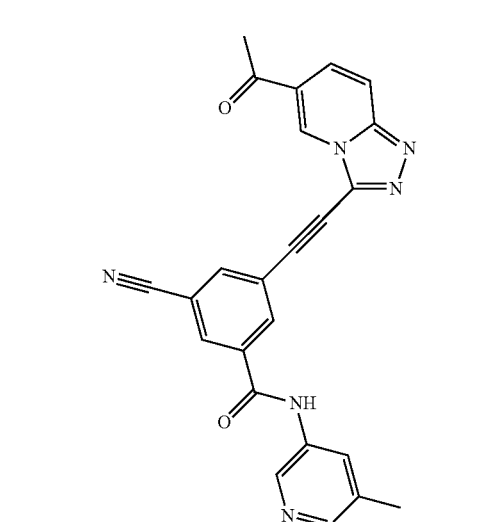 | 503.55 | 504 |
| 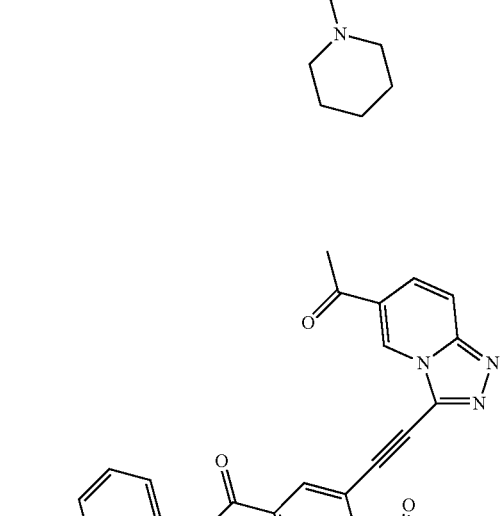 | 502.50 | 503 |

TABLE 8-continued
| Structure | MW | m/z |
|---|---|---|
| 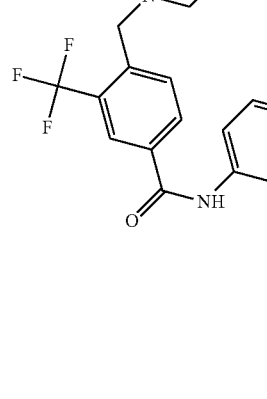 | 578.56 | 579 |
| 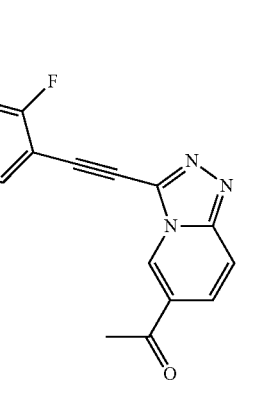 | 492.47 | 493 |
| 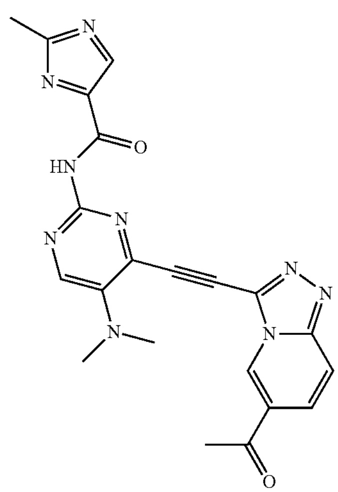 | 428.43 | 429 |
| 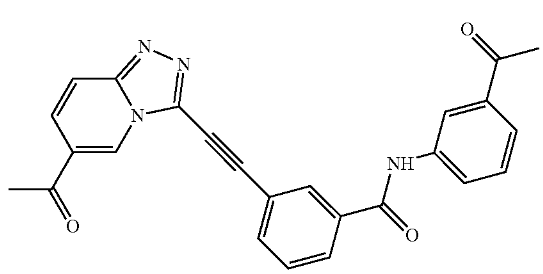 [SMILES: CC(=O)c1cccc(NC(=O)c2cccc(C#Cc3nnc4ccc(C(C)=O)cn34)c2)c1] | 422.44 | 423 |

TABLE 8-continued
| Structure | MW | m/z |
|---|---|---|
| 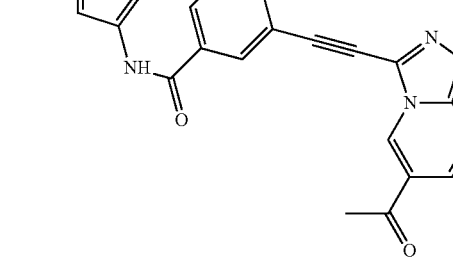 | 450.51 | 451 |
| 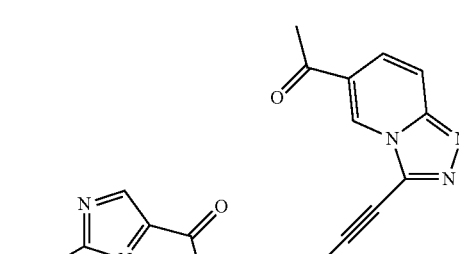 | 408.39 | 409 |
| 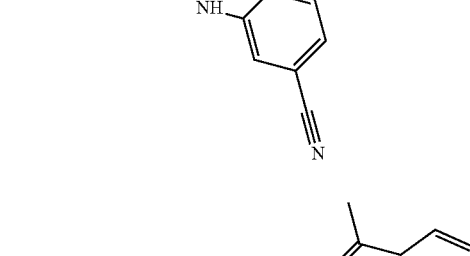 | 558.61 | 559 |
| 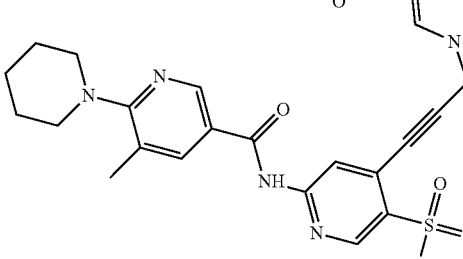 | 549.56 | 550 |

TABLE 8-continued
| Structure | MW | m/z |
|---|---|---|
| 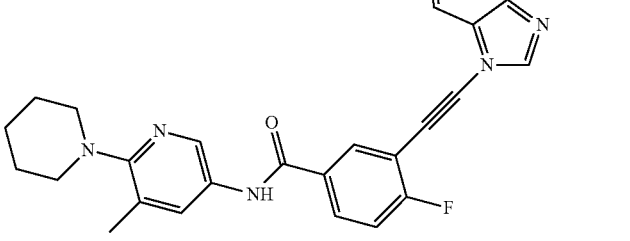 | 467.54 | 468 |
| 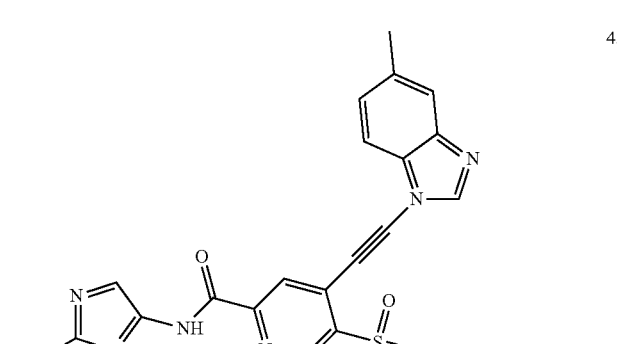 | 434.45 | 435 |
| 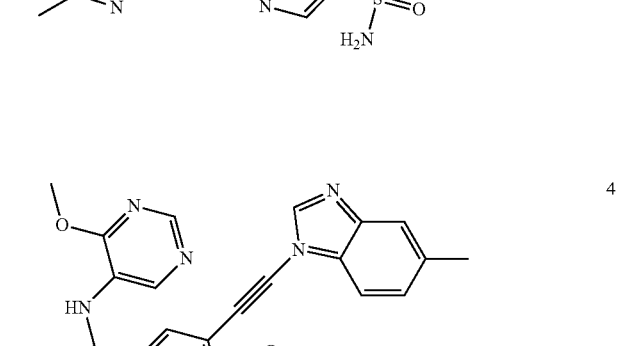 | 463.47 | 464 |
| 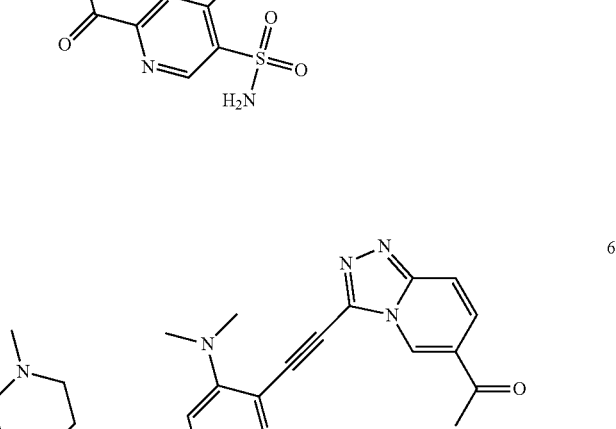 | 605.61 | 606 |

TABLE 8-continued
| Structure | MW | m/z |
|---|---|---|
| 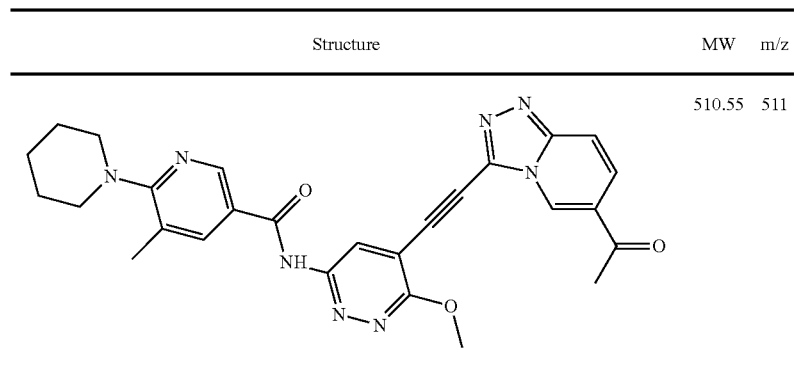 | 510.55 | 511 |
| 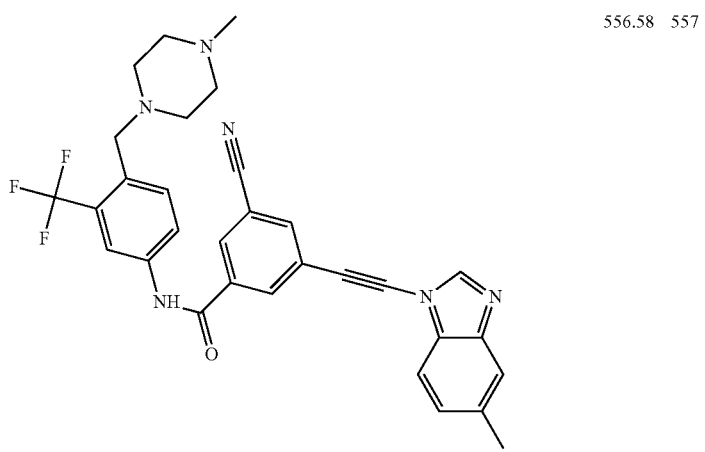 | 556.58 | 557 |
| 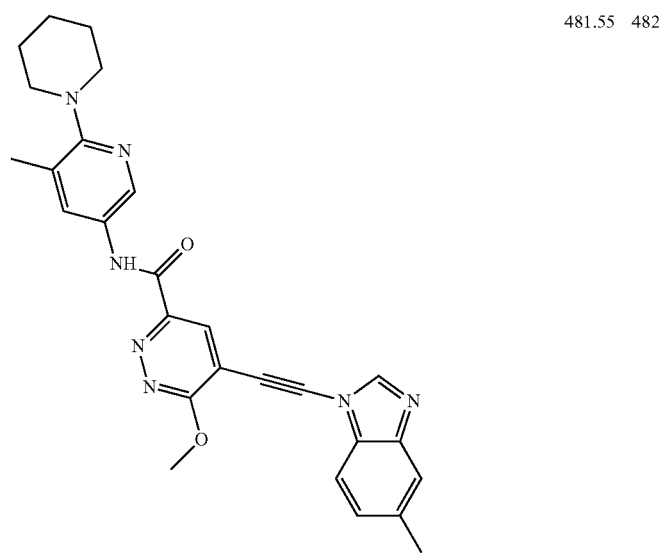 | 481.55 | 482 |

TABLE 8-continued
| Structure | MW | m/z |
|---|---|---|
| 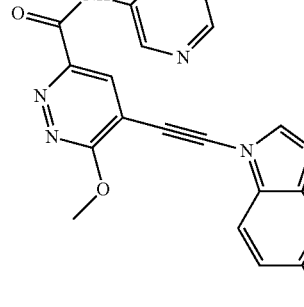 | 415.41 | 416 |
| 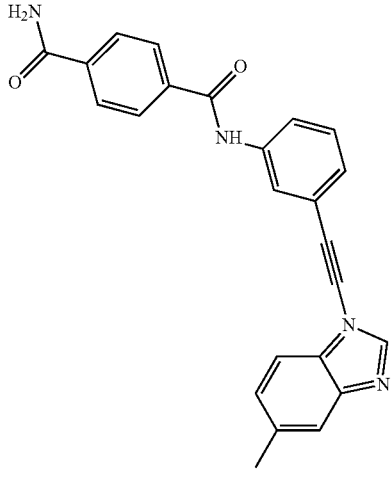 | 394.43 | 395 |
| 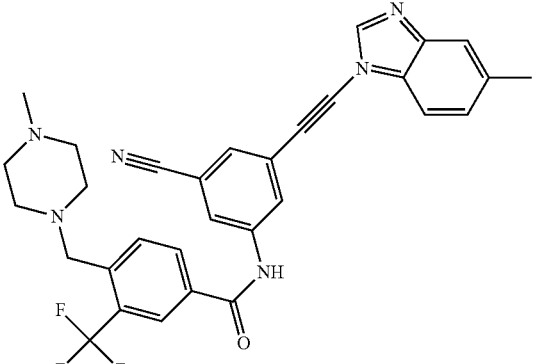 | 556.58 | 557 |

TABLE 8-continued

| Structure | MW | m/z |
|---|---|---|
| 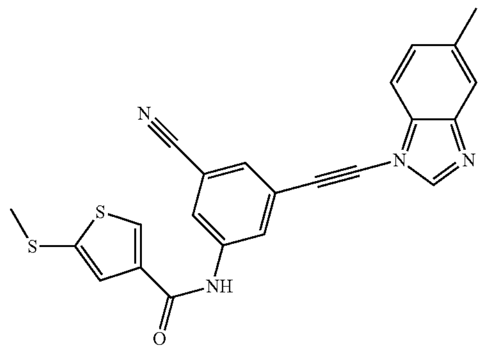 | 428.53 | 429 |
| 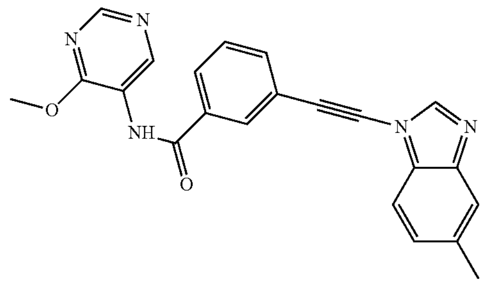 | 383.40 | 384 |
| 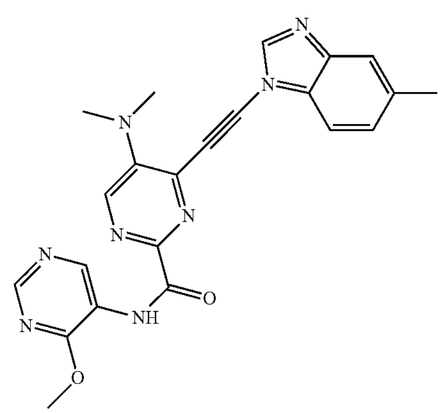 | 428.45 | 429 |
| 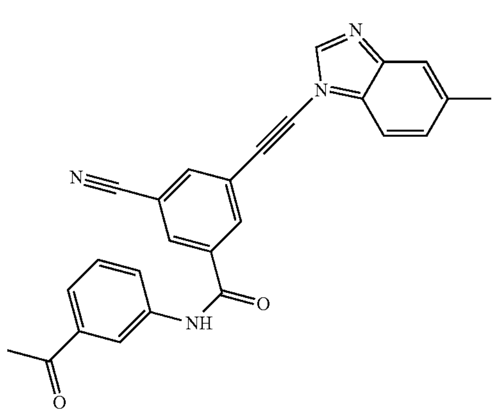 | 418.45 | 419 |

TABLE 8-continued
| Structure | MW | m/z |
|---|---|---|
| 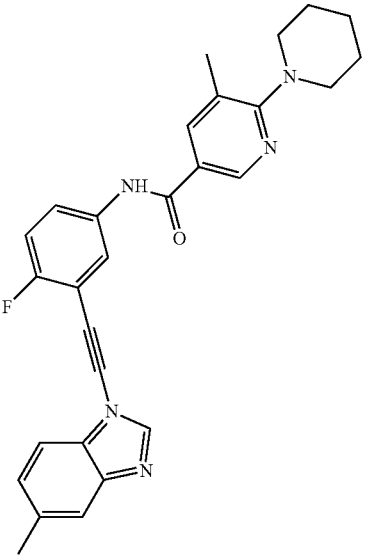 | 467.54 | 468 |
| 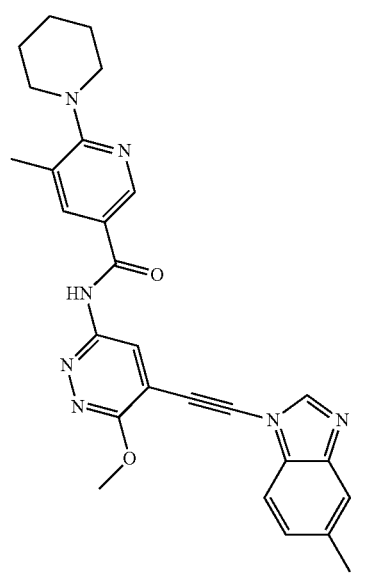 | 481.55 | 482 |

TABLE 8-continued
| Structure | MW | m/z |
|---|---|---|
| 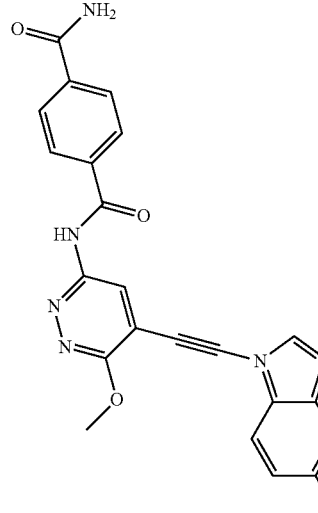 | 426.43 | 427 |
| 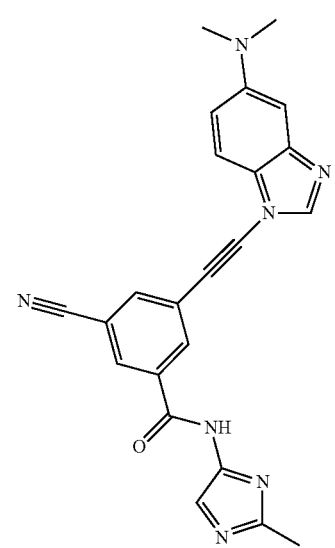 | 408.44 | 409 |
| 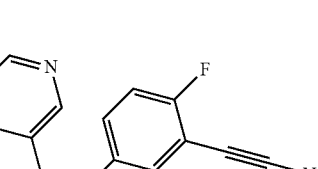 | 430.43 | 431 |

TABLE 8-continued

| Structure | MW | m/z |
|---|---|---|
| 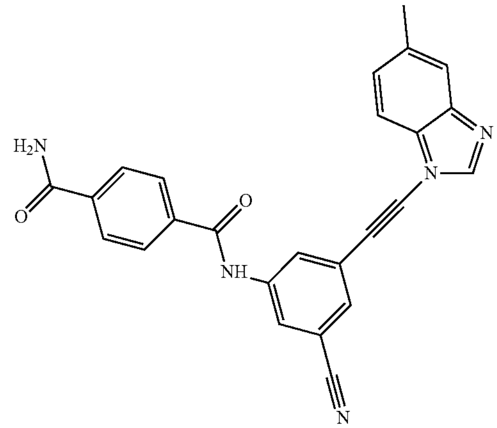 | 419.43 | 420 |
| 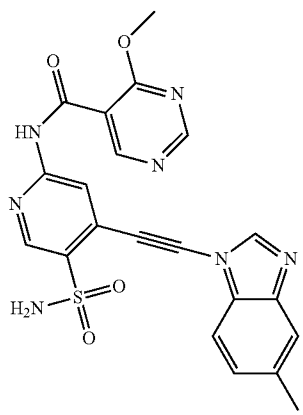 | 463.47 | 464 |
| 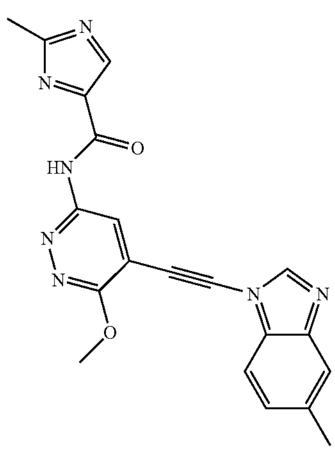 | 386.39 | 387 |

TABLE 8-continued
| Structure | MW | m/z |
|---|---|---|
| 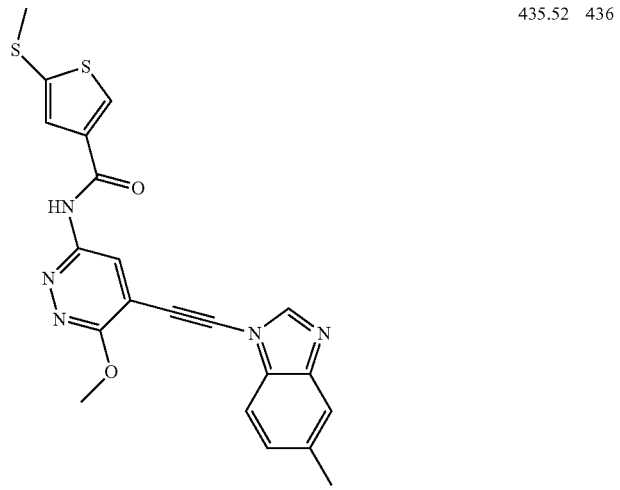 | 435.52 | 436 |
| 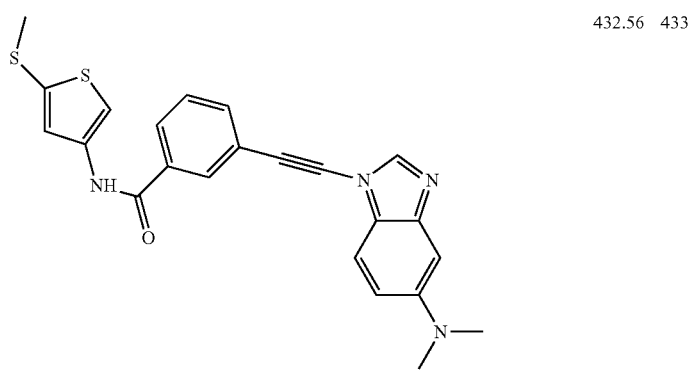 | 432.56 | 433 |
| 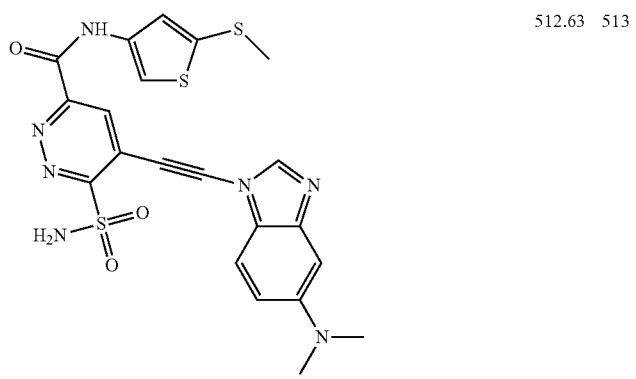 | 512.63 | 513 |

TABLE 8-continued

| Structure | MW | m/z |
|---|---|---|
| 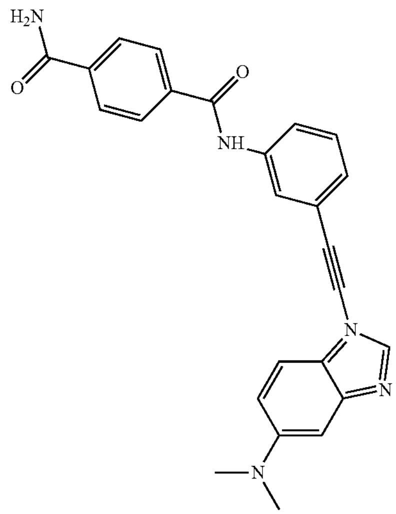 | 423.47 | 424 |
| 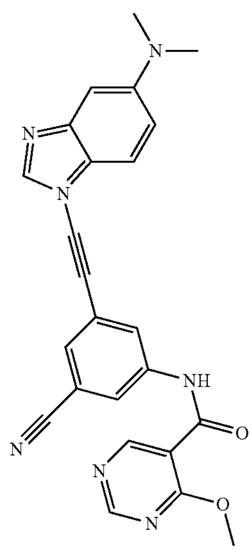 | 437.45 | 438 |
| 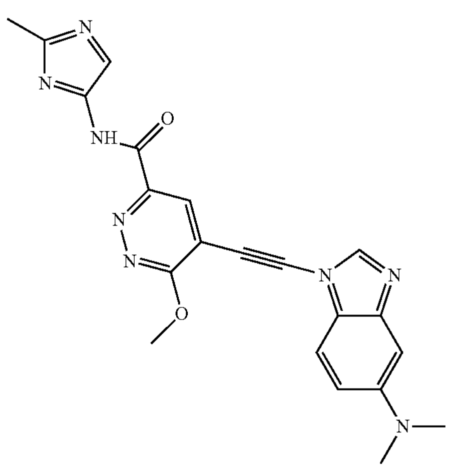 | 415.43 | 416 |

TABLE 8-continued

| Structure | MW | m/z |
|---|---|---|
| 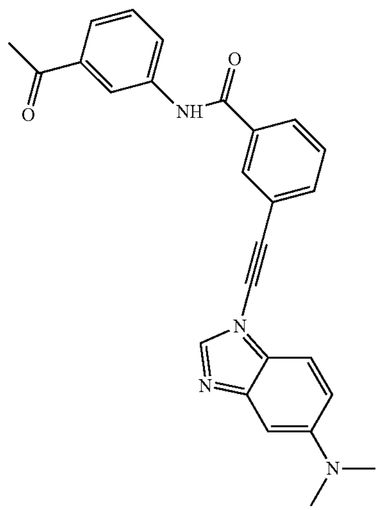 | 422.48 | 423 |
| 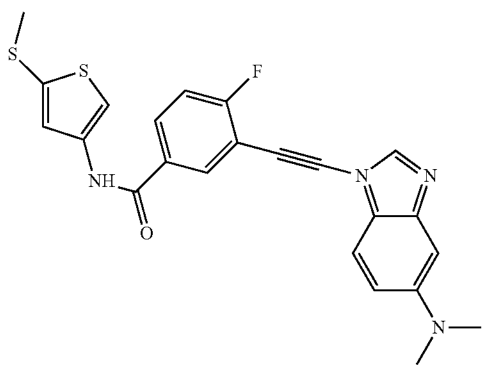 | 450.55 | 451 |
| 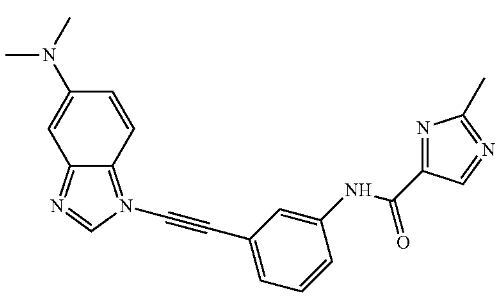 | 383.43 | 384 |

What is claimed is:
1. A compound selected from compounds of the following structures, or a pharmaceutically acceptable salt thereof:
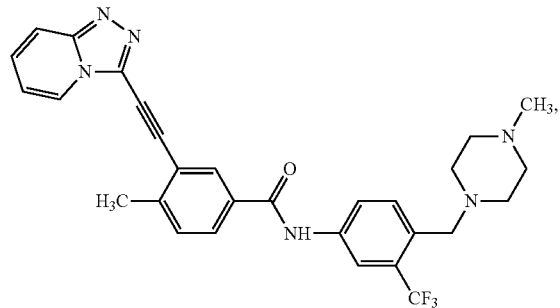
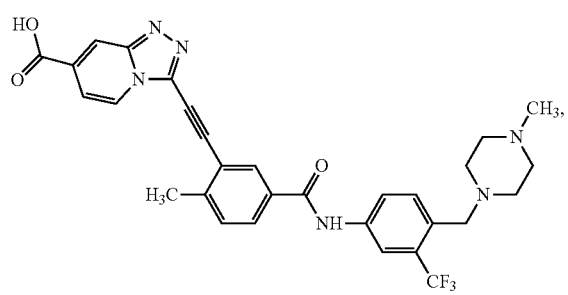 [SMILES: Cc1ccc(C(=O)Nc2ccc(CN3CCN(C)CC3)c(C(F)(F)F)c2)cc1C#Cc1nnc2cc(C(=O)O)ccn12]
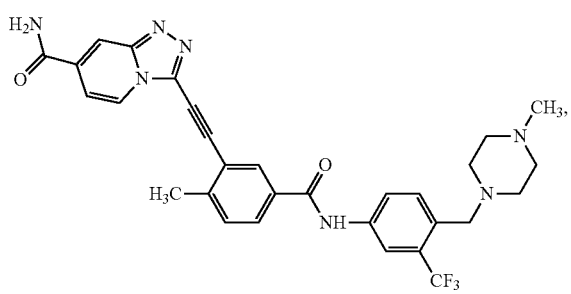
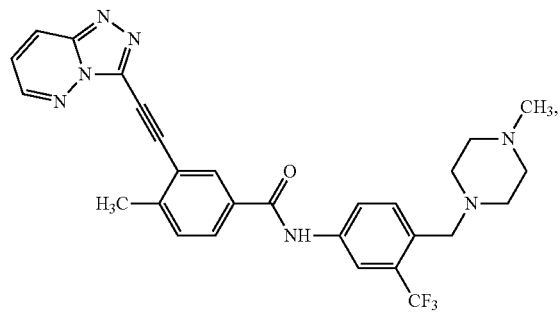
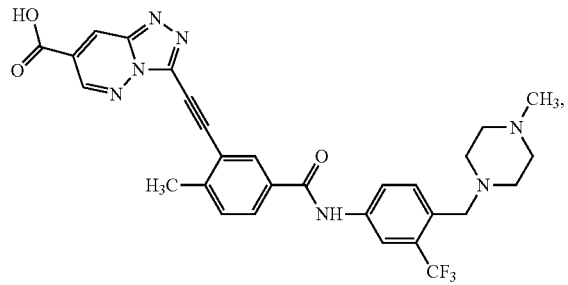
-continued
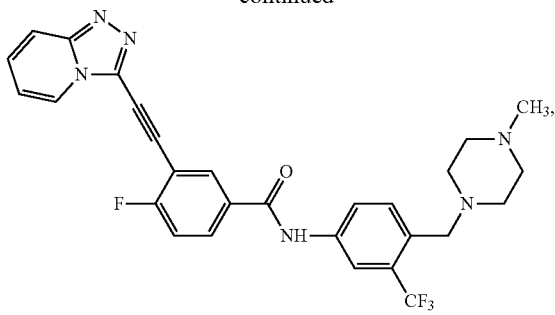
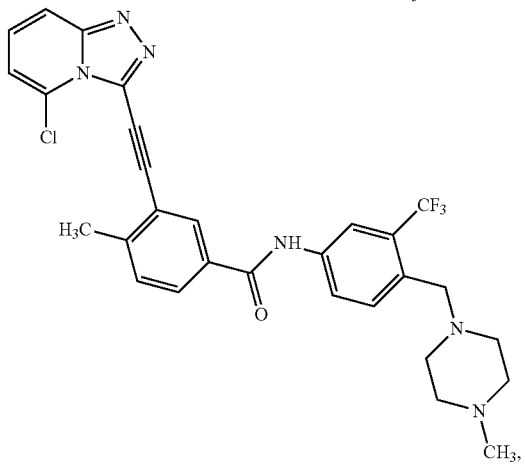
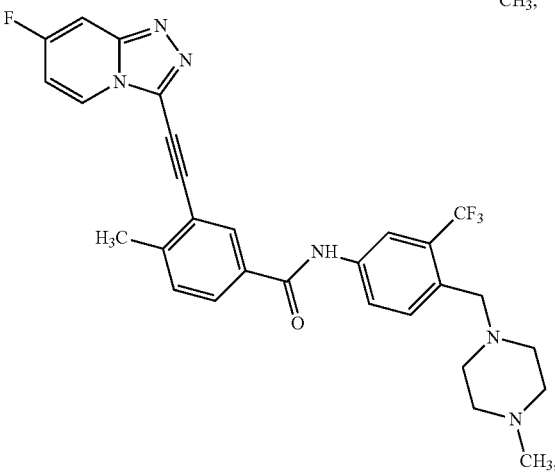
and
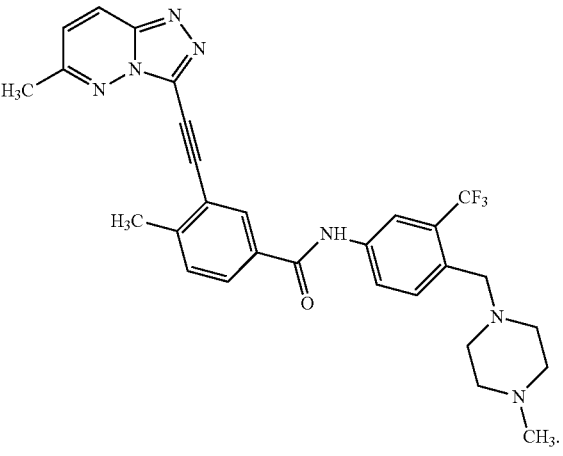

2. The compound or pharmaceutically acceptable salt thereof of claim 1, wherein the compound has the following structure:

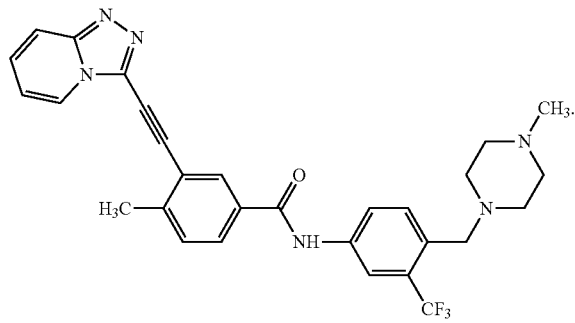 [SMILES: Cc1ccc(C(=O)Nc2ccc(CN3CCN(C)CC3)c(C(F)(F)F)c2)cc1C#Cc1nnc2cccnn12]

3. The compound of claim 2, wherein the compound inhibits Abl kinase with an IC$_{50}$ of less than 20 nM, inhibits Abl (T315I) kinase with an IC$_{50}$ of less than 20 nM and inhibits proliferation of K562 cells with an IC$_{50}$ of less than 100 nM.

4. The compound or pharmaceutically acceptable salt thereof of claim 1, wherein the compound has the following structure:

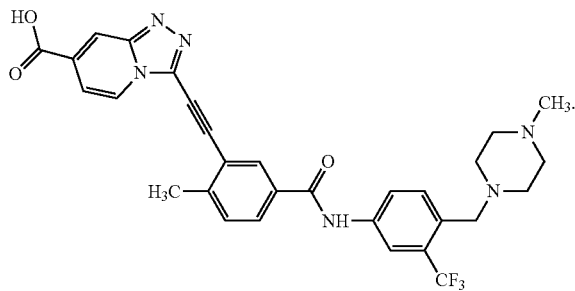 [SMILES: Cc1ccc(C(=O)Nc2ccc(CN3CCN(C)CC3)c(C(F)(F)F)c2)cc1C#Cc1nnc2cc(C(=O)O)cnn12]

5. The compound or pharmaceutically acceptable salt thereof of claim 1, wherein the compound has the following structure:

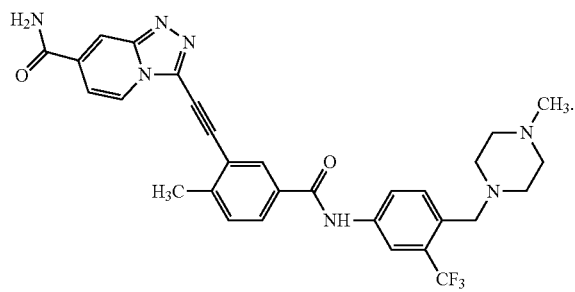

6. The compound or pharmaceutically acceptable salt thereof of claim 1, wherein the compound has the following structure:

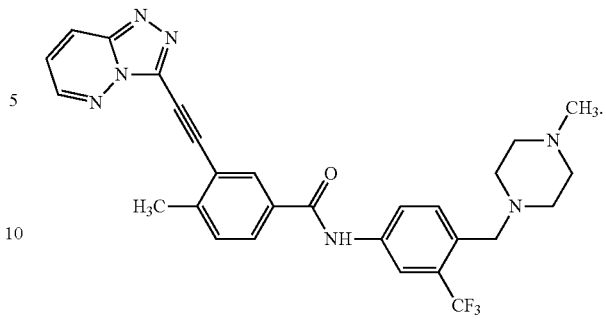

7. The compound or pharmaceutically acceptable salt thereof of claim 1, wherein the compound has the following structure:

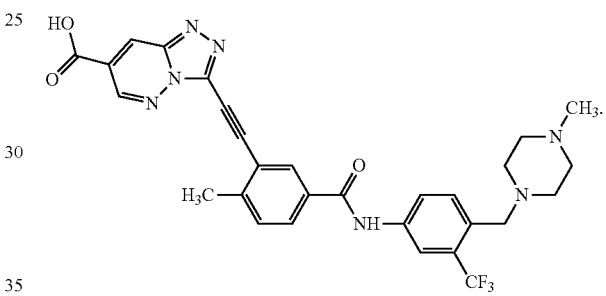

8. The compound or pharmaceutically acceptable salt thereof of claim 1, wherein the compound has the following structure:

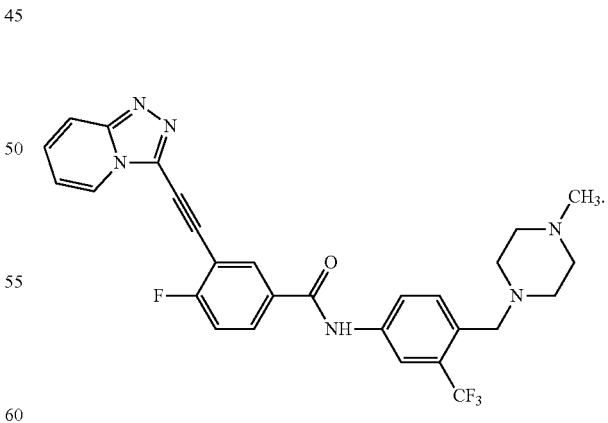

9. The compound of pharmaceutically acceptable salt thereof of claim 1, wherein the compound has the following structure:

10. The compound or pharmaceutically acceptable salt thereof of claim 1, wherein the compound has the following structure:

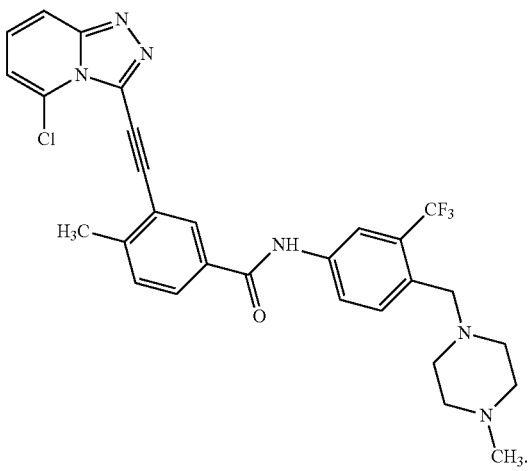 [SMILES: Cc1ccc(C(=O)Nc2ccc(CN3CCN(C)CC3)c(C(F)(F)F)c2)cc1C#Cc1nnc2cccc(Cl)n12]

11. The compound or pharmaceutically acceptable salt thereof of claim 1, wherein the compound has the following structure:

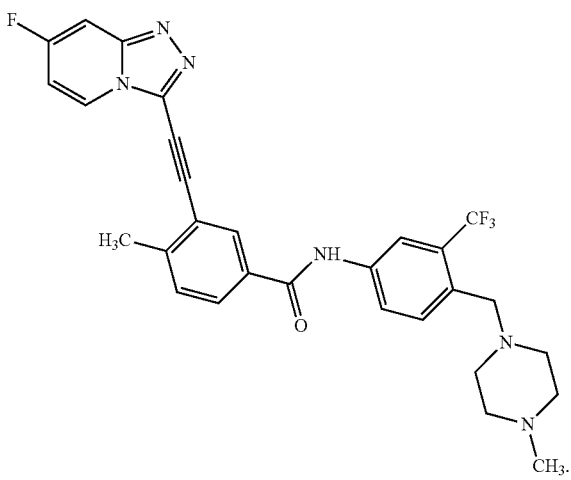 [SMILES: Cc1ccc(C(=O)Nc2ccc(CN3CCN(C)CC3)c(C(F)(F)F)c2)cc1C#Cc1nnc2cc(F)ccn12]

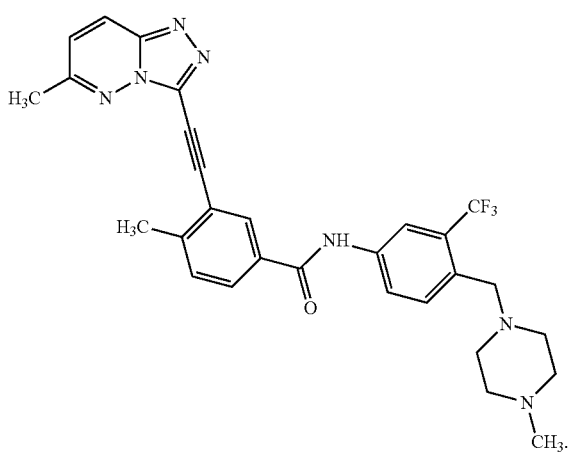 [SMILES: Cc1ccc2nnc(C#Cc3cc(C(=O)Nc4ccc(CN5CCN(C)CC5)c(C(F)(F)F)c4)ccc3C)n2n1]

12. A pharmaceutical composition comprising a compound or pharmaceutically acceptable salt thereof of claim 1, and a pharmaceutically acceptable carrier, solvent or filler.

13. A pharmaceutical composition comprising a compound or pharmaceutically acceptable salt thereof of claim 2, and a pharmaceutically acceptable carrier, solvent or filler.

14. A method of treating cancer, comprising administering to a subject in need of such treatment an effective amount of a compound or pharmaceutically acceptable salt thereof according to claim 1.

15. A method of treating a disease, wherein the disease is acute myelogenous leukemia, chronic myelogenous leukemia, hepatocellular carcinoma, non-small cell lung cancer or a gastrointestinal stromal tumor, comprising administering to a subject in need of such treatment an effective amount of a compound or pharmaceutically acceptable salt thereof according to claim 1.

16. A method of treating cancer, comprising administering to a subject in need of such treatment an effective amount of a compound or pharmaceutically acceptable salt thereof according to claim 2.

17. A method of treating a disease, wherein the disease is acute myelogenous leukemia, chronic myelogenous leukemia, hepatocellular carcinoma, non-small cell lung cancer or a gastrointestinal stromal tumor, comprising administering to a subject in need of such treatment an effective amount of a compound or pharmaceutically acceptable salt thereof according to claim 2.

18. A method of treating leukemia, comprising administering to a subject in need of such treatment an effective amount of a compound or pharmaceutically acceptable salt thereof according to claim 1.

19. The method of claim 18, wherein the leukemia is resistant to treatment with imatinib, or another kinase inhibitor.

20. A method of treating leukemia, comprising administering to a subject in need of such treatment an effective amount of a compound or pharmaceutically acceptable salt thereof according to claim 2.

21. The method of claim 20, wherein the leukemia is resistant to treatment with imatinib, or another kinase inhibitor.

22. A method of treating chronic myelogenous leukemia, comprising administering to a subject in need of such treatment an effective amount of a compound or pharmaceutically acceptable salt thereof according to claim 1.

23. The method of claim 22, wherein the leukemia is resistant to treatment with imatinib, dasatinib, or nilotinib, or another kinase inhibitor.

24. A method of treating chronic myelogenous leukemia, comprising administering to a subject in need of such treatment an effective amount of a compound or pharmaceutically acceptable salt thereof according to claim 2.

25. The method of claim 24, wherein the leukemia is resistant to treatment with imatinib, dasatinib, or nilotinib, or another kinase inhibitor.

26. A method of treating chronic myelogenous leukemia, comprising administering to a subject in need of such treatment an effective amount of a compound according to claim 3.

27. The method of claim 26, wherein the leukemia is resistant to treatment with imatinib, dasatinib, or nilotinib, or another kinase inhibitor.

28. A method of treating acute myelogenous leukemia, comprising administering to a subject in need of such treatment an effective amount of a compound or pharmaceutically acceptable salt thereof according to claim 1.

29. The method of claim 28, wherein the leukemia is resistant to treatment with imatinib, dasatinib, or nilotinib, or another kinase inhibitor.

30. A method of treating acute myelogenous leukemia, comprising administering to a subject in need of such treatment an effective amount of a compound or pharmaceutically acceptable salt thereof according to claim 2.

31. The method of claim 30, wherein the leukemia is resistant to treatment with imatinib, dasatinib, or nilotinib, or another kinase inhibitor.

32. A method of treating acute myelogenous leukemia, comprising administering to a subject in need of such treatment an effective amount of a compound according to claim 3.

33. The method of claim 32, wherein the leukemia is resistant to treatment with imatinib, dasatinib, or nilotinib, or another kinase inhibitor.

34. A method of treating Philadelphia chromosome-positive acute lymphoblastic leukemia, chronic myelogenous leukemia, hepatocellular carcinoma, non-small cell lung cancer or a gastrointestinal stromal tumor, comprising administering to a subject in need of such treatment an effective amount of a compound or pharmaceutically acceptable salt thereof according to claim 1.

35. A method of treating Philadelphia chromosome-positive acute lymphoblastic leukemia, chronic myelogenous leukemia, hepatocellular carcinoma, non-small cell lung cancer or a gastrointestinal stromal tumor, comprising administering to a subject in need of such treatment an effective amount of a compound or pharmaceutically acceptable salt thereof according to claim 2.

36. A method of treating Philadelphia chromosome-positive acute lymphoblastic leukemia, chronic myelogenous leukemia, hepatocellular carcinoma, non-small cell lung cancer or a gastrointestinal stromal tumor, comprising administering to a subject in need of such treatment an effective amount of a compound according to claim 3.

37. A pharmaceutically acceptable salt of the compound according to claim 2, wherein the compound inhibits Abl kinase with an $IC_{50}$ of less than 20 nM, inhibits Abl (T315I) kinase with an $IC_{50}$ of less than 20 nM and inhibits proliferation of K562 cells with an $IC_{50}$ of less than 100 nM.

38. A method of treating chronic myelogenous leukemia, comprising administering to a subject in need of such treatment a pharmaceutically acceptable salt according to claim 37.

39. A method of treating acute myelogenous leukemia, comprising administering to a subject in need of such treatment an effective amount of a pharmaceutically acceptable salt according to claim 37.

40. A method of treating Philadelphia chromosome-positive acute lymphoblastic leukemia, chronic myelogenous leukemia, hepatocellular carcinoma, non-small cell lung cancer or a gastrointestinal stromal tumor, comprising administering to a subject in need of such treatment an effective amount of a pharmaceutically acceptable salt according to claim 37.

41. The method of claim 14, wherein the cancer is a cancer wherein the inhibition of kinases is therapeutically beneficial.

42. The method of claim 16, wherein the cancer is a cancer wherein the inhibition of kinases is therapeutically beneficial.

43. The method of claim 14, wherein the cancer is a cancer wherein the inhibition of Abl or Abl (T315I) is therapeutically beneficial.

44. The method of claim 16, wherein the cancer is a cancer wherein the inhibition of Abl or Abl (T315I) is therapeutically beneficial.

45. The method of claim 14, wherein the cancer is a cancer that expresses Abl or Abl (T315I).

46. The method of claim 16, wherein the cancer is a cancer that expresses Abl or Abl (T315I).

47. The method of claim 14, wherein the cancer is a cancer wherein the inhibition of ABL2/ARG, DDR2, FMS, FRK, LCK, LYN, PDGFRA, RET, BLK, EPHA2, EPHA8, EPHB1, EPHB2, FGR, FLT4, FYN, HCK, KDR, or PDGFRb is therapeutically beneficial.

48. The method of claim 16, wherein the cancer is a cancer wherein the inhibition of ABL2/ARG, DDR2, FMS, FRK, LCK, LYN, PDGFRA, RET, BLK, EPHA2, EPHA8, EPHB1, EPHB2, FGR, FLT4, FYN, HCK, KDR, or PDGFRb is therapeutically beneficial.

49. The method of claim 14, wherein the cancer is a cancer that expresses ABL2/ARG, DDR2, FMS, FRK, LCK, LYN, PDGFRA, RET, BLK, EPHA2, EPHA8, EPHB1, EPHB2, FGR, FLT4, FYN, HCK, KDR, or PDGFRb.

50. The method of claim 16, wherein the cancer is a cancer that expresses ABL2/ARG, DDR2, FMS, FRK, LCK, LYN, PDGFRA, RET, BLK, EPHA2, EPHA8, EPHB1, EPHB2, FGR, FLT4, FYN, HCK, KDR, or PDGFRb.

* * * * *

UNITED STATES PATENT AND TRADEMARK OFFICE
CERTIFICATE OF CORRECTION

PATENT NO. : 9,522,910 B2  
APPLICATION NO. : 14/242241  
DATED : December 20, 2016  
INVENTOR(S) : Germes G. Chilov and Ilya Y. Titov Page 1 of 1

It is certified that error appears in the above-identified patent and that said Letters Patent is hereby corrected as shown below:

In the Claims

Column 236, Line 65 (Claim 9), delete "of" and insert -- or --, therefor.

Column 240, Line 19 (Claim 43), delete "(T3151 )" and insert -- (T3151) --, therefor.

Column 240, Line 22 (Claim 44), delete "(T3151 )" and insert -- (T3151) --, therefor.

Column 240, Line 25 (Claim 45), delete "(T3151 )" and insert -- (T3151) --, therefor.

Column 240, Line 27 (Claim 46), delete "(T3151 )" and insert -- (T3151) --, therefor.

Signed and Sealed this  
Eighteenth Day of June, 2019

Andrei Iancu  
*Director of the United States Patent and Trademark Office*